United States Patent [19]
Wissner et al.

[11] Patent Number: 4,640,913
[45] Date of Patent: Feb. 3, 1987

[54] PHOSPHOCHOLINE DERIVATIVES HAVING ANTIHYPERTENSIVE ACTION

[75] Inventors: Allan Wissner, Ardsley, N.Y.; Robert E. Schaub, Upper Saddle River, N.J.; Phaik E. Sum, New City, N.Y.

[73] Assignee: American Cyanamid Company, Stamford, Conn.

[21] Appl. No.: 457,097

[22] Filed: Jan. 10, 1983

[51] Int. Cl.$^4$ .......................... A61K 31/185; C07F 9/10
[52] U.S. Cl. .......................................... 514/77; 558/169
[58] Field of Search .................. 260/925; 424/199; 558/169; 514/77

[56] References Cited

U.S. PATENT DOCUMENTS 4,159,988  7/1979  Eibl et al. .............................. 260/925
4,329,302  5/1982  Hanahan et al. ...................... 424/199

OTHER PUBLICATIONS

Blank et al, "Res. Comm. in Chem. Path. & Pharmacology", vol. 39, No. 1, (1982), pp. 3-20.
Tence et al, "Agents and Actions", vol. 11, Nos. 6/7, (1981), pp. 558-559.
Tence et al, "Biochimie", vol. 63, (1981) pp. 723-727.
Benveniste et al, "C. R. Acad. Sc. Paris", vol. 289 (1979) pp. D-1037-1040.
Godfroid et al, "Feds. Letters", vol. 116, No. 2, (7/1980), pp. 161-164.

Primary Examiner—Anton H. Sutto
Attorney, Agent, or Firm—M-E. M. Timbers

[57] ABSTRACT

Phosphocholine derivatives and compositions are described which are useful as hypotensive agents and in the treatment of hypertension in warm-blooded animals.

29 Claims, 10 Drawing Figures

FLOWSHEET D

28

29

31

32

33

33

FLOWSHEET D (continued)

34

$\xrightarrow{\text{p-TSA, CH}_3\text{OH, THF}}$ 35

35

$\xrightarrow[\underline{4a} \quad\quad\quad \underline{4b}]{\text{Cl}_2\overset{\overset{O}{\|}}{P}\text{O(CH}_2)_p\text{-Br, or Cl-}\overset{\overset{O}{\|}}{\underset{\text{OH}}{P}}\text{-CH}_2(\text{CH}_2)_p\text{-Br, (C}_2\text{H}_5)_3\text{N}}$ $\xrightarrow{\text{NaOAc, H}_2\text{O}}$ 36

36

(1) $N(R_2)_3^+$ or $R_2\text{-N}$$(CH_2)_q$ 7           8

(2) AgCO₃

$\longrightarrow$ 37

36

FLOWSHEET D(continued)

37

38

27

FLOWSHEET E

FLOWSHEET F

FLOWSHEET F (continued)

51

51a

51

52

FLOWSHEET F (continued)

52

44a (1) $N(R_2)_3^+$ or $R_2-N\underset{8}{\phantom{xx}}(CH_2)q$
    $\phantom{(1) N(R_2)_3^+ or } \underline{7} \phantom{xxxx} \underline{8}$ (2) $Ag_2CO_3$ 44b

FLOWSHEET G

FLOWSHEET J

X'—CH2CCH2OH  $\xrightarrow{\text{NaBH}_4}$
   ‖
   O

<u>3</u>

X'—CH2CHCH2OH  $\xrightarrow{\text{TrCl, pyridine}}$
   ‖
   OH

<u>69</u>

X'—CH2CHCH2OC  $\xrightarrow{\text{R—J, NaH}}$
   |
   OH

<u>70</u>

$\xrightarrow{\text{p-TSA, CH}_3\text{OH\&THF}}$

<u>71</u>

FLOWSHEET J (continued)

72

73

68

PHOSPHOCHOLINE DERIVATIVES HAVING ANTIHYPERTENSIVE ACTION

BACKGROUND OF INVENTION

This invention pertains to novel phosphocholine derivatives, and to methods of preparation of such compounds. This invention is also concerned with compositions useful in the treatment of hypertention.

It is estimated that approximately fifteen percent (15%) or more of the adult population in the United States is hypertensive, i.e., having blood pressures greater than or equal to about 160/95 mm Hg. Of that population, approximately one-half is unaware of their hypertensive condition. An untreated hypertensive is at great risk of developing disabling or fatal left ventricular failure, myocardial infarction, cerebral hemorrhage or infarction, and renal failure at an early age. Hypertension is generally considered the most important risk factor predisposing to coronary and cerebral atherosclerosis. However, it is believed that effective medical control of hypertension will prevent or forestall all complications associated with hypertension, and will prolong the life of the hypertensive patient.

Drug therapy for hypertension includes use of diuretics, sympathetic depressants (e.g., α-blockers such as reserpine), vasodilators and finally blockers of sympathetic transmission at the neuroeffector junction (e.g., guanethidine or clonidine).

Among the vasodilators currently employed in hypertension therapy are diazoxide and sodium nitroprusside. Side effects of diazoxide therapy include nausea, vomiting, hyperglycemia and tachycardia. Side effects from sodium nitroprusside therapy include nausea, vomiting, agitation, muscular twitching and cutis anserina if blood pressure is reduced too rapidly. Minoxidil is also often used as a vasodilator in hypertension therapy. However, the side effects of minoxidil include sodium and water retention, and hirsutism. Hydralazine, a mild vasodilator, is also employed. Its side effects include headaches, tachycardia, fluid retention, aggravation of angina, gastrointestinal irritation, lupus-like syndrome, drug fever and psychosis.

Acetyl glyceryl ether phosphocholines have been recognized as having potent biological activity in platelet activation, and in vasoconstriciton and vasodilation. See, e.g., U.S. Pat. No. 4,329,302, which issued on May 11, 1982 to Hanahan et al. Such phosphocholines have been identified as both a platelet activation factor (PAF) and an antihypertensive polar renomedullary lipid (APRL). See R. L. Wykle et al., FEBS LETTERS, 141: 29-32 (1982); M. L. Blank et al., BIOCHEMICAL AND BIOPHYSICAL RESEARCH COMMUNICATIONS, 90: 1194–1200 (1979). Antihypertensive phospocholines do not occur as pre-formed components in the body; rather, such phosphocholines are synthesized by certain cells. See J. Benveniste et al., INT. ARCHS. ALLERGY APPL. IMMUNN., 66 (Supp. 1): 121–126 (1981); E. E. Muirhead, HYPERTENSION, 2: 444–464 (1980). APRL has been described as being accountable in great measure for the endocrine-type antihypertensive action exerted by the renal medullary and the renomedullary interstitial cells. M. L. Blank et al., ID.

BRIEF SUMMARY OF THE INVENTION

The phosphocholine derivatives of the present invention have the formula:

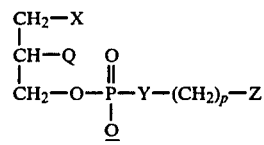

wherein X is selected from one or more of: (a) $C_1$-$C_{24}$ branched or straight chain alkyl; (b) $C_1$-$C_{24}$ branched or straight chain alkoxy; (c)

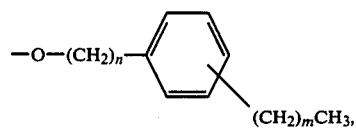

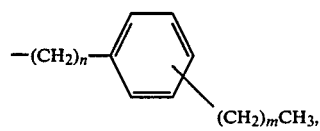

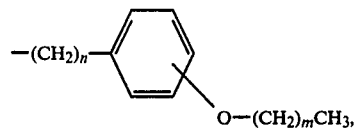

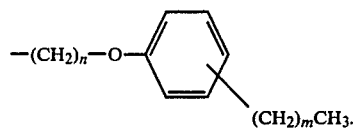

wherein n and m are integers from zero to 25 and the sum of n and m is less than or equal to 25; (d) phenyl; (e) substituted phenyl, wherein the substituents are selected form one or more of $C_1$-$C_{20}$ branched or straight chain alkyl, $C_1$-$C_{20}$ branched or straight chain alkoxy, halogen, trifluoromethyl, phenyl and substituted phenyl; (f) phenoxy, and (g) substituted phenoxy, wherein the substituents are selected from one or more of the group consisting of $C_1$-$C_{20}$ branched or straight chain alkyl, halogen, trifluoromethyl, phenyl and substituted phenyl;

wherein Q is selected from the group consisting of:

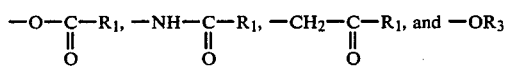

wherein $R_1$ is selected from the group consisting of hydrogen, $C_1$-$C_4$ branched or straight chain alkyl, $C_1$-$C_4$ branched or straight chain alkoxy and $C_1$-$C_4$ branched or straight chain alkylamino and $R_3$ is $C_1$-$C_4$ alkyl, with the provisos (1) Q is not

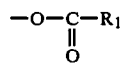

if at the same time $R_1$ is $C_1$-$C_4$ alkyl, X is $C_1$-$C_{24}$ branched or straight chain alkoxy and Y is oxygen; (2) Q is not —$OR_3$ when at the same time X is $C_1$-$C_{24}$ branched or straight chain alkoxy and Y is oxygen; (3) when Q is

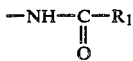

X is $C_1$-$C_{24}$ branched or straight chain alkoxy or

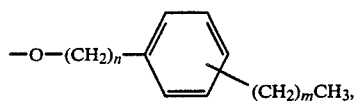

and (4) when Q is

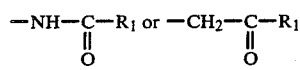

$R_1$ is $C_1$-$C_4$ branched or straight chain alkyl; wherein Y is oxygen or —$CH_2$; wherein p is an integer from 1 to 15 with the proviso that when Y is oxygen, p must be greater than 1; and wherein Z is selected from the group consisting of

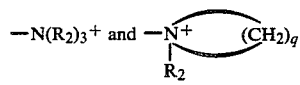

wherein $R_2$ may be the same or different and is selected from the group consisting of hydrogen and $C_1$-$C_4$ branched or straight chain alkyl and q is an integer from 4 to 7. Such phosphocholine derivatives have antihypertensive activity.

DETAILED DESCRIPTION OF THE INVENTION

Figure 1:
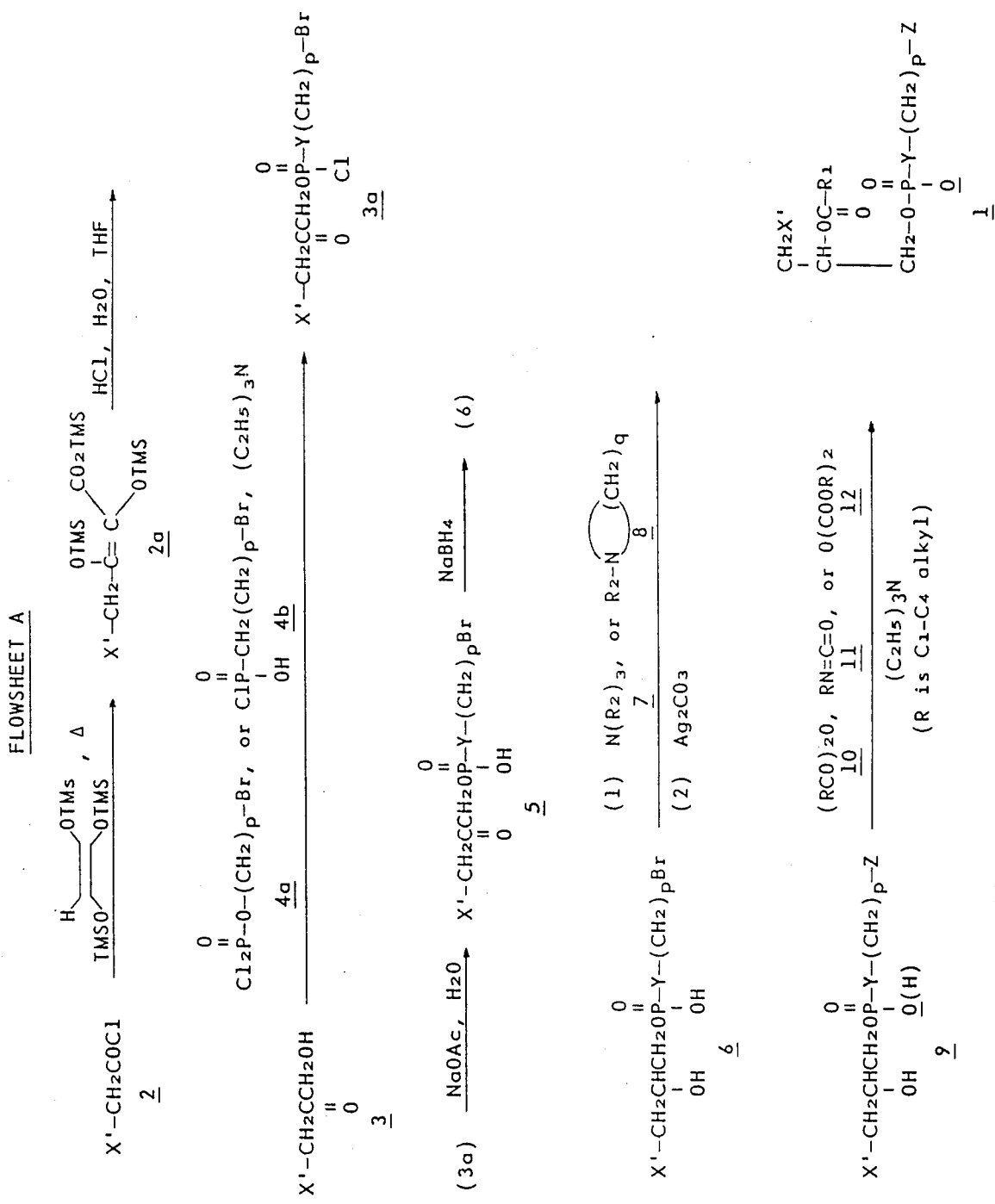

This invention is concerned with new compounds of the formula:

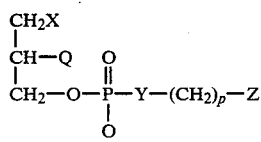

wherein X is selected from the group consisting of $C_1$-$C_{24}$ branched or straight chain alkyl, $C_1$-$C_{24}$ branched or straight chain alkoxy,

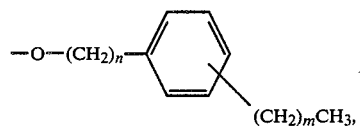

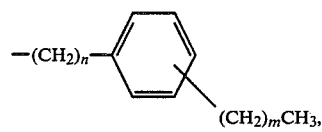

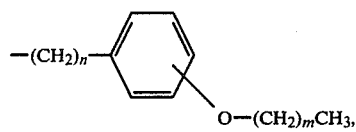

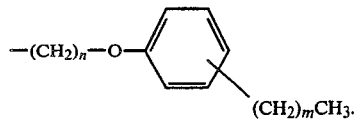

wherein n and m are integers from zero to 25 and the sum of n and m is less than or equal to 25, phenyl and substituted phenyl wherein the substituents are selected from the group consisting of $C_1$-$C_{20}$ branched or straight chain alkyl, $C_1$-$C_{20}$ branched or straight chain alkoxy, halogen, trifluoromethyl, phenyl and substituted phenyl, phenoxy and substituted phenoxy wherein the substituents are selected from the group consisting of $C_1$-$C_{20}$ branched or straight chain alkyl, $C_1$-$C_{20}$ branched or straight chain alkoxy, halogen, trifluoromethyl, phenyl and substituted phenyl. $R_1$ is selected from the group consisting of hydrogen, $C_1$-$C_4$ branched or straight chain alkyl, $C_1$-$C_4$ branched or straight chain alkoxy and $C_1$-$C_4$ branched or straight chain alkylamino; Y is oxygen or —$CH_2$—; p is an integer from 1 to 15 with the proviso that when Y is oxygen, p must be greater than 1; Q is selected from the group consisting of

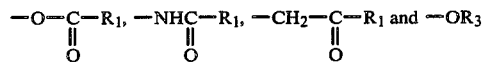

wherein $R_1$ is as defined above and $R_3$ is $C_1$-$C_4$ alkyl, with the proviso that Q cannot be

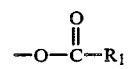

if $R_1$ is $C_1$-$C_4$ branched or straight chain alkyl when both X is $C_1$-$C_{24}$ branched or straight chain alkoxy and Y is oxygen, with the further proviso that Q cannot be —$OR_3$ when both X is $C_1$-$C_{24}$ alkoxy and Y is oxygen, with the further proviso that when Q is

X may only be $C_1$-$C_{24}$ branched or straight chain alkoxy or

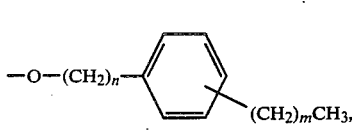

and with the further proviso that when Q is

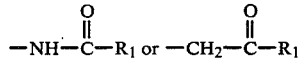

$R_1$ may only be $C_1$-$C_4$ branched or straight chain alkyl; and Z is selected from the group consisting of —$N(R_2)_3^+$, and

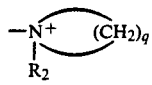

wherein $R_2$ may be the same or different and is selected from the group consisting of hydrogen and $C_1$-$C_4$ alkyl and q is an integer from 4 to 7.

The preparation of the compounds of this invention encompassed by Formula 1 is described hereinbelow in Flowsheet A, wherein X' is a $C_1$-$C_{24}$ branched or straight chain alkyl group,

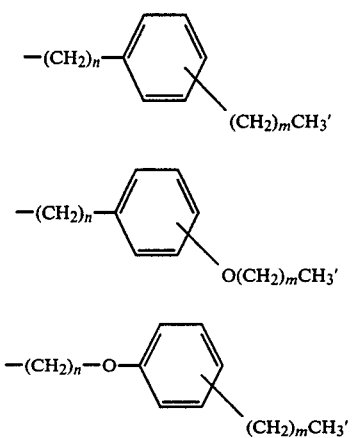

or a phenyl group optionally substituted with one or more of the following: $C_1$-$C_{20}$ branched or straight chain alkyl, $C_1$-$C_{20}$ branched or straight chain alkoxy, halogen, trifluoromethyl, phenyl and substituted phenyl; n and m are integers from zero to 25 and the sum of n and m is less than or equal to 25; $R_1$ is selected from the group consisting of hydrogen, branched or straight chain alkyl $C_1$-$C_4$, branched or straight chain alkoxy $C_1$-$C_4$ and branched or straight chain alkylamino $C_1$-$C_4$; Y is oxygen or —$CH_2$—; p is an integer from 1 to 15, with the proviso that when Y is oxygen, p must be greater than 1; Z is selected from the group consisting of —$N(R_2)_3^+$ and

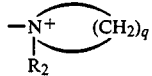

wherein $R_2$ is $C_1$-$C_4$ alkyl or hydrogen and q is an integer from 4 to 7; the $R_2$ groups within a molecule may be the same or different. Unless otherwise stated, all reactions are to be performed at room temperature (about 10° C. to about 25° C.) and at atmospheric pressure.

According to the sequence of reactions outlined in Flowsheet A, (FIG. 1) the carboxylic acid chloride 2 is heated at about 90°-125° C. with at least two equivalents of tris-trimethylsilyloxy ethylene [A. Wissner, J. ORG. CHEM., 44: 4617 (1979)], followed by hydrolysis of the resulting intermediate with dilute hydrochloric acid (about 0.01 to 1N) in tetrahydrofuran to furnish the hydroxymethyl ketone 3. Treatment of 3 with an excess of reagents 4a or 4b in carbon tetrachloride in the presence of at least one equivalent of an amine base, such as triethylamine, gives, after hydrolysis of the intermediate with a buffer such as sodium acetate solution, the compound 5.

The reagents 4a and 4b can be prepared by procedures well know in the art, such as those of E. Baer and N. Z. Stanacey, J. BIOL. CHEM., 240: 3754 (1965), A. Eberhard and F. H. Westheimer, J. AMER. CHEM. SOC., 87: 253 (1965), or W. Diembeck and H. Eibl, CHEM. PHY. LIPIDS, 24: 237 (1979).

Compound 5 can readily be reduced to alcohol 6 using sodium borohydride in an alcohol solvent such as ethanol or 1-butanol. Nucleophilic displacement of the bromine atom of 6 to give the compound 9 is accomplished by treatment of 6 with an excess of an amine such as 7 or 8, either in an inert solvent such as acetonitrile or tetrahydrofuran at elevated temperatures (about 50°-150° C.) in an enclosed vessel or by heating at about 60°-70° C. a solution of 6 and the amine in a mixture of chloroform, 1-propanol, dimethylformamide and water (about 3:5:5). When the compounds represented by structures 7 and 8 are tertiary amines, the products 9 of this reaction are quaternary ammonium salts; in these cases it may be desirable to prepare the internal salt by treatment of an aqueous-alcohol solution of the compound with a suspension of silver carbonate. The compounds represented by formula 9 can be converted to compounds 1 of this invention wherein $R_1$ is a $C_1$-$C_4$ alkyl group by the reaction of 9 with an anhydride 10 in the presence of a base catalyst such as triethylamine in an inert solvent such as chloroform.

The compounds represented by the formula 9 can be converted to the compounds 1 of this invention wherein $R_1$ is a $C_1$-$C_4$ alkoxy group by the reaction of 9 with a pyrocarbonate 12 in the absence of solvent at elevated temperature (about 50°-150° C.).

The compounds represented by the formula 9 can be converted to the compounds of 1 of this invention wherein $R_1$ is hydrogen by the reaction of 9 with 97% formic acid at room temperature for about 3 to 7 days.

The compounds represented by the formula 9 can be converted to the compounds 1 of this invention wherein $R_1$ is a $C_1$-$C_4$ alkylamino group by treatment of 9 with an isocyanate 11 in an inert solvent such as toluene at about 25°-100° C. for about 1 to 7 days.

Figure 2:
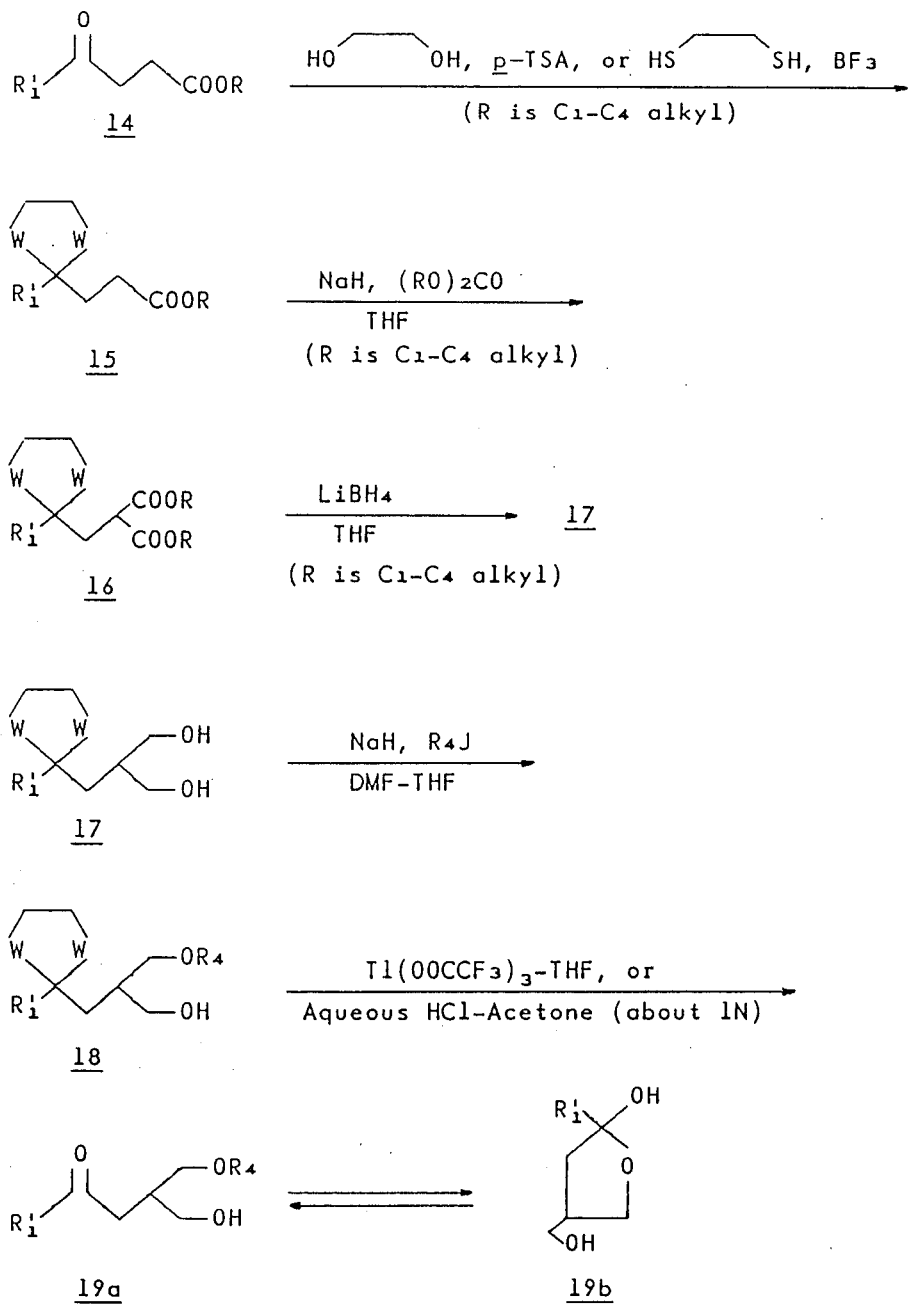
Figure 2:
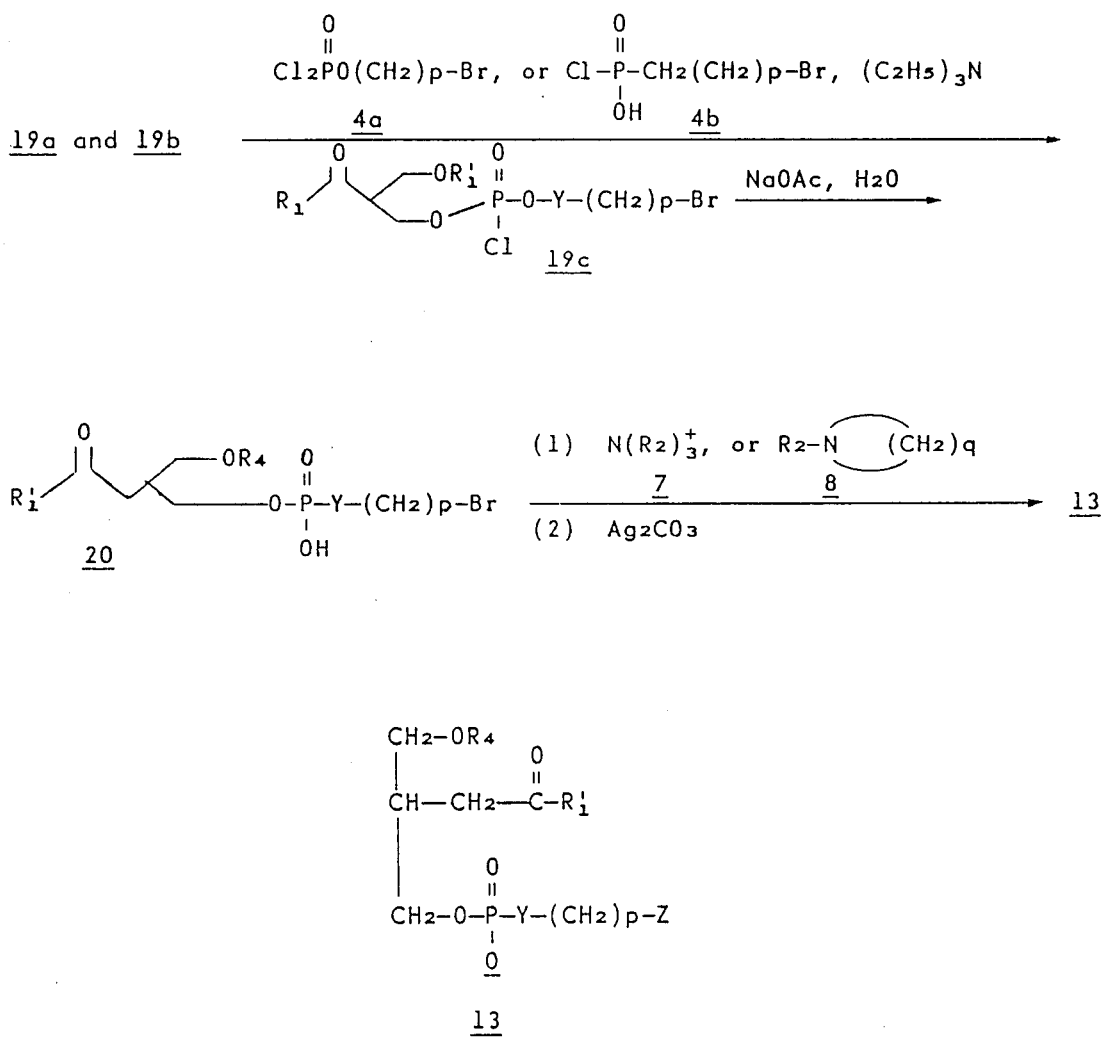

The preparation of the compounds of this invention encompassed by formula 13 is described hereinbelow in Flowsheet B, (FIG. 2) wherein $R_4$ is a $C_1$-$C_{24}$ branched or straight chain alkyl group or

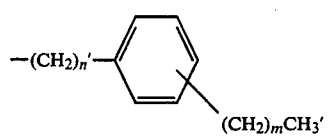

wherein n' and m are integers from zero to 25 and the sum of n' and m is equal to or less than 25 and n' must be greater than zero; $R_1'$ is a $C_1$-$C_4$ alkyl group; q, Y, p, Z, R and $R_2$ are defined as given hereinabove; W is oxygen or sulfur; and J is halogen (chlorine, bromine or iodine).

According to the sequence of reactions outlined in Flowsheet B, (FIG. 2) the ketone moiety of a 1,4-keto ester 14 is protected as either a dioxolane (15, W=oxygen) by refluxing a toluene solution of 14 and ethylene glycol in the presence of an acid catalyst such as p-toluenesulfonic acid into a Dean-Stark trap for about 5 to 24 hours, or as a thioketal (15, W=sulfur) by treating a solution of 14 and ethanedithiol in an alcohol solvent with boron trifluoride etherate. Acylation of 15 to give diester 16 is accomplished by the reaction of 15 with an alkyl carbonate and sodium hydride in refluxing inert solvent such as tetrahydrofuran. Both ester groups of 16 can be reduced to give diol 17 with lithium borohydride in a solvent such as tetrahydrofuran. Alkylation of one of the hydroxyl groups of 17 to give 18 is accomplished by the reaction of one equivalent of an alkyl halide with 17 using sodium hydride in a dimethylformamide-tetrahydrofuran mixture. Prepared in this manner, 18 is separated from unreacted 17 and dialkylated product using chromatographic procedures. The ketone protecting group can be removed in cases where W is sulfur using thallium trifluoroacetate in tetrahydrofuran followed by aqueous hydrolysis and for cases where W is oxygen by hydrolysis using aqueous hydrochloric acid in acetone (about 1N) at about 25°-80° C. The resulting deprotected product exists as a mixture of the keto (19a) and hemiketal (19b) isomers both of which react with either reagents 4a or 4b as described hereinabove to furnish, after hydrolysis in a buffer such as sodium acetate solution, the compound 20. The reaction of 20 with the amines 7 and 8 as described above furnishes the compounds of this invention represented by formula 13. As described above, compound 13 can be converted to the corresponding internal salt by treatment with silver carbonate.

The starting keto esters 14 are prepared by procedures well known in the art such as SYN., 490 (1980); CHEM. BER., 109: 2890 (1976); J. AMER. CHEM. SOC., 66: 46 (1944); ORG. SYN. COLL., Vol. 3: 601 (1955); CAN. J. CHEM., 50: 1105 (1972); AUST. J. CHEM., 20: 2441 (1967); and references cited therein.

The preparation of compounds of this invention encompassed by Formula 21 is described hereinbelow in Flowsheet C, (FIG. 2) wherein X', $R_1'$, Y, p, Z, W, J, R and $R_2$ are defined hereinabove.

Figure 3:
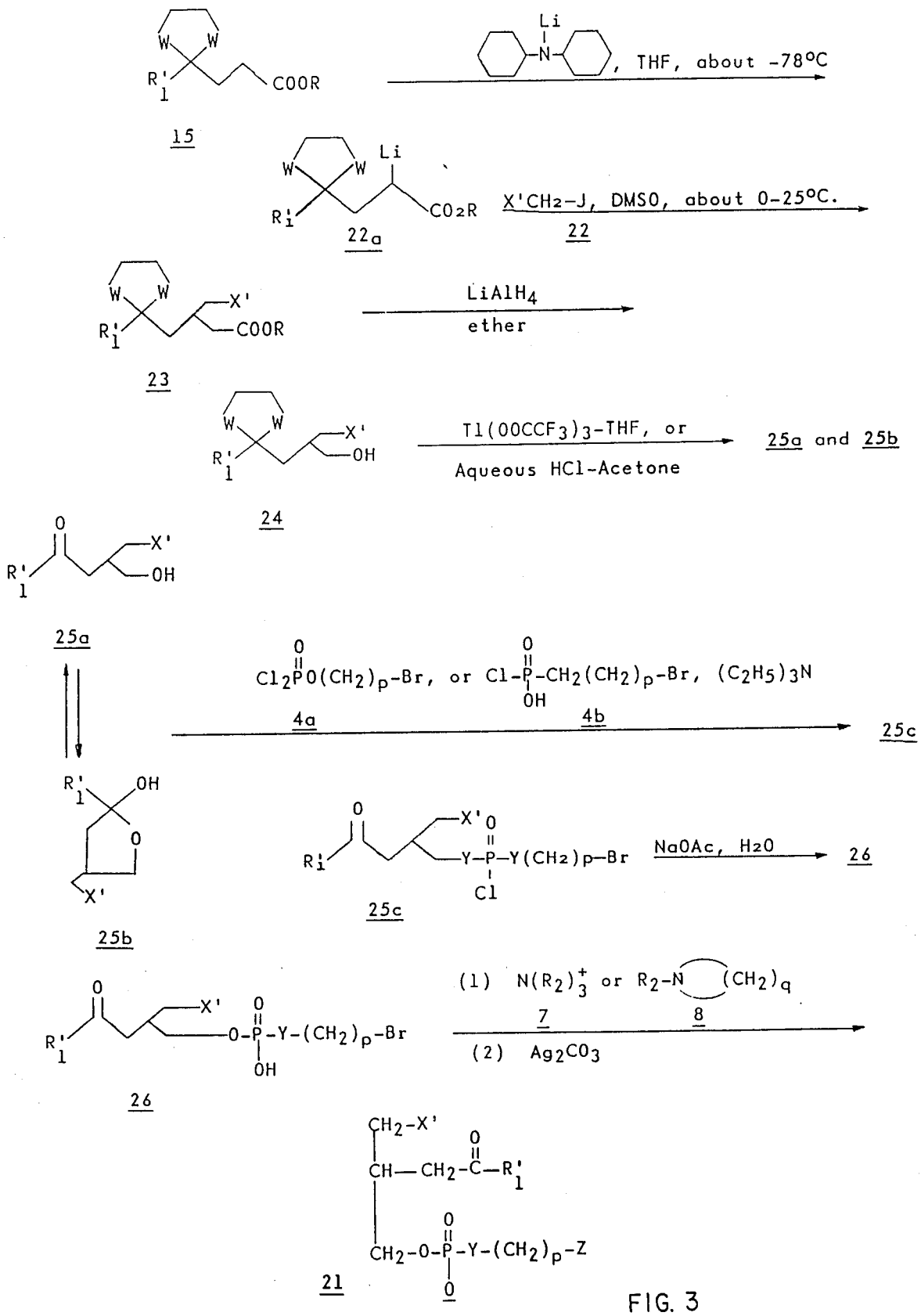

According to the sequence of reactions outlined in Flowsheet C, (FIG. 3) the Compound 15, the preparation of which is described hereinabove, is treated with an equivalent of an amide base such as lithium dicyclohexyl amide in an inert solvent such as ether or tetrahydrofuran at about −78° C. under an inert gas to form the corresponding lithium enolate ion. The enolate ion is added to a solution of the alkyl halide 22 in dimethyl sulfoxide or tetrahydrofuran containing hexamethyl phosphorous triamide and the solution is allowed to warm to about 0°-25° C. The resulting alkylated product 23 can be purified by chromatography. The ester group of 23 can be reduced to give the alcohol 24 using lithium aluminum hydride in an ether solvent. The ketone protecting group can be removed in cases where W is sulfur using thallium trifluoroacetate in tetrahydrofuran followed by aqueous hydrolysis and for cases where W is oxygen, by hydrolysis using aqueous hydrochloric acid in acetone or tetrahydrofuran (about 1N) at about 25°-80° C. The resulting deprotected product exists as a mixture of the keto (25a) and hemiketal (25b) isomers, both of which react with either reagents 4a or 4b as described hereinabove to furnish 26 after hydrolysis in a buffer such as sodium acetate solution. The reaction of 26 with the amines 7 and 8 as described above furnishes the compounds of this invention represented by Formula 21. As described above, Compound 21 can be converted to the corresponding internal salt by treatment with silver carbonate.

Figure 4:
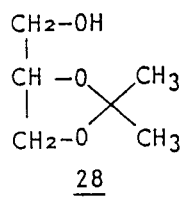
Figure 4:
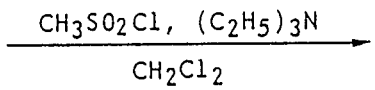
Figure 4:
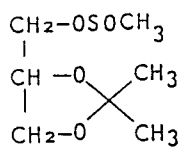
Figure 4:
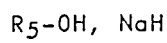
Figure 4:
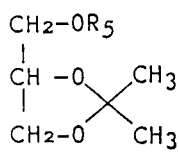
Figure 4:
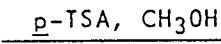
Figure 4:
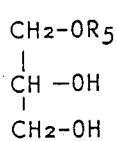
Figure 4:
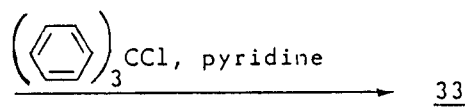
Figure 4:
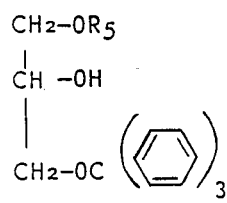
Figure 4:
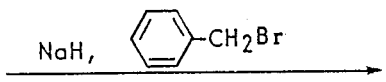
Figure 4:
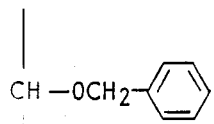
Figure 4:
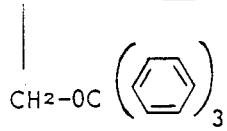
Figure 4:
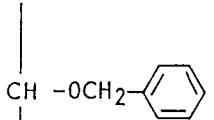
Figure 4:
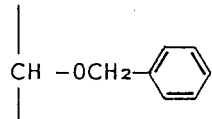
Figure 4:
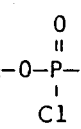
Figure 4:
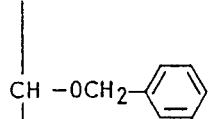
Figure 4:
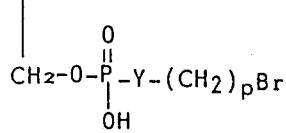
Figure 4:
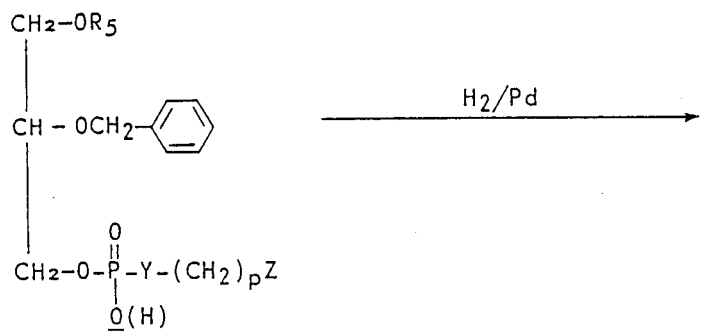
Figure 4:
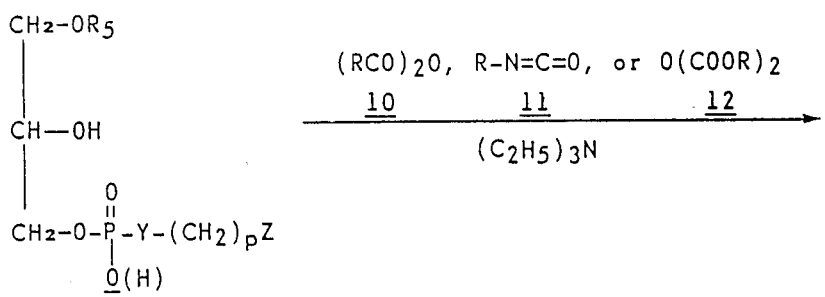
Figure 4:
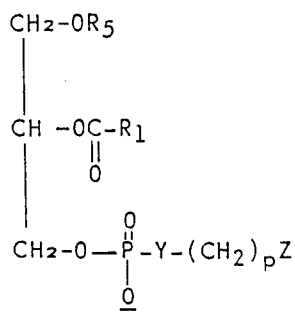

The preparation of the compounds of this invention encompassed by formula 27, both in the racemic form and in the form of the individual optical isomers is described hereinbelow in Flowsheet D, (FIG. 4) wherein $R_5$ is a $C_1$-$C_{24}$ branched or straight chain alkyl group or

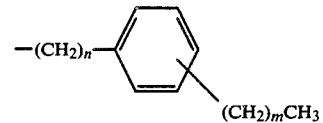

and q, y, p, Z, $R_2$, R, $R_1$, m and n are as defined hereinabove.

According to the sequence of reactions outlined in Flowsheet D, (FIG. 4) the compound 28 is converted to the mesylate 29 by the reaction of the alcohol 28 with an excess of mesyl chloride in an inert solvent such as methylene chloride in the presence of a base such as triethylamine.

Nucleophilic displacement of the mesylate group of 29 with an alcohol 30 to give the compound 31 can be accomplished using sodium hydride in dimethylformamide.

The diol protecting group of 31 can be removed using p-toluenesulfonic acid in methanol give the diol 32. The compound 32 is reacted with a reagent which only functionalizes the primary hydroxyl group; one such reagent is trityl chloride in pyridine; this provides the mono-protected compound 33, which is converted to the bis-protected compound 34 by the reaction with benzyl bromide and sodium hydride in an inert solvent The trityl protecting group of 34 can then be removed using p-toluenesulfonic acid in methanol or methanol-tetrahydrofuran mixtures (about 1:1), giving alcohol 35. Treatment of 35 with either reagents 4a or 4b as described hereinabove, furnishes, after hydrolysis with a sodium acetate buffer, the compound 36. The reaction of 36 with amines 7 and 8 as described above gives the compound 37.

When the compound represented by structures 7 and 8 are tertiary amines, the products (37) of this reaction are quaternary ammonium salts; in these cases it may be desirable to prepare the internal salt by treatment of an aqueous-alcohol solution of the compound with a suspension of silver carbonate. The benzyl protecting group of 37 can be removed by catalytic hydrogenation using a catalyst such as palladium on carbon (5%) to give the alcohol 38.

The compounds represented by the formula 38 can be converted to compounds 27 of this invention wherein $R_1$ is an alkyl group by the reaction of 38 with an anhydride 10 in the presence of a base catalyst such as triethylamine in an inert solvent such as chloroform.

The compounds represented by the formula 38 can be converted to compounds 27 of this invention wherein $R_1$ is a $C_1$-$C_4$ alkoxy group by the reaction of 38 with a pyrocarbonate 12 in the absence of solvent at elevated temperature (about 50°-150° C.).

The compounds represented by the formula 38 can be converted to compounds 27 of this invention wherein $R_1$ is hydrogen by the reaction of 38 with about 97% formic acid at room temperature for about 3 to 7 days.

The compounds represented by the formula 38 can be converted to compounds 27 of this invention wherein $R_1$ is a $C_1$-$C_4$ alkylamino group by treatment of 38 with an isocyanate 11 in an inert solvent such as toluene at about 25°–100° C. for about 1–7 days.

Since compound 28 is available in either the optically active R or S forms, or in the optically inactive racemic form, the compounds of this invention represented by the formula 27 can be prepared in the corresponding optically active R and S configurations or in the optically inactive racemic form by choosing the proper starting material [E. Baer, BIOCHEMICAL PREP., 2: 31 (1952); M. E. Jung and T. J. Shaw, J. AMER. CHEM. SOC., 102: 6304 (1980)].

Figure 5:
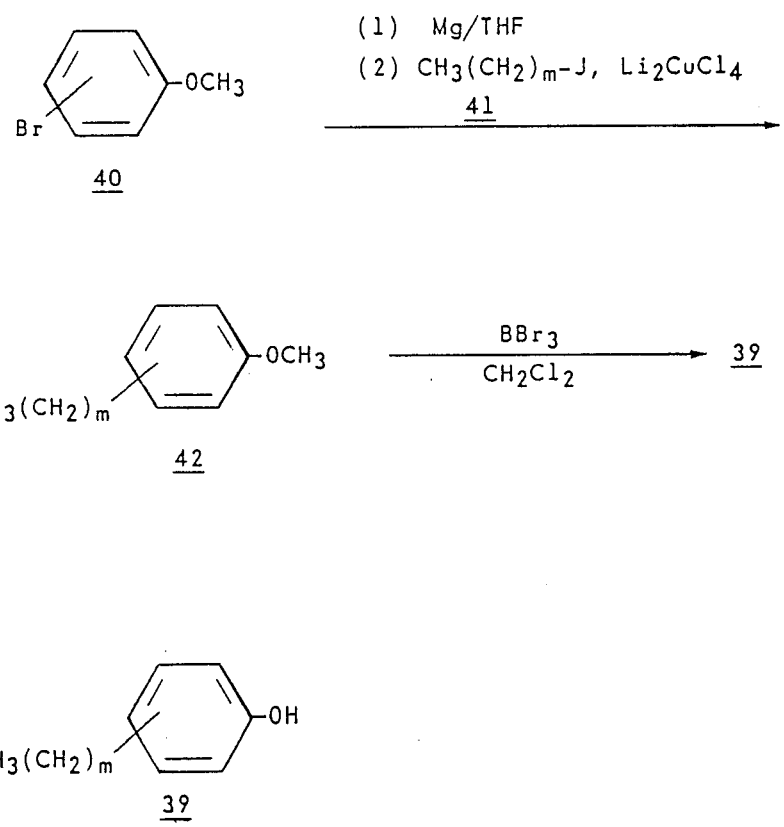

The preparation of alcohols 39 (a subclass of alcohols 30) needed to prepare some of the compounds of this invention is outlined in Flowsheet E (FIG. 5) given hereinbelow where J and m are defined as given above.

According to the sequence of reactions outlined in Flowsheet E (FIG. 5) an ortho, meta or para substituted bromobenzene 40 is reacted with magnesium in tetrahydrofuran to form the Grignard reagent which in turn is reacted with an alkyl halide 41 in the presence of $Li_2CuCl_4$. The resulting methyl ether 42 is cleaved to the phenol 39 using boron tribromide in an inert solvent such as methylene chloride.

Figure 6:
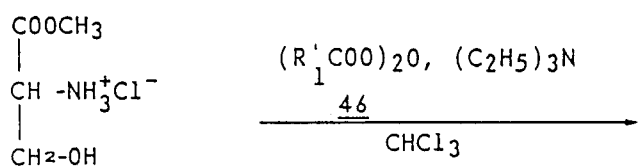
Figure 6:
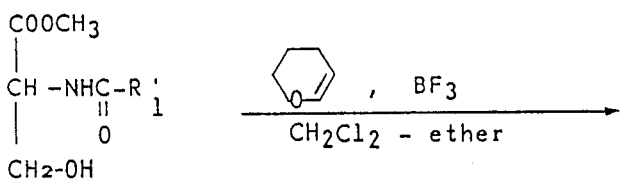
Figure 6:
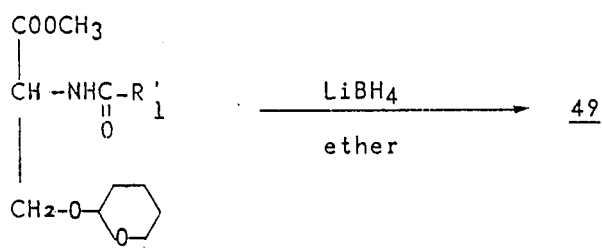
Figure 6:
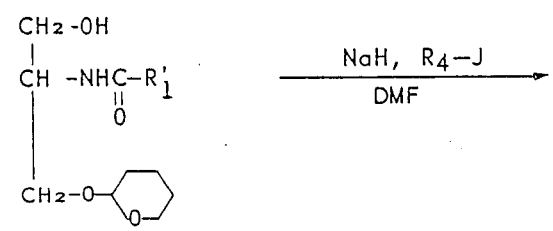
Figure 6:
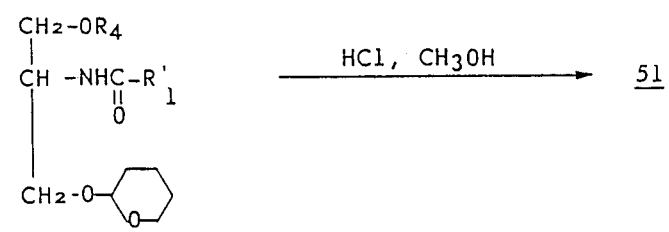
Figure 6:
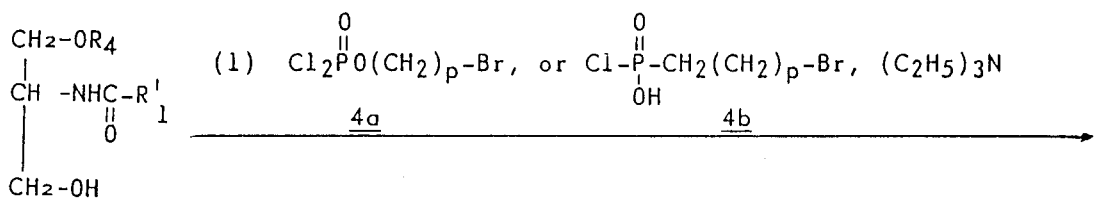
Figure 6:
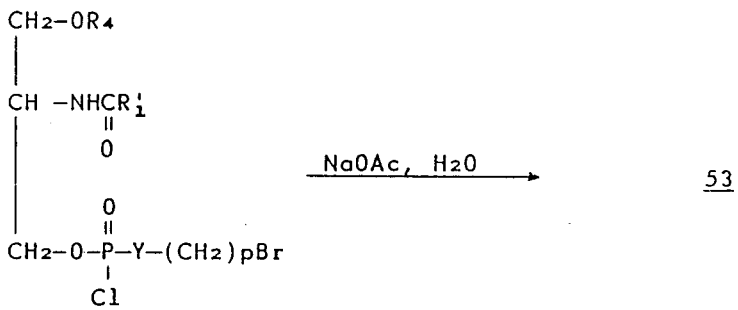
Figure 6:
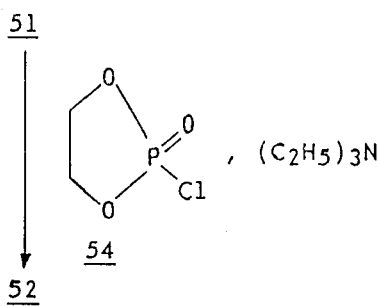
Figure 6:
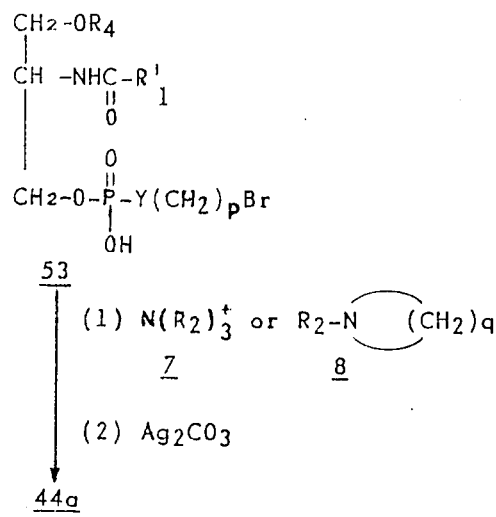
Figure 6:
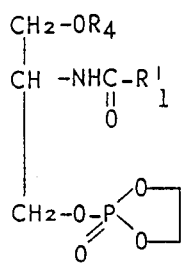
Figure 6:
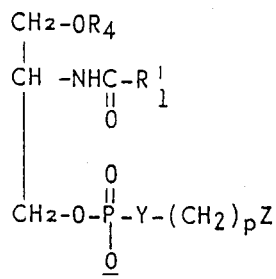
Figure 6:
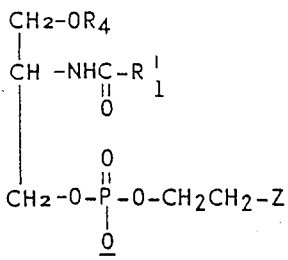

The compounds of this invention encompassed by the formulas 44a and 44b are prepared as shown hereinbelow in Flowsheet F, (FIG. 6) wherein $R_1'$ is a branched or straight chain alkyl group $C_1$–$C_4$ and $R_4$, p, Y, q, $R_2$ and Z are as described hereinabove.

According to the sequence of reactions outlined in Flowsheet F, (FIG. 6) Serine hydrochloride (45) in the optically active l or d forms or in the racemic dl form, is treated with an anhydride 46 in an inert solvent such as chloroform and a base catalyst such as triethylamine to give the amide 47. The alcohol group of 47 can be protected with a variety of protecting groups; for example the boron trifluoride catalyzed reaction of 47 with tetrahydropyran gives the THP ether 48. Reduction of the ester group of 48 to the alcohol 49 can be accomplished with lithium borohydride or similar hydride reducing agent in an inert solvent such as ether. Alkylation of 49 to give 50 is accomplished with sodium hydride in dimethylformamide. The THP group of 50 can be removed by treatment of a methanol solution with concentrated hydrochloric acid to give 51. The reaction of 51 with reagents 4a or 4b using a base such as triethylamine gives, after hydrolysis in a sodium acetate buffer, the compounds 53. Alternatively, the reaction of 51 with reagent 54 in an inert solvent using a base catalyst such as triethylamine gives compound 52. The reaction of 53 with amines 7 or 8 as described previously gives the compounds of this invention represented by formula 44a. Alternatively, treatment of 52 with amines 7 or 8 in an inert solvent at elevated temperature (about 50°–150° C.) gives the compounds of this invention represented by formula 44b.

Since the starting material 45 for the sequence of reactions outlined in Flowsheet F (FIG. 6) is readily available in the l, d or racemic forms, the products of this sequence 44a and 44b can be prepared in their optically active R and S forms or in the optically inactive racemic form simply by choosing the appropriate form of 45.

Figure 7:
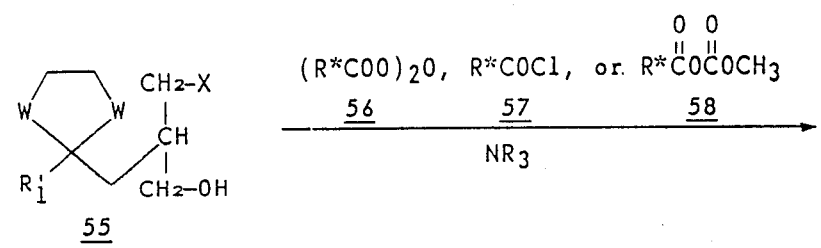
Figure 7:
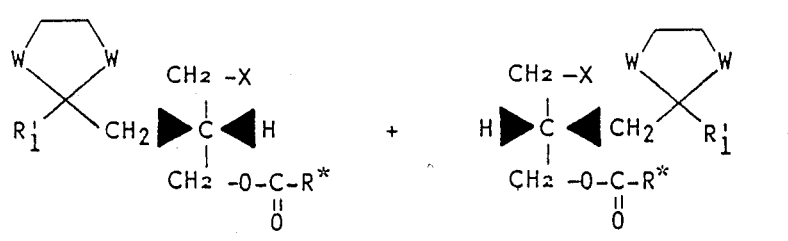
Figure 7:
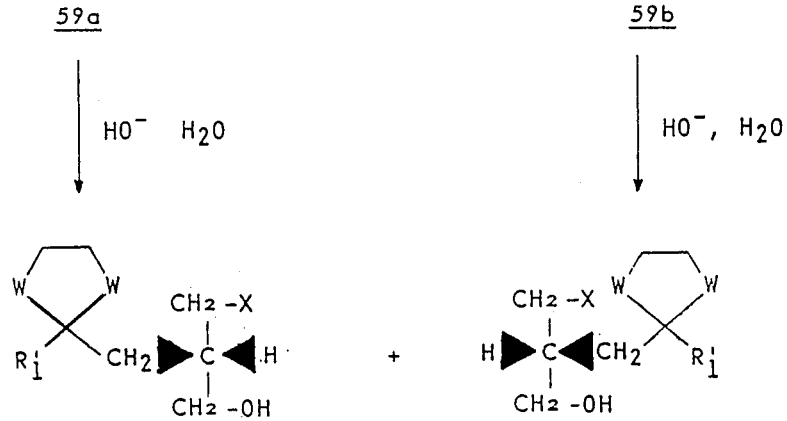
Figure 7:
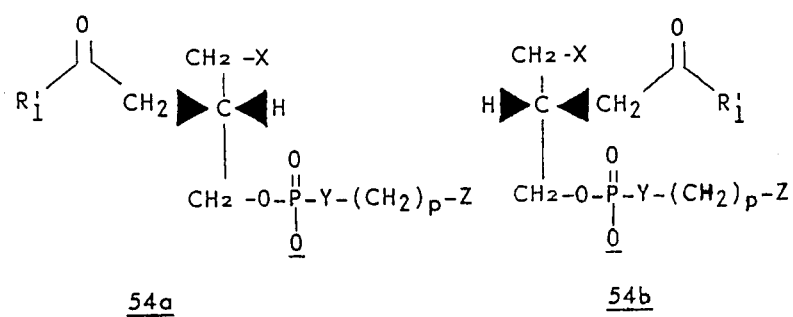

The compounds of this invention represented by formula 54:

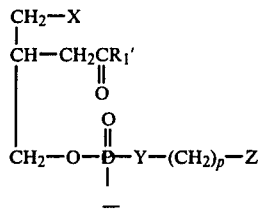

wherein X, $R_1'$, Y, p and Z are as defined hereinabove, can be prepared as the individual optically active R and S isomers (54a and 54b) by the resolution of the intermediate compounds of formula 55 as described hereinbelow in Flowsheet G, (FIG. 7) wherein R, X, $R'_1$, Y, p, Z and W are as previously described and the group

represents an optically active acyl moiety.

According to the sequence outlined in Flowsheet G, the racemic alcohol 55 is treated with a reactive derivative of an optically active carboxylic acid such as the anhydride 56, the acid chloride 57 or mixed anhydride 58 in an inert solvent in the presence of an equivalent of a trialkylamine base. The resulting esters 59a and 59b are diastereomers. In some cases it is possible to separate the mixture of 59a and 59b into its component parts by fractional recrystallization. In other cases the mixture can be separated using chromatographic techniques well known in the art, including high pressure liquid chromatography. The ester function in 59a and 59b can be cleaved by basic hydrolysis to give the resolved alcohols 60a and 60b. Taking compounds 60a and 60b through the sequences of reactions outlined hereinabove in Flowsheets B or C (FIG. 2 or 3) gives the optically active compounds of this invention 54a and 54b. Various optically active carboxylic acids which can be used in this process, as well as relevant procedures are described at length in the following reference: A. W. Ingersoll, "The Resolution of Alcohols", ORG. REACT., Chapter 9 (1944).

Figure 8:
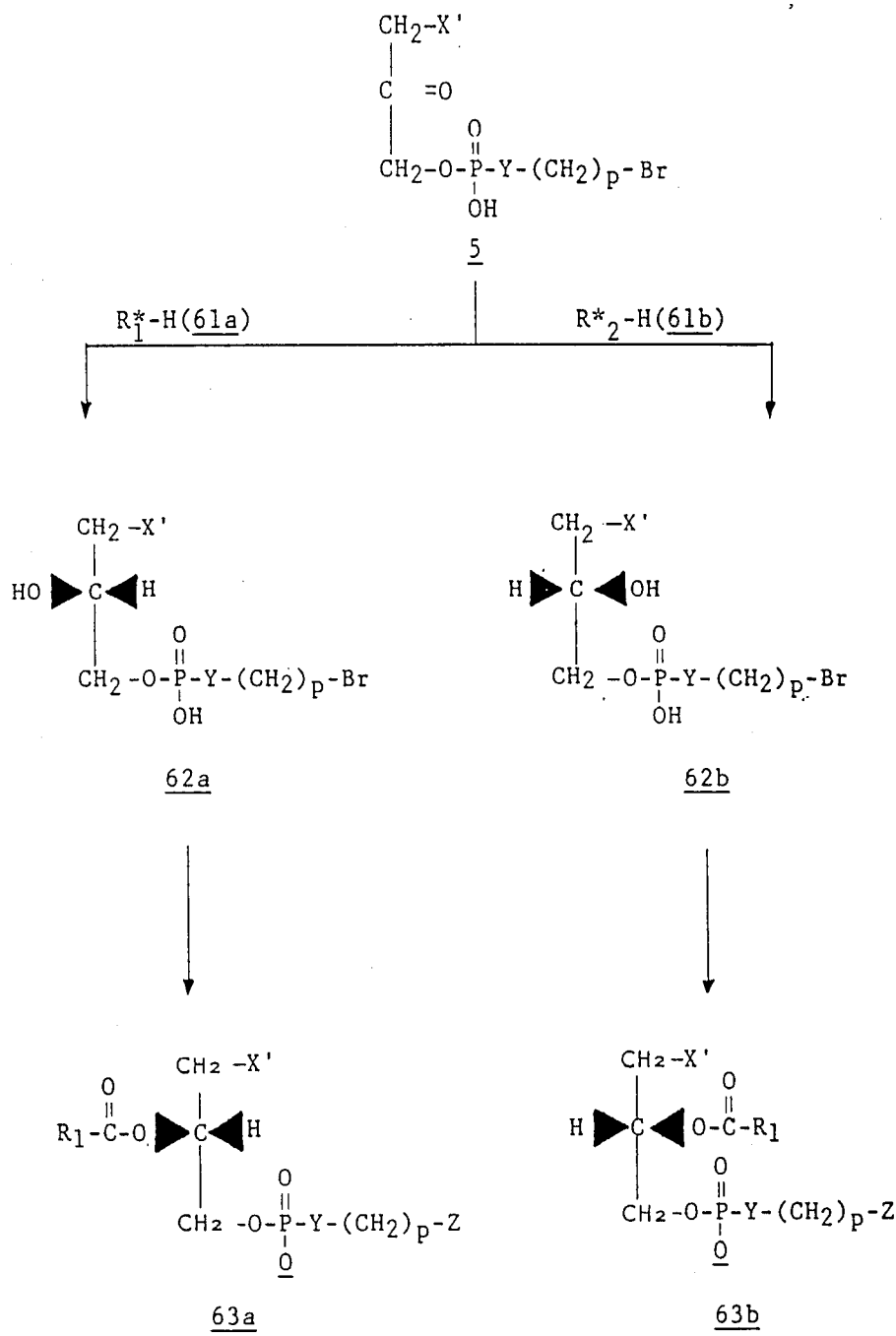

The compounds of this invention represented by formula 1, wherein X', R, Y, p and Z are as defined hereinabove can be prepared as the individual optically active R and S isomers (63a and 63b) by asymmetric reduction of the intermediate 5 as outlined hereinbelow in Flowsheet H (FIG. 8) wherein X', R, Y, p and Z are as defined above; the symbol $R_1^*$-H represents an asymmetric hydride reducing agent and the symbol $R_2^*$-H represents a reducing agent of opposite chirality.

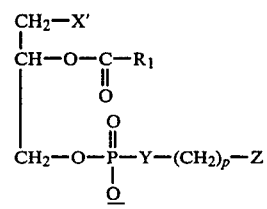

In accordance with the sequence of reactions outline in Flowsheet H, (FIG. 8) the ketone 5 can be treated with an asymmetric hydride reducing agent 61a in an inert solvent to give the chiral alcohol 62a. In a similar manner, treatment of 5 with 61b, a hydride reducing agent with chirality opposite to 61a, gives the alcohol 62b having chirality opposite to 62a. The various chiral reducing agents which can be used in this sequence as well as the various experimental procedures are described in detail in the following references:

R. Noyori, et al., J. AMER. CHEM. SOC., 101: 3129 (1979);
R. Noyori, et al., J. AMER. CHEM. SOC., 101: 5843 (1979);
R. S. Brinkmayer and V. M. Kapoor, J. AMER. CHEM. SOC., 99: 8339 (1977);
W. S. Johnson, et al., J. AMER. CHEM. SOC., 99: 8341 (1977);
T. Mukaiyama, et al., CHEM. LETT., 783 (1977);
M. M. Midland and P. E. Lee, J. ORG. CHEM., 46: 3933 (1981);
I. Ojima, et al., J. ORG. CHEM., 42: 1671 (1977);
J. D. Morrison and H. S. Mosher, "Asymmetric Organic Reactions", AMERICAN CHEMICAL SOC., Washington, D.C. (1976);
D. Valentine and J. W. Scott, SYN., 329 (1978);
H. B. Kagan and J. C. Fiaud, TOP. STEREOCHEM, 10: 175 (1978);
J. W. Opsimon and R. P. Seguin, TETRAHEDRON, 35: 2797 (1979).

By taking the chiral compounds 62a and 62b through the remaining sequence of reactions outlined hereinabove in Flowsheet A, (FIG. 1) the optically active compounds of this invention 63a and 63b, respectively are obtained.

Figure 9:
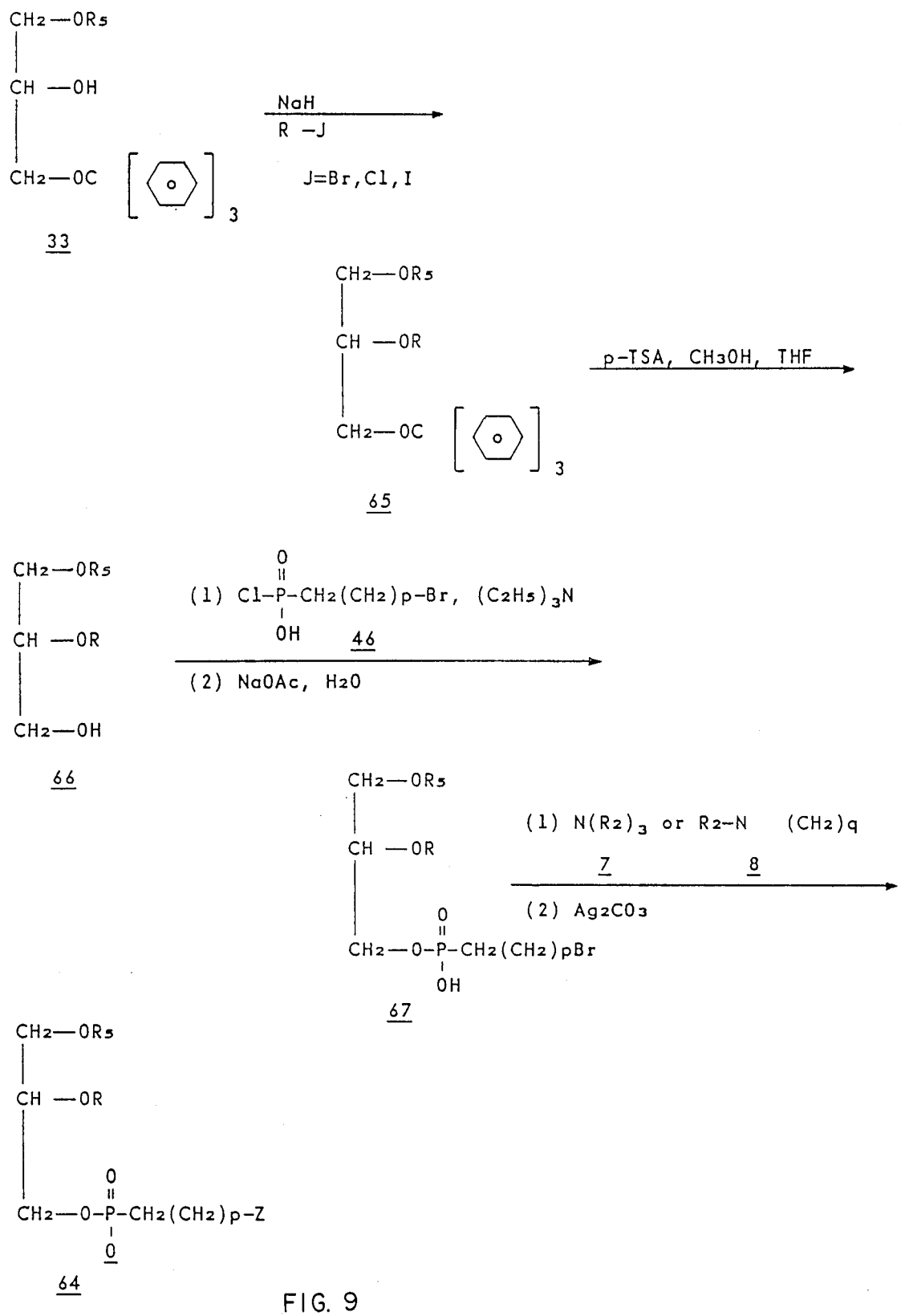

The preparation of compounds of this invention encompassed by formula 64 is described hereinbelow in Flowsheet I (FIG. 9) wherein $R_5$, p, q, and Z are as defined hereinabove and R is a $C_1$-$C_4$ alkyl group.

According to the reactions outlined below in Flowsheet I, (FIG. 9) the alcohol 33 (Flowsheet D) (FIG. 4) is alkylated with an alkyl halide R-J using sodium hydride in an inert solvent such as dimethylformamide or tetrahydrofuran at about 25°–150° C. to yield compound 65.

The trityl protecting group is removed by treatment of 65 with a 1:1 mixture of methanol and tetrahydrofuran with a catalytic amount of p-toluenesulfonic acid at about 25°–75° C. to yield alcohol 66. The reaction of 66 with reagent 46 as described above gives compound 67. The reaction of 67 with alkyl amines 7 or 8 as described previously furnishes the compounds of this inventions represented by formula 64.

Figure 10:
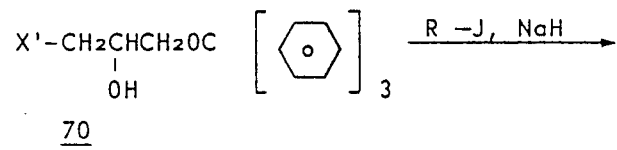
Figure 10:
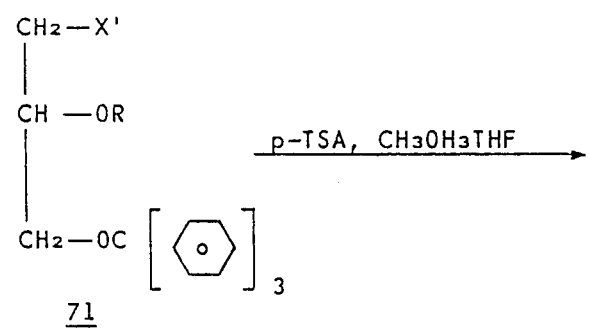
Figure 10:
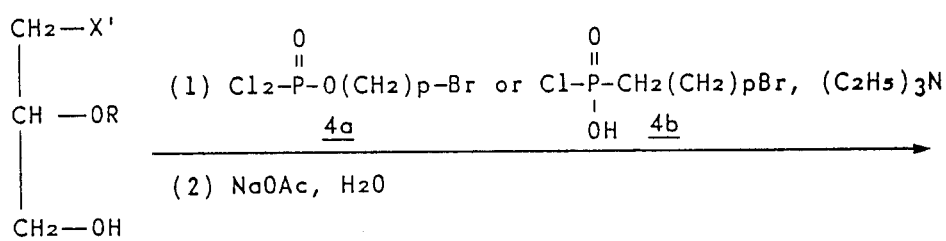
Figure 10:
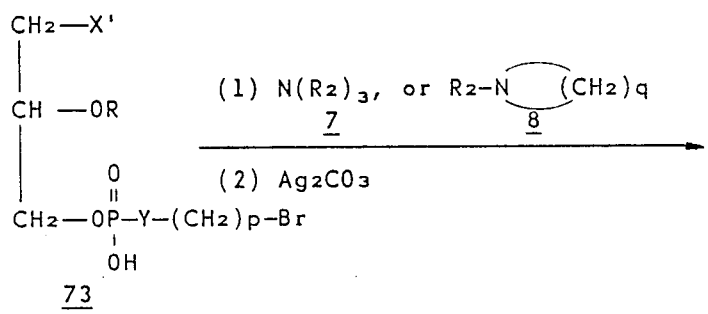
Figure 10:
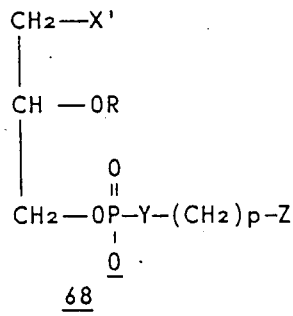

The compounds of this invention encompassed by formula 68 are prepared as described hereinbelow in Flowsheet J (FIG. 10) wherein X', R, Y, p, $R_2$, q, and J are defined as given hereinabove.

In accord with the steps outlined below in Flowsheet J, (FIG. 10) the compound 3 (Flowsheet A) (FIG. 1) is reduced with a hydride reducing agent such as sodium borohydride in an inert solvent such as ethanol or tetrahydrofuran to give the diol 69. Protection of the primary hydroxyl group of 69 as a trityl derivative is accomplished in the standard manner as described previously to give compound 70. Alkylation of 70 with an alkyl halide using sodium hydride in an inert solvent such as dimethylformamide or tetrahydrofuran gives compound 71. Detritylation of 71 using standard conditions gives alcohol 72 which is reacted with either reagent 4a or 4b to give after hydrolysis of the intermediate with sodium acetate buffer, the compound 73. The reaction of 73 with the alkylamine 7 or 8 as described above gives the compound 68 of this invention.

The compounds of the present invention are active as hypotensive agents as evidenced by their activity in the following test, the results of which are shown in Table I.

Under ether anesthesia, Weeks type cannulas (Peterson Technics) were surgically implanted in the abdominal aorta and vena cava of spontaneously hypertensive rats (Taconic Farms, Germantown, NY) and passed subcutaneously to the back of the neck where they were exteriorized. The cannulas were filled with saline, plugged and the rats returned to single cages where they were allowed food and water ad libitum.

At least three days following implantation of the cannulas, the rats were weighed and placed in Broome style restraining cages. The plug was removed from the aortic catheter which was connected to an arterial pressure transducer (Statham P23ID) using PE 100 polyethylene tubing and a stepdown connector fabricated from stainless steel hypodermic tubing. Mean arterial blood pressure was obtained by electrical damping of the pulse pressure channel. Heart rate was obtained from a tachograph triggered by the pulse pressure channel. All parameters were monitored on a Grass physiological recorder (Model 7).

The plug was removed from the vena cava catheter and a PE 20 polyethylene tubing extension was added using a piece of stainless steel hypodermic tubing. The other end was terminated with a 27G needle and one cc syringe.

All drugs were dissolved in saline or a mixture of ethanol and saline (25:75 V:V) such that the volume injected intravenously was 0.1 cc/100 g body weight. All drugs were flushed in with 0.2 cc saline.

| Compound | Dose (μg/kg) | No. of Rats | Peak Δ Mean Arterial Blood Pressure (mm Hg) |
|---|---|---|---|
| 7-(formyloxy)-4-hydroxy-N,N,N—trimethyl-3,5,9-trioxa-4-phosphaheptacosan-1-aminium, 4-oxide, hydroxide, inner salt | 30<br>100<br>300<br>1,000 | 4<br>4<br>4<br>4 | −9<br>−57<br>−97<br>−112 |
| 4-hydroxy-N,N,N—trimethyl-7-[(octadecyloxy)methyl]-9-oxo-3,5,8,10-tetraoxa-4-phosphadocecan-1-aminium, 4-oxide, hydroxide, inner salt | 30 | 2 | −51 |
| 7-heptadecyl-4-hydroxy-N,N,N—trimethyl-9-oxo-3,5,8-trioxa-4-phosphadecan-1-aminium, 4-oxide, hydroxide, inner salt | 300<br>1,000<br>3,000 | 4<br>4<br>4 | −45<br>−71<br>−88 |
| 8-(acetyloxy)-5-hydroxy-N,N,N—trimethyl-4,6,10-trioxa-5-phosphahexacosan-1-aminium, 5-oxide, hydroxide, inner salt | 1<br>3<br>10<br>30 | 4<br>4<br>4<br>4 | −43<br>−60<br>−76<br>−96 |
| 2-(acetyloxy)-3-(octadecyloxy)propyl-2-(dimethylamino)ethyl ester | 3,000 | 1 | −82 |
| 8-hydroxy-N,N,N—trimethyl-5-[(octadecyloxy)methyl]-3-oxo-4,7,9-trioxa-2-aza-8-phosphaundecan-11-aminium, 8-oxide, hydroxide, inner salt | 1<br>3<br>10 | 4<br>4<br>4 | −25<br>−45<br>−92 |
| 4-hydroxy-N,N,N—trimethyl-7-(2-oxopropyl)-3,5,9-trioxa-4-phosphaheptacosan-1-aminium, 4-oxide, hydroxide, | 30<br>100<br>300<br>1,000 | 6<br>6<br>6<br>6 | −13<br>−36<br>−74<br>−96 |

-continued

| Compound | Dose (μg/kg) | No. of Rats | Peak Δ Mean Arterial Blood Pressure (mm Hg) |
|---|---|---|---|
| inner salt | | | |
| 2-[[hydroxy[[4-oxo-2-[[4-(tetradecyloxy)phenyl]methyl]pentyl]oxy]phosphinyl]oxy]-N,N,N—trimethyl-ethanaminium, hydroxide, inner salt | 10,000 30,000 | 1 1 | −57 −75 |
| 2-[[2-(acetyloxy)-3-(octadecyloxy)propoxy]hydroxyphosphinyl]-N,N,N—trimethyl-ethanaminium, hydroxide, inner salt | 30 100 300 | 3 3 3 | −24 −67 −73 |
| 4-hydroxy-N,N,N—trimethyl-9-oxo-7-[[4-(tetradecyloxy)phenyl]methyl]-3,5,8-trioxaphosphadecan-1-aminium, 4-oxide, hydroxide, inner salt | 10,000 30,000 | 2 2 | −56 −96 |
| 7-(acetylamino)-4-hydroxy-N,N,N—trimethyl-3,5,9-trioxo-4-phosphaheptacosan-1-aminium, 4-oxide, hydroxide inner salt | 10 30 100 300 | 4 4 4 4 | −7 −26 −56 −60 |

When the compounds are employed for the above utility, they may be combined with one or more pharmaceutically acceptable carriers, e.g., solvents, diluents and the like, and may be administered orally in such forms as tablets, capsules, dispersible powders, granules, or suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. Such pharmaceutical preparations may contain, for example, from about 0.5% up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.005 mg to about 100 mg/kg of animal body weight, preferably given in divided doses two to four times a day, or in sustained release form. For most large mammals the total daily dosage is from about 500 mg to about 5,000 mg preferably from about 350 mg to 3,500 mg. Dosage forms suitable for internal use comprise from about 25 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are solid composition, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations should contain a preservative to prevent the growth of microorganisms.

The pharmaceutical forms suitable for injection use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

In addition to the above utilities, some of the compounds of this invention are useful for the preparation of other compounds of this invention.

The invention will be more fully described in conjunction with the following specific examples which are not to be construed as limiting the scope of the invention.

EXAMPLE 1

1-Hydroxy-2-nonadecanone

A mixture of about 96.5 g of octadecanoic acid chloride and about 205.06 g of tris-trimethylsilyloxyethylene was heated at about 110°–115° C. for about 2 hours. Another about 65 g of tris-trimethylsilyloxyethylene was added and heating was continued for about one more hour. The solution was poured slowly into a mixture of about 300 ml of tetrahydrofuran, about 300 ml of water and about 50 ml of concentrated hydrochloric acid with vigorous stirring (exothermic). The mixture was stirred at reflux for about 15 minutes and then diluted with about 1000 ml ethyl acetate. The water layer was separated from the hot mixture. The ethyl acetate layer was kept hot (about 0° C.), and saturated aqueous sodium bicarbonate was added. The resulting mixture was stirred for about 10 minutes. The organic layer was separated, dried, evaporated and recrystallized from methanol, giving about 81.3 g of the desired title compound as a white solid, mp 78°–80° C.

According to the method outlined hereinabove in Example 1, the acid chlorides derived from the carboxylic acids listed in Table I are converted to the hydroxymethyl ketones of the table which are needed to prepare the compounds of this invention.

TABLE I

| Carboxylic Acid | Hydroxymethyl Ketone |
| --- | --- |
| heptadecanoic acid | 1-hydroxy-2-decanone |
| nonadecanoic acid | 1-hydroxy-2-eicosanone |
| eicosanoic acid | 1-hydroxy-2-heneicosanone |
| heneicosanoic acid | 1-hydroxy-2-docosanone |
| docosanoic acid | 1-hydroxy-2-tricosanone |
| 4-methyl nonadecanoic acid | 1-hydroxy-5-methyl-2-eicosanone |

EXAMPLE 2

2-Bromoethyl 2-(oxononadecyl)phosphate

To a solution of about 65 g of 1-hydroxy-2-nonadecanone in about 1000 ml of warm carbon tetrachloride was added about 68.46 g of 2-bromoethyl phosphorodichlorodate, followed by about 28.64 g of triethylamine. After about two hours the mixture was filtered and the solvent removed. The residue was stirred overnight in a mixture of about 1000 ml of about 0.5M sodium acetate and about 1000 ml of tetrahydrofuran. Most of the tetrahydrofuran was removed, ether and concentrated hydrochloric acid (about 12N) were added and the mixture was extracted with ether. The ether extract was dried, evaporated and the residue was recrystallized twice from methanol. An about 50 g portion of this crude product was chromatographed on a florisil column, eluting first with chloroform and then with chloroform:methanol (1:1) to elute the product, which was then recrystallized twice from methanol:isopropanol, giving about 41.0 g of the desired title compound as a white solid, mp 94°–97° C.

EXAMPLE 3

2-Bromoethyl 2-hydroxynonadecyl phosphate

An about 34.0 g portion of 2-bromoethyl 2-(oxononadecyl)phosphate was heated on a steam bath in about 650 ml of isopropanol until solution was complete. This solution was partially cooled to about 40° C. in a water bath and while still warm, about 3.31 g of sodium borohydride were added, in portions, with stirring over a period of about 10 minutes. This mixture was stirred about 1.5 hours, most of the isopropanol was removed, the residue was diluted with dilute hydrochloric acid (about 1N) and extracted with ether. The ether extract was dried, evaporated and the residue recrystallized from hexane with cooling (at about 0° C.), giving about 32.8 g of the desired title compound, mp 68°–70° C.

EXAMPLE 4

2-[[Hydroxy[(2-hydroxynonadecyl)oxy]phosphinyl]oxy]N,N,N-trimethyl ethanaminium, hydroxide, inner salt A mixture of about 20.0 g of 2-bromoethyl 2-hydroxynonadecyl phosphate, about 600 ml of a mixture of chloroform:2-propanol:dimethylformamide (3:5:5) and about 375 ml of about 40% trimethylamine was stirred at about 55° C. for about 5 hours. The solvents were removed (with the addition of toluene to prevent foaming). The residue was dissolved in a mixture of about 200 ml of ethanol and about 100 ml of water, about 5.66 g of silver carbonate were added and the mixture was stirred overnight. The mixture was then filtered through celite, the solvent removed and the residue dissolved in a small amount of ethanol and precipitated with ether, giving about 17.2 g of the desired title compound as a white solid.

EXAMPLE 5

7-Heptadecyl-4-hydroxy-N,N,N-trimethyl-9-oxo-3,5,8-trioxa-4-phosphadecan-1-aminium, 4-oxide, hydroxide, inner salt A mixture of about 7.0 g of 2-[[hydroxy[(2-hydroxynonadecyl)oxy]phosphinyl]oxy]-N,N,N-trimethyl ethanaminium, hydroxide, inner salt, 0.62 g of sodium acetate and about 35 ml of acetic anhydride was refluxed for about 15 minutes. The excess anhydride was removed by distillation at reduced pressure. The residue was dissolved in chloroform, filtered through celite and the solvent removed. The residue was chromatographed on silica gel, eluting first with chloroform:methanol (70:30), then with chloroform:methanol (1:1) and finally the product was eluted with chloroform:methanol (30:70). The solvent was removed at room temperature and the residue slurried with moist ether overnight, giving about 4.5 g of the desired product as a hygroscopic powder, mp 204–225 (dec.).

By using the phosphorous reagents listed in Table VII, the amines of Table VIII and the appropriate starting materials prepared in Example 1 and listed in Table I and by following the methods described in detail hereinabove in Examples 1–5 and those described hereinbelow in Examples 34–36, the compounds of this invention listed below can be prepared. These compounds can be prepared as the individual optically active R and S enantiomers or as racemic mixtures as described in the above specifications.

7-hexadecyl-4-hydroxy-NNN-trimethyl-9-oxo-3,5,8-trioxa-4-phosphanonan-1-aminium, 4-oxide, hydroxide, inner salt 7-hexadecyl-4-hydroxy-NN-dimethyl-9-oxo-3,5,8-trioxa-4-phosphanonan-1-aminium, 4-oxide, hydroxide, inner salt 7-hexadecyl-4-hydroxy-N-methyl-9-oxo-3,5,8-trioxa-4-phosphanonan-1-aminium, 4-oxide, hydroxide, inner salt 7-hexadecyl-4-hydroxy-NN-tetramethylene-9-oxo-3,5,8-trioxa-4-phosphanonan-1-aminium, 4-oxide, hydroxide, inner salt 7-heptadecyl-4-hydroxy-NNN-trimethyl-9-oxo-3,5,8-trioxa-4-phosphanonan-1-aminium, 4-oxide, hydroxide, inner salt 7-heptadecyl-4-hydroxy-NN-dimethyl-9-oxo-3,5,8-trioxa-4-phosphanonan-1-aminium, 4-oxide, hydroxide, inner salt 7-heptadecyl-4-hydroxy-N-methyl-9-oxo-3,5,8-trioxa-4-phosphanonan-1-aminium, 4-oxide, hydroxide, inner salt 7-heptadecyl-4-hydroxy-NN-tetramethylene-9-oxo-3,5,8-trioxa-4-phosphanonan-1-aminium, 4-oxide, hydroxide, inner salt 7-octadecyl-4-hydroxy-NNN-trimethyl-9-oxo-3,5,8-trioxa-4-phosphanonan-1-aminium, 4-oxide, hydroxide, inner salt 7-octadecyl-4-hydroxy-NN-dimethyl-9-oxo-3,5,8-trioxa-4-phosphanonan-1-aminium, 4-oxide, hydroxide, inner salt 7-octadecyl-4-hydroxy-N-methyl-9-oxo-3,5,8-trioxa-4-phosphanonan-1-aminium, 4-oxide, hydroxide, inner salt 7-octadecyl-4-hydroxy-NN-tetramethylene-9-oxo-3,5,8-trioxa-4-phosphanonan-1-aminium, 4-oxide, hydroxide, inner salt 7-nonadecyl-4-hydroxy-NNN-trimethyl-9-oxo-3,5,8-trioxa-4-phosphanonan-1-aminium, 4-oxide, hydroxide, inner salt 7-nonadecyl-4-hydroxy-NN-dimethyl-9-oxo-3,5,8-trioxa-4-phosphanonan-1-aminium, 4-oxide, hydroxide, inner salt 7-nonadecyl-4-hydroxy-N-methyl-9-oxo-3,5,8-trioxa-4-phosphanonan-1-aminium, 4-oxide, hydroxide, inner salt 7-nonadecyl-4-hydroxy-NN-tetramethylene-9-oxo-3,5,8-trioxa-4-phosphanonan-1-aminium, 4-oxide, hydroxide, inner salt 7-eicosanyl-4-hydroxy-NNN-trimethyl-9-oxo-3,5,8-trioxa-4-phosphanonan-1-aminium, 4-oxide, hydroxide, inner salt 7-eicosanyl-4-hydroxy-NN-dimethyl-9-oxo-3,5,8-trioxa-4-phosphanonan-1-aminium, 4-oxide, hydroxide, inner salt 7-eicosanyl-4-hydroxy-N-methyl-9-oxo-3,5,8-trioxa-4-phosphanonan-1-aminium, 4-oxide, hydroxide, inner salt 7-eicosanyl-4-hydroxy-NN-tetramethylene-9-oxo-3,5,8-trioxa-4-phosphanonan-1-aminium, 4-oxide, hydroxide, inner salt 7-heneicosanyl-4-hydroxy-NNN-trimethyl-9-oxo-3,5,8-trioxa-4-phosphanonan-1-aminium, 4-oxide, hydroxide, inner salt 7-heneicosanyl-4-hydroxy-NN-dimethyl-9-oxo-3,5,8-trioxa-4-phosphanonan-1-aminium, 4-oxide, hydroxide, inner salt 7-heneicosanyl-4-hydroxy-N-methyl-9-oxo-3,5,8-trioxa-4-phosphanonan-1-aminium, 4-oxide, hydroxide, inner salt 7-heneicosanyl-4-hydroxy-NN-tetramethylene-9-oxo-3,5,8-trioxa-4-phosphanonan-1-aminium, 4-oxide, hydroxide, inner salt 7-(3-methyloctadecyl)-4-hydroxy-NNN-trimethyl-9-oxo-3,5,8-trioxa-4-phosphanonan-1-aminium, 4-oxide, hydroxide, inner salt 7-(3-methyloctadecyl)-4-hydroxy-NN-dimethyl-9-oxo-3,5,8-trioxa-4-phosphanonan-1-aminium, 4-oxide, hydroxide, inner salt 7-(3-methyloctadecyl)-4-hydroxy-N-methyl-9-oxo-3,5,8-trioxa-4-phosphanonan-1-aminium, 4-oxide, hydroxide, inner salt 7-(3-methyloctadecyl)-4-hydroxy-NN-tetramethylene-9-oxo-3,5,8-trioxa-4-phosphanonan-1-aminium, 4-oxide, hydroxide, inner salt 7-hexadecyl-4-hydroxy-NNN-trimethyl-9-oxo-3,5,8-trioxa-4-phosphadecan-1-aminium, 4-oxide, hydroxide, inner salt 7-hexadecyl-4-hydroxy-NN-dimethyl-9-oxo-3,5,8-trioxa-4-phosphadecan-1-aminium, 4-oxide, hydroxide, inner salt 7-hexadecyl-4-hydroxy-N-methyl-9-oxo-3,5,8-trioxa-4-phosphadecan-1-aminium, 4-oxide, hydroxide, inner salt 7-hexadecyl-4-hydroxy-NN-tetramethylene-9-oxo-3,5,8-trioxa-4-phosphadecan-1-aminium, 4-oxide, hydroxide, inner salt 7-heptadecyl-4-hydroxy-NNN-trimethyl-9-oxo-3,5,8-trioxa-4-phosphadecan-1-aminium, 4-oxide, hydroxide, inner salt 7-heptadecyl-4-hydroxy-NN-dimethyl-9-oxo-3,5,8-trioxa-4-phosphadecan-1-aminium, 4-oxide, hydroxide, inner salt 7-heptadecyl-4-hydroxy-N-methyl-9-oxo-3,5,8-trioxa-4-phosphadecan-1-aminium, 4-oxide, hydroxide, inner salt 7-heptadecyl-4-hydroxy-NN-tetramethylene-9-oxo-3,5,8-trioxa-4-phosphadecan-1-aminium, 4-oxide, hydroxide, inner salt 7-octadecyl-4-hydroxy-NNN-trimethyl-9-oxo-3,5,8-trioxa-4-phosphadecan-1-aminium, 4-oxide, hydroxide, inner salt 7-octadecyl-4-hydroxy-NN-dimethyl-9-oxo-3,5,8-trioxa-4-phosphadecan-1-aminium, 4-oxide, hydroxide, inner salt 7-octadecyl-4-hydroxy-N-methyl-9-oxo-3,5,8-trioxa-4-phosphadecan-1-aminium, 4-oxide, hydroxide, inner salt 7-octadecyl-4-hydroxy-NN-tetramethylene-9-oxo-3,5,8-trioxa-4-phosphadecan-1-aminium, 4-oxide, hydroxide, inner salt 7-nonadecyl-4-hydroxy-NNN-trimethyl-9-oxo-3,5,8-trioxa-4-phosphadecan-1-aminium, 4-oxide, hydroxide, inner salt 7-nonadecyl-4-hydroxy-NN-dimethyl-9-oxo-3,5,8-trioxa-4-phosphadecan-1-aminium, 4-oxide, hydroxide, inner salt 7-nonadecyl-4-hydroxy-N-methyl-9-oxo-3,5,8-trioxa-4-phosphadecan-1-aminium, 4-oxide, hydroxide, inner salt 7-nonadecyl-4-hydroxy-NN-tetramethylene-9-oxo-3,5,8-trioxa-4-phosphadecan-1-aminium, 4-oxide, hydroxide, inner salt 7-eicosanyl-4-hydroxy-NNN-trimethyl-9-oxo-3,5,8-trioxa-4-phosphadecan-1-aminium, 4-oxide, hydroxide, inner salt 7-eicosanyl-4-hydroxy-NN-dimethyl-9-oxo-3,5,8-trioxa-4-phosphadecan-1-aminium, 4-oxide, hydroxide, inner salt 7-eicosanyl-4-hydroxy-N-methyl-9-oxo-3,5,8-trioxa-4-phosphadecan-1-aminium, 4-oxide, hydroxide, inner salt 7-eicosanyl-4-hydroxy-NN-tetramethylene-9-oxo-3,5,8-trioxa-4-phosphadecan-1-aminium, 4-oxide, hydroxide, inner salt 7-heneicosanyl-4-hydroxy-NNN-trimethyl-9-oxo-3,5,8-trioxa-4-phosphadecan-1-aminium, 4-oxide, hydroxide, inner salt 7-heneicosanyl-4-hydroxy-NN-dimethyl-9-oxo-3,5,8-trioxa-4-phosphadecan-1-aminium, 4-oxide, hydroxide, inner salt 7-heneicosanyl-4-hydroxy-N-methyl-9-oxo-3,5,8-trioxa-4-phosphadecan-1-aminium, 4-oxide, hydroxide, inner salt 7-heneicosanyl-4-hydroxy-NN-tetramethylene-9-oxo-3,5,8-trioxa-4-phosphadecan-1-aminium, 4-oxide, hydroxide, inner salt 7-(3-methyloctadecyl)-4-hydroxy-NNN-trimethyl-9-oxo-3,5,8-trioxa-4-phosphadecan-1-aminium, 4-oxide, hydroxide, inner salt 7-(3-methyloctadecyl)-4-hydroxy-NN-dimethyl-9-oxo-3,5,8-trioxa-4-phosphadecan-1-aminium, 4-oxide, hydroxide, inner salt 7-(3-methyloctadecyl)-4-hydroxy-N-methyl-9-oxo-3,5,8-trioxa-4-phosphadecan-1-aminium, 4-oxide, hydroxide, inner salt 7-(3-methyloctadecyl)-4-hydroxy-NN-tetramethylene-9-oxo-3,5,8-trioxa-4-phosphadecan-1-aminium, 4-oxide, hydroxide, inner salt 7-hexadecyl-4-hydroxy-NNN-trimethyl-9-oxo-3,5,8-trioxa-4-phosphaundecan-1-aminium, 4-oxide, hydroxide, inner salt 7-hexadecyl-4-hydroxy-NN-dimethyl-9-oxo-3,5,8-trioxa-4-phosphaundecan-1-aminium, 4-oxide, hydroxide, inner salt 7-hexadecyl-4-hydroxy-N-methyl-9-oxo-3,5,8-trioxa-4-phosphaundecan-1-aminium, 4-oxide, hydroxide, inner salt 7-hexadecyl-4-hydroxy-NN-tetramethylene-9-oxo-3,5,8-trioxa-4-phosphaundecan-1-aminium, 4-oxide, hydroxide, inner salt 7-heptadecyl-4-hydroxy-NNN-trimethyl-9-oxo-3,5,8-trioxa-4-phosphaundecan-1-aminium, 4-oxide, hydroxide, inner salt 7-heptadecyl-4-hydroxy-NN-dimethyl-9-oxo-3,5,8-trioxa-4-phosphaundecan-1-aminium, 4-oxide, hydroxide, inner salt 7-heptadecyl-4-hydroxy-N-methyl-9-oxo-3,5,8-trioxa-4-phosphaundecan-1-aminium, 4-oxide, hydroxide, inner salt 7-heptadecyl-4-hydroxy-NN-tetramethylene-9-oxo-3,5,8-trioxa-4-phosphaundecan-1-aminium, 4-oxide, hydroxide, inner salt 7-octadecyl-4-hydroxy-NNN-trimethyl-9-oxo-3,5,8-trioxa-4-phosphaundecan-1-aminium, 4-oxide, hydroxide, inner salt 7-octadecyl-4-hydroxy-NN-dimethyl-9-oxo-3,5,8-trioxa-4-phosphaundecan-1-aminium, 4-oxide, hydroxide, inner salt 7-octadecyl-4-hydroxy-N-methyl-9-oxo-3,5,8-trioxa-4-phosphaundecan-1-aminium, 4-oxide, hydroxide, inner salt 7-octadecyl-4-hydroxy-NN-tetramethylene-9-oxo-3,5,8-trioxa-4-phosphaundecan-1-aminium, 4-oxide, hydroxide, inner salt 7-nonadecyl-4-hydroxy-NNN-trimethyl-9-oxo-3,5,8-trioxa-4-phosphaundecan-1-aminium, 4-oxide, hydroxide, inner salt 7-nonadecyl-4-hydroxy-NN-dimethyl-9-oxo-3,5,8-trioxa-4-phosphaundecan-1-aminium, 4-oxide, hydroxide, inner salt 7-nonadecyl-4-hydroxy-N-methyl-9-oxo-3,5,8-trioxa-4-phosphaundecan-1-aminium, 4-oxide, hydroxide, inner salt 7-nonadecyl-4-hydroxy-NN-tetramethylene-9-oxo-3,5,8-trioxa-4-phosphaundecan-1-aminium, 4-oxide, hydroxide, inner salt 7-eicosanyl-4-hydroxy-NNN-trimethyl-9-oxo-3,5,8-trioxa-4-phosphaundecan-1-aminium, 4-oxide, hydroxide, inner salt 7-eicosanyl-4-hydroxy-NN-dimethyl-9-oxo-3,5,8-trioxa-4-phosphaundecan-1-aminium, 4-oxide, hydroxide, inner salt 7-eicosanyl-4-hydroxy-N-methyl-9-oxo-3,5,8-trioxa-4-phosphaundecan-1-aminium, 4-oxide, hydroxide, inner salt 7-eicosanyl-4-hydroxy-NN-tetramethylene-9-oxo-3,5,8-trioxa-4-phosphaundecan-1-aminium, 4-oxide, hydroxide, inner salt 7-heneicosanyl-4-hydroxy-NNN-trimethyl-9-oxo-3,5,8-trioxa-4-phosphaundecan-1-aminium, 4-oxide, hydroxide, inner salt 7-heneicosanyl-4-hydroxy-NN-dimethyl-9-oxo-3,5,8-trioxa-4-phosphaundecan-1-aminium, 4-oxide, hydroxide, inner salt 7-heneicosanyl-4-hydroxy-N-methyl-9-oxo-3,5,8-trioxa-4-phosphaundecan-1-aminium, 4-oxide, hydroxide, inner salt 7-heneicosanyl-4-hydroxy-NN-tetramethylene-9-oxo-3,5,8-trioxa-4-phosphaundecan-1-aminium, 4-oxide, hydroxide, inner salt 7-(3-methyloctadecyl)-4-hydroxy-NNN-trimethyl-9-oxo-3,5,8-trioxa-4-phosphaundecan-1-aminium, 4-oxide, hydroxide, inner salt 7-(3-methyloctadecyl)-4-hydroxy-NN-dimethyl-9-oxo-3,5,8-trioxa-4-phosphaundecan-1-aminium, 4-oxide, hydroxide, inner salt 7-(3-methyloctadecyl)-4-hydroxy-N-methyl-9-oxo-3,5,8-trioxa-4-phosphaundecan-1-aminium, 4-oxide, hydroxide, inner salt 7-(3-methyloctadecyl)-4-hydroxy-NN-tetramethylene-9-oxo-3,5,8-trioxa-4-phosphaundecan-1-aminium, 4-oxide, hydroxide, inner salt 7-hexadecyl-4-hydroxy-NNN-trimethyl-9-oxo-3,5,8-trioxa-4-phosphadodecan-1-aminium, 4-oxide, hydroxide, inner salt 7-hexadecyl-4-hydroxy-NN-dimethyl-9-oxo-3,5,8-trioxa-4-phosphadodecan-1-aminium, 4-oxide, hydroxide, inner salt 7-hexadecyl-4-hydroxy-N-methyl-9-oxo-3,5,8-trioxa-4-phosphadodecan-1-aminium, 4-oxide, hydroxide, inner salt 7-hexadecyl-4-hydroxy-NN-tetramethylene-9-oxo-3,5,8-trioxa-4-phosphadodecan-1-aminium, 4-oxide, hydroxide, inner salt 7-heptadecyl-4-hydroxy-NNN-trimethyl-9-oxo-3,5,8-trioxa-4-phosphadodecan-1-aminium, 4-oxide, hydroxide, inner salt 7-heptadecyl-4-hydroxy-NN-dimethyl-9-oxo-3,5,8-trioxa-4-phosphadodecan-1-aminium, 4-oxide, hydroxide, inner salt 7-heptadecyl-4-hydroxy-N-methyl-9-oxo-3,5,8-trioxa-4-phosphadodecan-1-aminium, 4-oxide, hydroxide, inner salt 7-heptadecyl-4-hydroxy-NN-tetramethylene-9-oxo-3,5,8-trioxa-4-phosphadodecan-1-aminium, 4-oxide, hydroxide, inner salt 7-octadecyl-4-hydroxy-NNN-trimethyl-9-oxo-3,5,8-trioxa-4-phosphadodecan-1-aminium, 4-oxide, hydroxide, inner salt 7-octadecyl-4-hydroxy-NN-dimethyl-9-oxo-3,5,8-trioxa-4-phosphadodecan-1-aminium, 4-oxide, hydroxide, inner salt 7-octadecyl-4-hydroxy-N-methyl-9-oxo-3,5,8-trioxa-4-phosphadodecan-1-aminium, 4-oxide, hydroxide, inner salt 7-octadecyl-4-hydroxy-NN-tetramethylene-9-oxo-3,5,8-trioxa-4-phosphadodecan-1-aminium; 4-oxide, hydroxide, inner salt 7-nonadecyl-4-hydroxy-NNN-trimethyl-9-oxo-3,5,8-trioxa-4-phosphadodecan-1-aminium, 4-oxide, hydroxide, inner salt 7-nonadecyl-4-hydroxy-NN-dimethyl-9-oxo-3,5,8-trioxa-4-phosphadodecan-1-aminium, 4-oxide, hydroxide, inner salt 7-nonadecyl-4-hydroxy-N-methyl-9-oxo-3,5,8-trioxa-4-phosphadodecan-1-aminium, 4-oxide, hydroxide, inner salt 7-nonadecyl-4-hydroxy-NN-tetramethylene-9-oxo-3,5,8-trioxa-4-phosphadodecan-1-aminium, 4-oxide, hydroxide, inner salt 7-eicosanyl-4-hydroxy-NNN-trimethyl-9-oxo-3,5,8-trioxa-4-phosphadodecan-1-aminium, 4-oxide, hydroxide, inner salt 7-eicosanyl-4-hydroxy-NN-dimethyl-9-oxo-3,5,8-trioxa-4-phosphadodecan-1-aminium, 4-oxide, hydroxide, inner salt 7-eicosanyl-4-hydroxy-N-methyl-9-oxo-3,5,8-trioxa-4-phosphadodecan-1-aminium, 4-oxide, hydroxide, inner salt 7-eicosanyl-4-hydroxy-NN-tetramethylene-9-oxo-3,5,8-trioxa-4-phosphadodecan-1-aminium, 4-oxide, hydroxide, inner salt 7-heneicosanyl-4-hydroxy-NNN-trimethyl-9-oxo-3,5,8-trioxa-4-phosphadodecan-1-aminium, 4-oxide, hydroxide, inner salt 7-heneicosanyl-4-hydroxy-NN-dimethyl-9-oxo-3,5,8-trioxa-4-phosphadodecan-1-aminium, 4-oxide, hydroxide, inner salt 7-heneicosanyl-4-hydroxy-N-methyl-9-oxo-3,5,8-trioxa-4-phosphadodecan-1-aminium, 4-oxide, hydroxide, inner salt 7-heneicosanyl-4-hydroxy-NN-tetramethylene-9-oxo-3,5,8-trioxa-4-phosphadodecan-1-aminium, 4-oxide, hydroxide, inner salt 7-(3-methyloctadecyl)-4-hydroxy-NNN-trimethyl-9-oxo-3,5,8-trioxa-4-phosphadodecan-1-aminium, 4-oxide, hydroxide, inner salt 7-(3-methyloctadecyl)-4-hydroxy-NN-dimethyl-9-oxo-3,5,8-trioxa-4-phosphadodecan-1-aminium, 4-oxide, hydroxide, inner salt 7-(3-methyloctadecyl)-4-hydroxy-N-methyl-9-oxo-3,5,8-trioxa-4-phosphadodecan-1-aminium, 4-oxide, hydroxide, inner salt 7-(3-methyloctadecyl)-4-hydroxy-NN-tetramethylene-9-oxo-3,5,8-trioxa-4-phosphadodecan-1-aminium, 4-oxide, hydroxide, inner salt 8-hexadecyl-5-hydroxy-NNN-trimethyl-10-oxo-4,6,9-trioxa-5-phosphadecan-1-aminium, 5-oxide, hydroxide, inner salt 8-hexadecyl-5-hydroxy-NN-dimethyl-10-oxo-4,6,9-trioxa-5-phosphadecan-1-aminium, 5-oxide, hydroxide, inner salt 8-hexadecyl-5-hydroxy-N-methyl-10-oxo-4,6,9-trioxa-5-phosphadecan-1-aminium, 5-oxide, hydroxide, inner salt 8-hexadecyl-5-hydroxy-NN-tetramethylene-10-oxo-4,6,9-trioxa-5-phosphadecan-1-aminium, 5-oxide, hydroxide, inner salt 8-heptadecyl-5-hydroxy-NNN-trimethyl-10-oxo-4,6,9-trioxa-5-phosphadecan-1-aminium, 5-oxide, hydroxide, inner salt 8-heptadecyl-5-hydroxy-NN-dimethyl-10-oxo-4,6,9-trioxa-5-phosphadecan-1-aminium, 5-oxide, hydroxide, inner salt 8-heptadecyl-5-hydroxy-N-methyl-10-oxo-4,6,9-trioxa-5-phosphadecan-1-aminium, 5-oxide, hydroxide, inner salt 8-heptadecyl-5-hydroxy-NN-tetramethylene-10-oxo-4,6,9-trioxa-5-phosphadecan-1-aminium, 5-oxide, hydroxide, inner salt 8-octadecyl-5-hydroxy-NNN-trimethyl-10-oxo-4,6,9-trioxa-5-phosphadecan-1-aminium, 5-oxide, hydroxide, inner salt 8-octadecyl-5-hydroxy-NN-dimethyl-10-oxo-4,6,9-trioxa-5-phosphadecan-1-aminium, 5-oxide, hydroxide, inner salt 8-octadecyl-5-hydroxy-N-methyl-10-oxo-4,6,9-trioxa-5-phosphadecan-1-aminium, 5-oxide, hydroxide, inner salt 8-octadecyl-5-hydroxy-NN-tetramethylene-10-oxo-4,6,9-trioxa-5-phosphadecan-1-aminium, 5-oxide, hydroxide, inner salt 8-nonadecyl-5-hydroxy-NNN-trimethyl-10-oxo-4,6,9-trioxa-5-phosphadecan-1-aminium, 5-oxide, hydroxide, inner salt 8-nonadecyl-5-hydroxy-NN-dimethyl-10-oxo-4,6,9-trioxa-5-phosphadecan-1-aminium, 5-oxide, hydroxide, inner salt 8-nonadecyl-5-hydroxy-N-methyl-10-oxo-4,6,9-trioxa-5-phosphadecan-1-aminium, 5-oxide, hydroxide, inner salt 8-nonadecyl-5-hydroxy-NN-tetramethylene-10-oxo-4,6,9-trioxa-5-phosphadecan-1-aminium, 5-oxide, hydroxide, inner salt 8-eicosanyl-5-hydroxy-NNN-trimethyl-10-oxo-4,6,9-trioxa-5-phosphadecan-1-aminium, 5-oxide, hydroxide, inner salt 8-eicosanyl-5-hydroxy-NN-dimethyl-10-oxo-4,6,9-trioxa-5-phosphadecan-1-aminium, 5-oxide, hydroxide, inner salt 8-eicosanyl-5-hydroxy-N-methyl-10-oxo-4,6,9-trioxa-5-phosphadecan-1-aminium, 5-oxide, hydroxide, inner salt 8-eicosanyl-5-hydroxy-NN-tetramethylene-10-oxo-4,6,9-trioxa-5-phosphadecan-1-aminium, 5-oxide, hydroxide, inner salt 8-heneicosanyl-5-hydroxy-NNN-trimethyl-10-oxo-4,6,9-trioxa-5-phosphadecan-1-aminium, 5-oxide, hydroxide, inner salt 8-heneicosanyl-5-hydroxy-NN-dimethyl-10-oxo-4,6,9-trioxa-5-phosphadecan-1-aminium, 5-oxide, hydroxide, inner salt 8-heneicosanyl-5-hydroxy-N-methyl-10-oxo-4,6,9-trioxa-5-phosphadecan-1-aminium, 5-oxide, hydroxide, inner salt 8-heneicosanyl-5-hydroxy-NN-tetramethylene-10-oxo-4,6,9-trioxa-5-phosphadecan-1-aminium, 5-oxide, hydroxide, inner salt 8-(3-methyloctadecyl)-5-hydroxy-NNN-trimethyl-10-oxo-4,6,9-trioxa-5-phosphadecan-1-aminium, 5-oxide, hydroxide, inner salt 8-(3-methyloctadecyl)-5-hydroxy-NN-dimethyl-10-oxo-4,6,9-trioxa-5-phosphadecan-1-aminium, 5-oxide, hydroxide, inner salt 8-(3-methyloctadecyl)-5-hydroxy-N-methyl-10-oxo-4,6,9-trioxa-5-phosphadecan-1-aminium, 5-oxide, hydroxide, inner salt 8-(3-methyloctadecyl)-5-hydroxy-NN-tetramethylene-10-oxo-4,6,9-trioxa-5-phosphadecan-1-aminium, 5-oxide, hydroxide, inner salt 8-hexadecyl-5-hydroxy-NNN-trimethyl-10-oxo-4,6,9-trioxa-5-phosphaundecan-1-aminium, 5-oxide, hydroxide, inner salt 8-hexadecyl-5-hydroxy-NN-dimethyl-10-oxo-4,6,9-trioxa-5-phosphaundecan-1-aminium, 5-oxide, hydroxide, inner salt 8-hexadecyl-5-hydroxy-N-methyl-10-oxo-4,6,9-trioxa-5-phosphaundecan-1-aminium, 5-oxide, hydroxide, inner salt 8-hexadecyl-5-hydroxy-NN-tetramethylene-10-oxo-4,6,9-trioxa-5-phosphaundecan-1-aminium, 5-oxide, hydroxide, inner salt 8-heptadecyl-5-hydroxy-NNN-trimethyl-10-oxo-4,6,9-trioxa-5-phosphaundecan-1-aminium, 5-oxide, hydroxide, inner salt 8-heptadecyl-5-hydroxy-NN-dimethyl-10-oxo-4,6,9-trioxa-5-phosphaundecan-1-aminium, 5-oxide, hydroxide, inner salt 8-heptadecyl-5-hydroxy-N-methyl-10-oxo-4,6,9-trioxa-5-phosphaundecan-1-aminium, 5-oxide, hydroxide, inner salt 8-heptadecyl-5-hydroxy-NN-tetramethylene-10-oxo-4,6,9-trioxa-5-phosphaundecan-1-aminium, 5-oxide, hydroxide, inner salt 8-octadecyl-5-hydroxy-NNN-trimethyl-10-oxo-4,6,9-trioxa-5-phosphaundecan-1-aminium, 5-oxide, hydroxide, inner salt 8-octadecyl-5-hydroxy-NN-dimethyl-10-oxo-4,6,9-trioxa-5-phosphaundecan-1-aminium, 5-oxide, hydroxide, inner salt 8-octadecyl-5-hydroxy-N-methyl-10-oxo-4,6,9-trioxa-5-phosphaundecan-1-aminium, 5-oxide, hydroxide, inner salt 8-octadecyl-5-hydroxy-NN-tetramethylene-10-oxo-4,6,9-trioxa-5-phosphaundecan-1-aminium, 5-oxide, hydroxide, inner salt 8-nonadecyl-5-hydroxy-NNN-trimethyl-10-oxo-4,6,9-trioxa-5-phosphaundecan-1-aminium, 5-oxide, hydroxide, inner salt 8-nonadecyl-5-hydroxy-NN-dimethyl-10-oxo-4,6,9-trioxa-5-phosphaundecan-1-aminium, 5-oxide, hydroxide, inner salt 8-nonadecyl-5-hydroxy-N-methyl-10-oxo-4,6,9-trioxa-5-phosphaundecan-1-aminium, 5-oxide, hydroxide, inner salt 8-nonadecyl-5-hydroxy-NN-tetramethylene-10-oxo-4,6,9-trioxa-5-phosphaundecan-1-aminium, 5-oxide, hydroxide, inner salt 8-eicosanyl-5-hydroxy-NNN-trimethyl-10-oxo-4,6,9-trioxa-5-phosphaundecan-1-aminium, 5-oxide, hydroxide, inner salt 8-eicosanyl-5-hydroxy-NN-dimethyl-10-oxo-4,6,9-trioxa-5-phosphaundecan-1-aminium, 5-oxide, hydroxide, inner salt 8-eicosanyl-5-hydroxy-N-methyl-10-oxo-4,6,9-trioxa-5-phosphaundecan-1-aminium, 5-oxide, hydroxide, inner salt 8-eicosanyl-5-hydroxy-NN-tetramethylene-10-oxo-4,6,9-trioxa-5-phosphaundecan-1-aminium; 5-oxide, hydroxide, inner salt 8-heneicosanyl-5-hydroxy-NNN-trimethyl-10-oxo-4,6,9-trioxa-5-phosphaundecan-1-aminium, 5-oxide, hydroxide, inner salt 8-heneicosanyl-5-hydroxy-NN-dimethyl-10-oxo-4,6,9-trioxa-5-phosphaundecan-1-aminium, 5-oxide, hydroxide, inner salt 8-heneicosanyl-5-hydroxy-N-methyl-10-oxo-4,6,9-trioxa-5-phosphaundecan-1-aminium, 5-oxide, hydroxide, inner salt 8-heneicosanyl-5-hydroxy-NN-tetramethylene-10-oxo-4,6,9-trioxa-5-phosphaundecan-1-aminium, 5-oxide, hydroxide, inner salt 8-(3-methyloctadecyl)-5-hydroxy-NNN-trimethyl-10-oxo-4,6,9-trioxa-5-phosphaundecan-1-aminium, 5-oxide, hydroxide, inner salt 8-(3-methyloctadecyl)-5-hydroxy-NN-dimethyl-10-oxo-4,6,9-trioxa-5-phosphaundecan-1-aminium, 5-oxide, hydroxide, inner salt 8-(3-methyloctadecyl)-5-hydroxy-N-methyl-10-oxo-4,6,9-trioxa-5-phosphaundecan-1-aminium, 5-oxide, hydroxide, inner salt 8-(3-methyloctadecyl)-5-hydroxy-NN-tetramethylene-10-oxo-4,6,9-trioxa-5-phosphaundecan-1-aminium, 5-oxide, hydroxide, inner salt 8-hexadecyl-5-hydroxy-NNN-trimethyl-10-oxo-4,6,9-trioxa-5-phosphadodecan-1-aminium, 5-oxide, hydroxide, inner salt 8-hexadecyl-5-hydroxy-NN-dimethyl-10-oxo-4,6,9-trioxa-5-phosphadodecan-1-aminium, 5-oxide, hydroxide, inner salt 8-hexadecyl-5-hydroxy-N-methyl-10-oxo-4,6,9-trioxa-5-phosphadodecan-1-aminium, 5-oxide, hydroxide, inner salt 8-hexadecyl-5-hydroxy-NN-tetramethylene-10-oxo-4,6,9-trioxa-5-phosphadodecan-1-aminium, 5-oxide, hydroxide, inner salt 8-heptadecyl-5-hydroxy-NNN-trimethyl-10-oxo-4,6,9-trioxa-5-phosphadodecan-1-aminium; 5-oxide, hydroxide, inner salt 8-heptadecyl-5-hydroxy-NN-dimethyl-10-oxo-4,6,9-trioxa-5-phosphadodecan-1-aminium, 5-oxide, hydroxide, inner salt 8-heptadecyl-5-hydroxy-N-methyl-10-oxo-4,6,9-trioxa-5-phosphadodecan-1-aminium, 5-oxide, hydroxide, inner salt 8-heptadecyl-5-hydroxy-NN-tetramethylene-10-oxo-4,6,9-trioxa-5-phosphadodecan-1-aminium, 5-oxide, hydroxide, inner salt 8-octadecyl-5-hydroxy-NNN-trimethyl-10-oxo-4,6,9-trioxa-5-phosphadodecan-1-aminium, 5-oxide, hydroxide, inner salt 8-octadecyl-5-hydroxy-NN-dimethyl-10-oxo-4,6,9-trioxa-5-phosphadodecan-1-aminium, 5-oxide, hydroxide, inner salt 8-octadecyl-5-hydroxy-N-methyl-10-oxo-4,6,9-trioxa-5-phosphadodecan-1-aminium, 5-oxide, hydroxide, inner salt 8-octadecyl-5-hydroxy-NN-tetramethylene-10-oxo-4,6,9-trioxa-5-phosphadodecan-1-aminium, 5-oxide, hydroxide, inner salt 8-nonadecyl-5-hydroxy-NNN-trimethyl-10-oxo-4,6,9-trioxa-5-phosphadodecan-1-aminium, 5-oxide, hydroxide, inner salt 8-nonadecyl-5-hydroxy-NN-dimethyl-10-oxo-4,6,9-trioxa-5-phosphadodecan-1-aminium, 5-oxide, hydroxide, inner salt 8-nonadecyl-5-hydroxy-N-methyl-10-oxo-4,6,9-trioxa-5-phosphadodecan-1-aminium, 5-oxide, hydroxide, inner salt 8-nonadecyl-5-hydroxy-NN-tetramethylene-10-oxo-4,6,9-trioxa-5-phosphadodecan-1-aminium, 5-oxide, hydroxide, inner salt 8-eicosanyl-5-hydroxy-NNN-trimethyl-10-oxo-4,6,9-trioxa-5-phosphadodecan-1-aminium, 5-oxide, hydroxide, inner salt 8-eicosanyl-5-hydroxy-NN-dimethyl-10-oxo-4,6,9-trioxa-5-phosphadodecan-1-aminium, 5-oxide, hydroxide, inner salt 8-eicosanyl-5-hydroxy-N-methyl-10-oxo-4,6,9-trioxa-5-phosphadodecan-1-aminium, 5-oxide, hydroxide, inner salt 8-eicosanyl-5-hydroxy-NN-tetramethylene-10-oxo-4,6,9-trioxa-5-phosphadodecan-1-aminium, 5-oxide, hydroxide, inner salt
8-heneicosanyl-5-hydroxy-NNN-trimethyl-10-oxo-4,6,9-trioxa-5-phosphadodecan-1-aminium, 5-oxide, hydroxide, inner salt
8-heneicosanyl-5-hydroxy-NN-dimethyl-10-oxo-4,6,9-trioxa-5-phosphadodecan-1-aminium, 5-oxide, hydroxide, inner salt
8-heneicosanyl-5-hydroxy-N-methyl-10-oxo-4,6,9-trioxa-5-phosphadodecan-1-aminium, 5-oxide, hydroxide, inner salt
8-heneicosanyl-5-hydroxy-NN-tetramethylene-10-oxo-4,6,9-trioxa-5-phosphadodecan-1-aminium, 5-oxide, hydroxide, inner salt
8-(3-methyloctadecyl)-5-hydroxy-NNN-trimethyl-10-oxo-4,6,9-trioxa-5-phosphadodecan-1-aminium, 5-oxide, hydroxide, inner salt
8-(3-methyloctadecyl)-5-hydroxy-NN-dimethyl-10-oxo-4,6,9-trioxa-5-phosphadodecan-1-aminium, 5-oxide, hydroxide, inner salt
8-(3-methyloctadecyl)-5-hydroxy-N-methyl-10-oxo-4,6,9-trioxa-5-phosphadodecan-1-aminium, 5-oxide, hydroxide, inner salt
8-(3-methyloctadecyl)-5-hydroxy-NN-tetramethylene-10-oxo-4,6,9-trioxa-5-phosphadodecan-1-aminium, 5-oxide, hydroxide, inner salt
9-hexadecyl-6-hydroxy-NNN-trimethyl-11-oxo-5,7,10-trioxa-6-phosphaundecan-1-aminium, 6-oxide, hydroxide, inner salt
9-hexadecyl-6-hydroxy-NN-dimethyl-11-oxo-5,7,10-trioxa-6-phosphaundecan-1-aminium, 6-oxide, hydroxide, inner salt
9-hexadecyl-6-hydroxy-N-methyl-11-oxo-5,7,10-trioxa-6-phosphaundecan-1-aminium, 6-oxide, hydroxide, inner salt
9-hexadecyl-6-hydroxy-NN-tetramethylene-11-oxo-5,7,10-trioxa-6-phosphaundecan-1-aminium, 6-oxide, hydroxide, inner salt
9-heptadecyl-6-hydroxy-NNN-trimethyl-11-oxo-5,7,10-trioxa-6-phosphaundecan-1-aminium, 6-oxide, hydroxide, inner salt
9-heptadecyl-6-hydroxy-NN-dimethyl-11-oxo-5,7,10-trioxa-6-phosphaundecan-1-aminium, 6-oxide, hydroxide, inner salt
9-heptadecyl-6-hydroxy-N-methyl-11-oxo-5,7,10-trioxa-6-phosphaundecan-1-aminium, 6-oxide, hydroxide, inner salt
9-heptadecyl-6-hydroxy-NN-tetramethylene-11-oxo-5,7,10-trioxa-6-phosphaundecan-1-aminium, 6-oxide, hydroxide, inner salt
9-octadecyl-6-hydroxy-NNN-trimethyl-11-oxo-5,7,10-trioxa-6-phosphaundecan-1-aminium, 6-oxide, hydroxide, inner salt
9-octadecyl-6-hydroxy-NN-dimethyl-11-oxo-5,7,10-trioxa-6-phosphaundecan-1-aminium, 6-oxide, hydroxide, inner salt
9-octadecyl-6-hydroxy-N-methyl-11-oxo-5,7,10-trioxa-6-phosphaundecan-1-aminium, 6-oxide, hydroxide, inner salt
9-octadecyl-6-hydroxy-NN-tetramethylene-11-oxo-5,7,10-trioxa-6-phosphaundecan-1-aminium, 6-oxide, hydroxide, inner salt
9-nonadecyl-6-hydroxy-NNN-trimethyl-11-oxo-5,7,10-trioxa-6-phosphaundecan-1-aminium, 6-oxide, hydroxide, inner salt
9-nonadecyl-6-hydroxy-NN-dimethyl-11-oxo-5,7,10-trioxa-6-phosphaundecan-1-aminium, 6-oxide, hydroxide, inner salt
9-nonadecyl-6-hydroxy-N-methyl-11-oxo-5,7,10-trioxa-6-phosphaundecan-1-aminium, 6-oxide, hydroxide, inner salt
9-nonadecyl-6-hydroxy-NN-tetramethylene-11-oxo-5,7,10-trioxa-6-phosphaundecan-1-aminium, 6-oxide, hydroxide, inner salt
9-eicosanyl-6-hydroxy-NNN-trimethyl-11-oxo-5,7,10-trioxa-6-phosphaundecan-1-aminium, 6-oxide, hydroxide, inner salt
9-eicosanyl-6-hydroxy-NN-dimethyl-11-oxo-5,7,10-trioxa-6-phosphaundecan-1-aminium, 6-oxide, hydroxide, inner salt
9-eicosanyl-6-hydroxy-N-methyl-11-oxo-5,7,10-trioxa-6-phosphaundecan-1-aminium, 6-oxide, hydroxide, inner salt
9-eicosanyl-6-hydroxy-NN-tetramethylene-11-oxo-5,7,10-trioxa-6-phosphaundecan-1-aminium, 6-oxide, hydroxide, inner salt
9-heneicosanyl-6-hydroxy-NNN-trimethyl-11-oxo-5,7,10-trioxa-6-phosphaundecan-1-aminium, 6-oxide, hydroxide, inner salt
9-heneicosanyl-6-hydroxy-NN-dimethyl-11-oxo-5,7,10-trioxa-6-phosphaundecan-1-aminium, 6-oxide, hydroxide, inner salt
9-heneicosanyl-6-hydroxy-N-methyl-11-oxo-5,7,10-trioxa-6-phosphaundecan-1-aminium, 6-oxide, hydroxide, inner salt
9-heneicosanyl-6-hydroxy-NN-tetramethylene-11-oxo-5,7,10-trioxa-6-phosphaundecan-1-aminium, 6-oxide, hydroxide, inner salt
9-(3-methyloctadecyl)-6-hydroxy-NNN-trimethyl-11-oxo-5,7,10-trioxa-6-phosphaundecan-1-aminium, 6-oxide, hydroxide, inner salt
9-(3-methyloctadecyl)-6-hydroxy-NN-dimethyl-11-oxo-5,7,10-trioxa-6-phosphaundecan-1-aminium, 6-oxide, hydroxide, inner salt
9-(3-methyloctadecyl)-6-hydroxy-N-methyl-11-oxo-5,7,10-trioxa-6-phosphaundecan-1-aminium, 6-oxide, hydroxide, inner salt
9-(3-methyloctadecyl)-6-hydroxy-NN-tetramethylene-11-oxo-5,7,10-trioxa-6-phosphaundecan-1-aminium, 6-oxide, hydroxide, inner salt
9-hexadecyl-6-hydroxy-NNN-trimethyl-11-oxo-5,7,10-trioxa-6-phosphadodecan-1-aminium, 6-oxide, hydroxide, inner salt
9-hexadecyl-6-hydroxy-NN-dimethyl-11 -oxo-5,7,10-trioxa-6-phosphadodecan-1-aminium, 6-oxide, hydroxide, inner salt
9-hexadecyl-6-hydroxy-N-methyl-11-oxo-5,7,10-trioxa-6-phosphadodecan-1-aminium, 6-oxide, hydroxide, inner salt
9-hexadecyl-6-hydroxy-NN-tetramethylene-11-oxo-5,7,10-trioxa-6-phosphadodecan-1-aminium, 6-oxide, hydroxide, inner salt
9heptadecyl-6-hydroxy-NNN-trimethyl-11-oxo-5,7,10-trioxa-6-phosphadodecan-1-aminium, 6-oxide, hydroxide, inner salt
9-heptadecyl-6-hydroxy-NN-dimethyl-11-oxo-5,7,10-trioxa-6-phosphadodecan-1-aminium, 6-oxide, hydroxide, inner salt
9-heptadecyl-6-hydroxy-N-methyl-11-oxo-5,7,10-trioxa-6-phosphadodecan-1-aminium, 6-oxide, hydroxide, inner salt 9-heptadecyl-6-hydroxy-NN-tetramethylene-11-oxo-5,7,10-trioxa-6-phosphadodecan-1-aminium, 6-oxide, hydroxide, inner salt 9-octadecyl-6-hydroxy-N,N,N-trimethyl-11-oxo-5,7,10-trioxa-6-phosphadodecan-1-aminium, 6-oxide, hydroxide, inner salt 9-octadecyl-6-hydroxy-NN-dimethyl-11-oxo-5,7,10-trioxa-6-phosphadodecan-1-aminium, 6-oxide, hydroxide, inner salt 9-octadecyl-6-hydroxy-N-methyl-11-oxo-5,7,10-trioxa-6-phosphadodecan-1-aminium, 6-oxide, hydroxide, inner salt 9-octadecyl-6-hydroxy-NN-tetramethylene-11-oxo-5,7,10-trioxa-6-phosphadodecan-1-aminium, 6-oxide, hydroxide, inner salt 9-nonadecyl-6-hydroxy-NNN-trimethyl-11-oxo-5,7,10-trioxa-6-phosphadodecan-1-aminium, 6-oxide, hydroxide, inner salt 9-nonadecyl-6-hydroxy-NN-dimethyl-11-oxo-5,7,10-trioxa-6-phosphadodecan-1-aminium, 6-oxide, hydroxide, inner salt 9-nonadecyl-6-hydroxy-N-methyl-11-oxo-5,7,10-trioxa-6-phosphadodecan-1-aminium, 6-oxide, hydroxide, inner salt 9-nonadecyl-6-hydroxy-NN-tetramethylene-11-oxo-5,7,10-trioxa-6-phosphadodecan-1-aminium, 6-oxide, hydroxide, inner salt 9-eicosanyl-6-hydroxy-NNN-trimethyl-11-oxo-5,7,10-trioxa-6-phosphadodecan-1-aminium, 6-oxide, hydroxide, inner salt 9-eicosanyl-6-hydroxy-NN-dimethyl-11-oxo-5,7,10-trioxa-6-phosphadodecan-1-aminium, 6-oxide, hydroxide, inner salt 9-eicosanyl-6-hydroxy-N-methyl-11-oxo-5,7,10-trioxa-6-phosphadodecan-1-aminium, 6-oxide, hydroxide, inner salt 9-eicosanyl-6-hydroxy-NN-tetramethylene-11-oxo-5,7,10-trioxa-6-phosphadodecan-1-aminium, 6-oxide, hydroxide, inner salt 9-heneicosanyl-6-hydroxy-NNN-trimethyl-11-oxo-5,7,10-trioxa-6-phosphadodecan-1-aminium, 6-oxide, hydroxide, inner salt 9-heneicosanyl-6hydroxy-NN-dimethyl-11-oxo-5,7,10-trioxa-6-phosphadodecan-1-aminium, 6-oxide, hydroxide, inner salt 9-heneicosanyl-6-hydroxy-N-methyl-11-oxo-5,7,10-trioxa-6-phosphadodecan-1-aminium, 6-oxide, hydroxide, inner salt 9-heneicosanyl-6-hydroxy-NN-tetramethylene-11-oxo-5,7,10-trioxa-6-phosphadodecan-1-aminium, 6-oxide, hydroxide, inner salt 9-(3-methyloctadecyl)-6-hydroxy-NNN-trimethyl-11-oxo-5,7,10-trioxa-6-phosphadodecan-1-aminium, 6-oxide, hydroxide, inner salt 9-(3-methyloctadecyl)-6-hydroxy-NN-dimethyl-11-oxo-5,7,10-trioxa-6-phosphadodecan-1-aminium, 6-oxide, hydroxide, inner salt 9-(3-methyloctadecyl)-6-hydroxy-N-methyl-11-oxo-5,7,10-trioxa-6-phosphadodecan-1-aminium-6-oxide, hydroxide, inner salt 9-(3-methyloctadecyl)-6-hydroxy-NN-tetramethylene-11-oxo-5,7,10-trioxa-6-phosphadodecan-1-aminium, 6-oxide, hydroxide, inner salt 4-hydroxy-N,N,N-trimethyl-7-hexadecyl-9-oxo-3,5,8,10-tetraoxa-4-phosphaundecan-1-aminium, 4-oxide, hydroxide, inner salt 4hydroxy-N,N,N-trimethyl-7-hexadecyl-9-oxo-3,5,8,10-tetraoxa-4-phosphadodecan-1-aminium, 4-oxide, hydroxide, inner salt 4-hydroxy-N,N,N-trimethyl-7-hexadecyl-9-oxo-3,5,8-trioxa-10-aza-4-phosphaundecan-1-aminium, 4-oxide, hydroxide, inner salt 4-hydroxy-N,N,N-trimethyl-7-hexadecyl-9-oxo-3,5,8-trioxa-10-aza-4-phosphadodecan-1-aminium, 4-oxide, hydroxide, inner salt 4-hydroxy-N,N,N-trimethyl-7-heptadecyl-9-oxo-3,5,8,10-tetraoxa-4-phosphaundecan-1-aminium, 4-oxide, hydroxide, inner salt 4-hydroxy-N,N,N-trimethyl-7-heptadecyl-9-oxo-3,5,8,10-tetraoxa-4-phosphadodecan-1-aminium, 4-oxide, hydroxide, inner salt 4-hydroxy-N,N,N-trimethyl-7-heptadecyl-9-oxo-3,5,8-trioxa-10-aza-4-phosphaundecan-1-aminium, 4-oxide, hydroxide, inner salt 4-hydroxy-N,N,N-trimethyl-7-heptadecyl-9-oxo-3,5,8-trioxa-10-aza-4-phosphadodecan-1-aminium, 4-oxide, hydroxide, inner salt 4-hydroxy-N,N,N-trimethyl-7-octadecyl-9-oxo-3,5,8,10-tetraoxa-4-phosphaundecan-1-aminium, 4-oxide, hydroxide, inner salt 4-hydroxy-N,N,N-trimethyl-7-octadecyl-9-oxo-3,5,8,10-tetraoxa-4-phosphadodecan-1-aminium, 4-oxide, hydroxide, inner salt 4-hydroxy-N,N,N-trimethyl-7-octadecyl-9-oxo-3,5,8-trioxa-10-aza-4-phosphaundecan-1-aminium, 4-oxide, hydroxide, inner salt 4-hydroxy-N,N,N-trimethyl-7-octadecyl-9-oxo-3,5,8-trioxa-10-aza-4-phosphadodecan-1-aminium, 4-oxide, hydroxide, inner salt 4-hydroxy-N,N,N-trimethyl-7-nonadecyl-9-oxo-3,5,8,10-tetraoxa-4-phosphaundecan-1-aminium, 4-oxide, hydroxide, inner salt 4-hydroxy-N,N,N-trimethyl-7-nonadecyl-9-oxo-3,5,8,10-tetraoxa-4-phosphadodecan-1-aminium, 4-oxide, hydroxide, inner salt 4-hydroxy-N,N,N-trimethyl-7-nonadecyl-9-oxo-3,5,8-trioxa-10-aza-4-phosphaundecan-1-aminium, 4-oxide, hydroxide, inner salt 4-hydroxy-N,N,N-trimethyl-7-nonadecyl-9-oxo-3,5,8-trioxa-10-aza-4-phosphadodecan-1-aminium, 4-oxide, hydroxide, inner salt 4-hydroxy-N,N,N-trimethyl-7-eicosyl-9-oxo-3,5,8,10-tetraoxa-4-phosphaundecan-1-aminium, 4-oxide, hydroxide, inner salt 4-hydroxy-N,N,N-trimethyl-7-eicosyl-9-oxo-3,5,8,10-tetraoxa-4-phosphadodecan-1-aminium, 4-oxide, hydroxide, inner salt 4-hydroxy-N,N,N-trimethyl-7-eicosyl-9-oxo-3,5,8-trioxa-10-aza-4-phosphaundecan-1-aminium, 4-oxide, hydroxide, inner salt 4-hydroxy-N,N,N-trimethyl-7-eicosyl-9-oxo-3,5,8-trioxa-10-aza-4-phosphadodecan-1-aminium, 4-oxide, hydroxide, inner salt 4-hydroxy-N,N-dimethyl-7-hexadecyl-9-oxo-3,5,8,10-tetraoxa-4-phosphaundecan-1-aminium, 4-oxide, hydroxide, inner salt 4-hydroxy-N,N-dimethyl-7-hexadecyl-9-oxo-3,5,8,10-tetraoxa-4-phosphadodecan-1-aminium, 4-oxide, hydroxide, inner salt 4-hydroxy-N,N-dimethyl-7-hexadecyl-9-oxo-3,5,8-trioxa-10-aza-4-phosphaundecan-1-aminium, 4-oxide, hydroxide, inner salt 4-hydroxy-N,N-dimethyl-7-hexadecyl-9-oxo-3,5,8-trioxa-10-aza-4-phosphadodecan-1-aminium, 4-oxide, hydroxide, inner salt 4-hydroxy-N,N-dimethyl-7-heptadecyl-9-oxo-3,5,8,10-tetraoxa-4-phosphaundecan-1-aminium, 4-oxide, hydroxide, inner salt 4-hydroxy-N,N-dimethyl-7-heptadecyl-9-oxo-3,5,8,10-tetraoxa-4-phosphadodecan-1-aminium, 4-oxide, hydroxide, inner salt 4-hydroxy-N,N-dimethyl-7-heptadecyl-9-oxo-3,5,8-trioxa-10-aza-4-phosphaundecan-1-aminium, 4-oxide, hydroxide, inner salt 4-hydroxy-N,N-dimethyl-7-heptadecyl-9-oxo-3,5,8-trioxa-10-aza-4-phosphadodecan-1-aminium, 4-oxide, hydroxide, inner salt 4-hydroxy-N,N-dimethyl-7-octadecyl-9-oxo-3,5,8,10-tetraoxa-4-phosphaundecan-1-aminium, 4-oxide, hydroxide, inner salt 4-hydroxy-N,N-dimethyl-7-octadecyl-9-oxo-3,5,8,10-tetraoxa-4-phosphadodecan-1-aminium, 4-oxide, hydroxide, inner salt 4-hydroxy-N,N-dimethyl-7-octadecyl-9oxo-3,5,8-trioxa-10-aza-4-phosphaundecan-1-aminium, 4-oxide, hydroxide, inner salt 4-hydroxy-N,N-dimethyl-7-octadecyl-9-oxo-3,5,8-trioxa-10-aza-4-phosphadodecan-1-aminium, 4-oxide, hydroxide, inner salt 4-hydroxy-N,N-dimethyl-7-nonadecyl-9-oxo-3,5,8,10-tetraoxa-4-phosphaundecan-1-aminium, 4-oxide, hydroxide, inner salt 4-hydroxy-N,N-dimethyl-7-nonadecyl-9-oxo-3,5,8,10-tetraoxa-4-phosphadodecan-1-aminium, 4-oxide, hydroxide, inner salt 4-hydroxy-N,N-dimethyl-7-nonadecyl-9-oxo-3,5,8-trioxa-10-aza-4-phosphaundecan-1-aminium, 4-oxide, hydroxide, inner salt 4-hydroxy-N,N-dimethyl-7-nonadecyl-9-oxo-3,5,8-trioxa-10-aza-4-phosphadodecan-1-aminium, 4-oxide, hydroxide, inner salt 4-hydroxy-N,N-dimethyl-7-eicosyl-9-oxo-3,5,8,10-tetraoxa-4-phosphaundecan-1-aminium, 4-oxide, hydroxide, inner salt 4-hydroxy-N,N-dimethyl-7-eicosyl-9-oxo-3,5,8,10-tetraoxa-4-phosphadodecan-1-aminium, 4-oxide, hydroxide, inner salt 4-hydroxy-N,N-dimethyl-7-eicosyl-9-oxo-3,5,8-trioxa-10-aza-4-phosphaundecan-1-aminium, 4-oxide, hydroxide, inner salt 4-hydroxy-N,N-dimethyl-7-eicosyl-9-oxo-3,5,8-trioxa-10-aza-4-phosphadodecan-1-aminium, 4-oxide, hydroxide, inner salt 2-[[[2-(acetyloxy)eicosyl]oxy]hydroxyphosphinyl]-N,N,N-trimethyl-ethanaminium, hydroxide, inner salt 2-[[[2-(acetoxy)eicosyl]oxy]hydroxyphosphinyl]-N,N-dimethyl-ethanaminium, hydroxide, inner salt 2-[[[2-(acetyloxy)nonadecyl]oxy]hydroxyphosphinyl]-N,N,N-trimethyl-ethanaminium, hydroxide, inner salt 2-[[[2-(acetyloxy)nonadecyl]oxy]hydroxyphosphinyl]-N,N-dimethyl-ethanaminium, hydroxide, inner salt 2-[[[2-(acetyloxy)heneicosyl]oxy]hydroxyphosphinyl]-N,N,N-trimethyl-ethanaminium, hydroxide, inner salt 2-[[[2-(acetyloxy)heneicosyl]oxy]hydroxyphosphinyl]-N,N-dimethyl-ethanaminium, hydroxide, inner salt 3-[[[2-(acetyloxy)eicosyl]oxy]hydroxyphosphinyl]-N,N,N-trimethyl-propanaminium, hydroxide, inner salt 3-[[[2-(acetyloxy)eicosyl]oxy]hydroxyphosphinyl]-N,N-dimethyl-propanaminium, hydroxide, inner salt 3-[[[2-(acetyloxy)nonadecyl]oxy]hydroxyphosphinyl]-N,N,N-trimethyl-propanaminium, hydroxide, inner salt 3-[[[2-(acetyloxy)nonadecyl]oxy]hydroxyphosphinyl]-N,N-dimethyl-propanaminium, hydroxide, inner salt 3-[[[2-(acetyloxy)heneicosyl]oxy]hydroxyphosphinyl]-N,N,N-trimethyl-propanaminium, hydroxide, inner salt 3-[[[2-(acetyloxy)heneicosyl]oxy]hydroxyphosphinyl]-N,N-dimethyl-propanaminium, hydroxide, inner salt

EXAMPLE 6

(4-Tetradecyloxyphenyl)acetic acid

A mixture of about 75 g of 4-hydroxyphenylacetic acid, about 273.38 g of 1-tetradecylbromide, about 46.33 g of sodium hydroxide, about 5.0 g of trioctadecyl methylamine chloride and about 500 ml of water was refluxed for about 24 hours with stirring, cooled to room temperature, the aqueous layer decanted and the solid washed with water. The solid was refluxed for about 2 hours with stirring in about 500 ml of ethanol containing about 40 g of sodium hydroxide and about 40 ml of water. The solvents were removed and the residue heated at about 0.1 mm and about 200°–210° C. in a Kugelrohr. The residue was stirred with dilute hydrochloric acid and ethyl acetate on a steam bath until solution was complete. The warm solution was washed with brine, then the solvent was removed and the residue recrystallized sequentially from methanol and hexane, giving about 66 g of the desired title compound as a white solid, mp 86°–87° C.

As described hereinabove in Example 6, and hereinbelow in Example 19, the phenolic carboxylic acids listed below in Table II can be alkylated with the indicated alkyl halides to provide the ether carboxylic acids used to prepare the compounds of this invention.

TABLE II

| Phenolic Carboxylic Acid | Alkyl Halide | Ether Carboxylic Acid |
| --- | --- | --- |
| 4-hydroxyphenylacetic acid | 1-dodecyl-bromide | 4-dodecyloxyphenylacetic acid |
| 3-hydroxyphenylacetic acid | 1-tridecyl-bromide | 3-tridecyloxyphenylacetic acid |
| 2-hydroxyphenylacetic acid | 1-tetradecyl-bromide | 2-tetradecyloxyphenyl-acetic acid |
| 4-hydroxyphenylacetic acid | 1-dodecyl-bromide | 4-dodecyloxyphenylacetic acid |
| 3-(4-hydroxyphenyl)-propionic acid | 1-undecyl-bromide | 3-(4-undecyloxyphenyl)-propionic acid |
| 4-(4-hydroxyphenyl)-butanoic acid | 1-dodecyl-bromide | 4-(4-dodecyloxyphenyl)-butanoic acid |
| 3-(3-hydroxyphenyl)-propionic acid | 1-dodecyl-bromide | 3-(3-dodecyloxyphenyl)-propionic acid |

EXAMPLE 7

1-Hydroxy-3-[4-(tetradecyloxy)phenyl]-2-propanone

To a suspension of about 60.0 g of (4-tetradecyloxyphenyl)acetic acid in about 400 ml of methylene chloride containing about 0.63 ml of dimethylformamide was added, over about 10 minutes about 27.31 g of oxalyl chloride. After about 2 hours the solvent was removed, the residue was dissolved in hexane and filtered through celite. The solvent was removed and the residue dried in vacuo. An about 110.82 g portion of tris-trimethylsilyloxyethylene was added and the solution was heated at about 95° C., under argon, for about 5 hours. The solution was poured into a mixture of about 30 ml of concentrated hydrochloric acid (about 12N) about 170 ml of water and about 200 ml of tetrahydrofuran with stirring and heat. This mixture was refluxed about 10 minutes, ethyl acetate was added, the warm organic layer separated and washed with brine, saturated sodium bicarbonate solution, then brine, dried and the solvent removed, giving, after recrystallization from hexane, about 52 g of the desired title compound as a white solid, mp. 84°–85° C.

EXAMPLE 8

(2-Bromoethyl) [2-oxo-3-[4-tetradecyloxy)]phenyl]propyl phosphate

To a solution of about 45.0 g of 1-hydroxy-3-[4-(tetradecyloxy)phenyl]-2-propanone in about 600 ml of warm carbon tetrachloride was added about 36.02 g of 2-bromoethyl phosphorodichlorodate, followed by about 15.07 g of triethylamine. The mixture was stirred about 2 hours, then filtered through celite and the solvent remove. The residue was stirred in a mixture of about 600 ml of about 0.5M sodium acetate and about 600 ml of tetrhydrofuran overnight, then sodium chloride, concentrated hydrochloric acid (about 12N), and ethyl acetate were added. The organic layer was separated, washed with brine, dried and the solvent removed. The residue was chromatographed on florisil, eluting first with chloroform and then eluting the product with methanol:chloroform (1:1). The product was then dissolved in about 600 ml of hot ethanol, filtered and diluted with about 600 ml of water. The resulting solid was collected and washed with methanol, giving about 37.5 g of the desired title compound as a white solid, mp 86°–90° C. (dec.).

EXAMPLE 9

(2-Bromoethyl) [2-hydroxy-3-[4-(tetradecyloxy)phenyl]propyl]phosphate

An about 32.0 g portion of (2-bromoethyl) [2-oxo-3-[4-(tetradecyloxy)]phenyl]propyl phosphate was dissolved in about 600 ml of isopropanol by heating on a steam bath. The mixture was then stirred in a room temperature water bath as about 2.75 g of sodium borohydride were added portionwise over about 10 minutes. The mixture was then stirred at room temperature overnight, the isopropanol removed, dilute hydrochloric acid (about 1N) added and the mixture extracted with ether. The ether extract was dried and evaporated to a light yellow foam (about 18 g) which was the title compound.

EXAMPLE 10

2-[[Hydroxy[2-hydroxy-3-[4-(tetradecyloxy)phenyl]propoxy]phosphinyl]oxy]-N,N,N-trimethyl ethanaminium, hydroxide, inner salt An about 17.0 g portion of (2-bromoethyl) [2-hydroxy-3-[4-(tetradecyloxy)phenyl]propyl]phosphate was stirred in about 500 ml of mixture of chloroform:1-propanol:dimethylformamide (about 3:5:5) and about 300 ml of trimethylamine for about 5 hours at about 55°–60° C. The chloroform and 1-propanol were removed and about 4.25 g of silver carbonate and about 300 ml of ethanol were added. The mixture was then stirred for one hour, filtered through celite and the solvents removed. The residue was dissolved in a minimum amount of methanol and ether was added. The solid was collected, giving about 9.0 g of the desired title compound as a white solid, mp 225° C. (dec.).

EXAMPLE 11

4-Hydroxy-N,N,N-trimethyl-9-oxo-7-[[4-(tetradecyloxy)phenyl]methyl]-3,5,8-trioxa-4-phosphadecan-1-aminium, 4-oxide, hydroxide, inner salt A mixture of about 7.0 g of 2-[[hydroxy[2-hydroxy-3-[4-(tetradecyloxy)phenyl]propoxy]phosphinyl]oxy]-N,N,N-trimethyl ethanaminium, hydroxide, inner salt and about 28 ml of acetic anhydride was refluxed under argon for about 15 minutes. The excess anhydride was removed at reduced pressure and then the residue was chromatographed on silica gel, eluting first with chloroform:methanol (7:3), then chloroform:methanol (1:1) and finally eluting the product with chloroform:methanol (3:7). The solvent was removed at room temperature. The residue was dissolved in a small amount of tetrahydrofuran, diluted with a large volume of ether and the solid collected, giving about 5.0 g of the desired product, mp 220° C. (dec.).

EXAMPLE 12

Methyl 2-methyl-1,3-dithiolane-2-propanoate

Into a mixture of about 100 g of methyl levulinate and about 100 ml of ethanedithiol was slowly poured boron trifluoride etherate until reflux began. An about 500 ml portion of methanol was added followed by sufficient boron trifluoride etherate to make a total of about 100 ml of this reagent. The mixture was stirred overnight, the solvent removed and the residue poured into saturated sodium bi-carbonate. The mixture was extracted with ether. The ether extract was dried, the solvent removed and the residue distilled at about 97°–100° C., at about 0.55 mm, giving about 147 g of the desired title compound.

As described hereinabove in Example 12, the 1,4-keto esters methyl 4-oxo-hexanoate and methyl 4-oxo-heptanoate are converted to the 1,3-dithiolane derivatives methyl 2-methyl-1,3-dithiolane-2-butanoate and methyl 2-methyl-1,3-dithiolane-2-pentanoate respectively.

EXAMPLE 13

Dimethyl[(2-methyl-1,3-dithiolan-2-yl)methyl]propanedioate

A mixture of about 160 g of methyl 2-methyl-1,3-dithiolane-2-propanoate, about 174.63 g of dimethyl carbonate, about 74.41 g of sodium hydride and about 1000 ml of tetrahydrofuran was refluxed for about 19 hours under argon. The mixture was cooled to room temperature, added to a mixture of ice and dilute hydrochloric acid (about 1N) with stirring and saturated with sodium chloride. The organic layer was washed with saturated sodium bicarbonate then saturated sodium chloride, dried and the solvent removed. The residue was dissolved in ether, treated with charcoal, filtered through silica gel and the solvent removed. The residue was distilled via a Kugelrohr collecting the major fraction at about 180°–190° C., at about 0.5 mm giving about 96.26 g of the desired title product as a yellow oil.

EXAMPLE 14

2-[(2-Methyl-1,3-dithiolan-2-yl)methyl]-1,3-propanediol

To a solution of about 14.53 g of lithium borohydride in about 630 ml of tetrahydrofuran at about 0° C. was added about 84.0 g of dimethyl[(2-methyl-1,3-dithiolan-2-yl)methyl]propanedioate dropwise. After the exotherm ended the mixture was stirred at room temperature for about 18 hours, then about 4.15 g of lithium borohydride were added and stirring was continued for about 20 hours. The solution was cooled in an ice bath, about 400 ml of about 6N hydrochloric acid were added dropwise, the mixture was saturated with sodium chloride and then extracted with ether. The ether layer was washed with brine, then saturated sodium bicarbonate, dried and the solvent removed. Methanol was added and removed three times. The solid was recrystallized from carbon tetrachloride, giving about 56.77 g of the desired title compound, mp 72°-73° C.

EXAMPLE 15

2-Methyl-β-[(octadecyloxy)methyl]-1,3-dithiolan-2-propanol

To a suspension of about 14.92 g of washed (50%) sodium hydride in about 500 ml of dimethylformamide was added, under argon, with stirring, about 54.0 g of 2-[(2-methyl-1,3-dithiolan-2-yl)methyl]-1,3-propanediol. After about ½ hour, about 98.59 g of octadecyl iodide in about 80 ml of warm tetrahydrofuran was added (exothermic). After about 3.5 hours, water was added and the mixture was extracted with ether. The ether extract was dried, filtered through silica gel and the solvent removed. The residue was chromatographed on florisil, eluting first with hexane, then with about 10%, about 20% and finally about 30% ether in hexane to elute the product, giving about 43.5 g of the desired title compound as a waxy solid, mp 30°-31° C.

EXAMPLE 16

4-(Hydroxymethyl)-5-(octadecyloxy)-2-pentanone

To a solution of about 25.0 g of 2-methyl-β-[(octadeyloxy)methyl]-1,3-dithiolan-2-propanol in about 150 ml of tetrahydrofuran was added about 32.43 g of solid thallium trifluoroacetate. After stirring about 5 minutes, the mixture was poured into water and extracted twice with ether. The ether extracts were combined, washed with saturated sodium bicarbonate, filtered through silica gel and the solvent removed. The residue was dissolved in petroleum ether, filtered through celite and the solvent removed. The residue was purified by high performance liquid chromatography, using the system hexane:ether (about 10:1.5), giving about 7.7 g of the desired title compound as a white solid, mp 32°-33° C.

EXAMPLE 17

2-Bromoethyl 2-[(octadecyloxy)methyl]-4-oxopentyl phosphate

An about 14.3 g portion of 4-(hydroxymethyl)-5-(octadecyloxy)-2-pentanone was dissolved in about 200 ml of carbon tetrachloride, then about 19.78 g of 2-bromoethyl phosphorodichlorodate, 3-bromoethyl ester and about 8.28 g of triethyl-amine were added. After about 4 hours the mixture was filtered through celite and the solvent was removed. The residue was stirred overnight in a mixture of about 300 ml of about 0.5M sodium acetate and about 300 ml of tetrahydrofuran. The tetrahydrofuran was removed and the residue was acidified with hydrochloric acid and extracted with ether. The ether extract was dried, the solvent removed and the residue chromatographed on florisil, eluting first with chloroform and then eluting the product with chloroform:methanol (about 1:1) followed by recrystallization from methanol-water, giving about 4.4 g of the desired title compound as a white solid, mp 52°-54° C.

EXAMPLE 18

4-Hydroxy-N,N,N-trimethyl-7-(2-oxopropyl)-3,5,9-trioxa-4-phosphaheptacosan-1-aminium, 4-oxide, hydroxide, inner salt A mixture of about 3.4 g of 2-bromoethyl 2-[(octadecyloxy)methyl]-4-oxopentyl phosphate in about 100 ml of chloroform:1-propanol:dimethylformamide (about 3:5:5), containing about 64 ml of trimethylamine was stirred at about 60° C., for about 3 hours and then the solvents were removed. An about 75 ml portion of ethanol and about 75 ml of water were added, followed by about 0.82 g of silver carbonate. The mixture was stirred about 45 minutes, then filtered through celite, ethanol was added and the solvent removed. The residue was dissolved in a very small amount of chloroform and the product precipitated by the addition of ether, giving about 2.8 g of the desired product as a white solid, mp 63° C. (dec.).

By using the phosphorous reagents listed in Table VII, the amines of Table VIII and the appropriate starting materials prepared in Example 12 and those described immediately below Example 12 and by following the methods described in detail hereinabove in Examples 12–18, the compounds of this invention listed below can be prepared. These compounds can be prepared as the individual optically active R and S enantiomers or as racemic mixtures as described in the above specifications.

4-hydroxy-N,N,N-trimethyl-7-(2-oxopropyl)-3,5,9-trioxa-4-phosphaheptacosan-1-aminium, 4-oxide, hydroxide, inner salt 4-hydroxy-N,N,N-trimethyl-7-(2-oxopropyl)-3,5,9-trioxa-4-phosphapentacosan-1-aminium, 4-oxide, hydroxide, inner salt 4-hydroxy-N,N,N-trimethyl-7-(2-oxopropyl)-3,5,9-trioxa-4-phosphahexacosan-1-aminium, 4-oxide, hydroxide, inner salt 4-hydroxy-N,N,N-trimethyl-7-(2-oxopropyl)-3,5,9-trioxa-4-phosphaoctacosan-1-aminium, 4-oxide, hydroxide, inner salt 4-hydroxy-N,N,N-trimethyl-7-(2-oxopropyl)-3,5,9-trioxa-4-phosphanonacosan-1-aminium, 4-oxide, hydroxide, inner salt 4-hydroxy-N,N,N-trimethyl-7-(2-oxobutyl)-3,5,9-trioxa-4-phosphaheptacosan-1-aminium, 4-oxide, hydroxide, inner salt 4-hydroxy-N,N,N-trimethyl-7-(2-oxobutyl)-3,5,9-trioxa-4-phosphapentacosan-1-aminium, 4-oxide, hydroxide, inner salt 4-hydroxy-N,N,N-trimethyl-7-(2-oxopentyl)-3,5,9-trioxa-4-phosphaheptacosan-1-aminium, 4-oxide, hydroxide, inner salt 4-hydroxy-N,N,N-trimethyl-7-(2-oxapentyl)-3,5,9-trioxa-4-phosphapentacosan-1-aminium, 4-oxide, hydroxide, inner salt 4-hydroxy-N,N,N-trimethyl-7-(2-oxopentyl)-3,5,9-trioxa-4-phosphahexacosan-1-aminium, 4-oxide, hydroxide, inner salt 4-hydroxy-N,N-dimethyl-7-(2-oxopropyl)-3,5,9-trioxa-4-phosphaheptacosan-1-aminium, 4-oxide, hydroxide, inner salt 4-hydroxy-N,N-dimethyl-7-(2-oxopropyl)-3,5,9-trioxa-4-phosphapentacosan-1-aminium, 4-oxide, hydroxide, inner salt 4-hydroxy-N,N-dimethyl-7-(2-oxopropyl)-3,5,9-trioxa-4-phosphahexacosan-1-aminium, 4-oxide, hydroxide, inner salt 4-hydroxy-N,N-dimethyl-7-(2-oxopropyl)-3,5,9-trioxa-4-phosphaoctacosan-1-aminium, 4-oxide, hydroxide, inner salt 4-hydroxy-N,N-dimethyl-7-(2-oxopropyl)-3,5,9-trioxa-4-phosphanonacosan-1-aminium, 4-oxide, hydroxide, inner salt 4-hydroxy-N,N-dimethyl-7-(2-oxobutyl)-3,5,9-trioxa-4-phosphaheptacosan-1-aminium, 4-oxide, hydroxide, inner salt 4-hydroxy-N,N-dimethyl-7-(2-oxobutyl)-3,5,9-trioxa-4-phosphapentacosan-1-aminium, 4-oxide, hydroxide, inner salt 4-hydroxy-N,N-dimethyl-7-(2-oxopentyl)-3,5,9-trioxa-4-phosphaheptacosan-1-aminium, 4-oxide, hydroxide, inner salt 4-hydroxy-N,N-dimethyl-7-(2-oxopentyl)-3,5,9-trioxa-4-phosphapentacosan-1-aminium, 4-oxide, hydroxide, inner salt 4-hydroxy-N,N-dimethyl-7-(2-oxopentyl)-3,5,9-trioxa-4-phosphahexacosan-1-aminium, 4-oxide, hydroxide, inner salt 4-hydroxy-N-methyl-7-(2-oxopropyl)-3,5,9-trioxa-4-phosphaheptacosan-1-aminium, 4-oxide, hydroxide, inner salt 4-hydroxy-N-methyl-7-(2-oxopropyl)-3,5,9-trioxa-4-phosphapentacosan-1-aminium, 4-oxide, hydroxide, inner salt 4-hydroxy-N-methyl-7-(2-oxopropyl)-3,5,9-trioxa-4-phosphahexacosan-1-aminium, 4-oxide, hydroxide, inner salt 4-hydroxy-N-methyl-7-(2-oxopropyl)-3,5,9-trioxa-4-phosphaoctacosan-1-aminium, 4-oxide, hydroxide, inner salt 4-hydroxy-N-methyl-7-(2-oxopropyl)-3,5,9-trioxa-4-phosphanonacosan-1-aminium, 4-oxide, hydroxide, inner salt 4-hydroxy-N,N-tetramethylene-7-(2-oxopropyl)-3,5,9-trioxa-4-phosphaheptacosan-1-aminium, 4-oxide, hydroxide, inner salt 4-hydroxy-N,N-tetramethylene-7-(2-oxopropyl)-3,5,9-trioxa-4-phosphapentacosan-1-aminium, 4-oxide, hydroxide, inner salt 4-hydroxy-N,N-tetramethylene-7-(2-oxopropyl)-3,5,9-trioxa-4-phosphahexacosan-1-aminium, 4-oxide, hydroxide, inner salt 4-hydroxy-N,N-tetramethylene-7-(2-oxopropyl)-3,5,9-trioxa-4-phosphaoctacosan-1-aminium, 4-oxide, hydroxide, inner salt 4-hydroxy-N,N-tetramethylene-7-(2-oxopropyl)-3,5,9-trioxa-4-phosphanonacosan-1-aminium, 4-oxide, hydroxide, inner salt 4-hydroxy-N,N-tetramethylene-7-(2-oxopentyl)-3,5,9-trioxa-4-phosphaheptacosan-1-aminium, 4-oxide, hydroxide, inner salt 4-hydroxy-N,N-tetramethylene-7-(2-oxopentyl)-3,5,9-trioxa-4-phosphapentacosan-1-aminium, 4-oxide, hydroxide, inner salt 4-hydroxy-N,N-tetramethylene-7-(2-oxopentyl)-3,5,9-trioxa-4-phosphahexacosan-1-aminium, 4-oxide, hydroxide, inner salt 5-hydroxy-N,N,N-trimethyl-8-(2-oxopropyl)-4,6,10-trioxa-5-phosphaheptacosan-1-aminium, 5-oxide, hydroxide, inner salt 5-hydroxy-N,N,N-trimethyl-8-(2oxopropyl)-4,6,10-trioxa-5-phosphapentacosan-1-aminium, 5-oxide, hydroxide, inner salt 5-hydroxy-N,N,N-trimethyl-8-(2-oxopropyl)-4,6,10-trioxa-5-phosphahexacosan-1-aminium, 5-oxide, hydroxide, inner salt 5-hydroxy-N,N,N-trimethyl-8-(2-oxopropyl)-4,6,10-trioxa-5-phosphaoctacosan-1-aminium, 5-oxide, hydroxide, inner salt 5-hydroxy-N,N,N-trimethyl-8-(2-oxopropyl)-4,6,10-trioxa-5-phosphanonacosan-1-aminium, 5-oxide, hydroxide, inner salt 5-hydroxy-N,N,N-trimethyl-8-(2-oxobutyl)-4,6,10-trioxa-5-phosphaheptacosan-1-aminium, 5-oxide, hydroxide, inner salt 5-hydroxy-N,N,N-trimethyl-8-(2-oxobutyl)-4,6,10-trioxa-5-phosphapentacosan-1-aminium, 5-oxide, hydroxide, inner salt 5-hydroxy-N,N,N-trimethyl-8-(2-oxopentyl)-4,6,10-trioxa-5-phosphaheptacosan-1-aminium, 5-oxide, hydroxide, inner salt 5-hydroxy-N,N,N-trimethyl-8-(2-oxopentyl)-4,6,10-trioxa-5-phosphapentacosan-1-aminium, 5-oxide, hydroxide, inner salt 5-hydroxy-N,N,N-trimethyl-8-(2-oxopentyl)-4,6,10-trioxa-5-phosphahexacosan-1-aminium, 5-oxide, hydroxide, inner salt 5-hydroxy-N,N-dimethyl-8-(2-oxopropyl)-4,6,10-trioxa-5-phosphaheptacosan-1-aminium, 5-oxide, hydroxide, inner salt 5-hydroxy-N,N-dimethyl-8-(2-oxopropyl)-4,6,10-trioxa-5-phosphapentacosan-1-aminium, 5-oxide, hydroxide, inner salt 5-hydroxy-N,N-dimethyl-8-(2-oxopropyl)-4,6,10-trioxa-5-phosphahexacosan-1-aminium, 5-oxide, hydroxide, inner salt 5-hydroxy-N,N-dimethyl-8-(2-oxopropyl)-4,6,10-trioxa-5-phosphaoctacosan-1-aminium, 5-oxide, hydroxide, inner salt 5-hydroxy-N,N-dimethyl-8-(2-oxopropyl)-4,6,10-trioxa-5-phosphanonacosan-1-aminium, 5-oxide, hydroxide, inner salt 5-hydroxy-N,N-dimethyl-8-(2-oxobutyl)-4,6,10-trioxa-5-phosphaheptacosan-1-aminium, 5-oxide, hydroxide, inner salt 5-hydroxy-N,N-dimethyl-8-(2-oxobutyl)-4,6,10-trioxa-5-phosphapentacosan-1-aminium, 5-oxide, hydroxide, inner salt 5-hydroxy-N,N-dimethyl-8-(2-oxopentyl)-4,6,10-trioxa-5-phosphaheptacosan-1-aminium, 5-oxide, hydroxide, inner salt 5-hydroxy-N,N-dimethyl-8-(2-oxopentyl)-4,6,10-trioxa-5-phosphapentacosan-1-aminium, 5-oxide, hydroxide, inner salt 5-hydroxy-N,N-dimethyl-8-(2-oxopentyl)-4,6,10-5-phosphahexacosan-1-aminium, 5-oxide, hydroxide, inner salt 5-hydroxy-N-methyl-8-(2-oxopropyl)-4,6,10-trioxa-5-phosphaheptacosan-1-aminium, 5-oxide, hydroxide, inner salt 5-hydroxy-N-methyl-8-(2-oxopropyl)-4,6,10-trioxa-5-phosphapentacosan-1-aminium, 5-oxide, hydroxide, inner salt
5-hydroxy-N-methyl-8-(2-oxopropyl)-4,6,10-trioxa-5-phosphahexacosan-1-aminium, 5-oxide, hydroxide, inner salt
5-hydroxy-N-methyl-8-(2-oxopropyl)-4,6,10-trioxa-5-phosphaoctacosan-1-aminium, 5-oxide, hydroxide, inner salt
5-hydroxy-N-methyl-8-(2-oxopropyl)-4,6,10-trioxa-5-phosphanonacosan-1-aminium, 5-oxide, hydroxide, inner salt
5-hydroxy-N,N-tetramethylene-8-(2-oxopropyl)-4,6,10-trioxa-5-phosphaheptacosan-1-aminium, 5-oxide, hydroxide, inner salt
5-hydroxy-N,N-tetramethylene-8-(2-oxopropyl)-4,6,10-trioxa-5-phosphapentacosan-1-aminium, 5-oxide, hydroxide, inner salt
5-hydroxy-N,N-tetramethylene-8-(2-oxopropyl)-4,6,10-trioxa-5-phosphahexacosan-1-aminium, 5-oxide, hydroxide, inner salt
5-hydroxy-N,N-tetramethylene-8-(2-oxopropyl)-4,6,10-trioxa-5-phosphaoctacosan-1-aminium, 5-oxide, hydroxide, inner salt
5-hydroxy-N,N-tetramethylene-8-(2-oxopropyl)-4,6,10-trioxa-5-phosphanonacosan-1-aminium, 5-oxide, hydroxide, inner salt
5-hydroxy-N,N-tetramethylene-8-(2-oxopentyl)-4,6,10-trioxa-5-phosphaheptacosan-1-aminium, 5-oxide, hydroxide, inner salt
5-hydroxy-N,N-tetramethylene-8-(2-oxopentyl)-4,6,10-trioxa-5-phosphapentacosan-1-aminium, 5-oxide, hydroxide, inner salt
5-hydroxy-N,N-tetramethylene-8-(2-oxopentyl)-4,6,10-trioxa-5-phosphexacosan-1-aminium, 5-oxide, hydroxide, inner salt
6-hydroxy-N,N,N-trimethyl-9-(2-oxopropyl)-5,7,11-trioxa-6-phosphaheptacosan-1-aminium, 6-oxide, hydroxide, inner salt
6-hydroxy-N,N,N-trimethyl-9-(2-oxopropyl)-5,7,11-trioxa-6-phosphapentacosan-1-aminium, 6-oxide, hydroxide, inner salt
6-hydroxy-N,N,N-trimethyl-9-(2-oxopropyl)-5,7,11-trioxa-6-phosphahexacosan-1-aminium, 6-oxide, hydroxide, inner salt
6-hydroxy-N,N,N-trimethyl-9-(2-oxopropyl)-5,7,11-trioxa-6-phosphaoctacosan-1-aminium, 6-oxide, hydroxide, inner salt
6-hydroxy-N,N,N-trimethyl-9-(2-oxopropyl)-5,7,11-trioxa-6-phosphanonacosan-1-aminium, 6-oxide, hydroxide, inner salt
6-hydroxy-N,N,N-trimethyl-9-(2-oxobutyl)-5,7,11-trioxa-6-phosphaheptacosan-1-aminium, 6-oxide, hydroxide, inner salt
6-hydroxy-N,N,N-trimethyl-9-(2-oxobutyl)-5,7,11-trioxa-6-phosphapentacosan-1-aminium, 6-oxide, hydroxide, inner salt
6-hydroxy-N,N,N-trimethyl-9-(2-oxopentyl)-5,7,11-trioxa-6-phosphaheptacosan-1-aminium, 6-oxide, hydroxide, inner salt
6-hydroxy-N,N,N-trimethyl-9-(2-oxopentyl)-5,7,11-trioxa-6-phosphapentacosan-1-aminium, 6-oxide, hydroxide, inner salt
6-hydroxy-N,N,N-trimethyl-9-(2-oxopentyl)-5,7,11-trioxa-6-phosphahexacosan-1-aminium, 6-oxide, hydroxide, inner salt
6-hydroxy-N,N-dimethyl-9-(2-oxopropyl)-5,7,11-trioxa-6-phosphaheptacosan-1-aminium, 6-oxide, hydroxide, inner salt
6-hydroxy-N,N-dimethyl-9-(2-oxopropyl)-5,7,11-trioxa-6-phosphapentacosan-1-aminium, 6-oxide, hydroxide, inner salt
6-hydroxy-N,N-dimethyl-9-(2-oxopropyl)-5,7,11-trioxa-6-phosphahexacosan-1-aminium, 6-oxide, hydroxide, inner salt
6-hydroxy-N,N-dimethyl-9-(2-oxopropyl)-5,7,11-trioxa-6-phosphaoctacosan-1-aminium, 6-oxide, hydroxide, inner salt
6-hydroxy-N,N-dimethyl-9-(2-oxopropyl)-5,7,11-trioxa-6-phosphanonacosan-1-aminium, 6-oxide, hydroxide, inner salt
6-hydroxy-N,N-dimethyl-9-(2-oxobutyl)-5,7,11-trioxa-6-phosphaheptacosan-1-aminium, 6-hydroxide, inner salt
6-hydroxy-N,N-dimethyl-9-(2-oxobutyl)-5,7,11-trioxa-6-phosphapentacosan-1-aminium, 6-oxide, hydroxide, inner salt
6-hydroxy-N,N-dimethyl-9-(2-oxopentyl)-5,7,11-trioxa-6-phosphaheptacosan-1-aminium, 6-oxide, hydroxide, inner salt
6-hydroxy-N,N-dimethyl-9-(2-oxopentyl)-5,7,11-trioxa-6-phosphapentacosan-1-aminium, 6-oxide, hydroxide, inner salt
6-hydroxy-N,N-dimethyl-9-(2-oxopentyl)-5,7,11-trioxa-6-phosphahexacosan-1-aminium, 6-oxide, hydroxide, inner salt
6-hydroxy-N-methyl-9-(2-oxopropyl)-5,7,11-trioxa-6-phosphaheptacosan-1-aminium, 6-oxide, hydroxide, inner salt
6-hydroxy-N-methyl-9-(2-oxopropyl)-5,7,11-trioxa-6-phosphapentacosan-1-aminium, 6-oxide, hydroxide, inner salt
6-hydroxy-N-methyl-9-(2-oxopropyl)-5,7,11-trioxa-6-phosphahexacosan-1-aminium, 6-oxide, hydroxide, inner salt
6-hydroxy-N-methyl-9-(2-oxopropyl)-5,7,11-trioxa-6-phosphaoctacosan-1-aminium, 6-oxide, hydroxide, inner salt
6-hydroxy-N-methyl-9-(2-oxopropyl)-5,7,11-trioxa-6-phosphanonacosan-1-aminium, 6-oxide, hydroxide, inner salt
6-hydroxy-N,N-tetramethylene-9-(2-oxopropyl)-5,7,11-trioxa-6-phosphaheptacosan-1-aminium, 6-oxide, hydroxide, inner salt
6-hydroxy-N,N-tetramethylene-9-(2-oxopropyl)-5,7,11-trioxa-6-phosphapentacosan-1-aminium, 6-oxide, hydroxide, inner salt
6-hydroxy-N,N-tetramethylene-9-(2-oxopropyl)-5,7,11-trioxa-6-phosphahexacosan-1-aminium, 6-oxide, hydroxide, inner salt
6-hydroxy-N,N-tetramethylene-9-(2-oxopropyl)-5,7,11-trioxa-6-phosphaoctacosan-1-aminium, 6-oxide, hydroxide, inner salt
6-hydroxy-N,N-tetramethylene-9-(2-oxopropyl)-5,7,11-trioxa-6-phosphanonacosan-1-aminium, 6-oxide, hydroxide, inner salt
6-hydroxy-N,N-tetramethylene-9-(2-oxopentyl)-5,7,11-trioxa-6-phosphaheptacosan-1-aminium, 6-oxide, hydroxide, inner salt
6-hydroxy-N,N-tetramethylene-9-(2-oxopentyl)-5,7,11-trioxa-6-phosphapentacosan-1-aminium, 6-oxide, hydroxide, inner salt 6-hydroxy-N,N-tetramethylene-9-(2-oxopentyl)-5,7,11-trioxa-6-phosphahexacosan-1-aminium, 6-oxide, hydroxide, inner salt 2-[[[2-[(hexadecyloxy)methyl]-4-oxopentyl]oxy]hydroxyphosphinyl]-N,N,N-trimethyl-ethanaminium, hydroxide, inner salt 2-[[[2-[(hexadecyloxy)methyl]-4-oxopentyl]oxy]hydroxyphosphinyl]-N,N-dimethyl-ethanaminium, hydroxide, inner salt 2-[[[2-[(octadecyloxy)methyl]-4-oxopentyl]oxy]hydroxyphosphinyl]-N,N,N-trimethyl-ethanaminium, hydroxide, inner salt 2-[[[2-[(octadecyloxy)methyl]-4-oxopentyl]oxy]hydroxyphosphinyl]-N,N-dimethyl-ethanaminium, hydroxide, inner salt 2-[[[2-[(heptadecyloxy)methyl]-4-oxopentyl]oxy]hydroxyphosphinyl]-N,N,N-trimethyl-ethanaminium, hydroxide, inner salt 2-[[[2-[(heptadecyloxy)methyl]-4-oxopentyl]oxy]hydroxyphosphinyl]-N,N-dimethyl-ethanaminium, hydroxide, inner salt

EXAMPLE 19

2-(Octadecyloxy)phenylacetic acid

To a suspension of about 18.1 g of washed about 50% sodium hydride in about 350 ml of dimethylformamide was added about 114.36 g of octadecyl bromide and about 6.17 g of sodium iodide. At about 0° C. a solution of about 57 g of methyl-o-hydroxyphenyl acetate in about 350 ml of dimethylformamide was added with stirring, over about ½ hour. This mixture was stirred at room temperature for about 18 hours, then poured into dilute hydrochloric acid and the solid collected, washed twice with water and recrystallized from 2-propanol. The solid was then refluxed in a mixture of about 1000 ml of ethanol, about 50 ml of water and about 48.02 g of sodium hydroxide for about one hour. This mixture was poured into dilute hydrochloric acid and the solid was collected, washed with water and recrystallized successively from 2-propanol and ethanol, giving about 63.75 g of the desired title compound, mp 81°–82° C.

EXAMPLE 20

1-Hydroxy-3-[2-(octadecyloxy)phenyl]-2-propanone

To a solution of about 50 g of 2-(octadecyloxy)phenyl acetic acid in about 400 ml of methylene chloride was added about 19.6 g of oxalylchloride. After stirring about 3 hours the solvent was removed and the residue was dissolved in hexane and filtered through celite. The hexane was removed and to the residue was added about 79.5 g of tris-trimethylsilyloxyethylene. This mixture was stirred at about 90°–95° C. for 1.5 hours, then the oil was poured into a mixture of about 30 ml of concentrated (about 12N) hydrochloric acid, about 170 ml of water and about 200 ml of tetrahydrofuran and stirred at reflux for about ½ hour. The tetrahydrofuran was removed and the residue was extracted with ether. The ether extract was washed with dilute sodium bicarbonate, then brine and dried. The solvent was removed and the residue recrystallized from hexane, giving about 31 g of the desired title compound as a white solid, mp 59°–60° C.

EXAMPLE 21

2-Bromoethyl 3-[2-(octadecyloxy)phenyl]-2-oxopropyl phosphate

To a suspension of about 27 g of 1-hydroxy-3-[2-(octadecyloxy)phenyl]-2-propanone in about 500 ml of ether was added about 18.72 g of 2-bromoethyl phosphorodichlorodate and about 16.32 g of triethylamine. The mixture was stirred about 3 hours, then about 4.65 g of water and about 7.83 g of triethylamine were added. The mixture was refluxed about 1.5 hours, washed with dilute hydrochloric acid, then brine, dried and the solvent removed. The residue was chromatographed on florisil, eluting first with chloroform and then eluting the product with chloroform:methanol (about 1:1). The product was recrystallized by dissolving in about 250 ml of hot ether, concentrating to about 200 ml, adding about 200 ml of methanol and boiling off about 100 ml of solvent, giving about 5.73 g of the desired title compound, mp 111°–113° C.

EXAMPLE 22

2-Bromoethyl 2-hydroxy-3-[2-(octadecyloxy)phenyl]propyl phosphate

An about 5.2 g portion of 2-bromoethyl-3-[2-(octadecyloxy)phenyl]-2-oxypropyl phosphate ester was dissolved by heating to about 40° C. in a mixture of about 200 ml of 1-propanol and about 40 ml of tetrahydrofuran. To this hot, about 40° C., mixture, was added about 0.41 g of sodium borohydride. After stirring about one hour the solvent was removed and the residue mixed with dilute (about 1N) hydrochloric acid and then extracted with ether. The ether extract was dried and the solvent removed, giving about 5.1 g of the desired title compound as a colorless oil.

EXAMPLE 23

2-[[Hydroxy[2-hydroxy-3-[2-(octadecyloxy)phenyl]propoxy]phosphinyl]oxy]-N,N,N-trimethyl-ethanaminium, hydroxide, inner salt An about 5.2 g portion of 2-bromoethyl 2-hydroxy-3-[2-(octadecyloxy)phenyl]propyl phosphate in about 150 ml of chloroform:1-propanol:dimethylformamide (about 3:5:5) and about 300 ml of about 40% trimethylamine was stirred about 5 hours at about 55° C. and then about 12 hours at room temperature. About 75 ml of solvent was removed, about 1.42 g of silver carbonate was added and the mixture was stirred at about 50° C. for about one hour. This mixture was filtered through celite, ethanol was added and all the solvents were removed. The residue was dissolved in a minimum of methanol, ether was added and the precipitate collected, giving about 3.03 g of the desired title compound as a white solid, mp 211° C. (dec.).

EXAMPLE 24

4-Hydroxy-N,N,N-trimethyl-9-oxo-7-[[2-octadecyloxy)phenyl]methyl]-3,5,8-trioxa-4-phosphadecan-1-aminium, 4-oxide, hydroxide, inner salt A mixture of about 2.4 g of 2-[[hydroxy[2-hydroxy-3-[2-(octadecyloxy)phenyl]propoxy]phosphinyl]oxy]-N,N,N-trimethylethanaminium, hydroxide, inner salt, about 9.76 g of acetic anhydride, about 3.87 g of triethylamine and about 125 ml of chloroform was stirred at reflux for about 2 hours and 15 minutes. The chloroform was removed, the excess triethylamine and anhydride were removed at about 50° C. in vacuo and the residue was chromatographed on about 150 ml of silica gel eluting with chloroform:methanol (about 7:3), then about 1:1 and finally the product was eluted with about 3:7. The solvent was removed, the residue dissolved in a minimum of chloroform, filtered through glass wool, the solution diluted with about 500 ml of ether and stored at about 0° C. overnight. The solid was collected, giving about 2.1 g of the desired product as a white solid, mp 218° C. (dec.).

By using the phosphorous reagents listed in Table VII, the amines of Table VIII and the appropriate starting materials prepared in Examples 6 and 19 and those listed in Table II and by following the methods described in detail hereinabove in Examples 6–11 and 19–24, the compounds of this invention listed below can be prepared. These compounds can be prepared as the individual optically active R and S enantiomers or as racemic mixtures as described in the above specifications.

7-[[4-(tetradecyloxy)phenyl]methyl]-4-hydroxy-NNN-trimethyl-9-oxo-3,5,8-trioxa-4-phosphanonan-1-aminium, 4-oxide, hydroxide, inner salt 7-[[4-(tetradecyloxy)phenyl]methyl]-4-hydroxy-NN-dimethyl-9-oxo-3,5,8-trioxa-4-phosphanonan-1-aminium, 4-oxide, hydroxide, inner salt 7-[[4-(tetradecyloxy)phenyl]methyl]-4-hydroxy-N-methyl-9-oxo-3,5,8-trioxa-4-phosphanonan-1-aminium, 4-oxide, hydroxide, inner salt 7-[[4-(tetradecyloxy)phenyl]methyl]-4-hydroxy-NN-tetramethylene-9-oxo-3,5,8-trioxa-4-phosphanonan-1-aminium, 4-oxide, hydroxide, inner salt 7-[[3-(tridecyloxy)phenyl]methyl]-4-hydroxy-NNN-trimethyl-9-oxo-3,5,8-trioxa-4-phosphanonan-1-aminium, 4-oxide, hydroxide, inner salt 7-[[3-(tridecyloxy)phenyl]methyl]-4-hydroxy-NN-dimethyl-9-oxo-3,5,8-trioxa-4-phosphanonan-1-aminium, 4-oxide, hydroxide, inner salt 7-[[3-(tridecyloxy)phenyl]methyl]-4-hydroxy-N-methyl-9-oxo-3,5,8-trioxa-4-phosphanonan-1-aminium, 4-oxide, hydroxide, inner salt 7-[[3-(tridecyloxy)phenyl]methyl]-4-hydroxy-NN-tetramethylene-9-oxo-3,5,8-trioxa-4-phosphanonan-1-aminium, 4-oxide, hydroxide, inner salt 7-[[2-(octadecyloxy)phenyl]methyl]-4-hydroxy-NNN-trimethyl-9-oxo-3,5,8-trioxa-4-phosphanonan-1-aminium, 4-oxide, hydroxide, inner salt 7-[[2-(octadecyloxy)phenyl]methyl]-4-hydroxy-NN-dimethyl-9-oxo-3,5,8-trioxa-4-phosphanonan-1-aminium, 4-oxide, hydroxide, inner salt 7-[[2-(octadecyloxy)phenyl]methyl]-4-hydroxy-N-methyl-9-oxo-3,5,8-trioxa-4-phosphanonan-1-aminium, 4-oxide, hydroxide, inner salt 7-[[2-(octadecyloxy)phenyl]methyl]-4-hydroxy-NN-tetramethylene-9-oxo-3,5,8-trioxa-4-phosphanonan-1-aminium, 4-oxide, hydroxide, inner salt 7-[[2-(tetradecyloxy)phenyl]methyl]-4-hydroxy-NNN-trimethyl-9-oxo-3,5,8-trioxa-4-phosphanonan-1-aminium, 4-oxide, hydroxide, inner salt 7-[[2-(tetradecyloxy)phenyl]methyl]-4-hydroxy-NN-dimethyl-9-oxo-3,5,8-trioxa-4-phosphanonan-1-aminium, 4-oxide, hydroxide, inner salt 7-[[2-(tetradecyloxy)phenyl]methyl]-4-hydroxy-N-methyl-9-oxo-3,5,8-trioxa-4-phosphanonan-1-aminium, 4-oxide, hydroxide, inner salt 7-[[2-(tetradecyloxy)phenyl]methyl]-4-hydroxy-NN-tetramethylene-9-oxo-3,5,8-trioxa-4-phosphanonan-1-aminium, 4-oxide, hydroxide, inner salt 7-[[4-(dodecyloxy)phenyl]methyl]-4-hydroxy-NNN-trimethyl-9-oxo-3,5,8-trioxa-4-phosphanonan-1-aminium, 4-oxide, hydroxide, inner salt 7-[[4-(dodecyloxy)phenyl]methyl]-4-hydroxy-NN-dimethyl-9-oxo-3,5,8-trioxa-4-phosphanonan-1-aminium, 4-oxide, hydroxide, inner salt 7-[[4-(dodecyloxy)phenyl]methyl]-4-hydroxy-N-methyl-9-oxo-3,5,8-trioxa-4-phosphanonan-1-aminium, 4-oxide, hydroxide, inner salt 7-[[4-(dodecyloxy)phenyl]methyl]-4-hydroxy-NN-tetramethylene-9-oxo-3,5,8-trioxa-4-phosphanonan-1-aminium, 4-oxide, hydroxide, inner salt 7-[2-[4-(undecyloxy)phenyl]ethyl]-4-hydroxy-NNN-trimethyl-9-oxo-3,5,8-trioxa-4-phosphanonan-1-aminium, 4-oxide, hydroxide, inner salt 7-[2-[4-(undecyloxy)phenyl]ethyl]-4-hydroxy-NN-dimethyl-9-oxo-3,5,8-trioxa-4-phosphanonan-1-aminium, 4-oxide, hydroxide, inner salt 7-[2-[4-(undecyloxy)phenyl]ethyl]-4-hydroxy-N-methyl-9-oxo-3,5,8-trioxa-4-phosphanonan-1-aminium, 4-oxide, hydroxide, inner salt 7-[2-[4-(undecyloxy)phenyl]ethyl]-4-hydroxy-NN-tetramethylene-9-oxo-3,5,8-trioxa-4-phosphanonan-1-aminium, 4-oxide, hydroxide, inner salt 7-[3-[4-(dodecyloxy)phenyl]propyl]-4-hydroxy-NNN-trimethyl-9-oxo-3,5,8-trioxa-4-phosphanonan-1-aminium, 4-oxide, hydroxide, inner salt 7-[3-[4-(dodecyloxy)phenyl]propyl]-4-hydroxy-NN-dimethyl-9-oxo-3,5,8-trioxa-4-phosphanonan-1-aminium, 4-oxide, hydroxide, inner salt 7-[3-[4-(dodecyloxy)phenyl]propyl]-4-hydroxy-N-methyl-9-oxo-3,5,8-trioxa-4-phosphanonan-1-aminium, 4-oxide, hydroxide, inner salt 7-[3-[4-(dodecyloxy)phenyl]propyl]-4-hydroxy-NN-tetramethylene-9-oxo-3,5,8-trioxa-4-phosphanonan-1-aminium, 4-oxide, hydroxide, inner salt 7-[2-[3-(dodecyloxy)phenyl]ethyl]4-hydroxy-NNN-trimethyl-9-oxo-3,5,8-trioxa-4-phosphanonan-1-aminium, 4-oxide, hydroxide, inner salt 7-[2-[3-(dodecyloxy)phenyl]ethyl]-4-hydroxy-NN-dimethyl-9-oxo-3,5,8-trioxa-4-phosphanonan-1-aminium, 4-oxide, hydroxide, inner salt 7-[2-[3-(dodecyloxy)phenyl]ethyl]-4-hydroxy-N-methyl-9-oxo-3,5,8-trioxa-4-phosphanonan-1-aminium, 4-oxide, hydroxide, inner salt 7-[2-[3-(dodecyloxy)phenyl]ethyl]-4-hydroxy-NN-tetramethylene-9-oxo-3,5,8-trioxa-4-phosphanonan-1-aminium, 4-oxide, hydroxide, inner salt 7-[[4-(tetradecyloxy)phenyl]methyl]-4-hydroxy-NNN-trimethyl-9-oxo-3,5,8-trioxa-4-phosphadecan-1-aminium, 4-oxide, hydroxide, inner salt 7-[[4-(tetradecyloxy)phenyl]methyl]-4-hydroxy-NN-dimethyl-9-oxo-3,5,8-trioxa-4-phosphadecan-1-aminium, 4-oxide, hydroxide, inner salt 7-[[4-(tetradecyloxy)phenyl]methyl]-4-hydroxy-N-methyl-9-oxo-3,5,8-trioxa-4-phosphadecan-1-aminium, 4-oxide, hydroxide, inner salt 7-[[4-(tetradecyloxy)phenyl]methyl]-4-hydroxy-NN-tetramethylene-9-oxo-3,5,8-trioxa-4-phosphadecan-1-aminium, 4-oxide, hydroxide, inner salt 7-[[3-(tridecyloxy)phenyl]methyl]-4-hydroxy-NNN-trimethyl-9-oxo-3,5,8-trioxa-4-phosphadecan-1-aminium, 4-oxide, hydroxide, inner salt 7-[[3-(tridecyloxy)phenyl]methyl]-4-hydroxy-NN-dimethyl-9-oxo-3,5,8-trioxa-4-phosphadecan-1-aminium, 4-oxide, hydroxide, inner salt 7-[[3-(tridecyloxy)phenyl]methyl]-4-hydroxy-N-methyl-9-oxo-3,5,8-trioxa-4-phosphadecan-1-aminium, 4-oxide, hydroxide, inner salt 7-[[3-(tridecyloxy)phenyl]methyl]-4-hydroxy-NN-tetramethylene-9-oxo-3,5,8-trioxa-4-phosphadecan-1-aminium, 4-oxide, hydroxide, inner salt 7-[[2-(octadecyloxy)phenyl]methyl]-4-hydroxy-NNN-trimethyl-9-oxo-3,5,8-trioxa-4-phosphadecan-1-aminium, 4-oxide, hydroxide, inner salt 7-[[2-(octadecyloxy)phenyl]methyl]-4-hydroxy-NN-dimethyl-9-oxo-3,5,8-trioxa-4-phosphadecan-1-aminium, 4-oxide, hydroxide, inner salt 7-[[2-(octadecyloxy)phenyl]methyl]-4-hydroxy-N-methyl-9-oxo-3,5,8-trioxa-4-phosphadecan-1-aminium, 4-oxide, hydroxide, inner salt 7-[[2-(octadecyloxy)phenyl]methyl]-4-hydroxy-NN-tetramethylene-9-oxo-3,5,8-trioxa-4-phosphadecan-1-aminium, 4-oxide, hydroxide, inner salt 7-[[2-(tetradecyloxy)phenyl]methyl]-4-hydroxy-NNN-trimethyl-9-oxo-3,5,8-trioxa-4-phosphadecan-1-aminium, 4-oxide, hydroxide, inner salt 7-[[2-(tetradecyloxy)phenyl]methyl]-4-hydroxy-NN-dimethyl-9-oxo-3,5,8-trioxa-4-phosphadecan-1-aminium, 4-oxide, hydroxide, inner salt 7-[[2-(tetradecyloxy)phenyl]methyl]-4-hydroxy-N-methyl-9-oxo-3,5,8-trioxa-4-phosphadecan-1-aminium, 4-oxide, hydroxide, inner salt 7-[[2-(tetradecyloxy)phenyl]methyl]-4-hydroxy-NN-tetramethylene-9-oxo-3,5,8-trioxa-4-phosphadecan-1-aminium, 4-oxide, hydroxide, inner salt 7-[[4-(dodecyloxy)phenyl]methyl]-4-hydroxy-NNN-trimethyl-9-oxo-3,5,8-trioxa-4-phosphadecan-1-aminium, 4-oxide, hydroxide, inner salt 7-[[4-(dodecyloxy)phenyl]methyl]-4-hydroxy-NN-dimethyl-9-oxo-3,5,8-trioxa-4-phosphadecan-1-aminium, 4-oxide, hydroxide, inner salt 7-[[4-(dodecyloxy)phenyl]methyl]-4-hydroxy-N-methyl-9-oxo-3,5,8-trioxa-4-phosphadecan-1-aminium, 4-oxide, hydroxide, inner salt 7-[[4-(dodecyloxy)methyl]-4-hydroxy-NN-tetramethylene-9-oxo-3,5,8-trioxa-4-phosphadecan-1-aminium, 4-oxide, hydroxide, inner salt 7-[2-[4-(undecyloxy)phenyl]ethyl]-4-hydroxy-NNN-trimethyl-9-oxo-3,5,8-trioxa-4-phosphadecan-1-aminium, 4-oxide, hydroxide, inner salt 7-[2-[4-(undecyloxy)phenyl]ethyl]-4-hydroxy-NN-dimethyl-9-oxo-3,5,8-trioxa-4-phosphadecan-1-aminium, 4-oxide, hydroxide, inner salt 7-[2-[4-(undecyloxy)phenyl]ethyl]-4-hydroxy-N-methyl-9-oxo-3,5,8-trioxa-4-phosphadecan-1-aminium, 4-oxide, hydroxide, inner salt 7-[2-[4-(undecyloxy)phenyl]ethyl]-4-hydroxy-NN-tetramethylene-9-oxo-3,5,8-trioxa-4-phosphadecan-1-aminium, 4-oxide, hydroxide, inner salt 7-[3-[4-(dodecyloxy)phenyl]propyl]-4-hydroxy-NNN-trimethyl-9-oxo-3,5,8-trioxa-4-phosphadecan-1-aminium, 4-oxide, hydroxide, inner salt 7-[3-[4-(dodecyloxy)phenyl]propyl]-4-hydroxy-NN-dimethyl-9-oxo-3,5,8-trioxa-4-phosphadecan-1-aminium, 4-oxide, hydroxide, inner salt 7-[3-[4-(dodecyloxy)phenyl]propyl]-4-hydroxy-N-methyl-9-oxo-3,5,8-trioxa-4-phosphadecan-1-aminium, 4-oxide, hydroxide, inner salt 7-[3-[4-dodecyloxy)phenyl]propyl]-4-hydroxy-NN-tetramethylene-9-oxo-3,5,8-trioxa-4-phosphadecan-1-aminium, 4-oxide, hydroxide, inner salt 7-[2-[3-dodecyloxy)phenyl]ethyl]-4-hydroxy-NNN-trimethyl-9-oxo-3,5,8-trioxa-4-phosphadecan-1-aminium, 4-oxide, hydroxide, inner salt 7-[2-[3-(dodecyloxy)phenyl]ethyl]-4-hydroxy-NN-dimethyl-9-oxo-3,5,8-trioxa-4-phosphadecan-1-aminium, 4-oxide, hydroxide, inner salt 7-[2-[3-(dodecyloxy)phenyl]ethyl]-4-hydroxy-N-methyl-9-oxo-3,5,8-trioxa-4-phosphadecan-1-aminium, 4-oxide, hydroxide, inner salt 7-[2-[3-(dodecyloxy)phenyl]ethyl]-4-hydroxy-NN-tetramethylene-9-oxo-3,5,8-trioxa-4-phosphadecan-1-aminium, 4-oxide, hydroxide, inner salt 7-[[4-(tetradecyloxy)phenyl]methyl]-4-hydroxy-NNN-trimethyl-9-oxo-3,5,8-trioxa-4-phosphaundecan-1-aminium, 4-oxide, hydroxide, inner salt 7-[[4-(tetradecyloxy)phenyl]methyl]-4-hydroxy-NN-dimethyl-9-oxo-3,5,8-trioxa-4-phosphaundecan-1-aminium, 4-oxide, hydroxide, inner salt 7-[[4-(tetradecyloxy)phenyl]methyl]-4-hydroxy-N-methyl-9-oxo-3,5,8-trioxa-4-phosphaundecan-1-aminium, 4-oxide, hydroxide, inner salt 7-[[4-(tetradecyloxy)phenyl]methyl]-4-hydroxy-NN-tetramethylene-9-oxo-3,5,8-trioxa-4-phosphaundecan-1-aminium, 4-oxide, hydroxide, inner salt 7-[[3-(tridecyloxy)phenyl]methyl]-4-hydroxy-NNN-trimethyl-9-oxo-3,5,8-trioxa-4-phosphaundecan-1-aminium, 4-oxide, hydroxide, inner salt 7-[[3-(tridecyloxy)phenyl]methyl]-4-hydroxy-NN-dimethyl-9-oxo-3,5,8-trioxa-4-phosphaundecan-1-aminium, 4-oxide, hydroxide, inner salt 7-[[3-(tridecyloxy)phenyl]methyl]-4-hydroxy-N-methyl-9-oxo-3,5,8-trioxa-4-phosphaundecan-1-aminium, 4-oxide, hydroxide, inner salt 7-[[3-(tridecyloxy)phenyl]methyl]-4-hydroxy-NN-tetramethylene-9-oxo-3,5,8-trioxa-4-phosphaundecan-1-aminium, 4-oxide, hydroxide, inner salt 7-[[2-(octadecyloxy)phenyl]methyl]-4-hydroxy-NNN-trimethyl-9-oxo-3,5,8-trioxa-4-phosphaundecan-1-aminium, 4-oxide, hydroxide, inner salt 7-[[2-(octadecyloxy)phenyl]methyl]-4-hydroxy-NN-dimethyl-9-oxo-3,5,8-trioxa-4-phosphaundecan-1-aminium, 4-oxide, hydroxide, inner salt 7-[[2-(octadecyloxy)phenyl]methyl]-4-hydroxy-N-methyl-9-oxo-3,5,8-trioxa-4-phosphaundecan-1-aminium, 4-oxide, hydroxide, inner salt 7-[[2-(octadecyloxy)phenyl]methyl]-4-hydroxy-NN-tetramethylene-9-oxo-3,5,8-trioxa-4-phosphaundecan-1-aminium, 4-oxide, hydroxide, inner salt 7-[[2-(tetradecyloxy)phenyl]methyl]-4-hydroxy-NNN-trimethyl-9-oxo-3,5,8-trioxa-4-phosphaundecan-1-aminium, 4-oxide, hydroxide, inner salt 7-[[2-(tetradecyloxy)phenyl]methyl]-4-hydroxy-NN-dimethyl-9-oxo-3,5,8-trioxa-4-phosphaundecan-1-aminium, 4-oxide, hydroxide, inner salt 7-[[2-(tetradecyloxy)phenyl]methyl]-4-hydroxy-N-methyl-9-oxo-3,5,8-trioxa-4-phosphaundecan-1-aminium, 4-oxide, hydroxide, inner salt 7-[[2-(tetradecyloxy)phenyl]methyl]-4-hydroxy-NN-tetramethylene-9-oxo-3,5,8-trioxa-4-phosphaundecan-1-aminium, 4-oxide, hydroxide, inner salt 7-[[4-(dodecyloxy)phenyl]methyl]-4-hydroxy-NNN-trimethyl-9-oxo-3,5,8-trioxa-4-phosphaundecan-1-aminium, 4-oxide, hydroxide, inner salt 7-[[4-(dodecyloxy)phenyl]methyl]-4-hydroxy-NN-dimethyl-9-oxo-3,5,8-trioxa-4-phosphaundecan-1-aminium, 4-oxide, hydroxide, inner salt 7-[[4-(dodecyloxy)phenyl]methyl]-4-hydroxy-N-methyl-9-oxo-3,5,8-trioxa-4-phosphaundecan-1-aminium, 4-oxide, hydroxide, inner salt 7-[[4-(dodecyloxy)phenyl]methyl]-4-hydroxy-NN-tetramethylene-9-oxo-3,5,8-trioxa-4-phosphaundecan-1-aminium, 4-oxide, hydroxide, inner salt 7-[2-[4-(undecyloxy)phenyl]ethyl]-4-hydroxy-NNN-trimethyl-9-oxo-3,5,8-trioxa-4-phosphaundecan-1-aminium, 4-oxide, hydroxide, inner salt 7-[2-[4-(undecyloxy)phenyl]ethyl]-4-hydroxy-NN-dimethyl-9-oxo-3,5,8-trioxa-4-phosphaundecan-1-aminium, 4-oxide, hydroxide, inner salt 7-[2-[4-(undecyloxy)phenyl]ethyl]-4-hydroxy-N-methyl-9-oxo-3,5,8-trioxa-4-phosphaundecan-1-aminium, 4-oxide, hydroxide, inner salt 7-[2-[4-(undecyloxy)phenyl]ethyl]-4-hydroxy-NN-tetramethylene-9-oxo-3,5,8-trioxa-4-phosphaundecan-1-aminium, 4-oxide, hydroxide, inner salt 7-[3-[4-(dodecyloxy)phenyl]propyl]-4-hydroxy-NNN-trimethyl-9-oxo-3,5,8-trioxa-4-phosphaundecan-1-aminium, 4-oxide, hydroxide, inner salt p0 7-[3-[4-(dodecyloxy)phenyl]propyl]-4-hydroxy-NN-dimethyl-9-oxo-3,5,8-trioxa-4-phosphaundecan-1-aminium, 4-oxide, hydroxide, inner salt 7-[3-[4-(dodecyloxy)phenyl]propyl]-4-hydroxy-N-methyl-9-oxo-3,5,8-trioxa-4-phosphaundecan-1aminium, 4-oxide, hydroxide, inner salt 7-[3-[4-(dodecyloxy)phenyl]propyl]-4-hydroxy-NN-tetramethylene-9-oxo-3,5,8-trioxa-4-phosphaundecan-1-aminium, 4-oxide, hydroxide, inner salt 7-[2-[3-(dodecyloxy)phenyl]ethyl]-4-hydroxy-NNN-trimethyl-9-oxo-3,5,8-trioxa-4-phosphaundecan-1-aminium, 4-oxide, hydroxide, inner salt 7-[2-[3-(dodecyloxy)phenyl]ethyl]-4-hydroxy-NN-dimethyl-9-oxo-3,5,8-trioxa-4-phosphaundecan-1-aminium, 4-oxide, hydroxide, inner salt 7-[2-[3-(dodecyloxy)phenyl]ethyl]-4-hydroxy-N-methyl-9-oxo-3,5,8-trioxa-4-phosphaundecan-1-aminium, 4-oxide, hydroxide, inner salt 7-[2-[3-(dodecyloxy)phenyl]ethyl]-4-hydroxy-NN-tetramethylene-9-oxo-3,5,8-trioxa-4-phosphaundecan-1-aminium, 4-oxide, hydroxide, inner salt 7-[[4-(tetradecyloxy)phenyl]methyl]-4-hydroxy-NNN-trimethyl-9-oxo-3,5,8-trioxa-4-phosphadodecan-1-aminium, 4-oxide, hydroxide, inner salt 7-[[4-(tetradecyloxy)phenyl]methyl]-4-hydroxy-NN-dimethyl-9-oxo-3,5,8-trioxa-4-phosphadodecan-1-aminium, 4-oxide, hydroxide, inner salt 7-[[4-(tetradecyloxy)phenyl]methyl]-4-hydroxy-N-methyl-9-oxo-3,5,8-trioxa-4-phosphadodecan-1-aminium, 4-oxide, hydroxide, inner salt p0 7-[[4-(tetradecyloxy)phenyl]methyl]-4-hydroxy-NN-tetramethylene-9-oxo-3,5,8-trioxa-4-phosphadodecan-1-aminium, 4-oxide, hydroxide, inner salt 7-[[3-(tridecyloxy)phenyl]methyl]-4-hydroxy-NNN-trimethyl-9-oxo-3,5,8-trioxa-4-phosphadodecan-1-aminium, 4-oxide, hydroxide, inner salt 7-[[3-(tridecyloxy)phenyl]methyl]-4-hydroxy-NN-dimethyl-9-oxo-3,5,8-trioxa-4-phosphadodecan-1-aminium, 4-oxide, hydroxide, inner salt 7-[[3-(tridecyloxy)phenyl]methyl]-4-hydroxy-N-methyl-9-oxo-3,5,8-trioxa-4-phosphadodecan-1-aminium, 4-oxide, hydroxide, inner salt 7-[[3-(tridecyloxy)phenyl]methyl]-4-hydroxy-NN-tetramethylene-9-oxo-3,5,8-trioxa-4-phosphadodecan-1-aminium, 4-oxide, hydroxide, inner salt 7-[[2-(octadecyloxy)phenyl]methyl]-4-hydroxy-NNN-trimethyl-9-oxo-3,5,8-trioxa-4-phosphadodecan-1-aminium, 4-oxide, hydroxide, inner salt 7-[[2-(octadecyloxy)phenyl]methyl]-4-hydroxy-NN-dimethyl-9-oxo-3,5,8-trioxa-4-phosphadodecan-1-aminium, 4-oxide, hydroxide, inner salt 7-[[2-(octadecyloxy)phenyl]methyl]-4-hydroxy-N-methyl-9-oxo-3,5,8-trioxa-4-phosphadodecan-1-aminium, 4-oxide, hydroxide, inner salt 7-[[2-(octadecyloxy)phenyl]methyl]-4-hydroxy-NN-tetramethylene-9-oxo-3,5,8-trioxa-4-phosphadodecan-1-aminium, 4-oxide, hydroxide, inner salt 7-[[2-(tetradecyloxy)phenyl]methyl]-4-hydroxy-NNN-trimethyl-9-oxo-3,5,8-trioxa-4-phosphadodecan-1-aminium, 4-oxide, hydroxide, inner salt 7-[[2-(tetradecyloxy)phenyl]methyl]-4-hydroxy-NN-dimethyl-9-oxo-3,5,8-trioxa-4-phosphadodecan-1-aminium, 4-oxide, hydroxide, inner salt 7-[[2-(tetradecyloxy)phenyl]methyl]-4-hydroxy-N-methyl-9-oxo-3,5,8-trioxa-4-phosphadodecan-1-aminium, 4-oxide, hydroxide, inner salt 7-[[2-(tetradecyloxy)phenyl]methyl]-4-hydroxy-NN-tetramethylene-9-oxo-3,5,8-trioxa-4-phosphadodecan-1-aminium, 4-oxide, hydroxide, inner salt 7-[[4-(dodecyloxy)phenyl]methyl]-4-hydroxy-NNN-trimethyl-9-oxo-3,5,8-trioxa-4-phosphadodecan-1-aminium, 4-oxide, hydroxide, inner salt 7-[[4-(dodecyloxy)phenyl]methyl]-4-hydroxy-NN-dimethyl-9-oxo-3,5,8-trioxa-4-phosphadodecan-1-aminium, 4-oxide, hydroxide, inner salt 7-[[4-(dodecyloxy)phenyl]methyl]-4-hydroxy-N-methyl-9-oxo-3,5,8-trioxa-4-phosphadodecan-1-aminium, 4-oxide, hydroxide, inner salt 7-[[4-(dodecyloxy)phenyl]methyl]-4-hydroxy-NN-tetramethylene-9-oxo-3,5,8-trioxa-4-phosphadodecan-1-aminium, 4-oxide, hydroxide, inner salt 7-[2-[4-(undecyloxy)phenyl]ethyl]-4-hydroxy-NNN-trimethyl-9-oxo-3,5,8-trioxa-4-phosphadodecan-1-aminium, 4-oxide, hydroxide, inner salt 7-[2-[4-(undecyloxy)phenyl]ethyl]-4-hydroxy-NN-dimethyl-9-oxo-3,5,8-trioxa-4-phosphadodecan-1-aminium, 4-oxide, hydroxide, inner salt 7-[2-[4-(undecyloxy)phenyl]ethyl]-4-hydroxy-N-methyl-9-oxo-3,5,8-trioxa-4-phosphadodecan-1-aminium, 4-oxide, hydroxide, inner salt 7-[2-[4-(undecyloxy)phenyl]ethyl]-4-hydroxy-NN-tetramethylene-9-oxo-3,5,8-trioxa-4-phosphadodecan-1-aminium, 4-oxide, hydroxide, inner salt 7-[3-[4-(dodecyloxy)phenyl]propyl]-4-hydroxy-NNN-trimethyl-9-oxo-3,5,8-trioxa-4-phosphadodecan-1-aminium, 4-oxide, hydroxide, inner salt 7-[3-[4-(dodecyloxy)phenyl]propyl]-4-hydroxy-NN-dimethyl-9-oxo-3,5,8-trioxa-4-phosphadodecan-1-aminium, 4-oxide, hydroxide, inner salt 7-[3-[4-(dodecyloxy)phenyl]propyl]-4-hydroxy-N-methyl-9-oxo-3,5,8-trioxa-4-phosphadodecan-1-aminium, 4-oxide, hydroxide, inner salt 7-[3-[4-dodecyloxy)phenyl]propyl]-4-hydroxy-NN-tetramethylene-9-oxo-3,5,8-trioxa-4-phosphadodecan-1-aminium, 4-oxide, hydroxide, inner salt 7-[2-[3-dodecyloxy)phenyl]ethyl]-4-hydroxy-NNN-trimethyl-9-oxo-3,5,8-trioxa-4-phosphadodecan-1-aminium, 4-oxide, hydroxide, inner salt 7-[2-[3-(dodecyloxy)phenyl]ethyl]-4-hydroxy-NN-dimethyl-9-oxo-3,5,8-trioxa-4-phosphadodecan-1-aminium, 4-oxide, hydroxide, inner salt 7-[2-[3-(dodecyloxy)phenyl]ethyl]-4-hydroxy-N-methyl-9-oxo-3,5,8-trioxa-4-phosphadodecan-1-aminium, 4-oxide, hydroxide, inner salt 7-[2-[3-(dodecyloxy)phenyl]ethyl]-4-hydroxy-NN-tetramethylene-9-oxo-3,5,8-trioxa-4-phosphadodecan-1-aminium, 4-oxide, hydroxide, inner salt 8-[[4-(tetradecyloxy)phenyl]methyl]-5-hydroxy-NNN-trimethyl-10-oxo-4,6,9-trioxa-5-phosphadecan-1-aminium, 5-oxide, hydroxide, inner salt 8-[[4-(tetradecyloxy)phenyl]methyl]-5-hydroxy-NN-dimethyl-10-oxo-4,6,9-trioxa-5-phosphadecan-1-aminium, 5-oxide, hydroxide, inner salt 8-[[4-(tetradecyloxy)phenyl]methyl]-5-hydroxy-N-methyl-10-oxo-4,6,9-trioxa-5-phosphadecan-1-aminium, 5-oxide, hydroxide, inner salt 8-[[4-(tetradecyloxy)phenyl]methyl]-5-hydroxy-NN-tetramethylene-10-oxo-4,6,9-trioxa-5-phosphadecan-1-aminium, 5-oxide, hydroxide, inner salt 8-[[3-(tridecyloxy)phenyl]methyl]-5-hydroxy-NNN-trimethyl-10-oxo-4,6,9-trioxa-5-phosphadecan-1-aminium, 5-oxide, hydroxide, inner salt 8-[[3-(tridecyloxy)phenyl]methyl]-5-hydroxy-NN-dimethyl-10-oxo-4,6,9-trioxa-5-phosphadecan-1-aminium, 5-oxide, hydroxide, inner salt 8-[[3-(tridecyloxy)phenyl]methyl]-5-hydroxy-N-methyl-10-oxo-4,6,9-trioxa-5-phosphadecan-1-aminium, 5-oxide, hydroxide, inner salt 8-[[3-(tridecyloxy)phenyl]methyl]-5-hydroxy-NN-tetramethylene-10-oxo-4,6,9-trioxa-5-phosphadecan-1-aminium, 5-oxide, hydroxide, inner salt 8-[[2-(octadecyloxy)phenyl]methyl]-5-hydroxy-NNN-trimethyl-10-oxo-4,6,9-trioxa-5-phosphadecan-1-aminium, 5-oxide, hydroxide, inner salt 8-[[2-(octadecyloxy)phenyl]methyl]-5-hydroxy-NN-dimethyl-10-oxo-4,6,9-trioxa-5-phosphadecan-1-aminium, 5-oxide, hydroxide, inner salt 8-[[2-(octadecyloxy)phenyl]methyl]-5-hydroxy-N-methyl-10-oxo-4,6,9-trioxa-5-phosphadecan-1-aminium, 5-oxide, hydroxide, inner salt 8-[[2-(octadecyloxy)phenyl]methyl]-5-hydroxy-NN-tetramethylene-10-oxo-4,6,9-trioxa-5-phosphadecan-1-aminium, 5-oxide, hydroxide, inner salt 8-[[2-(tetradecyloxy)phenyl]methyl]-5-hydroxy-NNN-trimethyl-10-oxo-4,6,9-trioxa-5-phosphadecan-1-aminium, 5-oxide, hydroxide, inner salt 8-[[2-(tetradecyloxy)phenyl]methyl]-5-hydroxy-NN-dimethyl-10-oxo-4,6,9-trioxa-5-phosphadecan-1-aminium, 5-oxide, hydroxide, inner salt 8-[[2-(tetradecyloxy)phenyl]methyl]-5-hydroxy-N-methyl-10-oxo-4,6,9-trioxa-5-phosphadecan-1-aminium, 5-oxide, hydroxide, inner salt 8-[[2-(tetradecyloxy)phenyl]methyl]-5-hydroxy-NN-tetramethylene-10-oxo-4,6,9-trioxa-5-phosphadecan-1-aminium, 5-oxide, hydroxide, inner salt 8-[[4-(dodecyloxy)phenyl]methyl]-5-hydroxy-NNN-trimethyl-10-oxo-4,6,9-trioxa-5-phosphadecan-1-aminium, 5-oxide, hydroxide, inner salt 8-[[4-(dodecyloxy)phenyl]methyl]-5-hydroxy-NN-dimethyl-10-oxo-4,6,9-trioxa-5-phosphadecan-1-aminium, 5-oxide, hydroxide, inner salt 8-[[4-(dodecyloxy)phenyl]methyl]-5-hydroxy-N-methyl-10-oxo-4,6,9-trioxa-5-phosphadecan-1-aminium, 5-oxide, hydroxide, inner salt 8-[[4-(dodecyloxy)phenyl]methyl]-5-hydroxy-NN-tetramethylene-10-oxo-4,6,9-trioxa-5-phosphadecan-1-aminium, 5-oxide, hydroxide, inner salt 8-[[4-(tetradecyloxy)phenyl]methyl]-5-hydroxy-NNN-trimethyl-10-oxo-4,6,9-trioxa-5-phosphaundecan-1-aminium, 5-oxide, hydroxide, inner salt 8-[[4-(tetradecyloxy)phenyl]methyl]-5-hydroxy-NN-dimethyl-10-oxo-4,6,9-trioxa-5-phosphaundecan-1-aminium, 5-oxide, hydroxide, inner salt 8-[[4-(tetradecyloxy)phenyl]methyl]-5-hydroxy-N-methyl-10-oxo-4,6,9-trioxa-5-phosphaundecan-1-aminium, 5-oxide, hydroxide, inner salt 8-[[4-(tetradecyloxy)phenyl]methyl]-5-hydroxy-NN-tetramethylene-10-oxo-4,6,9-trioxa-5-phosphaundecan-1-aminium, 5-oxide, hydroxide, inner salt 8-[[3-(tridecyloxy)phenyl]methyl]-5-hydroxy-NNN-trimethyl-10-oxo-4,6,9-trioxa-5-phosphaundecan-1-aminium, 5-oxide, hydroxide, inner salt 8-[[3-(tridecyloxy)phenyl]methyl]-5-hydroxy-NN-dimethyl-10-oxo-4,6,9-trioxa-5-phosphaundecan-1-aminium, 5-oxide, hydroxide, inner salt 8-[[3-(tridecyloxy)phenyl]methyl]-5-hydroxy-N-methyl-10-oxo-4,6,9-trioxa-5-phosphaundecan-1-aminium, 5-oxide, hydroxide, inner salt 8-[[3-(tridecyloxy)phenyl]methyl]-5-hydroxy-NN-tetramethylene-10-oxo-4,6,9-trioxa-5-phosphaundecan-1-aminium, 5-oxide, hydroxide, inner salt 8-[[2-(octadecyloxy)phenyl]methyl]-5-hydroxy-NNN-trimethyl-10-oxo-4,6,9-trioxa-5-phosphaundecan-1-aminium, 5-oxide, hydroxide, inner salt 8-[[2-(octadecyloxy)phenyl]methyl]-5-hydroxy-NN-dimethyl-10-oxo-4,6,9-trioxa-5-phosphaundecan-1-aminium, 5-oxide, hydroxide, inner salt 8-[[2-(octadecyloxy)phenyl]methyl]-5-hydroxy-N-methyl-10-oxo-4,6,9-trioxa-5-phosphaundecan-1-aminium, 5-oxide, hydroxide, inner salt 8-[[2-(octadecyloxy)phenyl]methyl]-5-hydroxy-NN-tetramethylene-10-oxo-4,6,9-trioxa-5-phosphaundecan-1-aminium, 5-oxide, hydroxide, inner salt 8-[[2-(tetradecyloxy)phenyl]methyl]-5-hydroxy-NNN-trimethyl-10-oxo-4,6,9-trioxa-5-phosphaundecan-1-aminium, 5-oxide, hydroxide, inner salt 8-[[2-(tetradecyloxy)phenyl]methyl]-5-hydroxy-NN-dimethyl-10-oxo-4,6,9-trioxa-5-phosphaundecan-1-aminium, 5-oxide, hydroxide, inner salt 8-[[2-(tetradecyloxy)phenyl]methyl]-5-hydroxy-N-methyl-10-oxo-4,6,9-trioxa-5-phosphaundecan-1-aminium, 5-oxide, hydroxide, inner salt 8-[[2-(tetradecyloxy)phenyl]methyl]-5-hydroxy-NN-tetramethylene-10-oxo-4,6,9-trioxa-5-phosphaundecan-1-aminium, 5-oxide, hydroxide, inner salt 8-[[4-(dodecyloxy)phenyl]methyl]-5-hydroxy-NNN-trimethyl-10-oxo-4,6,9-trioxa-5-phosphaundecan-1-aminium, 5-oxide, hydroxide, inner salt 8-[[4-(dodecyloxy)phenyl]methyl]-5-hydroxy-NN-dimethyl-10-oxo-4,6,9-trioxa-5-phosphaundecan-1-aminium, 5-oxide, hydroxide, inner salt 8-[[4-dodecyloxy)phenyl]methyl]-5-hydroxy-N-methyl-10-oxo-4,6,9-trioxa-5-phosphaundecan-1-aminium, 5-oxide, hydroxide, inner salt 8-[[4-(dodecyloxy)phenyl]methyl]-5-hydroxy-NN-tetramethylene-10-oxo-4,6,9-trioxa-5-phosphaundecan-1-aminium, 5-oxide, hydroxide, inner salt 8-[[4-(tetradecyloxy)phenyl]methyl]-5-hydroxy-NNN-trimethyl-10-oxo-4,6,9-trioxa-5-phosphadodecan-1-aminium, 5-oxide, hydroxide, inner salt 8-[[4-(tetradecyloxy)phenyl]methyl]-5-hydroxy-NN-dimethyl-10-oxo-4,6,9-trioxa-5-phosphadodecan-1-aminium, 5-oxide, hydroxide, inner salt 8-[[4-(tetradecyloxy)phenyl]methyl]-5-hydroxy-N-methyl-10-oxo-4,6,9-trioxa-5-phosphadodecan-1-aminium, 5-oxide, hydroxide, inner salt 8-[[4-(tetradecyloxy)phenyl]methyl]-5-hydroxy-NN-tetramethylene-10-oxo-4,6,9-trioxa-5-phosphadodecan-1-aminium, 5-oxide, hydroxide, inner salt 8-[[3-(tridecyloxy)phenyl]methyl]-5-hydroxy-NNN-trimethyl-10-oxo-4,6,9-trioxa-5-phosphadodecan-1-aminium, 5-oxide, hydroxide, inner salt 8-[[3-(tridecyloxy)phenyl]methyl]-5-hydroxy-NN-dimethyl-10-oxo-4,6,9-trioxa-5-phosphadodecan-1-aminium, 5-oxide, hydroxide, inner salt 8-[[3-(tridecyloxy)phenyl]methyl]-5-hydroxy-N-methyl-10-oxo-4,6,9-trioxa-5-phosphadodecan-1-aminium, 5-oxide, hydroxide, inner salt 8-[[3-(tridecyloxy)phenyl]methyl]-5-hydroxy-NN-tetramethylene-10-oxo-4,6,9-trioxa-5-phosphadodecan-1-aminium, 5-oxide, hydroxide, inner salt 8-[[2-(octadecyloxy)phenyl]methyl]-5-hydroxy-NNN-trimethyl-10-oxo-4,6,9-trioxa-5-phosphadodecan-1-aminium, 5-oxide, hydroxide, inner salt 8-[[2-(octadecyloxy)phenyl]methyl]-5-hydroxy-NN-dimethyl-10-oxo-4,6,9-trioxa-5-phosphadodecan-1-aminium, 5-oxide, hydroxide, inner salt 8-[[2-(octadecyloxy)phenyl]methyl]-5-hydroxy-N-methyl-10-oxo-4,6,9-trioxa-5-phosphadodecan-1-aminium, 5-oxide, hydroxide, inner salt 8-[[2-(octadecyloxy)phenyl]methyl]-5-hydroxy-NN-tetramethylene-10-oxo-4,6,9-trioxa-5-phosphadodecan-1-aminium, 5-oxide, hydroxide, inner salt 8-[[2-(tetradecyloxy)phenyl]methyl]-5-hydroxy-NNN-trimethyl-10-oxo-4,6,9-trioxa-5-phosphadodecan-1-aminium, 5-oxide, hydroxide, inner salt 8-[[2-(tetradecyloxy)phenyl]methyl]-5-hydroxy-NN-dimethyl-10-oxo-4,6,9-trioxa-5-phosphadodecan-1-aminium, 5-oxide, hydroxide, inner salt 8-[[2-(tetradecyloxy)phenyl]methyl]-5-hydroxy-N-methyl-10-oxo-4,6,9-trioxa-5-phosphadodecan-1-aminium, 5-oxide, hydroxide, inner salt 8-[[2-(tetradecyloxy)phenyl]methyl]-5-hydroxy-NN-tetramethylene-10-oxo-4,6,9-trioxa-5-phosphadodecan-1-aminium, 5-oxide, hydroxide, inner salt 8-[[4-(dodecyloxy)phenyl]methyl]-5-hydroxy-NNN-trimethyl-10-oxo-4,6,9-trioxa-5-phosphadodecan-1-aminium, 5-oxide, hydroxide, inner salt 8-[[4-(dodecyloxy)phenyl]methyl]-5-hydroxy-NN-dimethyl-10-oxo-4,6,9-trioxa-5-phosphadodecan-1-aminium, 5-oxide, hydroxide, inner salt 8-[[4-(dodecyloxy)phenyl]methyl]-5-hydroxy-N-methyl-10-oxo-4,6,9-trioxa-5-phosphadodecan-1-aminium, 5-oxide, hydroxide, inner salt 8-[[4-(dodecyloxy)phenyl]methyl]-5-hydroxy-NN-tetramethylene-10-oxo-4,6,9-trioxa-5-phosphadodecan-1-aminium, 5-oxide, hydroxide, inner salt 9-[[4-(tetradecyloxy)phenyl]methyl]-6-hydroxy-NNN-trimethyl-11-oxo-5,7,10-trioxa-6-phosphaundecan-1-aminium, 6-oxide, hydroxide, inner salt 9-[[4-(tetradecyloxy)phenyl]methyl]-6-hydroxy-NN-dimethyl-11-oxo-5,7,10-trioxa-6-phosphaundecan-1-aminium, 6-oxide, hydroxide, inner salt 9-[[4-(tetradecyloxy)phenyl]methyl]-6-hydroxy-N-methyl-11-oxo-5,7,10-trioxa-6-phosphaundecan-1-aminium, 6-oxide, hydroxide, inner salt 9-[[4-(tetradecyloxy)phenyl]methyl]-6-hydroxy-NN-tetramethylene-11-oxo-5,7,10-trioxa-6-phosphaundecan-1-aminium, 6-oxide, hydroxide, inner salt 9-[[3-(tridecyloxy)phenyl]methyl]-6-hydroxy-NNN-trimethyl-11-oxo-5,7,10-trioxa-6-phosphaundecan-1-aminium, 6-oxide, hydroxide, inner salt 9-[[3-(tridecyloxy)phenyl]methyl]-6-hydroxy-NN-dimethyl-11-oxo-5,7,10-trioxa-6-phosphaundecan-1-aminium, 6-oxide, hydroxide, inner salt 9-[[3-(tridecyloxy)phenyl]methyl]-6-hydroxy-N-methyl-11-oxo-5,7,10-trioxa-6-phosphaundecan-1-aminium, 6-oxide, hydroxide, inner salt 9-[[3-(tridecyloxy)phenyl]methyl]-6-hydroxy-NN-tetramethylene-11-oxo-5,7,10-trioxa-6-phosphaundecan-1-aminium, 6-oxide, hydroxide, inner salt 9-[[2-(tetradecyloxy)phenyl]methyl]-6-hydroxy-NNN-trimethyl-11-oxo-5,7,10-trioxa-6-phosphaundecan-1-aminium, 6-oxide, hydroxide, inner salt 9-[[2-(tetradecyloxy)phenyl]methyl]-6-hydroxy-NN-dimethyl-11-oxo-5,7,10-trioxa-6-phosphaundecan-1-aminium, 6-oxide, hydroxide, inner salt 9-[[2-(tetradecyloxy)phenyl]methyl]-6-hydroxy-N-methyl-11-oxo-5,7,10-trioxa-6-phosphaundecan-1-aminium, 6-oxide, hydroxide, inner salt 9-[[2-(tetradecyloxy)phenyl]methyl]-6-hydroxy-NN-tetramethylene-11-oxo-5,7,10-trioxa-6-phosphaundecan-1-aminium, 6-oxide, hydroxide, inner salt 9-[[4-(dodecyloxy)phenyl]methyl]-6-hydroxy-NNN-trimethyl-11-oxo-5,7,10-trioxa-6-phosphaundecan-1-aminium, 6-oxide, hydroxide, inner salt 9-[[4-(dodecyloxy)phenyl]methyl]-6-hydroxy-NN-dimethyl-11-oxo-5,7,10-trioxa-6-phosphaundecan-1-aminium, 6-oxide, hydroxide, inner salt 9-[[4-(dodecyloxy)phenyl]methyl]-6-hydroxy-N-methyl-11-oxo-5,7,10-trioxa-6-phosphaundecan-1-aminium, 6-oxide, hydroxide, inner salt 9-[[4-(dodecyloxy)phenyl]methyl]-6-hydroxy-NN-tetramethylene-11-oxo-5,7,10-trioxa-6-phosphaundecan-1-aminium, 6-oxide, hydroxide, inner salt 9-[[4-(tetradecyloxy)phenyl]methyl]-6-hydroxy-NNN-trimethyl-11-oxo-5,7,10-trioxa-6-phosphadodecan-1-aminium, 6-oxide, hydroxide, inner salt 9-[[4-(tetradecyloxy)phenyl]methyl]-6-hydroxy-NN-dimethyl-11-oxo-5,7,10-trioxa-6-phosphadodecan-1-aminium, 6-oxide, hydroxide, inner salt 9-[[4-(tetradecyloxy)phenyl]methyl]-6-hydroxy-N-methyl-11-oxo-5,7,10-trioxa-6-phosphadodecan-1-aminium, 6-oxide, hydroxide, inner salt 9-[[4-(tetradecyloxy)phenyl]methyl]-6-hydroxy-NN-tetramethylene-11-oxo-5,7,10-trioxa-6-phosphadodecan-1-aminium, 6-oxide, hydroxide, inner salt 9-[[3-(tridecyloxy)phenyl]methyl]-6-hydroxy-NNN-trimethyl-11-oxo-5,7,10-trioxa-6-phosphadodecan-1-aminium, 6-oxide, hydroxide, inner salt 9-[[3-(tridecyloxy)phenyl]methyl]-6-hydroxy-NN-dimethyl-11-oxo-5,7,10-trioxa-6-phosphadodecan-1-aminium, 6-oxide, hydroxide, inner salt 9-[[3-(tridecyloxy)phenyl]methyl]-6-hydroxy-N-methyl-11-oxo-5,7,10-trioxa-6-phosphadodecan-1-aminium, 6-oxide, hydroxide, inner salt 9-[[3-(tridecyloxy)phenyl]methyl]-6-hydroxy-NN-tetramethylene-11-oxo-5,7,10-trioxa-6-phosphadodecan-1-aminium, 6-oxide, hydroxide, inner salt 9-[[2-(tetradecyloxy)phenyl]methyl]-6-hydroxy-NNN-trimethyl-11-oxo-5,7,10-trioxa-6-phosphadodecan-1-aminium, 6-oxide, hydroxide, inner salt 9-[[2-(tetradecyloxy)phenyl]methyl]-6-hydroxy-NN-dimethyl-11-oxo-5,7,10-trioxa-6-phosphadodecan-1-aminium, 6-oxide, hydroxide, inner salt 9-[[2-(tetradecyloxy)phenyl]methyl]-6-hydroxy-N-methyl-11-oxo-5,7,10-trioxa-6-phosphadodecan-1-aminium, 6-oxide, hydroxide, inner salt 9-[[2-(tetradecyloxy)phenyl]methyl]-6-hydroxy-NN-tetramethylene-11-oxo-5,7,10-trioxa-6-phosphadodecan-1-aminium, 6-oxide, hydroxide, inner salt 9-[[4-(dodecyloxy)phenyl]methyl]-6-hydroxy-NNN-trimethyl-11-oxo-5,7,10-trioxa-6-phosphadodecan-1-aminium, 6-oxide, hydroxide, inner salt 9-[[4-(dodecyloxy)phenyl]methyl]-6-hydroxy-NN-dimethyl-11-oxo-5,7,10-trioxa-6-phosphadodecan-1-aminium, 6-oxide, hydroxide, inner salt 9-[[4-(dodecyloxy)phenyl]methyl]-6-hydroxy-N-methyl-11-oxo-5,7,10-trioxa-6-phosphadodecan-1-aminium, 6-oxide, hydroxide, inner salt 9-[[4-(dodecyloxy)phenyl]methyl]-6-hydroxy-NN-tetramethylene-11-oxo-5,7,10-trioxa-6-phosphadodecan-1-aminium, 6-oxide, hydroxide, inner salt 2-[[2-(acetyloxy)-3-[4-(tetradecyloxy)phenyl]propoxy]-hydroxyphosphinyl-N,N,N-trimethyl-ethanaminium-hydroxide, inner salt 2-[[2-(acetyloxy)-3-[4-(dodecyloxy)phenyl]propoxy]hydroxyphosphinyl-N,N,N-trimethyl-ethanaminiumhydroxide, inner salt 2-[[2-(acetyloxy)-3-[2-(tetradecyloxy)phenyl]propoxy]-hydroxyphosphinyl-N,N,N-trimethyl-ethanaminium-hydroxide, inner salt 2-[[2-(acetyloxy)-3-[3-(tridecyloxy)phenyl]propoxy]hydroxyphosphinyl-N,N,N-trimethyl-ethanaminiumhydroxide, inner salt 3-[[2-(acetyloxy)-3-[4-(tetradecyloxy)phenyl]propoxy]-hydroxyphosphinyl-N,N,N-trimethyl-propanaminiumhydroxide, inner salt 3-[[2-(acetyloxy)-3-[4-(dodecyloxy)phenyl]propoxy]hydroxyphosphinyl-N,N,N-trimethyl-propanaminiumhydroxide, inner salt 3-[[2-(acetyloxy)-3-[2-tetradecyloxy)phenyl]propoxy]-hydroxyphosphinyl-N,N,N-trimethyl-propanaminiumhydroxide, inner salt 3-[[2-(acetyloxy)-3-[3-(tridecyloxy)phenyl]propoxy]hydroxyphosphinyl-N,N,N-trimethyl-propanaminiumhydroxide, inner salt

EXAMPLE 25

2-Phenyl-m-dioxan-5-ol

A mixture of about 184 g of glycerol, about 212.03 g of benzaldehyde and about 3.6 g of p-toluenesulfonic acid was refluxed for about 5 hours, using a Dean-Stark trap. The mixture was then cooled at about 0° C. for about 17 hours and the solid collected and dissolved in about 1200 ml of warm toluene containing about one gram of sodium methoxide. This solution was washed with about 600 ml of dilute (about 1%) dibasic sodium phosphate and dried. Dilution with petroleum ether gave a solid which was recrystallized from toluene-petroleum ether, giving about 76 g of the desired title compound as a white solid.

EXAMPLE 26

5-(Benzyloxy)-2-phenyl-m-dioxane

To a suspension of about 19.63 g of about 50% sodium hydride in about 450 ml of dimethylformamide was added, portionwise, over about 15 minutes about 67 g of 2-phenyl-m-dioxan-5-ol. After stirring about 20 minutes, the mixture was cooled in ice and about 69.95 g of benzyl bromide was added dropwise over about 20 minutes. The mixture was stirred at room temperature overnight, water was added and the solid collected. This solid was dissolved in hot toluene, dried, filtered and diluted with an equal volume of petroleum ether. After standing about 4 hours at about 0° C. the solid was collected, giving about 90.5 g of the desired title compound.

EXAMPLE 27

2-(Benzyloxy)-1,3-propanediol

A mixture of about 338 g of 5-(benzyloxy)-2-phenyl-m-dioxane, about 1500 ml of ethanol, about 500 ml of water and about 20 ml of sulfuric acid was refluxed for about 2 hours. The ethanol was removed, the acid neutralized with solid sodium bicarbonate, the mixture steam distilled to remove benzaldehyde and then saturated with potassium carbonate. This mixture was extracted three times with ether. The ether extracts were combined, dried and evaporated. Toluene was added and evaporated. The residue was distilled via a Kugelrohr (about 0.1 mm, 170° C.) giving an oil. This oil was dissolved in about 300 ml of toluene, cooled and diluted with two volumes of petroleum ether. Refrigeration produced about 184.69 g of the desired title compound as a solid.

EXAMPLE 28

3-(Hexadecyloxy)-2-(benzyloxy)-1-propanol

To a suspension of about 14.26 g of washed about 50% sodium hydride in about 500 ml of dimethylformamide was added about 49.2 g of 2-(benzyloxy)-1,3-propanediol over about 20 minutes. The mixture was stirred for about 40 minutes, then cooled to about 0° C. and about 95.13 g of hexadecyl iodide were added. After standing about 10 minutes, the mixture was stirred at room temperature for about 3 hours, then filtered through celite and diluted with about 1000 ml of water. This mixture was extracted with petroleum ether. The ether extract was dried and the solvent removed giving an oil. This oil was chromatographed on a column of florisil, eluting first with petroleum ether and then successively with about 5% and about 10% ether in petroleum ether to elute the product, giving about 28.8 g of the desired title compound as a light yellow oil.

EXAMPLE 29

2-(Benzyloxy)-3-(octadecyloxy)-1-propanol

To a suspension of about 26.07 g of washed about 50% sodium hydride in about 1000 ml of dimethylformamide was added about 90 g of 2-(benzyloxy)-1,3-propanediol with stirring under argon. An about 187.88 g portion of octadecyl iodide and about 150 ml of tetrahydrofuran were added and the thick mixture was stirred with a glass rod, and then with magnetic stirring for about 3 hours. Water was then added and the mixture was extracted with ether. The ether extract was washed with brine, dried and filtered through a pad of florisil. The solvent was removed and the residue chromatographed on florisil, eluting first with petroleum ether, then with about 10% ether in petroleum ether and finally eluting the product with about 30% ether in petroleum ether, giving about 73.3 g of the desired title compound as a waxy solid.

By following the methods outlined above in Examples 28 and 29, 2-(benzyloxy)-1,3-propanediol is alkylated with the indicated alkyl iodides to provide the 1-propanol derivatives listed in Table III below.

TABLE III

| 1-Propanol Derivative | Alkyl Iodide |
| --- | --- |
| 2-(benzyloxy)-3-(nonadecyloxy)-1-propanol | nonadecyl iodide |
| 2-(benzyloxy)-3-(heptadecyloxy)-1-propanol | heptadecyl iodide |
| 2-(benzyloxy)-3-(pentadecyloxy)-1-propanol | pentadecyl iodide |
| 2-(benzyloxy)-3-(tetradecyloxy)-1-propanol | tetradecyl iodide |
| 2-(benzyloxy)-3-(tridecyloxy)-1-propanol | tridecyl iodide |
| 2-(benzyloxy)-3-(2-methylhexadecyloxy)-1-propanol | 2-methylhexadecyl iodide |
| 2-(benzyloxy)-3-(3-ethylpentadecyloxy)-1-propanol | 3-ethylpentadecyl iodide |
| 2-(benzyloxy)-3-(2,4-dimethylhexadecyloxy)-1-propanol | 2,4-dimethylhexadecyl iodide |

EXAMPLE 30

2-(Benzyloxy)-3-(octadecyloxy)propyl 2-bromoethyl phosphate

To a solution of about 16.43 g of 2-bromoethyl phosphorodichlorodate in about 400 ml of carbon tetrachloride at about 0° C., was added with stirring 28 g of triethylamine followed by about 21.2 g of 2-(benzyloxy)-3-(octadecyloxy)-1-propanol. The mixture was stirred about 2 hours at room temperature, about 300 ml of toluene were added and the mixture was filtered. The solvent was removed and the residue stirred in a mixture of about 300 ml of about 0.5M sodium acetate and about 300 ml of tetrahydrofuran overnight. The tetrahydrofuran was removed and the aqueous mixture was neutralized to about pH 2 and extracted with ether. The ether extract was dried, filtered through florasil and the solvent removed, giving about 29.5 g of the desired title compound as a yellow oil which solidified on standing, mp 30°–31° C.

EXAMPLE 31

7-(Benzyloxy)-4-hydroxy-N,N,N-trimethyl-3,5,9-trioxa-4-phosphaheptacosan-1-aminium, 4-oxide, hydroxide, inner salt A mixture of about 15.0 g of 2-(benzyloxy)-3-(octadecyloxy)propyl 2-bromoethyl phosphate in about 400 ml of chloroform:2-propanol:dimethylformamide (about 3:5:5) and about 250 ml of about 40% trimethylamine was stirred at about 55° C. for about 6 hours. Most of the solvent was removed and about 100 ml of water and about 100 ml of methanol were added, followed by about 3.33 g of silver carbonate. This mixture was stirred overnight, filtered through celite and the solvents removed under reduced pressure. The residue was dissolved in methanol, filtered and the methanol removed. This residue was stirred for about one hour in about one liter of ether, then concentrated to about 300 ml and the solid collected, giving about 11 g of the desired title compound, mp 217°–219° C. (dec.).

EXAMPLE 32

4,7-Dihydroxy-N,N,N-trimethyl-3,5,9-trioxa-4-phosphaheptacosan-1-aminium, 4-oxide, hydroxide, inner salt A mixture of about 9.0 g of 7-(benzyloxy)-4-hydroxy-N,N,N-trimethyl-3,5,9-trioxa-4-phosphaheptacosan-1-aminium, 4-oxide, hydroxide in about 60 ml of acetic acid and about 60 ml of methanol containing about 0.9 g of about 5% palladium on carbon catalyst was shaken in a Parr apparatus for about 17 hours. The mixture was then filtered and the solvents removed under reduced pressure. Toluene was added and removed twice. The residue was dissolved in methanol, treated with charcoal and filtered. The filtrate was concentrated to about 50 ml, then diluted with ether, the solid collected, washed with ether and dried in vacuo, giving the desired title compound as about 6 g of a white powder, mp 230° C. (dec.).

EXAMPLE 23

7-(Acetyloxy)-4-hydroxy-N,N,N-trimethyl-3,5,9-trioxa-4-phosphaheptacosan-1-aminium, 4-oxide, hydroxide, inner salt An about 1.8 g portion of 4,7-dihydroxy-N,N,N-trimethyl-3,5,9-trioxa-4-phosphaheptacosan-1-aminium, 4-oxide, hydroxide, inner salt in about 11 ml of acetic anhydride was refluxed for about 15 minutes, then the excess anhydride was removed. The residue was chromatographed on a wet silica gel column, eluting successively with chloroform:methanol (about 70:30), (about 50:50) and then (about 30:70). The product was then eluted with methanol which was removed at room temperature, giving about 1.41 g of the desired product.

EXAMPLE 34

7-(Formyloxy)-4-hydroxy-N,N,N-trimethyl-3,5,9-trioxa-4-phosphaheptacosan-1-aminium, 4-oxide, hydroxide, inner salt A solution of about 0.2 g of 4,7-dihydroxy-N,N,N-trimethyl-3,5,9-trioxa-4-phosphaheptacosan-1-aminium, 4-oxide, hydroxide, inner salt in about 2 ml of about 97% formic acid was kept at room temperature, under argon, in a stoppered flask for about 72 hours, then heated at about 60° C. for about one hour, cooled and taken to dryness. The solid was triturated with ether and dried, giving the desired product.

EXAMPLE 35

4-Hydroxy-N,N,N-trimethyl-7-[(octadecyloxy)methyl]-9-oxo-3,5,8,10-tetraoxa-4-phosphadodecan-1-aminium, 4-oxide, hydroxide, inner salts A mixture of about 0.5 g of 4,7-dihydroxyu-N,N,N-trimethyl-3,5,9-trioxa-4-phosphaheptacosan-1-aminium, 4-oxide, hydroxide, inner salt in about 5 ml of diethylpyrocarbonate was stirred at about 75°–80° C., under an argon atmosphere for about 2 hours, then cooled to room temperature. The solvent was evaporated and the solid triturated with ether and collected, giving about 453 mg of the desired product as a white solid.

EXAMPLE 36

8-Hydroxy-N,N,N-trimethyl-5-[(octadecyloxy)methyl]-3-oxo-4,7,9-trioxa-2-aza-8-phosphaundecan-11-aminium, 8-oxide, hydroxide, inner salt A mixture of about 0.5 g of 4,7-dihydroxy-N,N,N-trimethyl-3,5,9-trioxa-4-phosphaheptacosan-1-aminium, 4-oxide, hydroxide, inner salt in about 15 ml of dry toluene was stirred at reflux, under argon at about 85°–90° C. until solution was complete. A mixture of about 2 ml of methyl isocyanate in about 3 ml of toluene was added with stirring. When the temperature fell to about 70° C., about 2 ml of methyl isocyanate in about 3 ml of toluene was added and the mixture was allowed

EXAMPLE 37

3-Bromopropyl-2-(benzyloxy)-3-(hexadecyloxy)propyl phosphate

To a solution of about 24.27 g of 3-bromopropyl phosphorodichlorodate in about 500 ml of carbon tetrachloride at about 0° C. was added with stirring about 39 g of triethylamine, dropwise followed by about 27.7 g of 3-(hexadecyloxy)-2-(benzyloxy)-1-propanol in a small amount of carbon tetrachloride. The mixture was stirred at room temperature for about 2 hours, added to about 375 ml of toluene, filtered and the solvents removed. The residue was stirred in about 420 ml of about 0.5M sodium acetate and about 420 ml of tetrahydrofuran overnight, the tetrahydrofuran was removed and the aqueous mixture acidified with concentrated hydrochloric acid (about 12N) to about pH 2. This mixture was extracted twice with ether, the extracts were combined, dried, treated with charcoal, filtered through magnesium aluminum silicate and evaporated in vacuo, giving about 30 g of the desired title compound.

EXAMPLE 38

5-Hydroxy-N,N,N-trimethyl-8-(benzyloxy)-4,6,10-trioxa-5-phosphahexacosan-1-aminium, 5-oxide, hydroxide, inner salt To a solution of about 15 g of 3-bromopropyl-2-(benzyloxy)-3-(hexadecyloxy)propyl phosphate in about 400 ml of a mixture of chloroform:2-propanol:dimelthylformamide (about 3:5:5) was added about 250 ml of about 40% trimethylamine. The mixture was stirred at about 55° C. for about 6 hours, then concentrated to about 60 ml and about 100 ml of water and about 100 ml of methanol were added followed by about 3.4 g of silver carbonate. The mixture was stirred overnight, filtered through celite, washed with methanol and the mother liquor taken to dryness. The solid was triturated with ether, collected and dried, giving about 9 g of the desired title compound as a white powder.

EXAMPLE 9

5,8-Dihydroxy-N,N,N-trimethyl-4,6,10-trioxa-5-phosphahexacosan-1-aminium, 5-oxide, hydroxide, inner salt An about 8.3 g portion of 5-hydroxy-N,N,N-trimethyl-8-(benzyloxy)-4,6,10-trioxa-5-phosphahexacosan-1-aminium, 5-oxide, hydroxide, inner salt was added to a Parr bottle containing about 0.8 g of about 5% palladium on carbon, about 60 ml of glacial acetic acid and about 60 ml of methanol. The mixture was hydrogenated at an initial pressure of about 25 psi for about 18 hours, then filtered through celite and washed with methanol. The mother liquor was taken to dryness and then evaporated twice from toluene leaving an oil. This oil was stirred with about 150 ml of ether and the solid was collected and dried, giving about 7 g of the desired title compound as a white powder, mp 130° C.

EXAMPLE 40

8-(Acetyloxy)-5-hydroxy-N,N,N-trimethyl-4,6,10-trioxa-5-phosphadexacosan-1-aminium, 5-oxide, hydroxide, inner salt An about 7 g portion of 5,8-dihydroxy-N,N,N-trimethyl-4,6,10-trioxa-5-phosphahexacosan-1-aminium, 5-oxide, hydroxide, inner salt was combined with about 8 ml of acetic anhydride and about 2 ml of pyridine and heated at about 70° C., under argon for about one hour, then allowed to stand at room temperature for about 67 hours. The mixture was then repeatedly chromatographed on a silica gel column using mixtures of methanol and chloroform. The product fractions were pooled, taken to dryness, triturated with ether and the solid collected, giving about 250 mg of the desired product.

EXAMPLE 41

4-Bromobutyl phosphorodichlorodate

To a solution of about 75 g of phosphorous oxychloride in about 250 ml of carbon tetrachloride was added dropwise, about 50 g of 4-bromo-1-butanol over about 30 minutes. The mixture was stirred overnight, taken to dryness, evaporated three times from toluene and dried, giving about 68.3 g of the desired reagent as a dark oil.

EXAMPLE 42

2-(Benzyloxy)-3-(octadecyloxy)propyl 4-bromobutyl phosphate

To a solution of about 11.5 g of 4-bromobutyl phosphorodichlorodate in about 290 ml of carbon tetrachloride, cooled in an ice bath under nitrogen was added with stirring about 19.89 g of triethylamine followed by about 15 g of 2-(benzyloxy)-3-(octadecyloxy)-1-propanol. The mixture was then stirred at room temperature for about 2 hours, about 200 ml of toluene were added and the mixture was filtered through celite and washed with toluene. The mother liquor was taken to dryness, about 215 ml of tetrahydrofuran and about 215 ml of about 0.5M sodium acetate were added and the mixture was stirred overnight. The tetrahydrofuran was removed, the mixture acidified with concentrated hydrochloric acid (about 12N) and extracted twice with ether. The ether extracts were combined, dried, evaporated to an oil and chromatographed on florasil, eluting the product with about 10% methanol in chloroform, giving about 11.2 g of the desired title compound as a yellow oil.

EXAMPLE 43

6-Hydroxy-N,N,N-trimethyl-9-(benzyloxy)-5,7,11-trioxa-6-phosphanonacosan-1-aminium, 6-oxide, hydroxide, inner salt To a solution of about 11.2 g of 2-(benzyloxy)-3-(octadecyloxy)propyl 4-bromobutyl phosphate in about 300 ml of a mixture of chloroform:2-propanol:dimethylformamide (about 3:5:5) was added about 190 ml of about 40% trimethylamine. The mixture was stirred at about 50°–55° C. for about 6 hours, then allowed to stand at room temperature overnight. Most of the solvent was removed, about 100 ml of water, about 100 ml of methanol and about 2.38 g of silver carbonate were added and the mixture was stirred overnight, filtered through celite and the mother liquor taken to dryness. The residue was dissolved in methanol, filtered through celite and the mother liquor taken to dryness. This residue was triturated with about 150 ml of ether and the solid collected and dried, giving about 7.1 g of the desired title compound as a white solid.

EXAMPLE 44

6,9-Dihydroxy-N,N,N-trimethyl-5,7,11-trioxa-6-phosphanonacosan-1-aminium, 6-oxide, hydroxide, inner salt A solution of about 7 g of 6-hydroxy-N,N,N-trimethyl-9-(benzyloxy)-5,7,11-trioxa-6-phosphanonacosan-1-aminium, 6-oxide, hydroxide, inner salt in about 55 ml of methanol was added to about 0.9 g of about 5% palladium on carbon in about 55 ml of glacial acetic acid in a Parr bottle and hydrogenated at an initial pressure of about 25 psi for about 18 hours. The mixture was filtered through celite, washed with methanol, the mother liquor taken to dryness and the residue evaporated three times with toluene. This residue was stirred with about 150 ml of ether for about 2 hours, the solid collected and dried, giving about 5.9 g of the desired title compound as a white powder.

EXAMPLE 45

9-(Acetyloxy)-6-hydroxy-N,N,N-trimethyl-5,7,11-trioxa-6-phosphanonacosan-1-aminium, 6-oxide, hydroxide, inner salt A mixture of about one gram of 6,9-dihydroxy-N,N,N-trimethyl-5,7,11-trioxa-6-phosphanonacosan-1-aminium, 6-oxide, hydroxide, inner salt and about 10 ml of acetic anhydride was stirred at reflux for about 15 minutes at about 140°–145° C., about 10 ml of toluene was added and the mixture taken to dryness and evaporated three times with toluene. The residue was chromatographed on a dry column of silica gel, eluting with chloroform:methanol:water (about 65:35:6). The product segments were combined, evaporated three times with toluene, the residue dissolved in chloroform, treated with charcoal and taken to near dryness. The residue was flooded with ether, chilled to about 0° C., and the solid collected and dried, giving 715 mg of the desired product.

EXAMPLE 46

Mono[3-(octadecyloxy)-2-(benzyloxy)propyl](2-bromoethyl)phosphonate (2-Bromoethyl)phosphonic acid monochloride was prepared from phosphorous pentachloride and (2-bromoethyl)phosphonic acid according to E. Baer and N. Z. Stanacey, J. BIOL. CHEM., 10: 3754 (1965). A portion of this reagent was dissolved in about 50 ml of anhydrous, ethanol-free chloroform, cooled in an ice-water bath to about 10° C. To this was added a portion of 2-(benzyloxy)-3-(octadecyloxy)-1-propanol and about 3.0 ml of dry triethylamine in about 50 ml of dry chloroform, under argon, with stirring over a period of one hour. The reaction was allowed to stand at room temperature about 48 hours, then was refrigerated at about 0° C. overnight and then taken to dryness. The residue was dissolved in toluene, filtered and the filtrate taken to dryness. The residue was extracted with ether, giving the desired title compound as a pale yellow syrup.

EXAMPLE 47

2-[Hydroxy-[3-(octadecyloxy)-2-(benzyloxy)propoxy]-phosphinyl]-N,N,N-trimethyl-ethanaminium, hydroxide, inner salt A solution of about 5.0 g of mono[3-(octadecyloxy)-2-(benzyloxy)propyl](2-bromoethyl)phosphonate in about 70 ml of a solution composed of about 33% trimethylamine in acetonitrile and about 50 ml of acetonitrile was placed in a beaker in a steel bomb, sealed and heated at about 50°–55° C. for about 3½ days. The reaction product was then evaporated under reduced pressure and the residue dissolved in a mixture of about 50 ml of chloroform, about 50 ml of methanol and about 5 ml of water and then stirred with 1.7 g of silver carbonate for about 2½ hours. The mixture was filtered through celite, washed with methanol, the mother liquor taken to dryness and the residue evaporated with toluene. The solid was triturated with ether, refrigerated at about 0° C. for about one hour and the solid collected, giving about 2.99 g of the desired title compound, mp 175°–177° C.

EXAMPLE 48

2-[Hydroxy-[2-hydroxy-3-(octadecyloxy)propoxy]-phosphinyl]-N,N,N-trimethyl-ethanaminium, hydroxide, inner salt A solution of about 1.3 g of 2-[hydroxy-[3-octadecyloxy)-2-(benzyloxy)propoxy]phosphinyl]-N,N,N-trimethyl-ethanaminium, hydroxide, inner salt in about 20 ml of acetic acid and about 20 ml of methanol containing about 200 mg of about 5% palladium on carbon was hydrogenated in a Parr shaker at an initial pressure of about 25 psi for about 18 hours. The mixture was filtered through celite, washed with methanol and the mother liquor taken to dryness under reduced pressure at about 35° C. This residue was evaporated twice with toluene, triturated with ether, refrigerated at about 0° C. for about 2 hours and then collected, giving about 850 mg of the desired title compound as a white solid, mp 160°–165° C.

EXAMPLE 49

2-[[2-(Acetyloxy)-3-(octadecyloxy)propoxy]hydroxyphosphinyl]-N,N,N-trimethyl-ethanaminium, hydroxide, inner salt A solution of about 740 mg of 2-[hydroxy-[2-hydroxy-3-(octadecyloxy)propoxy]phosphinyl]-N,N,N-trimethylethanaminium, hydroxide inner salt in about 50 ml of chloroform containing about 3.8 g of acetic anhydride and about 1.52 g of triethylamine was refluxed for about 2½ hours. The solvent was removed in vacuo at about 50° C., the residue evaporated twice with toluene, triturated with ether, refrigerated at about 0° C. and the solid collected, giving about 435 mg of the desired product as a white solid.

By using the phosphorous reagents listed in Table VII, the amines of Table VIII and the appropriate starting materials prepared in Examples 28 and 29 and those listed in Table III and by following the methods described in detail hereinabove in Examples 28, 29, and 46–49, the compounds of this invention listed below can be prepared. These compounds can be prepared as the individual optically active R and S enantiomers or as racemic mixtures as described in the above specifications.

2-[[2-(acetyloxy)-3-(octadecyloxy)propoxy]hydroxyphosphinyl]-N,N,N-trimethyl-ethanaminium, hydroxide, inner salt 2-[[2-(acetyloxy)-3-(octadecyloxy)propoxy]hydroxyphosphinyl]-N,N-dimethyl-ethanaminium, hydroxide, inner salt 2-[[2-(acetyloxy)-3-(octadecyloxy)propoxy]hydroxyphosphinyl]-N-methyl-ethanaminium, hydroxide, inner salt 2-[[2-(acetyloxy)-3-(octadecyloxy)propoxy]hydroxyphosphinyl]-N,N-tetramethylene-ethanaminium, hydroxide, inner salt
2-[[2-(acetyloxy)-3-(octadecyloxy)propoxy]hydroxyphosphinyl]-N,N-diethyl-ethanaminium, hydroxide, inner salt
2-[[2-(acetyloxy)-3-(nonadecyloxy)propoxy]hydroxyphosphinyl]-N,N,N-trimethyl-ethanaminium, hydroxide, inner salt
2-[[2-(acetyloxy)-3-(nonadecyloxy)propoxy]hydroxyphosphinyl]-N,N-dimethyl-ethanaminium, hydroxide, inner salt
2-[[2-(acetyloxy)-3-(nonadecyloxy)propoxy]hydroxyphosphinyl]-N-methyl-ethanaminium, hydroxide, inner salt
2-[[2-(acetyloxy)-3-(nonadecyloxy)propoxy]hydroxyphosphinyl]-N,N-tetramethylene-ethanaminium, hydroxide, inner salt
2-[[2-(acetyloxy)-3-(nonadecyloxy)propoxy]hydroxyphosphinyl]-N,N-diethyl-ethanaminium, hydroxide, inner salt
2-[[2-(acetyloxy)-3-(heptadecyloxy)propoxy]hydroxyphosphinyl]-N,N,N-trimethyl-ethanaminium, hydroxide, inner salt
2-[[2-(acetyloxy)-3-(heptadecyloxy)propoxy]hydroxyphosphinyl]-N,N-dimethyl-ethanaminium, hydroxide, inner salt
2-[[2-(acetyloxy)-3-(heptadecyloxy)propoxy]hydroxyphosphinyl]-N-methyl-ethanaminium, hydroxide, inner salt
2-[[2-(acetyloxy)-3-(heptadecyloxy)propoxy]hydroxyphosphinyl]-N,N-tetramethylene-ethanaminium, hydroxide, inner salt
2-[[2-(acetyloxy)-3-(heptadecyloxy)propoxy]hydroxyphosphinyl]-N,N-diethyl-ethanaminium, hydroxide, inner salt
2-[[2-(acetyloxy)-3-(hexadecyloxy)propoxy]hydroxyphosphinyl]-N,N,N-trimethyl-ethanaminium, hydroxide, inner salt
2-[[2-(acetyloxy)-3-(hexadecyloxy)propoxy]hydroxyphosphinyl]-N,N-dimethyl-ethanaminium, hydroxide, inner salt
2-[[2-(acetyloxy)-3-(hexadecyloxy)propoxy]hydroxyphosphinyl]-N-methyl-ethanaminium, hydroxide, inner salt
2-[[2-(acetyloxy)-3-(hexadecyloxy)propoxy]hydroxyphosphinyl]-N,N-tetramethylene-ethanaminium, hydroxide, inner salt
2-[[2-(acetyloxy)-3-(hexadecyloxy)propoxy]hydroxyphosphinyl]-N,N-diethyl-ethanaminium, hydroxide, inner salt
2-[[2-(acetyloxy)-3-(pentadecyloxy)propoxy]hydroxyphosphinyl]-N,N,N-trimethyl-ethanaminium, hydroxide, inner salt
2-[[2-(acetyloxy)-3-(pentadecyloxy)propoxy]hydroxyphosphinyl]-N,N-dimethyl-ethanaminium, hydroxide, inner salt
2-[[2-(acetyloxy)-3-(pentadecyloxy)propoxy]hydroxyphosphinyl]-N-methyl-ethanaminium, hydroxide, inner salt
2-[[2-(acetyloxy)-3(pentadecyloxy)propoxy]hydroxyphosphinyl]-N,N-tetramethylene-ethanaminium, hydroxide, inner salt
2-[[2-(acetyloxy)-3-(pentadecyloxy)propoxy]hydroxyphosphinyl]-N,N-diethyl-ethanaminium, hydroxide, inner salt
2-[[2-(acetyloxy)-3-(2-methylhexadecyloxy)propoxy]hydroxyphosphinyl]-N,N,N-trimethyl-ethanaminium, hydroxide, inner salt
2-[[2-(acetyloxy)-3-(2-methylhexadecyloxy)propoxy]hydroxyphosphinyl]-N,N-dimethyl-ethanaminium, hydroxide, inner salt
2-[[2-(acetyloxy)-3-(2-methylhexadecyloxy)propoxy]hydroxyphosphinyl]-N-methyl-ethanaminium, hydroxide, inner salt
2-[[2-(acetyloxy)-3-(2-methylhexadecyloxy)propoxy]hydroxyphosphinyl]-N,N-tetramethylene-ethanaminium, hydroxide, inner salt
2-[[2-(acetyloxy)-3-(3-ethylpentadecyloxy)propoxy]hydroxyphosphinyl]-N,N,N-trimethyl-ethanaminium, hydroxide, inner salt
2-[[2-(acetyloxy)-3-(3-ethylpentadecyloxy)propoxy]hydroxyphosphinyl]-N,N-dimethyl-ethanaminium, hydroxide, inner salt
2-[[2-(acetyloxy)-3-(3-ethylpentadecyloxy)propoxy]hydroxyphosphinyl]-N,N-tetramethylene-ethanaminium, hydroxide, inner salt
2-[[2-(acetyloxy)-3-(3-ethylpentadecyloxy)propoxy]hydroxyphosphinyl]-N,N-diethyl-ethanaminium, hydroxide, inner salt
2-[[2-(acetyloxy)-3-(2,4-dimethylhexadecyloxy)propoxy]hydroxyphosphinyl]-N,N,N-trimethyl-ethanaminium, hydroxide, inner salt
2-[[2-(acetyloxy)-3-(2,4-dimethylhexadecyloxy)propoxy]hydroxyphosphinyl]-N,N-dimethyl-ethanaminium, hydroxide, inner salt
2-[[2-(acetyloxy)-3-(2,4-dimethylhexadecyloxy)propoxy]hydroxyphosphinyl]-N-methyl-ethanaminium, hydroxide, inner salt
2-[[2-(acetyloxy)-3-(2,4-dimethylhexadecyloxy)propoxy]hydroxyphosphinyl]-N,N-diethyl-ethanaminium, hydroxide, inner salt
2-[[2-(formyloxy)-3-(octadeyloxy)propoxy]hydroxyphosphinyl]-N,N,N-trimethyl-ethanaminium, hydroxide, inner salt
2-[[2-(formyloxy)-3-(octadeyloxy)propoxy]hydroxyphosphinyl]-N,N-dimethyl-ethanaminium, hydroxide, inner salt
2-[[2-(formyloxy)-3-(octadeyloxy)propoxy]hydroxyphosphinyl]-N-methyl-ethanaminium, hydroxide, inner salt
2-[[2-(formyloxy)-3-(octadecyloxy)propoxy]hydroxyphosphinyl]-N,N-tetramethylene-ethanaminium, hydroxide, inner salt
2-[[2-(formyloxy)-3-(octadecyloxy)propoxy]hydroxyphosphinyl]-N,N-diethyl-ethanaminium, hydroxide, inner salt
2-[[2-(formyloxy)-3-(nonadecyloxy)propoxy]hydroxyphosphinyl]-N,N,N-trimethyl-ethanaminium, hydroxide, inner salt
2-[[2-(formyloxy)-3-(nonadecyloxy)propoxy]hydroxyphosphinyl]-N,N-dimethyl-ethanaminium, hydroxide, inner salt
2-[[2-(formyloxy)-3-(nonadecyloxy)propoxy]hydroxyphosphinyl]-N-methyl-ethanaminium, hydroxide, inner salt
2-[[2-(formyloxy)-3-(nonadecyloxy)propoxy]hydroxyphosphinyl]-N,N-tetramethylene-ethanaminium, hydroxide, inner salt
2-[[2-(formyloxy)-3-(nonadecyloxy)propoxy]hydroxyphosphinyl]-N,N-diethyl-ethanaminium, hydroxide, inner salt 2-[[2-(formyloxy)-3-(heptadecyloxy)propoxy]hydroxy-phosphinyl]-N,N,N-trimethyl-ethanaminium, hydroxide, inner salt
2-[[2-(formyloxy)-3-(heptadecyloxy)propoxy]hydroxy-phosphinyl]-N,N-dimethyl-ethanaminium, hydroxide, inner salt
2-[[2-(formyloxy)-3-(heptadecyloxy)propoxy]hydroxy-phosphinyl]-N-methyl-ethanaminium, hydroxide, inner salt
2-[[2-(formyloxy)-3-(heptadecyloxy)propoxy]hydroxy-phosphinyl]-N,N-tetramethylene-ethanaminium, hydroxide, inner salt
2-[[2-(formyloxy)-3-(heptadecyloxy)propoxy]hydroxy-phosphinyl]-N,N-diethyl-ethanaminium, hydroxide, inner salt
2-[[2-(formyloxy)-3-(hexadecyloxy)propoxy]hydroxy-phosphinyl]-N,N,N-trimethyl-ethanaminium, hydroxide, inner salt
2-[[2-(formyloxy)-3-(hexadecyloxy)propoxy]hydroxy-phosphinyl]-N,N-dimethyl-ethanaminium, hydroxide, inner salt
2-[[2-(formyloxy)-3-(hexadecyloxy)propoxy]hydroxy-phosphinyl]-N-methyl-ethanaminium, hydroxide, inner salt
2-[[2-(formyloxy)-3-(hexadecyloxy)propoxy]hydroxy-phosphinyl]-N,N-tetramethylene-ethanaminium, hydroxide, inner salt
2-[[2-(formyloxy)-3-(hexadecyloxy)propoxy]hydroxy-phosphinyl]-N,N-diethyl-ethanaminium, hydroxide, inner salt
2-[[2-(formyloxy)-3-(pentadecyloxy)propoxy]hydroxy-phosphinyl]-N,N,N-trimethyl-ethanaminium, hydroxide, inner salt
2-[[2-(formyloxy)-3-(pentadecyloxy)propoxy]hydroxy-phosphinyl]-N,N-dimethyl-ethanaminium, hydroxide, inner salt
2-[[2-(formyloxy)-3-(pentadecyloxy)propoxy]hydroxy-phosphinyl]-N-methyl-ethanaminium, hydroxide, inner salt
2-[[2-(formyloxy)-3-(pentadecyloxy)propoxy]hydroxy-phosphinyl]-N,N-tetramethylene-ethanaminium, hydroxide, inner salt
2-[[2-(formyloxy)-3-(pentadecyloxy)propoxy]hydroxy-phosphinyl]-N,N-diethyl-ethanaminium, hydroxide, inner salt
2-[[2-(formyloxy)-3-(2-methylhexadecyloxy)propoxy]-hydroxyphosphinyl]-N,N,N-trimethyl-ethanaminium, hydroxide, inner salt
2-[[2-(formyloxy)-3-(2-methylhexadecyloxy)propoxy]-hydroxyphosphinyl]-N,N-dimethyl-ethanaminium, hydroxide, inner salt
2-[[2-(formyloxy)-3-(2-methylhexadecyloxy)propoxy]-hydroxyphosphinyl]-N-methyl-ethanaminium, hydroxide, inner salt
2-[[2-(formyloxy)-3-(2-methylhexadecyloxy)propoxy]-hydroxyphosphinyl]-N,N-tetramethylene-ethanaminium, hydroxide, inner salt
2-[[2-(formyloxy)-3-(3-ethylpentadecyloxy)propoxy]-hydroxyphosphinyl]-N,N,N-trimethyl-ethanaminium, hydroxide, inner salt
2-[[2-(formyloxy)-3-(3-ethylpentadecyloxy)propoxy]-hydroxyphosphinyl]-N,N-dimethyl-ethanaminium, hydroxide, inner salt
2-[[2-(formyloxy)-3-(3-ethylpentadecyloxy)propoxy]-hydroxyphosphinyl]-N,N-tetramethylene-ethanaminium, hydroxide, inner salt
2-[[2-(formyloxy)-3-(3-ethylpentadecyloxy)propoxy]-hydroxyphosphinyl]-N,N-diethyl-ethanaminium, hydroxide, inner salt
2-[[2-(formyloxy)-3-(2,4-dimethylhexadecyloxy)-propoxy]hydroxyphosphinyl]-N,N,N-trimethyl-ethanaminium, hydroxide, inner salt
2-[[2-(formyloxy)-3-(2,4-dimethylhexadecyloxy)-propoxy]hydroxyphosphinyl]-N,N-dimethyl-ethanaminium, hydroxide, inner salt
2-[[2-(formyloxy)-3-(2,4-dimethylhexadecyloxy)-propoxy]hydroxyphosphinyl]-N-methyl-ethanaminium, hydroxide, inner salt
2-[[2-(formyloxy)-3-(2,4-dimethylhexadecyloxy)-propoxy]hydroxyphosphinyl]-N,N-diethyl-ethanaminium, hydroxide, inner salt
2-[[2-(propionyloxy)-3-(octadeyloxy)propoxy]hydroxy-phosphinyl]-N,N,N-trimethyl-ethanaminium, hydroxide, inner salt
2-[[2-(propionyloxy)-3-(octadeyloxy)propoxy]hydroxy-phosphinyl]-N,N-dimethyl-ethanaminium, hydroxide, inner salt
2-[[2-(propionyloxy)-3-(octadeyloxy)propoxy]hydroxy-phosphinyl]-N-methyl-ethanaminium, hydroxide, inner salt
2-[[2-(propionyloxy)-3-(octadeyloxy)propoxy]hydroxy-phosphinyl]-N,N-tetramethylene-ethanaminium, hydroxide, inner salt
2-[[2-(propionyloxy)-3-(octadeyloxy)propoxy]hydroxy-phosphinyl]-N,N-diethyl-ethanaminium, hydroxide, inner salt
2-[[2-(propionyloxy)-3-(nonadecyloxy)propoxy]hy-droxyphosphinyl]-N,N,N-trimethyl-ethanaminium, hydroxide, inner salt
2-[[2-(propionyloxy)-3-(nonadecyloxy)propoxy]hy-droxyphosphinyl]-N,N-dimethyl-ethanaminium, hydroxide, inner salt
2-[[2-(propionyloxy)-3-(nonadecyloxy)propoxy]hy-droxyphosphinyl]-N-methyl-ethanaminium, hydroxide, inner salt
2-[[2-(propionyloxy)-3-(nonadecyloxy)propoxy]hy-droxyphosphinyl]-N,N-tetramethylene-ethanaminium, hydroxide, inner salt
2-[[2-(propionyloxy)-3-(nonadecyloxy)propoxy]hy-droxyphosphinyl]-N,N-diethyl-ethanaminium, hydroxide, inner salt
2-[[2-(propionyloxy)-3-(heptadecyloxy)propoxy]hy-droxyphosphinyl]-N,N,N-trimethyl-ethanaminium, hydroxide, inner salt
2-[[2-(propionyloxy)-3-(heptadecyloxy)propoxy]hy-droxyphosphinyl]-N,N-dimethyl-ethanaminium, hydroxide, inner salt
2-[[2-(propionyloxy)-3-(heptadecyloxy)propoxy]hy-droxyphosphinyl]-N-methyl-ethanaminium, hydroxide, inner salt
2-[[2-(propionyloxy)-3-(heptadecyloxy)propoxy]hy-droxyphosphinyl]-N,N-tetramethylene-ethanaminium, hydroxide, inner salt
2-[[2-(propionyloxy)-3-(heptadecyloxy)propoxy]hy-droxyphosphinyl]-N,N-diethyl-ethanaminium, hydroxide, inner salt
2-[[2-(propionyloxy)-3-(hexadecyloxy)propoxy]hy-droxyphosphinyl]-N,N,N-trimethyl-ethanaminium, hydroxide, inner salt
2-[[2-(propionyloxy)-3-(hexadecyloxy)propoxy]hy-droxyphosphinyl]-N,N-dimethyl-ethanaminium, hydroxide, inner salt 2-[[2-(propionyloxy)-3-(hexadecyloxy)-propoxy]hydroxyphosphinyl]-N-methyl-ethanaminium, hydroxide, inner salt 2-[[2-(propionyloxy)-3-(hexadecyloxy)propoxy]hydroxyphosphinyl]-N,N-tetramethylene-ethanaminium, hydroxide, inner salt 2-[[2-(propionyloxy)-3-(hexadecyloxy)propoxy]hydroxyphosphinyl]-N,N-diethyl-ethanaminium, hydroxide, inner salt 2-[[2-(propionyloxy)-3-(pentadecyloxy)propoxy]hydroxyphosphinyl]-N,N,N-trimethyl-ethanaminium, hydroxide, inner salt 2-[[2-(propionyloxy)-3-(pentadecyloxy)propoxy]hydroxyphosphinyl]-N,N-dimethyl-ethanaminium, hydroxide, inner salt 2-[[2-(propionyloxy)-3-(pentadecyloxy)propoxy]hydroxyphosphinyl]-N-methyl-ethanaminium, hydroxide, inner salt 2-[[2-(propionyloxy)-3-(pentadecyloxy)propoxy]hydroxyphosphinyl]-N,N-tetramethylene-ethanaminium, hydroxide, inner salt 2-[[2-(propionyloxy)-3-(pentadecyloxy)propoxy]hydroxyphosphinyl]-N,N-diethyl-ethanaminium, hydroxide, inner salt 2-[[2-(propionyloxy)-3-(2-methylhexadecyloxy)propoxy]hydroxyphosphinyl]-N,N,N-trimethyl-ethanaminium, hydroxide, inner salt 2-[[2-(propionyloxy)-3-(2-methylhexadecyloxy)propoxy]hydroxyphosphinyl]-N,N-dimethyl-ethanaminium, hydroxide, inner salt 2-[[2-(propionyloxy)-3-(2-methylhexadecyloxy)propoxy]hydroxyphosphinyl]-N-methyl-ethanaminium, hydroxide, inner salt 2-[[2-(propionyloxy)-3-(2-methylhexadecyloxy)propoxy]hydroxyphosphinyl]-N,N-tetramethylene-ethanaminium, hydroxide, inner salt 2-[[2-(propionyloxy)-3-(3-ethylpentadecyloxy)propoxy]hydroxyphosphinyl]-N,N,N-trimethyl-ethanaminium, hydroxide, inner salt 2-[[2-(propionyloxy)-3-(3-ethylpentadecyloxy)propoxy]hydroxyphosphinyl]-N,N-dimethyl-ethanaminium, hydroxide, inner salt 2-[[2-(propionyloxy)-3-(3-ethylpentadecyloxy)propoxy]hydroxyphosphinyl]-N,N-tetramethylene-ethanaminium, hydroxide, inner salt 2-[[2-(propionyloxy)-3-(3-ethylpentadecyloxy)propoxy]hydroxyphosphinyl]-N,N-diethyl-ethanaminium, hydroxide, inner salt 2-[[2-(propionyloxy)-3-(2,4-dimethylhexadecyloxy)propoxy]hydroxyphosphinyl]-N,N,N-trimethyl-ethanaminine, hydroxide, inner salt 2-[[2-(propionyloxy)-3-(2,4-dimethylhexadecyloxy)propoxy]hydroxyphosphinyl]-N,N-dimethyl-ethanaminium, hydroxide, inner salt 2-[[2-(propionyloxy)-3-(2,4-dimethylhexadecyloxy)propoxy]hydroxyphosphinyl]-N-methyl-ethanaminium, hydroxide, inner salt 2-[[2-(propionyloxy)-3-(2,4-dimethylhexadecyloxy)propoxy]hydroxyphosphinyl]-N,N-diethyl-ethanaminium, hydroxide, inner salt 2-[[2-(butyryloxy)-3-(octadecyloxy)propoxy]hydroxyphosphinyl]-N,N,N-trimethyl-ethanaminium, hydroxide, inner salt 2-[[2-(butyryloxy)-3-(octadeyloxy)propoxy]hydroxyphosphinyl]-N,N-dimethyl-ethanaminium, hydroxide, inner salt 2-[[2-(butyryloxy)-3-(octadeyloxy)propoxy]hydroxyphosphinyl]-N-methyl-ethanaminium, hydroxide, inner salt 2-[[2-(butyryloxy)-3-(octadecyloxy)propoxy]hydroxyphosphinyl]-N,N-tetramethylene-ethanaminium, hydroxide, inner salt 2-[[2-(butyryloxy)-3-(octadecyloxy)propoxy]hydroxyphosphinyl]-N,N-diethyl-ethanaminium, hydroxide, inner salt 2-[[2-(butyryloxy)-3-(nonadecyloxy)propoxy]hydroxyphosphinyl]-N,N,N-trimethyl-ethanaminium, hydroxide, inner salt 2-[[2-(butyryloxy)-3-(nonadecyloxy)propoxy]hydroxyphosphinyl]-N,N-dimethyl-ethanaminium, hydroxide, inner salt 2-[[2-(butyryloxy)-3-(nonadecyloxy)propoxy]hydroxyphosphinyl]-N-methyl-ethanaminium, hydroxide, inner salt 2-[[2-(butyryloxy)-3-(nonadecyloxy)propoxy]hydroxyphosphinyl]-N,N-tetramethylene-ethanaminium, hydroxide, inner salt 2-[[2-(butyryloxy)-3-(nonadecyloxy)propoxy]hydroxyphosphinyl]-N,N-diethyl-ethanaminium, hydroxide, inner salt 2-[[2-(butyryloxy)-3-(heptadecyloxy)propoxy]hydroxyphosphinyl]-N,N,N-trimethyl-ethanaminium, hydroxide, inner salt 2-[[2-(butyryloxy)-3-(heptadecyloxy)propoxy]hydroxyphosphinyl]-N,N-dimethyl-ethanaminium, hydroxide, inner salt 2-[[2-(butyryloxy)-3-(heptadecyloxy)propoxy]hydroxyphosphinyl]-N-methyl-ethanaminium, hydroxide, inner salt 2-[[2-(butyryloxy)-3-(heptadecyloxy)propoxy]hydroxyphosphinyl]-N,N-tetramethylene-ethanaminium, hydroxide, inner salt 2-[[2-(butyryloxy)-3-(heptadecyloxy)propoxy]hydroxyphosphinyl]-N,N-diethyl-ethanaminium, hydroxide, inner salt 2-[[2-(butyryloxy)-3-(hexadecyloxy)propoxy]hydroxyphosphinyl]-N,N,N-trimethyl-ethanaminium, hydroxide, inner salt 2-[[2-(butyryloxy)-3-(hexadecyloxy)propoxy]hydroxyphosphinyl]-N,N-dimethyl-ethanaminium, hydroxide, inner salt 2-[[2-(butyryloxy)-3-(hexadecyloxy)propoxy]hydroxyphosphinyl]-N-methyl-ethanaminium, hydroxide, inner salt 2-[[2-(butyryloxy)-3-(hexadecyloxy)propoxy]hydroxyphosphinyl]-N,N-tetramethylene-ethanaminium, hydroxide, inner salt 2-[[2-(butyryloxy)-3-(hexadecyloxy)propoxy]hydroxyphosphinyl]-N,N-diethyl-ethanaminium, hydroxide, inner salt 2-[[2-(butyryloxy)-3-(pentadecyloxy)propoxy]hydroxyphosphinyl]-N,N,N-trimethyl-ethanaminium, hydroxide, inner salt 2-[[2-(butyryloxy)-3-(pentadecyloxy)propoxy]hydroxyphosphinyl]-N,N-dimethyl-ethanaminium, hydroxide, inner salt 2-[[2-(butyryloxy)-3-(pentadecyloxy)propoxy]hydroxyphosphinyl]-N-methyl-ethanaminium, hydroxide, inner salt 2-[[2-(butyryloxy)-3-(pentadecyloxy)propoxy]hydroxyphosphinyl]-N,N-tetramethylene-ethanaminium, hydroxide, inner salt 2-[[2-(butyryloxy)-3-(pentadecyloxy)propoxy]hydroxyphosphinyl]-N,N-diethyl-ethanaminium, hydroxide, inner salt 2-[[2-(butyryloxy)-3-(2-methylhexadecyloxy)propoxy]hydroxyphosphinyl]-N,N,N-trimethyl-ethanaminium, hydroxide, inner salt 2-[[2-(butyryloxy)-3-(2-methylhexadecyloxy)propoxy]hydroxyphosphinyl]-N,N-dimethyl-ethanaminium, hydroxide, inner salt 2-[[2-(butyryloxy)-3-(2-methylhexadecyloxy)propoxy]hydroxyphosphinyl]-N-methyl-ethanaminium, hydroxide, inner salt 2-[[2-(butyryloxy)-3-(2-methylhexadecyloxy)propoxy]hydroxyphosphinyl]-N,N-tetramethylene-ethanaminium, hydroxide, inner salt 2-[[2-(butyryloxy)-3-(3-ethylpentadecyloxy)propoxy]hydroxyphosphinyl]-N,N,N-trimethyl-ethanaminium, hydroxide, inner salt 2-[[2-(butyryloxy)-3-(3-ethylpentadecyloxy)propoxy]hydroxyphosphinyl]-N,N-dimethyl-ethanaminium, hydroxide, inner salt 2-[[2-(butyryloxy)-3-(3-ethylpentadecyloxy)propoxy]hydroxyphosphinyl]-N,N-tetramethylene-ethanaminium, hydroxide, inner salt 2-[[2-(butyryloxy)-3-(3-ethylpentadecyloxy)propoxy]hydroxyphosphinyl]-N,N-diethyl-ethanaminium, hydroxide, inner salt 2-[[2-(butyryloxy)-3-(2,4-dimethylhexadecyloxy)propoxy]hydroxyphosphinyl]-N,N,N-trimethyl-ethanaminium, hydroxide, inner salt 2-[[2-(butyryloxy)-3-(2,4-dimethylhexadecyloxy)propoxy]hydroxyphosphinyl]-N,N-dimethyl-ethanaminium, hydroxide, inner salt 2-[[2-(butyryloxy)-3-(2,4-dimethylhexadecyloxy)propoxy]hydroxyphosphinyl]-N-methyl-ethanaminium, hydroxide, inner salt 2-[[2-(butyryloxy)-3-(2,4-dimethylhexadecyloxy)propoxy]hydroxyphosphinyl]-N,N-diethyl-ethanaminium, hydroxide, inner salt 3-[[2-(acetyloxy)-3-(octadeyloxy)propoxy]hydroxyphosphinyl]-N,N,N-trimethyl-proanaminium, hydroxide, inner salt 3-[[2-(acetyloxy)-3-(octadeyloxy)propoxy]hydroxyphosphinyl]-N,N-dimethyl-proanaminium, hydroxide, inner salt 3-[[2-(acetyloxy)-3-(octadeyloxy)propoxy]hydroxyphosphinyl]-N-methyl-proanaminium, hydroxide, inner salt 3-[[2-(acetyloxy)-3-(octadeyloxy)propoxy]hydroxyphosphinyl]-N,N-tetramethylene-proanaminium, hydroxide, inner salt 3-[[2-(acetyloxy)-3-(pentadecyloxy)propoxy]hydroxyphosphinyl]-N,N,N-trimethyl-proanaminium, hydroxide, inner salt 3-[[2-(acetyloxy)-3-(pentadecyloxy)propoxy]hydroxyphosphinyl]-N,N-dimethyl-proanaminium, hydroxide, inner salt 3-[[2-(acetyloxy)-3-(pentadecyloxy)propoxy]hydroxyphosphinyl]-N-methyl-proanaminium, hydroxide, inner salt 3-[[2-(acetyloxy)-3-(pentadecyloxy)propoxy]hydroxyphosphinyl]-N,N-tetramethylene-proanaminium, hydroxide, inner salt 3-[[2-(acetyloxy)-3-(2-methylhexadecyloxy)propoxy]hydroxyphosphinyl]-N,N,N-trimethyl-proanaminium, hydroxide, inner salt 3-[[2-(acetyloxy)-3-(2-methylhexadecyloxy)propoxy]hydroxyphosphinyl]-N,N-dimethyl-proanaminium, hydroxide, inner salt 3-[[2-(acetyloxy)-3-(2-methylhexadecyloxy)propoxy]hydroxyphosphinyl]-N-methyl-proanaminium, hydroxide, inner salt 3-[[2-(acetyloxy)-3-(2-methylhexadecyloxy)propoxy]hydroxyphosphinyl]-N,N-tetramethylene-proanaminium, hydroxide, inner salt 3-[[2-(propionyloxy)-3-(octadecyloxy)propoxy]hydroxyphosphinyl]-N,N,N-trimethyl-proanaminium, hydroxide, inner salt 3-[[2-(propionyloxy)-3-(octadeyloxy)propoxy]hydroxyphosphinyl]-N,N-dimethyl-proanaminium, hydroxide, inner salt 3-[[2-(propionyloxy)-3-(octadeyloxy)propoxy]hydroxyphosphinyl]-N-methyl-proanaminium, hydroxide, inner salt 3-[[2-(propionyloxy)-3-(octadeyloxy)propoxy]hydroxyphosphinyl]-N,N-tetramethylene-proanaminium, hydroxide, inner salt 3-[[2-(propionyloxy)-3-(pentadecyloxy)propoxy]hydroxyphosphinyl]-N,N,N-trimethyl-proanaminium, hydroxide, inner salt 3-[[2-(propionyloxy)-3-(pentadecyloxy)propoxy]hydroxyphosphinyl]-N,N-dimethyl-proanaminium, hydroxide, inner salt 3-[[2-(propionyloxy)-3-(pentadecyloxy)propoxy]hydroxyphosphinyl]-N-methyl-proanaminium, hydroxide, inner salt 3-[[2-(propionyloxy)-3-(pentadecyloxy)propoxy]hydroxyphosphinyl]-N,N-tetramethylene-proanaminium, hydroxide, inner salt 3-[[2-(propionyloxy)-3-(2-methylhexadecyloxy)propoxy]hydroxyphosphinyl]-N,N,N-trimethyl-proanaminium, hydroxide, inner salt 3-[[2-(propionyloxy)-3-(2-methylhexadecyloxy)propoxy]hydroxyphosphinyl]-N,N-dimethyl-proanaminium, hydroxide, inner salt 3-[[2-(propionyloxy)-3-(2-methylhexadecyloxy)propoxy]hydroxyphosphinyl]-N-methyl-proanaminium, hydroxide, inner salt 3-[[2-(propionyloxy)-3-(2-methylhexadecyloxy)propoxy]hydroxyphosphinyl]-N,N-tetramethylene-proanaminium, hydroxide, inner salt 4-[[2-(acetyloxy)-3-(octadeyloxy)propoxy]hydroxyphosphinyl]-N,N,N-trimethyl-butanaminium, hydroxide, inner salt 4-[[2-(acetyloxy)-3-(octadeyloxy)propoxy]hydroxyphosphinyl]-N,N-dimethyl-butanaminium, hydroxide, inner salt 4-[[2-(acetyloxy)-3-(octadeyloxy)propoxy]hydroxyphosphinyl]-N-methyl-butanaminium, hydroxide, inner salt 4-[[2-(acetyloxy)-3-(octadeyloxy)propoxy]hydroxyphosphinyl]-N,N-diethyl-butanaminium, hydroxide, inner salt 4-[[2-(acetyloxy)-3-(heptadecyloxy)propoxy]hydroxyphosphinyl]-N,N,N-trimethyl-butanaminium, hydroxide, inner salt 4-[[2-(acetyloxy)-3-(heptadecyloxy)propoxy]hydroxyphosphinyl]-N,N-dimethyl-butanaminium, hydroxide, inner salt 4-[[2-(acetyloxy)-3-(heptadecyloxy)propoxy]hydroxyphosphinyl]-N-methyl-butanaminium, hydroxide, inner salt 4-[[2-(acetyloxy)-3-(heptadecyloxy)propoxy]hydroxy-
phosphinyl]-N,N-diethyl-butanaminium, hydroxide,
inner salt 4-[[2-(acetyloxy)-3-(hexadecyloxy)propoxy]hydroxy-
phosphinyl]-N,N,N-trimethyl-butanaminium, hydroxide, inner salt 4-[[2-(acetyloxy)-3-(hexadecyloxy)propoxy]hydroxy-
phosphinyl]-N,N-dimethyl-butanaminium, hydroxide, inner salt 4-[[2-(acetyloxy)-3-(hexadecyloxy)propoxy]hydroxy-
phosphinyl]-N-methyl-butanaminium, hydroxide, inner salt 4-[[2-(acetyloxy)-3-(hexadecyloxy)propoxy]hydroxy-
phosphinyl]-N,N-diethyl-butanaminium, hydroxide, inner salt 4-[[2-(acetyloxy)-3-(2-methylhexadecyloxy)propoxy]-
hydroxyphosphinyl]-N,N,N-trimethyl-
butanaminium, hydroxide, inner salt

EXAMPLE 50

4-Hydroxy-N,N,-dimethyl-7-(benzyloxy)-3,5,9-trioxa-
4-phosphaheptacosan-1-aminium, 4-oxide, hydroxide,
inner salt To a mixture of about 5.0 g of 2-bromoethyl 2-(benzyloxy)-3-(octadecyloxy)propyl phosphate in about 130 ml of a mixture of chloroform:2-propanol:dimethylformamide (about 3:5:5) was added about 85 ml of about 40% dimethylamine. This solution was stirred at about 55° C. for about 6 hours and then at room temperature for about 66 hours. The mixture was taken to dryness, then evaporated three time with toluene, giving a glass. This glass was dissolved in chloroform and chromatographed on a silica gel column, developing with chloroform and collecting about 50 ml fractions. Fractions 6–9 were combined, and evaporated, giving about 4.7 g of the desired title compound.

EXAMPLE 51

4,7-dihydroxy-N,N-dimethyl-3,5,9-trioxa-4-phosphaheptacosan-1-aminium, 4-oxide, hydroxide, inner salt An about 4.2 g portion of 4-hydroxy-N,N-dimethyl-7-(benzyloxy)-3,5,9-trioxa-4-phosphaheptacosan-1-aminium, 4-oxide, hydroxide, inner salt was added to a Parr bottle containing about 0.402 g of about 5% palladium on carbon, about 26 ml of glacial acetic acid and about 26 ml of methanol. This mixture was hydrogenated at an initial pressure of about 24 psi for about 18 hours. The mixture was filtered through celite, washed with methanol, the mother liquor taken to dryness and evaporated twice from toluene. The solid was triturated with ether and dried, giving about 3.2 g of the desired title compound as a white solid.

EXAMPLE 52

4-Hydroxy-N,N-dimethyl-7-(acetyloxy)-3,5,9-trioxa-4-phosphaheptacosan-1-aminium, 4-oxide, hydroxide, inner salt An about 0.4 g portion of 4,7-dihydroxy-N,N-dimethyl-3,5,9-trioxa-4-phosphaheptacosan-1-aminium, 4-oxide, hydroxide, inner salt in about 4 ml of acetic anhydride was heated to about 75° C. for several hours, then heated at about 80° C. overnight. The solution was cooled, flooded with ether and the solid collected, giving about 160 mg of the desired product as a white solid.

EXAMPLE 53

4-Hydroxy-N,N-trimethylene-7-(benzyloxy)-3,5,9-trioxa-4-phosphaheptacosan-1-aminium, 4-oxide,
hydroxide inner salt To a mixture of about 5.0 g of 2-bromoethyl-2-(benzyloxy)-3-(octadecyloxy)propyl phosphate in about 130 ml of a mixture of chloroform:2-propanol:dimethylformamide (about 3:5:5) was added about 85 ml of about 40% pyrrolidine in water. The mixture was stirred at about 55° C. for about 6 hours, allowed to stand at room temperature overnight, most of the solvents were removed and the residue was evaporated with toluene. This residue was dissolved in chloroform, chromatographed on a wet column of silica gel and eluted first with chloroform, then with about 10% methanol in chloroform, collecting about 50 ml fractions. Fractions 5–10 were combined and evaporated, giving about 4.53 g of the desired title compound as a solid.

EXAMPLE 54

4,7-Dihydroxy-N,N-trimethylene-3,5,9-trioxa-4-phosphaheptacosan-1-aminium, 4-oxide, hydroxide inner salt An about 4.1 g portion of 4-hydroxy-N,N-trimethylene-7-(benzyloxy)-3,5,9-trioxa-4-phosphaheptacosan-1-aminium, 4-oxide, hydroxide, inner salt was added to a Parr bottle containing about 0.4 g of about 5% palladium on carbon, about 25 ml of glacial acetic acid and about 25 ml of methanol. This mixture was hydrogenated at an initial pressure of about 25 psi for about 18 hours. The mixture was then filtered through celite, washed with methanol, the mother liquor taken to dryness and evaporated twice from toluene. The solid was triturated with ether and dried, giving about 2.02 g of the desired title compound as a solid.

EXAMPLE 55

Ethyl 4-tetradecyloxybenzoate

To a stirred mixture of about 39.7 g of about 50% sodium hydride, about 13.5 g of sodium iodide and about 208.58 g of tetradecylbromide in about 750 ml of dimethylformamide at about 0° C. was added a solution of about 125 g of ethyl p-hydroxybenzoate in about 400 ml of dimethylformamide over about ½ hour. The mixture was stirred at room temperature for about 67 hours and then poured into about 2 liters of water. The solid was collected, washed with water, mixed with hot (about 50° C.) ethyl acetate, washed with water and dried. The solvent was removed and the residue recrystallized from ethanol, giving about 144.57 g of the desired title compound, mp 34°–35° C.

EXAMPLE 56

4-(Tetradecyloxy) benzyl alcohol

To about 13.61 g of lithium aluminum hydride in about 200 ml of tetrahydrofuran was added, over about ½ hour, a solution of about 130 g of 4-tetradecyloxybenzoate in about 400 ml of tetrahydrofuran, in an ice bath with stirring and maintaining the temperature below about 40° C. After stirring about 2 hours the mixture was cooled to about 0° C., about 9 ml of water was added dropwise followed by the dropwise addition of about 18 ml of about 15% sodium hydroxide and about 30 ml of water. This mixture was filtered through celite, the solvent was removed and the residue recrystallized from ethanol, giving about 94.5 g of the desired title compound as a white solid, mp 75°–76° C.

EXAMPLE 57

1-(Bromomethyl)-4-(tetradecyloxy)benzene

Hydrogen bromide was bubbled into about 400 ml of chloroform for about 5 minutes, then about 40 g of 4-(tetradecyloxy)benzyl alcohol was added and hydrogen bromide was bubbled in for about 3 more minutes. After stirring for about one hour the solution was washed with saturated sodium bicarbonate, dried and the solvent removed. The residue was recrystallized from petroleum ether at about −30° C., giving the desired title compound, mp 54°–55° C.

As described hereinabove in Examples 55–57, the hydroxy esters listed in Table IV are alkylated with the indicated alkyl halides. Reduction with lithium aluminum hydride followed by treatment of the resulting alcohol with either hydrogen bromide in chloroform or phosphorous tribromide in chloroform gives the bromides of Table IV needed to prepare some of the compounds of this invention.

TABLE IV

| Hydroxy Ester | Alkyl Halide | Bromide |
| --- | --- | --- |
| ethyl p-hydroxybenzoate | 1-dodecylbromide | 1-(bromomethyl)-4-(dodecyloxy)-benzene |
| ethyl m-hydroxybenzoate | 1-tridecylbromide | 1-(bromomethyl)-3-(tridecyloxy)-benzene |
| ethyl o-hydroxybenzoate | 1-octadecylbromide | 1-(bromomethyl)-2-(octadecyloxy)-benzene |
| ethyl p-hydroxyphenylacetate | 1-undecylbromide | 2-[4-(undecyloxy)phenyl]ethyl-bromide |
| ethyl 3-(p-hydroxyphenyl)propionate | 1-dodecylbromide | 1-bromo-2-[4-(dodecyloxy)phenyl]-propane |

EXAMPLE 58

Ethyl levulinate ethylene ketal

A mixture of about 110.86 g of ethylene glycol, about 2 g of p-toluenesulfonic acid and about 800 ml of toluene was refluxed using a Dean-Stark trap until no more water came off. An about 250 g portion of ethyl levulinate was added and refluxing was continued until no more water came off. The mixture was then cooled to room temperature, poured into saturated sodium bicarbonate, the organic layer dried and the solvent removed. The residue was distilled (about 67°–70° C., 0.35 mm) and the distillate stirred for about 20 minutes with about 6 g of sodium borohydride in ethanol. The solvent was removed, the residue dissolved in ether, washed with saturated sodium bicarbonate, dried and then distilled (about 41°–45° C., 0.3 mm), giving about 83 g of the desired title compound.

As described hereinabove in Example 58, ethyl 4-oxo-hexanoate and ethyl 4-oxo-heptanoate are converted to ethyl 4-oxo-hexanoate ethylene ketal and ethyl 4-oxo-heptanoate ethylene ketal, respectively.

EXAMPLE 59

2-Methyl-α-[[4-(tetradecyloxy)phenyl]methyl]-1,3-dioxolane-2-propanoic acid, ethyl ester A mixture of about 33 g of 1-(bromomethyl)-4-(tetradecyloxy)benzene, about 16.2 g of ethyl levulinate ethylene ketal, about 4.54 g of about 50% sodium hydride and about 350 ml of tetrahydrofuran was refluxed with stirring, under argon for about 18 hours and then filtered through celite. The solvent was removed and the residue was dissolved in ether. The ether solution was washed with aqueous monobasic sodium phosphate, dried and the solvent removed. The residue was subjected to high performance liquid chromatography (HPLC), using the system hexane:ethyl acetate (about 9:1), giving about 22.1 g of the desired title compound as a light yellow oil).

EXAMPLE 60

2-Methyl-β-[[4-(tetradecyloxy)phenyl]methyl]-1,3-dioxolane-2-propanol

To a suspension of about 2.38 g of lithium aluminum hydride in about 40 ml of ether was added dropwise, over about ½ hour, a solution of about 20.5 g of 2-methyl-α-[[4-(tetradecyloxy)phenyl]methyl]-1,3-dioxolane-2-propanoic acid, ethyl ester in about 70 ml of ether at about 0° C. The mixture was stirred about ½ hour at room temperature, recooled to about 0° C. and about 10 ml of ethyl acetate, about one ml of water, about 2 ml of about 15% sodium hydroxide and about 3 ml of water were added dropwise. The mixture was filtered through celite, the solids were washed with ether and the ether removed from the combined solutions, which was then purified by HPLC, using the system hexane:ethyl acetate (about 3:7), giving a colorless oil which solidified on standing, giving about 15.28 g of the desired title compound, mp 28°–29° C.

EXAMPLE 61

4-(Hydroxymethyl)-5-[4-(tetradecyloxy)phenyl]-2-pentanone

A mixture of about 12.0 g of 2-methyl-β-[[4-(tetradecyloxy)phenyl]methyl]-1,3-dioxolane-2-propanol, about 50 ml of about 1N hydrochloric acid and about 300 ml of dioxane was stirred for about 3 hours. The dioxane was then removed, the residue diluted with water and extracted with ether. The ether extract was washed with saturated aqueous sodium bicarbonate, dried and the solvent removed, giving an oil, which crystallized on standing, giving about 10.5 g of the desired title compound.

EXAMPLE 62

2-Bromoethyl 4-oxo-2-[[4-tetradecyloxy)phenyl]methyl]pentyl phosphate

A mixture of about 11 g of 4-(hydroxymethyl)-5-[4-(tetradecyloxy)phenyl]-2-pentanone, about 13.81 g of 2-bromoethyl phosphorodichlorodate, about 5.78 g of triethylamine and about 200 ml of carbon tetrachloride was stirred overnight, filtered through celite and the solvent removed. The residue was stirred in a mixture of about 300 ml of about 0.5N sodium acetate and about 300 ml of tetrahydrofuran for about 4 hours, the tetrahydrofuran was removed, the mixture acidified with hydrochloric acid and extracted with ether. The ether extract was dried, the solvent removed and the residue chromatographed on florisil, using chloroform as initial elutant and then chloroform:methanol to elute the product. This product was dissolved in ether, filtered, concentrated and diluted with hexane, giving about 3.5 g of the desired title compound as a light yellow glassy solid.

EXAMPLE 63

2-[[Hydroxy[[4-oxo-2-[[4-(tetradecyloxy)phenyl]methyl]pentyl]oxy]phosphinyl]oxy]-N,N,N-trimethylethanaminium, hydroxide, inner salt A mixture of about 5.0 g of 2-bromoethyl 4-oxo-2-[[4-tetradecyloxy)phenyl]methyl]pentyl phosphate, about 150 ml of a mixture of chloroform:1-propanol:dimethylformamide (about 3:5:5) and about 250 ml of about 40% trimethylamine was stirred at about 60° C. for about 5 hours and then at room temperature for about 12 hours. The solution was then concentrated to about ½ volume and about 1.4 g of silver carbonate were added. The mixture was stirred about ½ hour, filtered through celite, ethanol was added to the filtrate and the solvent was removed. The residue was chromatographed on a wet column of silica gel eluting with chloroform:methanol (about 7:3) then (about 1:1) and finally (about 3:7) to elute the product. The product was dissolved in chloroform, filtered, concentrated and diluted with ether, giving about 3.5 g of the desired product as a solid.

By using the phosphorous reagents listed in Table VII, the amines of Table VIII, the appropriate bromo compounds prepared in Example 57 and listed in Table IV, and the appropriate ketal esters prepared in Example 58 and listed immediately below Example 58 and by following the methods described in detail hereinabove in Examples 59-63, the compounds of this invention listed below can be prepared. These compounds can be prepared as the individual optically active R and S enantiomers or as racemic mixtures as described in the above specifications.

2-[[hydroxy[[4-oxo-2-[[4-(tetradecyloxy)phenyl]methyl]pentyl]oxy]phosphinyl]oxy]-N,N,N-trimethylethanaminium, hydroxide, inner salt 2-[[hydroxy[[4-oxo-2-[[4-(tetradecyloxy)phenyl]methyl]pentyl]oxy]phosphinyl]oxy]-N,N-dimethylethanaminium, hydroxide, inner salt 2-[[hydroxy[[4-oxo-2-[[4-(tetradecyloxy)phenyl]methyl]pentyl]oxy]phosphinyl]oxy]-N-methylethanaminium, hydroxide, inner salt 2-[[hydroxy[[4-oxo-2-[[4-(tetradecyloxy)phenyl]methyl]pentyl]oxy]phosphinyl[oxy]-N,N-dimethyl-N-ethyl-ethanaminium, hydroxide, inner salt 2-[[hydroxy[[4-oxo-2-[[4-(tetradecyloxy)phenyl]methyl]hexyl]oxy]phosphinyl]oxy]-N,N,N-trimethylethanaminium, hydroxide, inner salt 2-[[hydroxy[[4-oxo-2-[[4-(tetradecyloxy)phenyl]methyl]hexyl]oxy]phosphinyl]oxy]-N,N-dimethylethanaminium, hydroxide, inner salt 2-[[hydroxy[[4-oxo-2-[[4-(tetradecyloxy)phenyl]methyl]hexyl]oxy]phosphinyl]oxy]-N-methylethanaminium, hydroxide, inner salt 2-[[hydroxy[[4-oxo-2-[[4-(tetradecyloxy)phenyl]methyl]hexyl]oxy]phosphinyl]oxy]-N,N-dimethyl-N-ethyl-ethanaminium, hydroxide, inner salt 2-[[hydroxy[[4-oxo-2-[[4-(tetradecyloxy)phenyl]methyl]heptyl]oxy]phosphinyl]oxy]-N,N,N-trimethylethanaminium, hydroxide, inner salt 2-[[hydroxy[[4-oxo-2-[[4-(tetradecyloxy)phenyl]methyl]heptyl]oxy]phosphinyl]oxy]-N,N-dimethylethanaminium, hydroxide, inner salt 2-[[hydroxy[[4-oxo-2-[[4-(tetradecyloxy)phenyl]methyl]heptyl]oxy]phosphinyl]oxy]N-methyl-ethanaminium, hydroxide, inner salt 2-[[hydroxy[[4-oxo-2-[[4-(tetradecyloxy)phenyl]methyl]heptyl]oxy]phosphinyl]oxy]-N,N-dimethyl-N-ethyl-ethanaminium, hydroxide, inner salt 2-[[hydroxy[[4-oxo-2-[[3-(tridecyloxy)phenyl]methyl]pentyl]oxy]phosphinyl]oxy]-N,N,N-trimethylethanaminium, hydroxide, inner salt 2-[[hydroxy[[4-oxo-2-[[3-(tridecyloxy)phenyl]methyl]pentyl]oxy]phosphinyl]oxy]-N,N-dimethylethanaminium, hydroxide, inner salt 2-[[hydroxy[[4-oxo-2-[[3-(tridecyloxy)phenyl]methyl]pentyl]oxy]phosphinyl]oxy]-N-methylethanaminium, hydroxide, inner salt 2-[[hydroxy[[4-oxo-2-[[3-(tridecyloxy)phenyl]methyl]pentyl]oxy]phosphinyl]oxy]-N,N-dimethyl-N-ethyl-ethanaminium, hydroxide, inner salt 2-[[hydroxy[[4-oxo-2-[[3-(tridecyloxy)phenyl]methyl]hexyl]oxy]phosphinyl]oxy]-N,N,N-trimethylethanaminium, hydroxide, inner salt 2-[[hydroxy[[4-oxo-2-[[3-(tridecyloxy)phenyl]methyl]hexyl]oxy]phosphinyl]oxy]-N,N-dimethylethanaminium, hydroxide, inner salt 2-[[hydroxy[[4-oxo-2-[[3-(tridecyloxy)phenyl]methyl]hexyl]oxy]phosphinyl]oxy]-N-methyl-ethanaminium, hydroxide, inner salt 2-[[hydroxy[[4-oxo-2-[[3-(tridecyloxy)phenyl]methyl]hexyl]oxy]phosphinyl]oxy]-N,N-dimethyl-N-ethyl-ethanaminium, hydroxide, inner salt 2-[[hydroxy[[4-oxo-2-[[3-(tridecyloxy)phenyl]methyl]heptyl]oxy]phosphinyl]oxy]-N,N,N-trimethylethanaminium, hydroxide, inner salt 2-[[hydroxy[[4-oxo-2-[[3-(tridecyloxy)phenyl]methyl]heptyl]oxy]phosphinyl]oxy]-N,N-dimethylethanaminium, hydroxide, inner salt 2-[[hydroxy[[4-oxo-2-[[3-(tridecyloxy)phenyl]methyl]heptyl]oxy]phosphinyl]oxy]-N-methylethanaminium, hydroxide, inner salt 2-[[hydroxy[[4-oxo-2-[[3-(tridecyloxy)phenyl]methyl]heptyl]oxy]phosphinyl]oxy]-N,N-dimethyl-N-ethyl-ethanaminium, hydroxide, inner salt 2-[[hydroxy[[4-oxo-2-[[2-(octadecyloxy)phenyl]methyl]pentyl]oxy]phosphinyl]oxy]-N,N,N-trimethylethanaminium, hydroxide, inner salt 2-[[hydroxy[[4-oxo-2-[[2-(octadecyloxy)phenyl]methyl]pentyl]oxy]phosphinyl]oxy]-N,N-dimethylethanaminium, hydroxide, inner salt 2-[[hydroxy[[4-oxo-2-[[2-(octadecyloxy)phenyl]methyl]pentyl]oxy]phosphinyl]oxy-N-methylethanaminium, hydroxide, inner salt 2-[[hydroxy[[4-oxo-2-[[2-(octadecyloxy)phenyl]methyl]pentyl]oxy]phosphinyl]oxy-N,N-dimethyl-N-ethyl-ethanaminium, hydroxide, inner salt 2-[[hydroxy[[4-oxo-2-[[2-(octadecyloxy)phenyl]methyl]hexyl]oxy]phosphinyl]oxy]-N,N,N-trimethylethanaminium, hydroxide, inner salt 2-[[hydroxy[[4-oxo-2-[[2-(octadecyloxy)phenyl]methyl]hexyl]oxy]phosphinyl]oxy]-N,N-dimethylethanaminium, hydroxide, inner salt 2-[[hydroxy[[4-oxo-2-[[2-(octadecyloxy)phenyl]methyl]hexyl]oxy]phosphinyl]oxy]-N-methylethanaminium, hydroxide, inner salt 2-[[hydroxy[[4-oxo-2-[[2-(octadecyloxy)phenyl]methyl]hexyl]oxy]phosphinyl]oxy]-N,N-dimethyl-N-ethyl-ethanaminium, hydroxide, inner salt
2-[[hydroxy[[4-oxo-2-[[2-(octadecyloxy)phenyl]methyl]heptyl]oxy]phosphinyl]oxy]-N,N,N-trimethyl-ethanaminium, hydroxide, inner salt
2-[[hydroxy[[4-oxo-2-[[2-(octadecyloxy)phenyl]methyl]heptyl]oxy]phosphinyl]oxy]-N,N-dimethyl-ethanaminium, hydroxide, inner salt
2-[[hydroxy[[4-oxo-2-[[2-(octadecyloxy)phenyl]methyl]heptyl]oxy]phosphinyl]oxy]-N-methyl-ethanaminium, hydroxide, inner salt
2-[[hydroxy[[4-oxo-2-[[2-(octadecyloxy)phenyl]methyl]heptyl]oxy]phosphinyl]oxy]-N,N-dimethyl-N-ethyl-ethanaminium, hydroxide, inner salt
2-[[hydroxy[[4-oxo-2-[[4-(dodecyloxy)phenyl]methyl]pentyl]oxy;9 phosphinyl]oxy]-N,N,N-trimethyl-ethanaminium, hydroxide, inner salt
2-[[hydroxy[[4-oxo-2-[[4-(dodecyloxy)phenyl]methyl]pentyl]oxy]phosphinyl]oxy]-N,N-dimethyl-ethanaminium, hydroxide, inner salt
2-[[hydroxy[[4-oxo-2-[[4-(dodecyloxy)phenyl]methyl]pentyl]oxy]phosphinyl]oxy]-N-methyl-ethanaminium, hydroxide, inner salt
2-[[hydroxy[[4-oxo-2-[[4-(dodecyloxy)phenyl]methyl]pentyl]oxy]phosphinyl]oxy]-N,N-dimethyl-N-ethyl-ethanaminium, hydroxide, inner salt
2-[[hydroxy[[4-oxo-2-[[4-(dodecyloxy)phenyl]methyl]hexyl]oxy]phosphinyl]oxy]-N,N,N-trimethyl-ethanaminium, hydroxide, inner salt
2-[[hydroxy[[4-oxo-2-[[4-(dodecyloxy)phenyl]methyl]hexyl]oxy]phosphinyl]oxy]-N,N-dimethyl-ethanaminium, hydroxide, inner salt
2-[[hydroxy[[4-oxo-2-[[4-(dodecyloxy)phenyl]methyl]hexyl]oxy]phosphinyl]oxy]-N-methyl-ethanaminium, hydroxide, inner salt
2-[[hydroxy[[4-oxo-2-[[4-(dodecyloxy)phenyl]methyl]hexyl]oxy]phosphinyl]oxy]-N,N-dimethyl-N-ethyl-ethanaminium, hydroxide, inner salt
2-[[hydroxy[[4-oxo-2-[[4-(dodecyloxy)phenyl]methyl]heptyl]oxy]phosphinyl]oxy]-N,N,N-trimethyl-ethanaminium, hydroxide, inner salt
2-[[hydroxy[[4-oxo-2-[[4-(dodecyloxy)phenyl]methyl]heptyl]oxy]phosphinyl]oxy]-N,N-dimethyl-ethanaminium, hydroxide, inner salt
2-[[hydroxy[[4-oxo-2-[[4-(dodecyloxy)phenyl]methyl]heptyl]oxy]phosphinyl]oxy]-N-methyl-ethanaminium, hydroxide, inner salt
2-[[hydroxy[[4-oxo-2-[[4-(dodecyloxy)phenyl]methyl]heptyl]oxy]phosphinyl]oxy]-N,N-dimethyl-N-ethyl-ethanaminium, hydroxide, inner salt
2-[[hydroxy[[4-oxo-2-[2-[4-(undecyloxy)phenyl]ethyl]pentyl]oxy]phosphinyl]oxy]-N,N,N-trimethyl-ethanaminium, hydroxide, inner salt
2-[[hydroxy[[4-oxo-2-[2-[4-(undecyloxy)phenyl]ethyl]pentyl]oxy]phosphinyl]oxy]-N,N-dimethyl-ethanaminium, hydroxide, inner salt
2-[[hydroxy[[4-oxo-2-[2-[4-(undecyloxy)phenyl]ethyl]pentyl]oxy]phosphinyl]oxy]-N-methyl-ethanaminium, hydroxide, inner salt
2-[[hydroxy[[4-oxo-2-[2-[4-(undecyloxy)phenyl]ethyl]pentyl]oxy]phosphinyl]oxy]-N,N-dimethyl-N-ethyl-ethanaminium, hydroxide, inner salt
2-[[hydroxy[[4-oxo-2-[2-[4-(undecyloxy)phenyl]ethyl]hexyl]oxy]phosphinyl]oxy]-N,N,N-trimethyl-ethanaminium, hydroxide, inner salt
2-[[hydroxy[[4-oxo-2-[2-[4-(undecyloxy)phenyl]ethyl]hexyl]oxy]phosphinyl]oxy]-N,N-dimethyl-ethanaminium, hydroxide, inner salt
2-[[hydroxy[[4-oxo-2-[2-[4-(undecyloxy)phenyl]ethyl]hexyl]oxy]phosphinyl]oxy]-N-methyl-ethanaminium, hydroxide, inner salt
2-[[hydroxy[[4-oxo-2-[2-[4-(undecyloxy)phenyl]ethyl]hexyl]oxy]phosphinyl]oxy]-N,N-dimethyl-N-ethyl-ethanaminium, hydroxide, inner salt
2-[[hydroxy[[4-oxo-2-[2-[4-(undecyloxy)phenyl]ethyl]heptyl]oxy]phosphinyl]oxy]-N,N,N-trimethyl-ethanaminium, hydroxide, inner salt
2-[[hydroxy[[4-oxo-2-[2-[4-(undecyloxy)phenyl]ethyl]heptyl]oxy]phosphinyl]oxy]-N,N-dimethyl-ethanaminium, hydroxide, inner salt
2-[[hydroxy[[4-oxo-2-[2-[4-(undecyloxy)phenyl]ethyl]heptyl]oxy]phosphinyl]oxy]-N-methyl-ethanaminium, hydroxide, inner salt
2-[[hydroxy[[4-oxo-2-[2-[4-(undecyloxy)phenyl]ethyl]heptyl]oxy]phosphinyl]oxy]-N,N-dimethyl-N-ethyl-ethanaminium, hydroxide, inner salt
2-[[hydroxy[[4-oxo-2-[3-[4-(dodecyloxy)phenyl]propyl]pentyl]oxy]phosphinyl]oxy]-N,N,N-trimethyl-ethanaminium, hydroxide, inner salt
2-[[hydroxy[[4-oxo-2-[3-[4-(dodecyloxy)phenyl]propyl]pentyl]oxy]phosphinyl]oxy]-N,N-dimethyl-ethanaminium, hydroxide, inner salt
2-[[hydroxy[[4-oxo-2-[3-[4-(dodecyloxy)phenyl]propyl]pentyl]oxy]phosphinyl]oxy]-N-methyl-ethanaminium, hydroxide, inner salt
2-[[hydroxy[[4-oxo-2-[3-[4-(dodecyloxy)phenyl]propyl]pentyl]oxy]phosphinyl]oxy]-N,N-dimethyl-N-ethyl-ethanaminium, hydroxide, inner salt
2-[[hydroxy[[4-oxo-2-[3-[4-(dodecyloxy)phenyl]propyl]hexyl]oxy]phosphinyl]oxy]-N,N,N-trimethyl-ethanaminium, hydroxide, inner salt
2-[[hydroxy[[4-oxo-2-[3-[4-(dodecyloxy)phenyl]propyl]hexyl]oxy]phosphinyl]oxy]-N,N-dimethyl-ethanaminium, hydroxide, inner salt
2-[[hydroxy[[4-oxo-2-[3-[4-(dodecyloxy)phenyl]hexyl]oxy]phosphinyl]oxy]-N-methyl-ethanaminium, hydroxide, inner salt
2-[[hydroxy[[4-oxo-2-[3-[4-(dodecyloxy)phenyl]propyl]hexyl]oxy]phosphinyl]oxy]-N,N-dimethyl-N-ethyl-ethanaminium, hydroxide, inner salt
2-[[hydroxy[[4-oxo-2-[3-[4-(dodecyloxy)phenyl]propyl]heptyl]oxy]phosphinyl]oxy]-N,N,N-trimethyl-ethanaminium, hydroxide, inner salt
2-[[hydroxy[[4-oxo-2-[3-[4-(dodecyloxy)phenyl]propyl]heptyl]oxy]phosphinyl]oxy]-N,N-dimethyl-ethanaminium, hydroxide, inner salt
2-[[hydroxy[[4-oxo-2-[3-[4-(dodecyloxy)phenyl]propyl]heptyl]oxy]phosphinyl]oxy]-N-methyl-ethanaminium, hydroxide, inner salt
2-[[hydroxy[[4-oxo-2-[3-[4-(dodecyloxy)phenyl]propyl]heptyl]oxy]phosphinyl]oxy]-N,N-dimethyl-N-ethyl-ethanaminium, hydroxide, inner salt
3-[[hydroxy[[4-oxo-2-[[4-(tetradecyloxy)phenyl]methyl]pentyl]oxy]phosphinyl]oxy]-N,N,N-trimethyl-propanaminium, hydroxide, inner salt
3-[[hydroxy[[4-oxo-2-[[4-(tetradecyloxy)phenyl]methyl]pentyl]oxy]phosphinyl]oxy]-N,N-dimethyl-propanaminium, hydroxide, inner salt
3-[[hydroxy[[4-oxo-2-[[4-(tetradecyloxy)phenyl]methyl]pentyl]oxy]phosphinyl]oxy]-N-methyl-propanaminium, hydroxide, inner salt 3-[[hydroxy[[4-oxo-2-[[4-(tetradecyloxy)phenyl]methyl]pentyl]oxy]phosphinyl]oxy]-N,N-dimethyl-N-ethyl-propanaminium, hydroxide, inner salt 3-[[hydroxy[[4-oxo-2-[[4-(tetradecyloxy)phenyl]methyl]hexyl]oxy]phosphinyl]oxy]-N,N,N-trimethyl-propanaminium, hydroxide, inner salt 3-[[hydroxy[[4-oxo-2-[[4-(tetradecyloxy)phenyl]methyl]hexyl]oxy]phosphinyl]oxy]-N,N-dimethyl-propanaminium, hydroxide, inner salt 3-[[hydroxy[[4-oxo-2-[[4-(tetradecyloxy)phenyl]methyl]hexyl]oxy]phosphinyl]oxy]-N-methyl-propanaminium, hydroxide, inner salt 3-[[hydroxy[[4-oxo-2-[[4-(tetradecyloxy)phenyl]methyl]hexyl]oxy]phosphinyl]oxy]-N,N-dimethyl-N-ethyl-propanaminium, hydroxide, inner salt 3-[[hydroxy[[4-oxo-2[[4-(tetradecyloxy)phenyl]methyl]heptyl]oxy]phosphinyl]oxy]-N,N,N-trimethyl-propanaminium, hydroxide, inner salt 3-[[hydroxy[[4-oxo-2-[[4-(tetradecyloxy)phenyl]methyl]heptyl]oxy]phosphinyl]oxy]-N,N-dimethyl-propanaminium, hydroxide, inner salt 3-[[hydroxy[[4-oxo-2-[[4-(tetradecyloxy)phenyl]methyl]heptyl]oxy]phosphinyl]oxy]-N-methyl-propanaminium, hydroxide, inner salt 3-[[hydroxy[[4-oxo-2-[[4-(tetradecyloxy)phenyl]methyl]heptyl]oxy]phosphinyl]oxy]-N,N-dimethyl-N-ethyl-propaninium, hydroxide, inner salt 3-[[hydroxy[[4-oxo-2-[[3-(tridecyloxy)phenyl]methyl]pentyl]oxy]phosphinyl]oxy]-N,N,N-trimethyl-propanaminium, hydroxide, inner salt 3-[[hydroxy[[4-oxo-2-[[3-(tridecyloxy)phenyl]methyl]pentyl]oxy]phosphinyl]oxy]-N,N-dimethyl-propanaminium, hydroxide, inner salt 3-[[hydroxy[[4-oxo-2-[[3-(tridecyloxy)phenyl]methyl]pentyl]oxy]phosphinyl]oxy]-N-methyl-propanaminium, hydroxide, inner salt 3-[[hydroxy[[4-oxo-2-[[3-(tridecyloxy)phenyl]methyl]pentyl]oxy]phosphinyl]oxy]-N,N-dimethyl-N-ethyl-propanaminium, hydroxide, inner salt 3-[[hydroxy[[4-oxo-2-[[3-(tridecyloxy)phenyl]methyl]hexyl]oxy]phosphinyl]oxy]-N,N,N-trimethyl-propanaminium, hydroxide, inner salt 3-[[hydroxy[[4-oxo-2-[[3-(tridecyloxy)phenyl]methyl]hexyl]oxy]phosphinyl]oxy]-N,N-dimethyl-propanaminium, hydroxide, inner salt 3-[[hydroxy[[4-oxo-2-[[3-(tridecyloxy)phenyl]methyl]hexyl]oxy]phosphinyl]oxy]-N-methyl-propanaminium, hydroxide, inner salt 3-[[hydroxy[[4-oxo-2-[[3-(tridecyloxy)phenyl]methyl]hexyl]oxy]phosphinyl]oxy]-N,N-dimethyl-N-ethyl-propanaminium, hydroxide, inner salt 3-[[hydroxy[[4-oxo-2-[[3-(tridecyloxy)phenyl]methyl]heptyl]oxy]phosphinyl]oxy]-N,N,N-trimethyl-propanaminium, hydroxide, inner salt 3-[[hydroxy[[4-oxo-2-[[3-(tridecyloxy)phenyl]methyl]heptyl]oxy]phosphinyl]oxy]-N,N-dimethyl-propanaminium, hydroxide, inner salt 3-[[hydroxy[[4-oxo-2-[[3-(tridecyloxy)phenyl]methyl]heptyl]oxy]phosphinyl]oxy]-N-methyl-propanaminium, hydroxide, inner salt 3-[[hydroxy[[4-oxo-2-[[3-(tridecyloxy)phenyl]methyl]heptyl]oxy]phosphinyl]oxy]-N,N-dimethyl-N-ethyl-propanaminium, hydroxide, inner salt 3-[[hydroxy[[4-oxo-2-[[2-(octadecyloxy)phenyl]methyl]pentyl]oxy]phosphinyl]oxy]-N,N,N-trimethyl-propanaminium, hydroxide, inner salt 3-[[hydroxy[[4-oxo-2-[[2-(octadecyloxy)phenyl]methyl]pentyl]oxy]phosphinyl]oxy]-N,N-dimethyl-propanaminium, hydroxide, inner salt 3-[[hydroxy[[4-oxo-2-[[2-(octadecyloxy)phenyl]methyl]pentyl]oxy]phosphinyl]oxy]-N-methyl-propanaminium, hydroxide, inner salt 3-[[hydroxy[[4-oxo-2-[[2-(octadecyloxy)phenyl]methyl]pentyl]oxy]phosphinyl]oxy]-N,N-dimethyl-N-ethyl-propanaminium, hydroxide, inner salt 3-[[hydroxy[[4-oxo-2-(octadecyloxy)phenyl]methyl]hexyl]oxy]phosphinyl]oxy]-N,N,N-trimethyl-propanaminium, hydroxide, inner salt 3-[[hydroxy[[4-oxo-2-[[2-(octadecyloxy)phenyl]methyl]hexyl]oxy]phosphinyl]oxy]-N,N-dimethyl-propanaminium, hydroxide, inner salt 3-[[hydroxy[[4-oxo-2-[[2-(octadecyloxy)phenyl]methyl]hexyl]oxy]phosphinyl]oxy]-N-methyl-propanaminium, hydroxide, inner salt 3-[[hydroxy[[4-oxo-2-[[2-(octadecyloxy)phenyl]methyl]hexyl]oxy]phosphinyl]oxy]-N,N-dimethyl-N-ethyl-propanaminium, hydroxide, inner salt 3-[[hydroxy[[4-oxo-2-[[2-(octadecyloxy)phenyl]methyl]heptyl]oxy]phosphinyl]oxy]-N,N,N-trimethyl-propanaminium, hydroxide, inner salt 3-[[hydroxy[[4-oxo-2-[[2-(octadecyloxy)phenyl]methyl]heptyl]oxy]phosphinyl]oxy]-N,N-dimethyl-propanaminium, hydroxide, inner salt 3-[[hydroxy[[4-oxo-2-[[2-(octadecyloxy)phenyl]methyl]hepty]oxy]phosphinyl]oxy]-N-methyl-propanaminium, hydroxide, inner salt 3-[[hydroxy[[4-oxo-2-[[2-(octadecyloxy)phenyl]methyl]heptyl]oxy]phosphinyl]oxy]-N,N-dimethyl-N-ethyl-propanaminium, hydroxide, inner salt 3-[[hydroxy[[4-oxo-2-[[4-(dodecyloxy)phenyl]methyl]pentyl]oxy]phosphinyl]oxy]-N,N,N-trimethyl-propanaminium, hydroxide, inner salt 3-[[hydroxy[[4-(dodecyloxy)phenyl]methyl]pentyl]oxy]phosphinyl]oxy]-N,N-dimethyl-propanaminium, hydroxide, inner salt 3-[[hydroxy[[4-oxo-2-[[4-(dodecyloxy)phenyl]methyl]pentyl]oxy]phosphinyl]oxy]-N-methyl-propanaminium, hydroxide, inner salt 3-[[hydroxy[[4-oxo-2-[[4-(dodecyloxy)phenyl]methyl]pentyl]oxy]phosphinyl]oxy-N,N-dimethyl-N-ethyl-propanaminium, hydroxide, inner salt 3-[[hydroxy[[4-oxo-2-[[4-(dodecyloxy)phenyl]methyl]hexyl]oxy]phosphinyl]oxy]-N,N,N-trimethyl-propanaminium, hydroxide, inner salt 3-[[hydroxy[[4-oxo-2-[[4-(dodecyloxy)phenyl]methyl]hexyl]oxy]phosphinyl]oxy]-N,N-dimethyl-propanaminium, hydroxide, inner salt 3-[[hydroxy[[4-oxo-2-[[4-(dodecyloxy)phenyl]methyl]hexyl]oxy]phosphinyl]oxy]-N-methyl-propanaminium, hydroxide, inner salt 3-[[hydroxy[[4-oxo-2-[[4-(dodecyloxy)phenyl]methyl]hexyl]oxy]phosphinyl]oxy]-N,N-dimethyl-N-ethyl-propanaminium, hydroxide, inner salt 3-[[hydroxy[[4-oxo-2-[[4-(dodecyloxy)phenyl]methyl]heptyl]oxy]phosphinyl]oxy]-N,N,N-trimethyl-propanaminium, hydroxide, inner salt 3-[[hydroxy[[4-oxo-2-[[4-(dodecyloxy)phenyl]methyl]heptyl]oxy]phosphinyl]oxy]-N,N-dimethyl-propanaminium, hydroxide, inner salt 3-[[hydroxy[[4-oxo-2-[[4-(dodecyloxy)phenyl]methyl]heptyl]oxy]phosphinyl]oxy]-N-methyl-propanaminium, hydroxide, inner salt 3-[[hydroxy[[4-oxo-2-[[4-(dodecyloxy)phenyl]methyl]-
heptyl]oxy]phosphinyl]oxy]-N,N-dimethyl-N-ethyl-
propanaminium, hydroxide, inner salt 4-[[hydroxy[[4-oxo-2-[[4-(tetradecyloxy)phenyl]me-
thyl]pentyl]oxy]phosphinyl]oxy]-N,N,N-trimethyl-
butanaminium, hydroxide, inner salt 4-[[hydroxy[[4-oxo-2-[[4-(tetradecyloxy)phenyl]me-
thyl]pentyl]oxy]phosphinyl]oxy]-N,N-dimethyl-
butanaminium, hydroxide, inner salt 4-[[hydroxy[[4-oxo-2-[[4-(tetradecyloxy)phenyl]me-
thyl]pentyl]oxy]phosphinyl]oxy]-N-methyl-
butanaminium, hydroxide, inner salt 4-[[hydroxy[[4-oxo-2-[[4-(tetradecyloxy)phenyl]me-
thyl]pentyl]oxy]phosphinyl]oxy]-N,N-dimethyl-N-
ethyl-butanaminium, hydroxide, inner salt 4-[[hydroxy[[4-oxo-2-[[4-(tetradecyloxy)phenyl]me-
thyl]hexyl]oxy]phosphinyl]oxy]-N,N,N-trimethyl-
butanaminium, hydroxide, inner salt 4-[[hydroxy[[4-oxo-2-[[4-(tetradecyloxy)phenyl]me-
thyl]hexyl]oxy]phosphinyl]-N,N-dimethyl-
butanaminium, hydroxide, inner salt 4-[[hydroxy[[4-oxo-2-[[4-(tetradecyloxy)phenyl]me-
thyl]hexyl]oxy]phosphinyl]oxy]-N-methyl-
butanaminium, hydroxide, inner salt 4-[[hydroxy[[4-oxo-2-[[4-(tetradecyloxy)phenyl]me-
thyl]hexyl]oxy]phosphinyl]oxy]-N,N-dimethyl-N-
ethyl-butanaminium, hydroxide, inner salt 4-[[hydroxy[[4-oxo-2-[[4-(tetradecyloxy)phenyl]me-
thyl]heptyl]oxy]phosphinyl]oxy]-N,N,N-trimethyl-
butanaminium, hydroxide, inner salt 4-[[hydroxy[[4-oxo-2-[[4-(tetradecyloxy)phenyl]me-
thyl]heptyl]oxy]phosphinyl]oxy]-N,N-dimethyl-
butanaminium, hydroxide, inner salt 4-[[hydroxy[[4-oxo-2-[[4-(tetradecyloxy)phenyl]me-
thyl]heptyl]oxy]phosphinyl]oxy]-N-methyl-
butanaminium, hydroxide, inner salt 4-[[hydroxy[[4-oxo-2-[[4-(tetradecyloxy)phenyl]me-
thyl]heptyl]oxy]phosphinyl]oxy]-N,N-dimethyl-N-
ethyl-butanaminium, hydroxide, inner salt 4-[[hydroxy[[4-oxo-2-[[3-(tridecyloxy)phenyl]methyl]-
pentyl]oxy]phosphinyl]oxy]-N,N,N-trimethyl-
butanaminium, hydroxide, inner salt 4-[[hydroxy[[4-oxo-2-[[3-(tradecyloxy)phenyl]methyl]-
pentyl]oxy]phosphinyl]oxy]-N,N-dimethyl-
butanaminium, hydroxide, inner salt 4-[[hydroxy[[4-oxo-2-[[3-(tridecyloxy)phenyl]methyl]-
pentyl]oxy]phosphinyl]oxy]-N-methyl-
butanaminium, hydroxide, inner salt 4-[[hydroxy[[4-oxo-2-[[3-(tridecyloxy)phenyl]methyl]-
pentyl]oxy]phosphinyl]oxy]-N,N-dimethyl-N-ethyl-
butanaminium, hydroxide, inner salt 4-[[hydroxy[[4-oxo-2-[[3-(tridecyloxy)phenyl]methyl]-
hexyl]oxy]phosphinyl]oxy]-N,N,N-trimethyl-
butanaminium, hydroxide, inner salt 4-[[hydroxy[[4-oxo-2-[[3-(tridecyloxy)phenyl]methyl]-
hexyl]oxy]phosphinyl]oxy]-N,N-dimethyl-
butanaminium, hydroxide, inner salt 4-[[hydroxy[[4-oxo-2-[[3-(tridecyloxy)phenyl]methyl]-
hexyl]oxy]phosphinyl]oxy]-N-methyl-butanaminium,
hydroxide, inner salt 4-[[hydroxy[[4-oxo-2-[[3-(tridecyloxy)phenyl]methyl]-
hexyl]oxy]phosphinyl]oxy]-N,N-dimethyl-N-ethyl-
butanaminium, hydroxide, inner salt 4-[[hydroxy[[4-oxo-2-[[3-(tridecyloxy)phenyl]methyl]-
heptyl]oxy]phosphinyl]oxy]-N,N,N-trimethyl-
butanaminium, hydroxide, inner salt 4-[[hydroxy[[4-oxo-2-[[3-(tridecyloxy)phenyl]methyl]-
heptyl]oxy]phosphinyl]oxy]-N,N-dimethyl-
butanaminium, hydroxide, inner salt 4-[[hydroxy[[4-oxo-2-[[3-(tridecyloxy)phenyl]methyl]-
heptyl]oxy]phosphinyl]oxy]-N-methyl-
butanaminium, hydroxide, inner salt 4-[[hydroxy[[4-oxo-2-[[3-tridecyloxy)phenyl]methyl]-
heptyl]oxy]phosphinyl]oxy]-N,N-dimethyl-N-ethyl-
butanaminium, hydroxide, inner salt 4-[[hydroxy[[4-oxo-2-[[2-(octadecyloxy)phenyl]me-
thyl]pentyl]oxy]phosphinyl]oxy]-N,N,N-trimethyl-
butanaminium, hydroxide, inner salt 4-[[hydroxy[[4-oxo-2-[[2-(octadecyloxy)phenyl]me-
thyl]pentyl]oxy]phosphinyl]oxy]-N,N-dimethyl-
butanaminium, hydroxide, inner salt 4-[[hydroxy[[4-oxo-2-[[2-(octadecyloxy)phenyl]me-
thyl]pentyl]oxy]phosphinyl]oxy]-N-methyl-
butanaminium, hydroxide, inner salt 4-[[hydroxy[[4-oxo-2-[[2-(octadecyloxy)phenyl]me-
thyl]pentyl]oxy]phosphinyl]oxy]-N,N-dimethyl-N-
ethyl-butanaminium, hydroxide, inner salt 4-[[hydroxy[[4-oxo-2-[[2-(octadecyloxy)phenyl]me-
thyl]hexyl]oxy]phosphinyl]oxy]-N,N,N-trimethyl-
butanaminium, hydroxide, inner salt 4-[[hydroxy[[4-oxo-2-[[2-(octadecyloxy)phenyl]me-
thyl]hexyl]oxy]phosphinyl]oxy]-N,N-dimethyl-
butanaminium, hydroxide, inner salt 4-[[hydroxy[[4-oxo-2-[[2-(octadecyloxy)phenyl]me-
thyl]hexyl]oxy]phosphinyl]oxy]-N-methyl-
butanaminium, hydroxide, inner salt 4-[[hydroxy[[4-oxo-2-[[2-(octadecyloxy)phenyl]me-
thyl]hexyl]oxy]phosphinyl]oxy]-N,N-dimethyl-N-
ethyl-butanaminium, hydroxide, inner salt 4-[[hydroxy[[4-oxo-2-[[2-(octadecyloxy)phenyl]me-
thyl]heptyl]oxy]phosphinyl]oxy]-N,N,N-trimethyl-
butanaminium, hydroxide, inner salt 4-[[hydroxy[[4-oxo-2-[[2-(octadecyloxy)phenyl]me-
thyl]heptyl]oxy]phosphinyl]oxy]-N,N-dimethyl-
butanaminium, hydroxide, inner salt 4-[[hydroxy[[4-oxo-2-[[2-(octadecyloxy)phenyl]me-
thyl]heptyl]oxy]phosphinyl]oxy]-N-methyl-
butanaminium, hydroxide, inner salt 4-[[hydroxy[[4-oxo-2-[[2-(octadecyloxy)phenyl]me-
thyl]heptyl]oxy]phosphinyl]oxy]-N,N-dimethyl-N-
ethyl-butanaminium, hydroxide, inner salt 4-[[hydroxy[[4-oxo-2-[[4-(dodecyloxy)phenyl]methyl]-
pentyl]oxy]phosphinyl]oxy]-N,N,N-trimethyl-
butanaminium, hydroxide, inner salt 4-[[hydroxy[[4-oxo-2-[[4-(dodecyloxy)phenyl]methyl]-
pentyl]oxy]phosphinyl]oxy]-N,N-dimethyl-
butanaminium, hydroxide, inner salt 4-[[hydroxy[[4-oxo-2-[[4-(dodecyloxy)phenyl]methyl]-
pentyl]oxy]phosphinyl]oxy]-N-methyl-
butanaminium, hydroxide, inner salt 4-[[hydroxy[[4-oxo-2-[[4-(dodecyloxy)phenyl]methyl]-
pentyl]oxy]phosphinyl]oxy]-N,N-dimethyl-N-ethyl-
butanaminium, hydroxide, inner salt 4-[[hydroxy[[4-oxo-2-[[4-(dodecyloxy)phenyl]methyl]-
hexyl]oxy]phosphinyl]oxy]-N,N,N-trimethyl-
butanaminium, hydroxide, inner salt 4-[[hydroxy[[4-oxo-2-[[4-(dodecyloxy)phenyl]methyl]-
hexyl]oxy]phosphinyl]oxy]-N,N-dimethyl-
butanaminium, hydroxide, inner salt 4-[[hydroxy[[4-oxo-2-[[4-(dodecyloxy)phenyl]methyl]-
hexyl]oxy]phosphinyl]oxy]-N-methyl-butanaminium,
hydroxide, inner salt 4-[[hydroxy[[4-oxo-2-[[4-(dodecyloxy)phenyl]methyl]-
hexyl]oxy]phosphinyl]oxy]-N,N-dimethyl-N-ethyl-
butanaminium, hydroxide, inner salt 4-[[hydroxy[[4-oxo-2-[[4-(dodecyloxy)phenyl]methyl]-
heptyl]oxy]phosphinyl]oxy]-N,N,N-trimethyl-
butanaminium, hydroxide, inner salt 4-[[hydroxy[[4-oxo-2-[[4-(dodecyloxy)phenyl]methyl]-
heptyl]oxy]phosphinyl]oxy]-N,N-dimethyl-
butanaminium, hydroxide, inner salt 4-[[hydroxy[[4-oxo-2-[[4-(dodecyloxy)phenyl]methyl]-
heptyl]oxy]phosphinyl]oxy]-N-methyl-
butanaminium, hydroxide, inner salt 4-[[hydroxy[[4-oxo-2-[[4-(dodecyloxy)phenyl]methyl]-
heptyl]oxy]phosphinyl]oxy]-N,N-dimethyl-N-ethyl-
butanaminium, hydroxide, inner salt 2-[hydroxy[[4-oxo-2-[[4-(tetradecyloxy)phenyl]me-
thyl]pentyl]oxy]phosphinyl]-N,N,N-trimethyl-
ethanaminium, hydroxide, inner salt 2-[hydroxy[[4-oxo-2-[[3-(tridecyloxy)phenyl]methyl]-
pentyl]oxy]phosphinyl]-N,N,N-trimethyl-
ethanaminium, hydroxide, inner salt 2-[hydroxy[[4-oxo-2-[[4-(dodecyloxy)phenyl]methyl]-
pentyl]oxy]phosphinyl]-N,N,N-trimethyl-
ethanaminium, hydroxide, inner salt 2-[hydroxy[[4-oxo-2-[[2-(tetradecyloxy)penyl]methyl]-
pentyl]oxy]phosphinyl]-N,N,N-trimethyl-
ethanaminium, hydroxide, inner salt 3-[hydroxy[[4-oxo-2-[[4-(tetradecyloxy)phenyl]me-
thyl]pentyl]oxy]phosphinyl]-N,N,N-trimethyl-
propanaminium, hydroxide, inner salt 3-[hydroxy[[4-oxo-2-[[3-(tridecyloxy)phenyl]methyl]-
pentyl]oxy]phosphinyl]-N,N,N-trimethyl-
propanaminium, hydroxide, inner salt 3-[hydroxy[[4-oxo-2-[[4-(dodecyloxy)phenyl]methyl]-
pentyl]oxy]phosphinyl]-N,N,N-trimethyl-
propanaminium, hydroxide, inner salt 3-[hydroxy[[4-oxo-2-[[2-(tetradecyloxy)phenyl]me-
thyl]pentyl]oxy]phosphinyl]-N,N,N-trimethyl-
propanaminium, hydroxide, inner salt

EXAMPLE 64

2-Methyl-α-octadecyl-1,3-dioxolan-2-propanoic acid, ethyl ester

To a solution of about 34.35 g of isopropylcyclohex-ylamine in about 150 ml of tetrahydrofuran at about −20° C. was added about 156.89 ml of an about 1.55M n-butyllithium, at a rate so that the final temperature reached about 10° C. The solution was then cooled to about −70° C. and about 25 g of ethyl levulinate ethylene ketal was added dropwise. After about 15 minutes, the solution was warmed to about −30° C. and maintained at that temperature while it was added rapidly, dropwise to a stirred solution of about 80.44 g of octadecyl iodide in about 150 ml of dimethyl sulfoxide and about 50 ml of tetrahydrofuran at room temperature. This mixture was stirred overnight, the volatile solvents were removed and water was added. The resulting solid was collected by filtration and extracted with ether giving a solution and a solid. This solution and original filtrate were combined and extracted with ether. This ether extract was dried and the solvent removed giving an oil. This oil was subjected to HPLC, eluting with hexane:ether (about 9:1). The product band was collected and the solvent removed, giving about 30.76 g of the desired title compound as a solid, mp 33°-34° C.

EXAMPLE 65

2-Methyl-β-octadecyl-1,3-dioxolan-2-propanol

To a suspension of about 3.75 g of lithium aluminum hydride in about 100 ml of ether at about 0° C., was added dropwise, under argon, over about 20 minutes, a solution of about 29 g of 2-methyl-α-octadecyl-1,3-dioxolan-2-propanoic acid, ethyl ester in about 200 ml of ether. This mixture was stirred about 40 minutes at room temperature, then about 15 ml of ethyl acetate were added dropwise, followed by about 1.5 ml of water, about 3 ml of about 15% sodium hydroxide and about 4 ml of water. The mixture was then filtered through celite and the solid washed with ether. The solvent was removed from the filtrate, giving an oil which crystallized on standing, giving about 24.1 g of the desired title compound, mp 34°-35° C.

EXAMPLE 66

4-(Hydroxymethyl)-2-docosanone

A mixture of about 21 g of 2-methyl-β-octadecyl-1,3-dioxolan-2-propanol in about 220 ml of acetone, about one ml of concentrated (about 12N) hydrochloric acid and about 15 ml of water was refluxed for about 20 minutes, poured into a solution of saturated sodium chloride and extracted with ether. The ether extract was washed with aqueous sodium bicarbonate, dried and the solvent removed. The residue was chromatographed via HPLC, eluting with hexane:ethyl acetate (about 9:1). The solvent was removed from the product fraction, giving about 12.3 g of the desired title compound as a white solid.

EXAMPLE 67

2-Bromoethyl 2-(2-oxopropyl)eicosyl phosphate

To a solution of about 7.0 g of 4-(hydroxymethyl)-2-docosanone in about 100 ml of carbon tetrachloride was added about 3.5 g of triethylamine, followed by about 8.35 g of 2-bromoethyl phosphorodichlorodate. The mixture was stirred about 2 hours, diluted with ether, filtered through celite and the solvent removed. The residue was stirred in a mixture of about 250 ml of about 0.5M sodium acetate and about 250 ml of tetrahydrofuran overnight. The tetrahydrofuran was removed, ether was added and the mixture was acidified with hydrochloric acid. The ether layer was washed with brine, dried and the solvent removed. The residue was chromatographed on a wet column of florasil, eluting first with chloroform and then eluting the product with chloroform:methanol (about 7:3). The product was dissolved in ether, filtered and the ether removed, giving about 8.27 g of the desired title compound as a glassy solid, mp 57°-59° C.

EXAMPLE 68

2-[[Hydroxy-[[2-(2-oxopropyl)eicosyl]oxy]phosphinyl]oxy]-N,N,N-trimethyl-ethanaminium, hydroxide, inner salt A mixture of about 7.2 g of 2-bromoethyl 2-(2-oxopropyl)eicosyl phosphate and about 150 ml of about 40% trimethylamine in about 260 ml of a mixture of chloroform:2-propanol:dimethylformamide (about 3:5:5) was stirred at about 65°-70° C. for about 4 hours. The solution was concentrated to about ½ volume, about 2.0 g of silver carbonate were added and the mixture was stirred for about one hour. This mixture was filtered through celite and the solvent removed with the repeated addition of ethanol to prevent foaming. The residue was dried in vacuo and then chromatographed on a dry column of silica gel, eluting the product with methanol:chloroform (about 7:3). The solvent was removed and the residue dissolved in chloroform, filtered through celite and the filtrate concentrated and diluted with ether, giving the desired title compound as a white solid, mp 109° C.

By using the phosphorous reagents listed in Table VII, the amines of Table VIII, the appropriate alkyl halides and the appropriate ketal esters prepared in Example 58 and listed immediately below Example 58 and by following the methods described in detail hereinabove in Examples 64–68, the compounds of this invention listed below can be prepared. These compounds can be prepared as the individual optically active R and S enantiomers or as racemic mixtures as described in the above specifications.

2-[[hydroxy[[2-(2-oxopropyl)hexadecyl]oxy]phosphinyl]oxy]-N,N,N-trimethyl-ethanaminium, hydroxide, inner salt 2-[[hydroxy[[2-(2-oxopropyl)hexadecyl]oxy]phosphinyl]oxy]-N,N-dimethyl-ethanaminium, hydroxide, inner salt 2-[[hydroxy[[2-(2-oxopropyl)octadecyl]oxy]phosphinyl]oxy]-N,N,N-trimethyl-ethanaminium, hydroxide, inner salt 2-[[hydroxy[[2-(2-oxopropyl)octadecyl]oxy]phosphinyl]oxy]-N,N-dimethyl-ethanaminium, hydroxide, inner salt 2-[[hydroxy[[2-(2-oxopropyl)octadecyl]oxy]phosphinyl]oxy]N-methyl-ethanaminium, hydroxide, inner salt 2-[[hydroxy[[2-(2-oxopropyl)octadecyl]oxy]phosphinyl]oxy]-N,N-tetramethylene-ethanaminium, hydroxide, inner salt 2-[[hydroxy[[2-(2-oxopropyl)nonadecyl]oxy]phosphinyl]oxy]-N,N,N-trimethyl-ethanaminium, hydroxide, inner salt 2-[[hydroxy[[2-(2-oxopropyl)nonadecyl]oxy]phosphinyl]oxy]-N,N-dimethyl-ethanaminium, hydroxide, inner salt 2-[[hydroxy[[2-(2-oxopropyl)eicosyl]oxy]phosphinyl]oxy]-N,N,N-trimethyl-ethanaminium, hydroxide, inner salt 2-[[hydroxy[[2-(2-oxopropyl)eicosyl]oxy]phosphinyl]oxy]-N,N-dimethyl-ethanaminium, hydroxide, inner salt 2-[[hydroxy[[2-(2-oxopropyl)eicosyl]oxy]phosphinyl]oxy]N-methyl-ethanminium, hydroxide, inner salt 2-[[hydroxy[[2-(2-oxopropyl)eicosyl]oxy]phosphinyl]oxy]-N,N-tetramethylene-ethanaminium, hydroxide, inner salt 2-[[hydroxy[[2-(2-oxopropyl)heneicosyl]oxy]phosphinyl]oxy]-N,N,N-trimethyl-ethanaminium, hydroxide, inner salt 2-[[hydroxy[[2-(2-oxopropyl)heneicosyl]oxy]phosphinyl]oxy]-N,N-dimethyl-ethanaminium, hydroxide, inner salt 2-[[hydroxy[[2-(2-oxopropyl)heneicosyl]oxy]phosphinyl]oxy]N-methyl-ethanaminium, hydroxide, inner salt 2-[[hydroxy[[2-(2-oxopropyl)heneicosyl]oxy]phosphinyl]oxy]-N,N-tetramethylene-ethanaminium, hydroxide, inner salt 2-[[hydroxy[[2-(2-oxopropyl)docosyl]oxy]phosphinyl]oxy]-N,N,N-trimethyl-ethanaminium, hydroxide, inner salt 2-[[hydroxy[[2-(2-oxobutyl)octadecyl]oxy]phosphinyl]oxy]-N,N,N-trimethyl-ethanaminium, hydroxide, inner salt 2-[[hydroxy[[2-(2-oxobutyl)octadecyl]oxy]phosphinyl]oxy]-N,N-dimethyl-ethanaminium, hydroxide, inner salt 2-[[hydroxy[[2-(2-oxobutyl)octadecyl]oxy]phosphinyl]oxy]N-methyl-ethanaminium, hydroxide, inner salt 2-[[hydroxy[[2-(2-oxobutyl)octadecyl]oxy]phosphinyl]oxy]-N,N-tetramethylene-ethanaminium, hydroxide, inner salt 2-[[hydroxy[[2-(2-oxobutyl)nonadecyl]oxy]phosphinyl]oxy]-N,N,N-trimethyl-ethanaminium, hydroxide, inner salt 2-[[hydroxy[[2-(2-oxobutyl)nonadecyl]oxy]phosphinyl]oxy]-N,N-dimethyl-ethanaminium, hydroxide, inner salt 2-[[hydroxy[[2-(2-oxobutyl)eicosyl]oxy]phosphinyl]oxy]-N,N,N-trimethyl-ethanaminium, hydroxide, inner salt 2-[[hydroxy[[2-(2-oxobutyl)eicosyl]oxy]phosphinyl]oxy]-N,N-dimethyl-ethanaminium, hydroxide, inner salt 2-[[hydroxy[[2-(2-oxobutyl)eicosyl]oxy]phosphinyl]oxy]N-methyl-ethanaminium, hydroxide, inner salt 2-[[hydroxy[[2-(2-oxobutyl)eicosyl]oxy]phosphinyl]oxy]-N,N-tetramethylene-ethanaminium, hydroxide, inner salt 2-[[hydroxy[[2-(2-oxobutyl)heneicosyl]oxy]phosphinyl]oxy]-N,N,N-trimethyl-ethanaminium, hydroxide, inner salt 2-[[hydroxy[[2-(2-oxobutyl)heneicosyl]oxy]phosphinyl]oxy]-N,N-dimethyl-ethanaminium, hydroxide, inner salt 2-[[hydroxy[[2-(2-oxobutyl)heneicosyl]oxy]phosphinyl]oxy]N-methyl-ethanaminium, hydroxide, inner salt 2-[[hydroxy[[2-(2-oxobutyl)heneicosyl]oxy]phosphinyl]oxy]-N,N-tetramethylene-ethanaminium, hydroxide, inner salt 2-[[hydroxy[[2-(2-oxopentyl)octadecyl]oxy]phosphinyl]oxy]-N,N,N-trimethyl-ethanaminium, hydroxide, inner salt 2-[[hydroxy[[2-(2-oxopentyl)octadecyl]oxy]phosphinyl]oxy]-N,N-dimethyl-ethanaminium, hydroxide, inner salt 2-[[hydroxy[[2-(2-oxopentyl)octadecyl]oxy]phosphinyl]oxy]N-methyl-ethanaminium, hydroxide, inner salt 2-[[hydroxy[[2-(2-oxopentyl)octadecyl]oxy]phosphinyl]oxy]-N,N-tetramethylene-ethanaminium, hydroxide, inner salt 2-[[hydroxy[[2-(2-oxopentyl)eicosyl]oxy]phosphinyl]oxy]-N,N,N-trimethyl-ethanaminium, hydroxide, inner salt 2-[[hydroxy[[2-(2-oxopentyl)eicosyl]oxy]phosphinyl]oxy]-N,N-dimethyl-ethanaminium, hydroxide, inner salt 2-[[hydroxy[[2-(2-oxopentyl)eicosyl]oxy]phosphinyl]oxy]N-methyl-ethanaminium, hydroxide, inner salt 2-[[hydroxy[[2-(2-oxopentyl)eicosyl]oxy]phosphinyl]oxy]-N,N-tetramethylene-ethanaminium, hydroxide, inner salt 2-[[hydroxy[[2-(2-oxopentyl)heneicosyl]oxy]phosphinyl]oxy]-N,N,N-trimethyl-ethanaminium, hydroxide, inner salt 2-[[hydroxy[[2-(2-oxopentyl)heneicosyl]oxy]phosphinyl]oxy]-N,N-dimethyl-ethanaminium, hydroxide, inner salt 2-[[hydroxy[[2-(2-oxopentyl)heneicosyl]oxy]phosphinyl]oxy]N-methyl-ethanaminium, hydroxide, inner salt 2-[[hydroxy[[2-(2-oxopentyl)heneicosyl]oxy]phosphinyl]oxy]-N,N-tetramethylene-ethanaminium, hydroxide, inner salt 3-[[hydroxy[[2-(2-oxopropyl)octadecyl]oxy]phosphinyl]oxy]-N,N,N-trimethyl-propanaminium, hydroxide, inner salt 3-[[hydroxy[[2-(2-oxopropyl)octadecyl]oxy]phosphinyl]oxy]-N,N-dimethyl-propanaminium, hydroxide, inner salt 3-[[hydroxy[[2-(2-oxopropyl)octadecyl]oxy]phoshinyl]oxy]N-methyl-propanaminium, hydroxide, inner salt 3-[[hydroxy[[2-(2-oxopropyl)octadecyl]oxy]phosphinyl]oxy]-N,N-tetramethylene-propanaminium, hydroxide, inner salt 3-[[hydroxy[[2-(2-oxopropyl)nonadecyl]oxy]phosphinyl]oxy]-N,N,N-trimethyl-propanaminium, hydroxide, inner salt 3-[[hydroxy[[2-(2-oxopropyl)nonadecyl]oxy]phosphinyl]oxy]-N,N-dimethyl-propanaminium, hydroxide, inner salt 3-[[hydroxy[[2-(2-oxopropyl)eicosyl]oxy]phosphinyl]oxy]-N,N,N-trimethyl-propanaminium, hydroxide, inner salt 3-[[hydroxy[[2-(2-oxopropyl)eicosyl]oxy]phosphinyl]oxy]-N,N-dimethyl-propanaminium, hydroxide, inner salt 3-[[hydroxy[[2-(2-oxopropyl)eicosyl]oxy]phosphinyl]oxy]N-methyl-propanaminium, hydroxide, inner salt 3-[[hydroxy[[2-(2-oxopropyl)eicosyl]oxy]phosphinyl]oxy]-N,N-tetramethylene-propanaminium, hydroxide, inner salt 3-[[hydroxy[[2-(2-oxopropyl)heneicosyl]oxy]phosphinyl]oxy]-N,N,N-trimethyl-propanaminium, hydroxide, inner salt 3-[[hydroxy[[2-(2-oxopropyl)heneicosyl]oxy]phosphinyl]oxy]-N,N-dimethyl-propanaminium, hydroxide, inner salt 3-[[hydroxy[[2-(2-oxopropyl)heneicosyl]oxy]phosphinyl]oxy]N-methyl-propanaminium, hydroxide, inner salt 3-[[hydroxy[[2-(2-oxopropyl)heneicosyl]oxy]phosphinyl]oxy]-N,N-tetramethylene-propanaminium, hydroxide, inner salt 3-[[hydroxy[[2-(2-oxobutyl)octadecyl]oxy]phosphinyl]oxy]-N,N,N-trimethyl-propanaminium, hydroxide, inner salt 3-[[hydroxy[[2-(2-oxobutyl)octadecyl]oxy]phosphinyl]oxy]-N,N-dimethyl-propanaminium, hydroxide, inner salt 3-[[hydroxy[[2-(2-oxobutyl)octadecyl]oxy]phosphinyl]oxy]N-methyl-propanaminium, hydroxide, inner salt 3-[[hydroxy[[2-(2-oxobutyl)octadecyl]oxy]phosphinyl]oxy]-N,N-tetramethylene-propanaminium, hydroxide, inner salt 3-[[hydroxy[[2-(2-oxobutyl)nonadecyl]oxy]phosphinyl]oxy]-N,N,N-trimethyl-propanaminium, hydroxide, inner salt 3-[[hydroxy[[2-(2-oxobutyl)nonadecyl]oxy]phosphinyl]oxy]-N,N-dimethyl-propanaminium, hydroxide, inner salt 3-[[hydroxy[[2-(2-oxobutyl)eicosyl]oxy]phosphinyl]oxy]-N,N,N-trimethyl-propanaminium, hydroxide, inner salt 3-[[hydroxy[[2-(2-oxobutyl)eicosyl]oxy]phosphinyl]oxy]-N,N-dimethyl-propanaminium, hydroxide, inner salt 3-[[hydroxy[[2-(2-oxobutyl)eicosyl]oxy]phosphinyl]oxy]-N-methyl-propanaminium, hydroxide inner salt 3-[[hydroxy[[2-(2-oxobutyl)eicosyl]oxy]phosphinyl]oxy]-N,N-tetramethylene-propanaminium, hydroxide, inner salt 3-[[hydroxy[[2-(2-oxobutyl)heneicosyl]oxy]phosphinyl]oxy]-N,N,N-trimethyl-propanaminium, hydroxide, inner salt 3-[[hydroxy[[2-(2-oxobutyl)heneicosyl]oxy]phosphinyl]oxy]-N,N-dimethyl-propanaminium, hydroxide, inner salt 3-[[hydroxy[[2-(2-oxobutyl)heneicosyl]oxy]phosphinyl]oxy]N-methyl-propanaminium, hydroxide, inner salt 3-[[hydroxy[[2-(2-oxobutyl)heneicosyl]oxy]phosphinyl]oxy]-N,N-tetramethylene-propanaminium, hydroxide, inner salt 3-[[hydroxy[[2-(2-oxopentyl)octadecyl]oxy]phosphinyl]oxy]-N,N,N-trimethyl-propanaminium, hydroxide, inner salt 3-[[hydroxy[[2-(2-oxopentyl)octadecyl]oxy]phosphinyl]oxy]-N,N-dimethyl-propanaminium, hydroxide, inner salt 3-[[hydroxy[[2-(2-oxopentyl)octadecyl]oxy]phosphinyl]oxy]N-methyl-propanaminium, hydroxide, inner salt 3-[[hydroxy[[2-(2-oxopentyl)octadecyl]oxy]phosphinyl]oxy]-N,N-tetramethylene-propanaminium, hydroxide, inner salt 3-[[hydroxy[[2-(2-oxopentyl)eicosyl]oxy]phosphinyl]oxy]-N,N,N-trimethyl-propanaminium, hydroxide, inner salt 3-[[hydroxy[[2-(2-oxopentyl)eicosyl]oxy]phosphinyl]oxy]-N,N-dimethyl-propanaminium, hydroxide, inner salt 3-[[hydroxy[[2-(2-oxopentyl)eicosyl]oxy]phosphinyl]oxy]N-methyl-propanaminium, hydroxide, inner salt 3-[[hydroxy[[2-(2-oxopentyl)eicosyl]oxy]phosphinyl]oxy]-N,N-tetramethylene-propanaminium, hydroxide, inner salt 3-[[hydroxy[[2-(2-oxopentyl)heneicosyl]oxy]phosphinyl]oxy]-N,N,N-trimethyl-propanaminium, hydroxide, inner salt 3-[[hydroxy[[2-(2-oxopentyl)heneicosyl]oxy]phosphinyl]oxy]-N,N-dimethyl-propanaminium, hydroxide, inner salt 3-[[hydroxy[[2-(2-oxopentyl)heneicosyl]oxy]phosphinyl]oxy]N-methyl-propanaminium, hydroxide, inner salt 3-[[hydroxy[[2-(2-oxopentyl)heneicosyl]oxy]phosphinyl]oxy]-N,N-tetramethylene-propanaminium, hydroxide, inner salt 4-[[hydroxy[[2-(2-oxopropyl)octadecyl]oxy]phosphinyl]oxy]-N,N,N-trimethyl-butanaminium, hydroxide, inner salt 4-[[hydroxy[[2-(2-oxopropyl)octadecyl]oxy]phosphinyl]oxy]-N,N-dimethyl-butanaminium, hydroxide, inner salt 4-[[hydroxy[[2-(2-oxopropyl)octadecyl]oxy]phosphinyl]oxy]N-methyl-butanaminium, hydroxide, inner salt 4-[[hydroxy[[2-(2-oxopropyl)octadecyl]oxy]phosphinyl]oxy]-N,N-tetramethylene-butanaminium, hydroxide, inner salt 4-[[hydroxy[[2-(2-oxopropyl)nonadecyl]oxy]phosphinyl]oxy]-N,N,N-trimethyl-butanaminium, hydroxide, inner salt 4-[[hydroxy[[2-(2-oxopropyl)nonadecyl]oxy]phosphinyl]oxy]-N,N-dimethyl-butanaminium, hydroxide, inner salt 4-[[hydroxy[[2-(2-oxopropyl)eicosyl]oxy]phosphinyl]oxy]-N,N,N-trimethyl-butanaminium, hydroxide, inner salt 4-[[hydroxy[[2-(2-oxopropyl)eicosyl]oxy]phosphinyl]oxy]-N,N-dimethyl-butanaminium, hydroxide, inner salt 4-[[hydroxy[[2-(2-oxopropyl)eicosyl]oxy]phosphinyl]oxy]N-methyl-butanaminium, hydroxide, inner salt 4-[[hydroxy[[2-(2-oxopropyl)eicosyl]oxy]phosphinyl]oxy]-N,N-tetramethylene-butanaminium, hydroxide, inner salt 4-[[hydroxy[[2-(2-oxobutyl)octadecyl]oxy]phosphinyl]oxy]-N,N,N-trimethyl-butanaminium, hydroxide, inner salt 4-[[hydroxy[[2-(2-oxobutyl)octadecyl]oxy]phosphinyl]oxy]-N,N-dimethyl-butanaminium, hydroxide, inner salt 4-[[hydroxy[[2-(2-oxobutyl)octadecyl]oxy]phosphinyl]oxy]N-methyl-butanaminium, hydroxide, inner salt 4-[[hydroxy[[2-(2-oxobutyl)octadecyl]oxy]phosphinyl]oxy]-N,N-tetramethylene-butanaminium, hydroxide, inner salt 4-[[hydroxy[[2-(2-oxobutyl)nonadecyl]oxy]phosphinyl]oxy]-N,N,N-trimethyl-butanaminium, hydroxide, inner salt 4-[[hydroxy[[2-(2-oxobutyl)nonadecyl]oxy]phosphinyl]oxy]-N,N-dimethyl-butanaminium, hydroxide, inner salt 4-[[hydroxy[[2-(2-oxobutyl)eicosyl]oxy]phosphinyl]oxy]-N,N,N-trimethyl-butanaminium, hydroxide, inner salt 4-[[hydroxy[[2-(2-oxobutyl)eicosyl]oxy]phosphinyl]oxy]-N,N-dimethyl-butanaminium, hydroxide, inner salt 4-[[hydroxy[[2-(2-oxobutyl)eicosyl]oxy]phosphinyl]oxy]N-methyl-butanaminium, hydroxide, inner salt 4-[[hydroxy[[2-(2-oxobutyl)eicosyl]oxy]phosphinyl]oxy]-N,N-tetramethylene-butanaminium, hydroxide, inner salt 4-[[hydroxy[[2-(2-oxopentyl)octadecyl]oxy]phosphinyl]oxy]-N,N,N-trimethyl-butanaminium, hydroxide, inner salt 4-[[hydroxy[[2-(2-oxopentyl)octadecyl]oxy]phosphinyl]oxy]-N,N -dimethyl-butanaminium, hydroxide, inner salt 4-[[hydroxy[[2-(2-oxopentyl)octadecyl]oxy]phosphinyl]oxy]N-methyl-butanaminium, hydroxide, inner salt 4-[[hydroxy[[2-(2-oxopentyl)octadecyl]oxy]phosphinyl]oxy]-N,N-tetramethylene-butanaminium, hydroxide, inner salt 4-[[hydroxy[[2-(2-oxopentyl)eicosyl]oxy]phosphinyl]oxy]-N,N,N-trimethyl-butanaminium, hydroxide, inner salt 4-[[hydroxy[[2-(2-oxopentyl)eicosyl]oxy]phosphinyl]oxy]-N,N-dimethyl-butanaminium, hydroxide, inner salt 4-[[hydroxy[[2-(2-oxopentyl)eicosyl]oxy]phosphinyl]oxy]N-methyl-butanaminium, hydroxide, inner salt 4-[[hydroxy[[2-(2-oxopentyl)eicosyl]oxy]phosphinyl]oxy]-N,N-tetramethylene-butanaminium, hydroxide, inner salt 2-[hydroxy[[2-(2-oxopropyl)eicosyl]oxy]phosphinyl]-N,N,N-trimethyl-ethanaminium, hydroxide, inner salt 2-[hydroxy[[2-(2-oxopropyl)nonadecyl]oxy]phosphinyl]-N,N,N-trimethyl-ethanaminium, hydroxide, inner salt 2-[hydroxy[[2-(2-oxopropyl)heneicosyl]oxy]phosphinyl]-N,N,N-trimethyl-ethanaminium, hydroxide, inner salt 2-[hydroxy[[2-(2-oxobutyl)eicosyl]oxy]phosphinyl]-N,N,N-trimethyl-ethanaminium, hydroxide, inner salt 2-[hydroxy[[2-(2-oxobutyl)nonadecyl]oxy]phosphinyl]-N,N,N-trimethyl-ethanaminium, hydroxide, inner salt 2-[hydroxy[[2-(2-oxobutyl)heneicosyl]oxy]phosphinyl]-N,N,N-trimethyl-ethanaminium, hydroxide, inner salt 3-[hydroxy[[2-(2-oxopropyl)eicosyl]oxy]phosphinyl]-N,N,N-trimethyl-propanaminium, hydroxide, inner salt 3-[hydroxy[[2-(2-oxopropyl)nonadecyl]oxy]phosphinyl]-N,N,N-trimethyl-propanaminium, hydroxide, inner salt 3-[hydroxy[[2-(2-oxopropyl)heneicosyl]oxy]phosphinyl]-N,N,N-trimethyl-propanaminium, hydroxide, inner salt 3-[hydroxy[[2-(2-oxobutyl)eicosyl]oxy]phosphinyl]-N,N,N-trimethyl-propanaminium, hydroxide, inner salt 3-[hydroxy[[2-(2-oxobutyl)nonadecyl]oxy]phosphinyl]-N,N,N-trimethyl-propanaminium, hydroxide, inner salt 3-[hydroxy[[2-(2-oxobutyl)heneicosyl]oxy]phosphinyl]-N,N,N-trimethyl-propanaminium, hydroxide, inner salt

EXAMPLE 69

3-Bromopropyl phosphorodichlorodate

To a solution of about 198 g of phosphorous oxychloride in about 500 ml of carbon tetrachloride was added dropwise, with stirring about 119.7 g of 3-bromo-1-propanol over about 30 minutes. The solution was warmed slightly (about 40° C.), then stirred at room temperature overnight and taken to dryness. The residue was evaporated twice from toluene, giving an orange oil which was distilled (at about 85°–87° C., 0.6 mm), giving about 32 g of the desired reagent as a yellow-orange oil.

EXAMPLE 70

(2-Bromoethyl)phosphonic acid compound with benzeneamine (1:1)

A solution of about 50 g of diethyl-2-bromoethylphosphonate in about 255 ml of about 48% hydrobromic acid was kept at reflux (about 95°–100° C.) overnight. The solvent was removed under reduced pressure and the residue evaporated twice with toluene, giving a syrup. This syrup was dissolved in about 65 ml of about 99% ethanol, about 20 g of aniline was added dropwise and the solid was collected, washed with cold about 99% ethanol (at about 0° C.) and dried in vacuo, giving about 30.6 g of the desired reagent, mp 157°–158° C.

EXAMPLE 71a (2-Bromoethyl)phosphonic acid

An about 33 g portion of (2-bromoethyl)phosphonic acid compound with benzeneamine (about 1:1) was dissolved in about 600 ml of about 50% ethanol in water by warming to about 50° C. This warm mixture was passed through a column of about 200 ml of Amberlite ® IR-120 (H+form) anion exchange resin.

The column was then washed with about 135 ml of about 50% ethanol in water, the effluents combined and taken to dryness under reduced pressure at about 40° C. The resulting solid was dissolved in about 400 ml of boiling chloroform, then allowed to stand at room temperature and the solid collected, giving about 19.34 g of the desired reagent, mp 95.5°–96.5° C.

EXAMPLE 71b (2-Bromoethyl)phosphonic acid monochloride

To a solution of about 3.78 g of dry (2-bromoethyl)phosphonic acid in about 50 ml of dry alcohol free chloroform was added about 4.16 g of phosphorous pentachloride. The solution was refluxed for about 10 minutes and the solvent was removed, giving the title compound.

EXAMPLE 72

N-Acetyl-L-serine, methyl ester

To a suspension of about 46.57 g of L-serine methyl ester hydrochloride in about 3 liters of chloroform was added about 84 ml of triethylamine. This mixture was stirred until solution was complete, then about 21 ml of acetyl chloride was added dropwise. The mixture was then stirred under argon for about 2 days and the chloroform removed under reduced pressure. The residue was suspended in ethanol, filtered through a sintered glass funnel and the ethanol removed, giving about 49 g of the desired title compound $[\alpha]_D^{26} = +36° \pm 1°$ (CHCl$_3$, 1.039%).

As described hereinabove in Example 72, the reaction of L-serine methyl ester hydrochloride with propionyl chloride or butyryl chloride gives N-propionyl-L-serine, methyl ester and N-butyryl-L-serine, methyl ester, respectively. In a similar manner using D-serine methyl ester hydrochloride or racemic serine methyl ester hydrochloride furnishes the compounds with opposite chirality and the racemic compounds, respectively.

EXAMPLE 73

N-Acetyl-O-(tetrahydro-2H-pyran-2-yl)-L-serine, methyl ester

To a solution of about 4.50 g of N-acetyl-L-serine, methyl ester in about 100 ml of dry methylene chloride was added about 2.93 ml of distilled tetrahydro-2H-pyran and about 0.34 ml of borontrifluoroetherate. The mixture was stirred under argon for about 7 hours, then washed with saturated sodium bicarbonate and brine, dried and the solvent removed under reduced pressure, giving about 6 g of the desired title compound.

EXAMPLE 74

N-[1-(Hydroxymethyl)-2-[(tetrahydro-2H-pyran-2-yl)oxy]ethyl]acetamide

An about 76 mg portion of lithium borohydride was weighed into a 100 ml round bottom flask which had been flushed with argon. An about 50 ml portion of anhydrous ether was added, under argon. To this was added a solution of about 857.5 mg of N-acetyl-O-(tetrahydro-2H-pyran-2-yl)-L-serine, methyl ester in ether. The mixture was stirred for about 7 hours, the reaction quenched with water and brine, the organic layer separated and saved and the aqueous layer extracted several times with ethyl acetate. The organic layers were combined, dried and the solvent evaporated under reduced pressure. This crude material was purified by chromatography on silica gel, using the systems hexane:ethyl acetate:ethanol (about 1:1:0.3) followed by ethyl acetate:ethanol (about 8:1), giving about 397 mg of the desired compound, $[\alpha]_D^{26°} = +7° \pm 2°$ (CHCl$_3$, 0.66%).

EXAMPLE 75

N-[1-[(Octadecyloxy)methyl]-2-[(tetrahydro-2H-pyran-2-yl)oxy]ethyl]acetamide

A solution of about 10.85 g of N-[1-(hydroxymethyl)-2-[(tetrahydro-2H-pyran-2-yl)oxy]ethyl]acetamide in about 240 ml of dry dimethylformamide was added dropwise to a suspension of about 3.12 g of about 50% sodium hydride (pre-washed with anhydrous ether). After stirring about one hour a solution of about 22.8 g of octadecyl iodide in about 150 ml of tetrahydrofuran was added, stirring was continued for about 24 hours, then the mixture was diluted with ether and washed with a minimum amount of brine. The organic layer was dried, the solvents evaporated and the crude material purified by chromatography on silica gel, eluting with ethyl acetate:hexane:ethanol (about 1:1:0.2), giving about 8 g of the desired title compound, mp 52°–55° C.

According to the procedures described in Examples 73–75, the amides of L-serine methyl ester listed below in Table V are protected with tetrahydro-2H-pyran. The resulting THP ethers are then alkylated with the indicated alkyl halides to give the compounds of Table V needed to prepare some of the compounds of this invention. In a similar manner the reactions outlined in Examples 73–75 can be performed using the D or racemic amides of serine methyl ester to furnish the compounds with opposite chirality and the racemic compounds, respectively.

TABLE V

| | |
|---|---|
| AMIDE: | N—acetyl-L-serine, methyl ester |
| ALKYL HALIDE: | octadecyl iodide |
| PRODUCT: | N—[1-[(octadecyloxy)methyl]-2-[(tetrahydro-2H—pyran-2-yl)oxy]ethyl]acetamide |
| AMIDE: | N—acetyl-L-serine, methyl ester |
| ALKYL HALIDE: | pentadecyl iodide |
| PRODUCT: | N—[1-[(pentadecyloxy)methyl]-2-[(tetrahydro-2H—pyran-2-yl)oxy]ethyl]acetamide |
| AMIDE: | N—acetyl-L-serine, methyl ester |
| ALKYL HALIDE: | hexadecyl iodide |
| PRODUCT: | N—[1-[(hexadecyloxy)methyl]-2-[(tetrahydro-2H—pyran-2-yl)oxy]ethyl]acetamide |
| AMIDE: | N—propionyl-L-serine, methyl ester |
| ALKYL HALIDE: | octadecyl iodide |
| PRODUCT: | N—[1-[(pentadecyloxy)methyl]-2-[(tetrahydro-2H—pyran-2-yl)oxy]ethyl]propionamide |
| AMIDE: | N—propionyl-L-serine, methyl ester |

TABLE V-continued

| | |
|---|---|
| ALKYL HALIDE: | pentadecyl iodide |
| PRODUCT: | N—[1-[(pentadecyloxy)methyl]-2-[(tetrahydro-2H—pyran-2-yl)oxy]ethyl]propionamide |
| AMIDE: | N—propionyl-L-serine, methyl ester |
| ALKYL HALIDE: | hexadecyl iodide |
| PRODUCT: | N—[1-[(hexadecyloxy)methyl]-2-[(tetrahydro-2H—pyran-2-yl)oxy]ethyl]propionamide |
| AMIDE: | N—butyryl-L-serine, methyl ester |
| ALKYL HALIDE: | octadecyl iodide |
| PRODUCT: | N—[1-[(octadecyloxy)methyl]-2-[(tetrahydro-2H—pyran-2-yl)oxy]ethyl]butyramide |
| AMIDE: | N—butyryl-L-serine, methyl ester |
| ALKYL HALIDE: | pentadecyl iodide |
| PRODUCT: | N—[1-[(pentadecyloxy)methyl]-2-[(tetrahydro-2H—pyran-2-yl)oxy]ethyl]butyramide |
| AMIDE: | N—butyryl-L-serine, methyl ester |
| ALKYL HALIDE: | hexadecyl iodide |
| PRODUCT: | N—[1-[(hexadecyloxy)methyl]-2-[(tetrahydro-2H—pyran-2-yl)oxy]ethyl]butyramide |
| AMIDE: | N—acetyl-L-serine, methyl ester |
| ALKYL HALIDE: | heptadecyl iodide |
| PRODUCT: | N—[1-[(heptadecyloxy)methyl]-2-[(tetrahydro-2H— pyran-2-yl)oxy]ethyl]acetamide |
| AMIDE: | N—acetyl-L-serine, methyl ester |
| ALKYL HALIDE: | 2-methylhexadecyl iodide |
| PRODUCT: | N—[1-[(2-methylhexadecyloxy)methyl]-2-[(tetrahydro-2H—pyran-2-yl)oxy]ethyl]acetamide |
| AMIDE: | N—acetyl-L-serine, methyl ester |
| ALKYL HALIDE: | 3-ethylpentadecyl iodide |
| PRODUCT: | N—[1-[(3-ethylpentadecyloxy)methyl]-2-[(tetrahydro-2H—pyran-2-yl)oxy]ethyl]ethyl]acetamide |
| AMIDE: | N—propionyl-L-serine, methyl ester |
| ALKYL HALIDE: | heptadecyl iodide |
| PRODUCT: | N—[1-[(heptadecyloxy)methyl]-2-[(tetrahydro-2H—pyran-2-yl)oxy]ethyl]propionamide |
| AMIDE: | N—propionyl-L-serine, methyl ester |
| ALKYL HALIDE: | 2-methylhexadecyl iodide |
| PRODUCT: | N—[1-[(2-methylhexadecyloxy)methyl]-2-[(tetrahydro-2H—pyran-2-yl)oxy]ethyl]propionamide |
| AMIDE: | N—propionyl-L-serine, methyl ester |
| ALKYL HALIDE: | 3-ethylpentadecyl iodide |
| PRODUCT: | N—[1-[(3-ethylpentadecyloxy)methyl]-2-[(tetrahydro-2H—pyran-2-yl)oxy]ethyl]propionamide |
| AMIDE: | N—butyryl-L-serine, methyl ester |
| ALKYL HALIDE: | heptadecyl iodide |
| PRODUCT: | N—[1-[(heptadecyloxy)methyl]-2-[(tetrahydro-2H—pyran-2-yl)oxy]ethyl]butyramide |
| AMIDE: | N—butyryl-L-serine, methyl ester |
| ALKYL HALIDE: | 2-methylhexadecyl iodide |
| PRODUCT: | N—[1-[(2-methylhexadecyloxy)methyl]-2-[(tetrahydro-2H—pyran-2-yl)oxy]ethyl]butyramide |
| AMIDE: | N—butyryl-L-serine, methyl ester |
| ALKYL HALIDE: | 3-ethylpentadecyl iodide |
| PRODUCT: | N—[1-[(3-ethylpentadecyloxy)methyl]-2-[(tetrahydro-2H—pyran-2-yl)oxy]ethyl]butyramide |

EXAMPLE 76

N-[1-(Hydroxymethyl)-2-(octadecyloxy)ethyl]acetamide

A mixture of about 4.69 g of N-[1-[(octadecyloxy)methyl]-2-[(tetrahydro-2H-pyran-2-yl)oxy]ethyl]acetamide in about 200 ml of methanol and about 4 ml of about 1N hydrochloric acid was stirred for about 24 hours and the methanol removed under reduced pressure. The residue was dissolved in ethyl acetate, washed with aqueous sodium bicarbonate, dried and the solvent removed, giving about 3.2 g of the desired title compound, mp 82°–85° C.

EXAMPLE 77

2-Chloro-1,3,2-dioxophospholane, 2-oxide

A stream of oxygen was bubbled into a solution of about 90 g of ethylene chlorophosphite in about 300 ml of toluene until the exothermic reaction was complete. The toluene was removed and the crude product distilled using a Kugelrohr (about 110° C., 1 mm) giving about 45 g of the desired title compound.

EXAMPLE 78

N-[1-[(1,3,2-Dioxophospholan-2-yloxy)methyl]-2-(octadecyloxy)ethyl]acetamide, 2-oxide To a mixture of about 240 mg of N-[1-(hydroxymethyl)-2-(octadecyloxy)ethyl]acetamide and about 88.7 mg of 2-chloro-1,3,2-dioxophospholane, 2-oxide in about 15 ml of dry toluene was added dropwise a solution of about 6.3 mg of triethylamine in about 2 ml of toluene. The mixture was stirred under argon for about 24 hours and then filtered through a thin layer of celite on a sintered glass funnel. The filtrate was evaporated, giving about 340 mg of the desired title compound.

EXAMPLE 79

7-(acetylamino)-4-hydroxy-N,N,N-trimethyl-3,5,9-trioxo-4-phosphaheptacosan-1-aminium, 4-oxide, hydroxide, inner salt An about 340 mg portion of N-[1-[(1,3,2-dioxophospholan-2-yloxy)methyl]-2-(octadecyloxy)ethyl]acetamide, 2-oxide was dissolved in about 30 ml of acetonitrile and about 6 ml of a solution of about 33.3% trimethylamine in acetonitrile was added. The mixture was refluxed for about 24 hours, cooled and the acetonitrile removed under reduced pressure. The residue was purified by preparative TLC on silica gel, eluting with chloroform:methanol:water (about 65:25:4), giving about 160 mg of the desired product, $[\alpha]_D^{26°} = -9° \pm 1°$ (CHCl$_3$, 0.837%).

By using the phosphorous reagents listed in Table VII, the amines of Table VIII and the appropriate starting materials prepared in Example 75 and listed in Table V and by following the methods described in detail hereinabove in Examples 76, 78 and 79, the compounds of this invention listed below can be prepared. These compounds can be prepared as the individual optically active R and S enantiomers or as racemic mixtures as described in the above specifications.

7-(acetylamino)-4-hydroxy-N,N,N-trimethyl-3,5,9-trioxo-4-phosphatetracosan-1-aminium, 4-oxide, hydroxide, inner salt 7-(acetylamino)-4-hydroxy-N,N-dimethyl-3,5,9-trioxo-4-phosphatetracosan-1-aminium, 4-oxide, hydroxide, inner salt 7-(acetylamino)-4-hydroxy-N-methyl-3,5,9-trioxo-4-phosphatetracosan-1-aminium, 4-oxide, hydroxide, inner salt 7-(acetylamino)-4-hydroxy-N,N-tetramethylene-3,5,9-trioxo-4-phosphatetracosan-1-aminium, 4-oxide, hydroxide, inner salt 7-(propionylamino)-4-hydroxy-N,N,N-trimethyl-3,5,9-trioxo-4-phosphatetracosan-1-aminium, 4-oxide, hydroxide, inner salt 7-(propionylamino)-4-hydroxy-N,N-dimethyl-3,5,9-trioxo-4-phosphatetracosan-1-aminium, 4-oxide, hydroxide, inner salt 7-(butyrylamino)-4-hydroxy-N,N,N-trimethyl-3,5,9-trioxo-4-phosphatetracosan-1-aminium, 4-oxide, hydroxide, inner salt 7-(butyrylamino)-4-hydroxy-N,N-dimethyl-3,5,9-trioxo-4-phosphatetracosan-1-aminium, 4-oxide, hydroxide, inner salt 7-(acetylamino)-4-hydroxy-N,N,N-trimethyl-3,5,9-trioxo-4-phosphahexacosan-1-aminium, 4-oxide, hydroxide, inner salt 7-(acetylamino)-4-hydroxy-N,N-dimethyl-3,5,9-trioxo-4-phosphahexacosan-1-aminium, 4-oxide, hydroxide, inner salt 7-(acetylamino)-4-hydroxy-N-methyl-3,5,9-trioxo-4-phosphahexacosan-1-aminium, 4-oxide, hydroxide, inner salt 7-(acetylamino)-4-hydroxy-N,N-tetramethylene-3,5,9-trioxo-4-phosphahexacosan-1-aminium, 4-oxide, hydroxide, inner salt 7-(propionylamino)-4-hydroxy-N,N,N-trimethyl-3,5,9-trioxo-4-phosphahexacosan-1-aminium, 4-oxide, hydroxide, inner salt 7-(propionylamino)-4-hydroxy-N,N-dimethyl-3,5,9-trioxo-4-phosphahexacosan-1-aminium, 4-oxide, hydroxide, inner salt 7-(butyrylamino)-4-hydroxy-N,N,N-trimethyl-3,5,9-trioxo-4-phosphahexacosan-1-aminium, 4-oxide, hydroxide, inner salt 7-(butyrylamino)-4-hydroxy-N,N-dimethyl-3,5,9-trioxo-4-phosphahexacosan-1-aminium, 4-oxide, hydroxide, inner salt 7-(acetylamino)-4-hydroxy-N,N,N-trimethyl-3,5,9-trioxo-4-phosphaheptacosan-1-aminium, 4-oxide, hydroxide, inner salt 7-(acetylamino)-4-hydroxy-N,N-dimethyl-3,5,9-trioxo-4-phosphaheptacosan-1-aminium, 4-oxide, hydroxide, inner salt 7-(acetylamino)-4-hydroxy-N-methyl-3,5,9-trioxo-4-phospha heptacosan-1-aminium, 4-oxide, hydroxide, inner salt 7-(acetylamino)-4-hydroxy-N,N-tetramethylene-3,5,9-trioxo-4-phospha heptacosan-1-aminium, 4-oxide, hydroxide, inner salt 7-(propionylamino)-4-hydroxy-N,N,N-trimethyl-3,5,9-trioxo-4-phospha heptacosan-1-aminium, 4-oxide, hydroxide, inner salt 7-(propionylamino)-4-hydroxy-N,N-dimethyl-3,5,9-trioxo-4-phospha heptacosan-1-aminium, 4-oxide, hydroxide, inner salt 7-(butyrylamino)-4-hydroxy-N,N,N-trimethyl-3,5,9-trioxo-4-phospha heptacosan-1-aminium, 4-oxide, hydroxide, inner salt 7-(butyrylamino)-4-hydroxy-N,N-dimethyl-3,5,9-trioxo-4-phospha heptacosan-1-aminium, 4-oxide, hydroxide, inner salt 7-(acetylamino)-4-hydroxy-N,N,N-trimethyl-3,5,9-trioxo-4-phospha pentacosan-1-aminium, 4-oxide, hydroxide, inner salt 7-(propionylamino)-4-hydroxy-N,N,N-trimethyl-3,5,9-trioxo-4-phospha pentacosan-1-aminium, 4-oxide, hydroxide, inner salt 7-(butyrylamino)-4-hydroxy-N,N,N-trimethyl-3,5,9-trioxo-4-phospha pentacosan-1-aminium, 4-oxide, hydroxide, inner salt 8-(acetylamino)-5-hydroxy-N,N,N-trimethyl-4,6,10-trioxo-5-phospha tetracosan-1-aminium, 5-oxide, hydroxide, inner salt 8-(acetylamino)-5-hydroxy-N,N-dimethyl-4,6,10-trioxo-5-phospha tetracosan-1-aminium, 5-oxide, hydroxide, inner salt 8-(acetylamino)-5-hydroxy-N-methyl-4,6,10-trioxo-5-phospha tetracosan-1-aminium, 5-oxide, hydroxide, inner salt 8-(acetylamino)-5-hydroxy-N,N-tetramethylene-4,6,10-trioxo-5-phospha tetracosan-1-aminium, 5-oxide, hydroxide, inner salt 8-(propionylamino)-5-hydroxy-N,N,N-trimethyl-4,6,10-trioxo-5-phospha tetracosan-1-aminium, 5-oxide, hydroxide, inner salt 8-(propionylamino)-5-hydroxy-N,N-dimethyl-4,6,10-trioxo-5-phospha tetracosan-1-aminium, 5-oxide, hydroxide, inner salt 8-(butyrylamino)-5-hydroxy-N,N,N-trimethyl-4,6,10-trioxo-5-phospha tetracosan-1-aminium, 5-oxide, hydroxide, inner salt 8-(butyrylamino)-5-hydroxy-N,N-dimethyl-4,6,10-trioxo-5-phospha tetracosan-1-aminium, 5-oxide, hydroxide, inner salt 8-(acetylamino)-5-hydroxy-N,N,N-trimethyl-4,6,10-trioxo-5-phospha pentacosan-1-aminium, 5-oxide, hydroxide, inner salt 8-(acetylamino)-5-hydroxy-N,N-dimethyl-4,6,10-trioxo-5-phospha pentacosan-1-aminium, 5-oxide, hydroxide, inner salt 8-(acetylamino)-5-hydroxy-N-methyl-4,6,10-trioxo-5-phospha pentacosan-1-aminium, 5-oxide, hydroxide, inner salt 8-(acetylamino)-5-hydroxy-N,N-tetramethylene-4,6,10-trioxo-5-phospha pentacosan-1-aminium, 5-oxide, hydroxide, inner salt 8-(propionylamino)-5-hydroxy-N,N,N-trimethyl-4,6,10-trioxo-5-phospha pentacosan-1-aminium, 5-oxide, hydroxide, inner salt 8-(propionylamino)-5-hydroxy-N,N-dimethyl-4,6,10-trioxo-5-phospha pentacosan-1-aminium, 5-oxide, hydroxide, inner salt 8-(butyrylamino)-5-hydroxy-N,N,N-trimethyl-4,6,10-trioxo-5-phospha pentacosan-1-aminium, 5-oxide, hydroxide, inner salt 8-(butyrylamino)-5-hydroxy-N,N-dimethyl-4,6,10-trioxo-5-phospha pentacosan-1-aminium, 5-oxide, hydroxide, inner salt 8-(acetylamino)-5-hydroxy-N,N,N-trimethyl-4,6,10-trioxo-5-phospha hexacosan-1-aminium, 5-oxide, hydroxide, inner salt 8-(acetylamino)-5-hydroxy-N,N-dimethyl-4,6,10-trioxo-5-phospha hexacosan-1-aminium, 5-oxide, hydroxide, inner salt 8-(acetylamino)-5-hydroxy-N-methyl-4,6,10-trioxo-5-phospha hexacosan-1-aminium, 5-oxide, hydroxide, inner salt 8-(acetylamino)-5-hydroxy-N,N-tetramethylene-4,6,10-trioxo-5-phospha hexacosan-1-aminium, 5-oxide, hydroxide, inner salt 8-(propionylamino)-5-hydroxy-N,N,N-trimethyl-4,6,10-trioxo-5-phospha hexacosan-1-aminium, 5-oxide, hydroxide, inner salt 8-(propionylamino)-5-hydroxy-N,N-dimethyl-4,6,10-trioxo-5-phospha hexacosan-1-aminium, 5-oxide, hydroxide, inner salt 8-(butyrylamino)-5-hydroxy-N,N,N-trimethyl-4,6,10-trioxo-5-phospha hexacosan-1-aminium, 5-oxide, hydroxide, inner salt 8-(butyrylamino)-5-hydroxy-N,N-dimethyl-4,6,10-trioxo-5-phospha hexacosan-1-aminium, 5-oxide, hydroxide, inner salt 8-(acetylamino)-5-hydroxy-N,N,N-trimethyl-4,6,10-trioxo-5-phospha heptacosan-1-aminium, 5-oxide, hydroxide, inner salt 8-(acetylamino)-5-hydroxy-N,N-dimethyl-4,6,10-trioxo-5-phospha heptacosan-1-aminium, 5-oxide, hydroxide, inner salt 8-(acetylamino)-5-hydroxy-N-methyl-4,6,10-trioxo-5-phospha heptacosan-1-aminium, 5-oxide, hydroxide, inner salt 8-(acetylamino)-5-hydroxy-N,N-tetramethylene-4,6,10-trioxo-5-phospha heptacosan-1-aminium, 5-oxide, hydroxide, inner salt 8-(propionylamino)-5-hydroxy-N,N,N-trimethyl-4,6,10-trioxo-5-phospha heptacosan-1-aminium, 5-oxide, hydroxide, inner salt 8-(propionylamino)-5-hydroxy-N,N-dimethyl-4,6,10-trioxo-5-phospha heptacosan-1-aminium, 5-oxide, hydroxide, inner salt 8-(butyrylamino)-5-hydroxy-N,N,N-trimethyl-4,6,10-trioxo-5-phospha heptacosan-1-aminium, 5-oxide, hydroxide, inner salt 8-(butyrylamino)-5-hydroxy-N,N-dimethyl-4,6,10-trioxo-5-phospha heptacosan-1-aminium, 5-oxide, hydroxide, inner salt 9-(acetylamino)-6-hydroxy-N,N,N-trimethyl-5,7,11-trioxo-6-phospha tetracosan-1-aminium, 6-oxide, hydroxide, inner salt 9-(acetylamino)-6-hydroxy-N,N-dimethyl-5,7,11-trioxo-6-phospha tetracosan-1-aminium, 6-oxide, hydroxide, inner salt 9-(acetylamino)-6-hydroxy-N-methyl-5,7,11-trioxo-6-phospha tetracosan-1-aminium, 6-oxide, hydroxide, inner salt 9-(acetylamino)-6-hydroxy-N,N-tetramethylene-5,7,11-trioxo-6-phospha tetracosan-1-aminium, 6-oxide, hydroxide, inner salt 9-(propionylamino)-6-hydroxy-N,N,N-trimethyl-5,7,11-trioxo-6-phospha tetracosan-1-aminium, 6-oxide, hydroxide, inner salt 9-(propionylamino)-6-hydroxy-N,N-dimethyl-5,7,11-trioxo-6-phospha tetracosan-1-aminium, 6-oxide, hydroxide, inner salt 9-(butyrylamino)-6-hydroxy-N,N,N-trimethyl-5,7,11-trioxo-6-phospha tetracosan-1-aminium, 6-oxide, hydroxide, inner salt 9-(butyrylamino)-6-hydroxy-N,N-dimethyl-5,7,11-trioxo-6-phospha tetracosan-1-aminium, 6-oxide, hydroxide, inner salt 9-(acetylamino)-6-hydroxy-N,N,N-trimethyl-5,7,11-trioxo-6-phospha pentacosan-1-aminium, 6-oxide, hydroxide, inner salt 9-(acetylamino)-6-hydroxy-N,N-dimethyl-5,7,11-trioxo-6-phospha pentacosan-1-aminium, 6-oxide, hydroxide, inner salt 9-(acetylamino)-6-hydroxy-N-methyl-5,7,11-trioxo-6-phospha pentacosan-1-aminium, 6-oxide, hydroxide, inner salt 9-(acetylamino)-6-hydroxy-N,N-tetramethylene-5,7,11-trioxo-6-phospha pentacosan-1-aminium, 6-oxide, hydroxide, inner salt 9-(propionylamino)-6-hydroxy-N,N,N-trimethyl-5,7,11-trioxo-6-phospha pentacosan-1-aminium, 6-oxide, hydroxide, inner salt 9-(propionylamino)-6-hydroxy-N,N-dimethyl-5,7,11-trioxo-6-phospha pentacosan-1-aminium, 6-oxide, hydroxide, inner salt 9-(butyrylamino)-6-hydroxy-N,N,N-trimethyl-5,7,11-trioxo-6-phospha pentacosan-1-aminium, 6-oxide, hydroxide, inner salt 9-(butyrylamino)-6-hydroxy-N,N-dimethyl-5,7,11-trioxo-6-phospha pentacosan-1-aminium, 6-oxide, hydroxide, inner salt 9-(acetylamino)-6-hydroxy-N,N,N-trimethyl-5,7,11-trioxo-6-phospha hexacosan-1-aminium, 6-oxide, hydroxide, inner salt 9-(acetylamino)-6-hydroxy-N,N-dimethyl-5,7,11-trioxo-6-phospha hexacosan-1-aminium, 6-oxide, hydroxide, inner salt 9-(acetylamino)-6-hydroxy-N-methyl-5,7,11-trioxo-6-phospha hexacosan-1-aminium, 6-oxide, hydroxide, inner salt 9-(acetylamino)-6-hydroxy-N,N-tetramethylene-5,7,11-trioxo-6-phospha hexacosan-1-aminium, 6-oxide, hydroxide, inner salt 9-(propionylamino)-6-hydroxy-N,N,N-trimethyl-5,7,11-trioxo-6-phospha hexacosan-1-aminium, 6-oxide, hydroxide, inner salt 9-(propionylamino)-6-hydroxy-N,N-dimethyl-5,7,11-trioxo-6-phospha hexacosan-1-aminium, 6-oxide, hydroxide, inner salt 9-(butyrylamino)-6-hydroxy-N,N,N-trimethyl-5,7,11-trioxo-6-phospha hexacosan-1-aminium, 6-oxide, hydroxide, inner salt 9-(butyrylamino)-6-hydroxy-N,N-dimethyl-5,7,11-trioxo-6-phospha hexacosan-1-aminium, 6-oxide, hydroxide, inner salt 9-(acetylamino)-6-hydroxy-N,N,N-trimethyl-5,7,11-trioxo-6-phospha heptacosan-1-aminium, 6-oxide, hydroxide, inner salt 9-(acetylamino)-6-hydroxy-N,N-dimethyl-5,7,11-trioxo-6-phospha heptacosan-1-aminium, 6-oxide, hydroxide, inner salt 9-(acetylamino)-6-hydroxy-N-methyl-5,7,11-trioxo-6-phospha heptacosan-1-aminium, 6-oxide, hydroxide, inner salt 9-(acetylamino)-6-hydroxy-N,N-tetramethylene-5,7,11-trioxo-6-phospha heptacosan-1-aminium, 6-oxide, hydroxide, inner salt 9-(propionylamino)-6-hydroxy-N,N,N-trimethyl-5,7,11-trioxo-6-phospha heptacosan-1-aminium, 6-oxide, hydroxide, inner salt 9-(propionylamino)-6-hydroxy-N,N-dimethyl-5,7,11-trioxo-6-phospha heptacosan-1-aminium, 6-oxide, hydroxide, inner salt 9-(butyrylamino)-6-hydroxy-N,N,N-trimethyl-5,7,11-trioxo-6-phospha heptacosan-1-aminium, 6-oxide, hydroxide, inner salt 9-(butyrylamino)-6-hydroxy-N,N-dimethyl-5,7,11-trioxo-6-phospha heptacosan-1-aminium, 6-oxide, hydroxide, inner salt 9-(acetylamino)-6-hydroxy-N,N,N-trimethyl-5,7,11-trioxo-6-phospha pentacosan-1-aminium, 6-oxide, hydroxide, inner salt 9-(propionylamino)-6-hydroxy-N,N,N-trimethyl-5,7,11-trioxo-6-phospha pentacosan-1-aminium, 6-oxide, hydroxide, inner salt 9-(butyrylamino)-6-hydroxy-N,N,N-trimethyl-5,7,11-trioxo-6-phospha pentacosan-1-aminium, 6-oxide, hydroxide, inner salt 7-(acetylamino)-4-hydroxy-N,N,N-trimethyl-3,5,9-trioxo-10-methyl-4-phospha pentacosan-1-aminium, 4-oxide, hydroxide, inner salt 7-(propionylamino)-4-hydroxy-N,N,N-trimethyl-3,5,9-trioxo-10-methyl-4-phospha pentacosan-1-aminium, 4-oxide, hydroxide, inner salt 7-(butyrylamino)-4-hydroxy-N,N,N-trimethyl-3,5,9-trioxo-10-methyl-4-phospha pentacosan-1-aminium, 4-oxide, hydroxide, inner salt 7-(acetylamino)-4-hydroxy-N,N,N-trimethyl-3,5,9-trioxo-11-ethyl-4-phospha tetracosan-1-aminium, 4-oxide, hydroxide, inner salt 7-(acetylamino)-4-hydroxy-N,N-dimethyl-3,5,9-trioxo-11-ethyl-4-phospha tetracosan-1-aminium, 4-oxide, hydroxide, inner salt 7-(acetylamino)-4-hydroxy-N-methyl-3,5,9-trioxo-11-ethyl-4-phospha tetracosan-1-aminium, 4-oxide, hydroxide, inner salt 7-(acetylamino)-4-hydroxy-N,N-tetramethylene-3,5,9-trioxo-11-ethyl-4-phospha tetracosan-1-aminium, 4-oxide, hydroxide, inner salt 7-(propionylamino)-4-hydroxy-N,N,N-trimethyl-3,5,9-trioxo-11-ethyl-4-phospha tetracosan-1-aminium, 4-oxide, hydroxide, inner salt 7-(propionylamino)-4-hydroxy-N,N-dimethyl-3,5,9-trioxo-11-ethyl-4-phospha tetracosan-1-aminium, 4-oxide, hydroxide, inner salt 7-(butyrylamino)-4-hydroxy-N,N,N-trimethyl-3,5,9-trioxo-11-ethyl-4-phospha tetracosan-1-aminium, 4-oxide, hydroxide, inner salt 7-(butyrylamino)-4-hydroxy-N,N-dimethyl-3,5,9-trioxo-11-ethyl-4-phospha tetracosan-1-aminium, 4-oxide, hydroxide, inner salt 2-[[2-(acetylamino)-3-(octadecyloxy)propoxy]hydroxyphosphinyl]-N,N,N-trimethyl-ethanaminium, hydroxide, inner salt 2-[[2-(acetylamino)-3-(octadecyloxy)propoxy]hydroxyphosphinyl]-N,N-dimethyl-ethanaminium, hydroxide, inner salt 2-[[2-(acetylamino)-3-(hexadecyloxy)propoxy]hydroxyphosphinyl]-N,N,N-trimethyl-ethanaminium, hydroxide, inner salt 2-[[2-(acetylamino)-3-(hexadecyloxy)propoxy]hydroxyphosphinyl]-N,N-dimethyl-ethanaminium, hydroxide, inner salt

EXAMPLE 80

4-Methoxy-1-tetradecyl-benzene

An about 3.70 g portion of magnesium was placed in a 100 ml, two-necked round bottom flask. The flask was flamed several times and about 28.5 g of p-bromoanisole and tetrahydrofuran were added. As soon as the reaction stopped it was refluxed for about 2 hours and then added to a boiling solution of about 21.07 g of tetradecyl bromide in tetrahydrofuran. Then about 9 ml of lithium cupric chloride was added and the mixture was refluxed for about 2 hours, then stirred at room temperature for about 16 hours, quenched with dilute hydrochloric acid, washed with ammonium chloride solution, sodium bicarbonate solution, brine and dried, giving about 23 g of the desired title compound, mp 38° C.

EXAMPLE 81

4-Tetradecylphenol

Boron tribromide was added dropwise, under argon to an about −78° C. solution of about 12.16 g of 4-methoxy-1-tetradecyl-benzene in about 125 ml of methylene chloride. The reaction was stirred for about 2½ hours at about −78° C., then water was added dropwise, the organic layer separated, washed with sodium bicarbonate solution and evaporated, giving about 11.8 g of the desired title compound, mp 70°–71° C.

According to the methods described hereinabove in Examples 80 and 81 and hereinbelow in Examples 91 and 92, the phenols listed in Table VI are prepared from the indicated bromoanisole and alkylhalide.

TABLE VI

| Bromo Anisole | Alkyl Halide | Phenol |
| --- | --- | --- |
| p-bromoanisole | dodecyl bromide | 4-dodecylphenol |
| m-bromoanisole | tetradecyl bromide | 3-tetradecylphenol |
| o-bromoanisole | tetradecyl bromide | 2-tetradecylphenol |
| m-bromoanisole | tridecyl iodide | 3-tridecylphenol |
| o-bromoanisole | pentadecyl bromide | 2-pentadecylphenol |
| o-bromoanisole | hexadecyl iodide | 2-hexadecylphenol |

The phosphorous reagents listed hereinbelow in Table VII which are used to prepare the compounds of this invention are prepared by following the methods outlined hereinabove in Examples 41, 69, 70, 71a, 71b, and 77 and those methods described in the following references: E. Baer and N. Z. Stanacey, J. BIOL. CHEM., 240: 3754 (1965); A. Eberhard and F. H. Westheimer, J. AMER. CHEM. SOC., 37: 253 (1965); W. Diembeck and H. Eibl, CHEM. PHY. LIPIDS 24: 237 (1979).

TABLE VII

| Phosphorous Reagents |
| --- |
| 2-bromoethyl phosphorodichlorodate |
| 3-bromopropyl phosphorodichlorodate |
| 4-bromobutyl phosphorodichlorodate |
| 5-bromopentyl phosphorodichlorodate |
| (2-bromoethyl) phosphoric acid monochloride |
| (3-bromopropyl) phosphoric acid monochloride |
| (4-bromobutyl) phosphonic acid monochloride |
| (5-bromopentyl) phosphonic acid monochloride |
| 2-chloro-1,3,2-dioxophospholane, 2-oxide |

Some of the alkyl amines which can be used to prepare the compounds of this invention are listed hereinbelow in Table VIII.

TABLE VIII

| Alkyl Amines |
| --- |
| trimethyl amine |
| dimethyl amine |
| methyl amine |
| triethyl amine |
| diethyl amine |

TABLE VIII-continued
Alkyl Amines ethyl amine
tripropyl amine
dipropyl amine
propyl amine
pyrrolidine
N—methyl pyrrolidine
butyl amine
ammonia

EXAMPLE 82

2,2-Dimethyl-4-[(4-tetradecylphenoxy)methyl]-1,3-dioxolane

To a prewashed suspension of about 10.8 g of sodium hydride in about 800 ml of dimethylformamide was added about 43.5 g of 4-tetradecylphenol. The reaction was then refluxed about 2 hours, cooled to room temperature and about 37.8 g of freshly prepared 2,2-dimethyl-4-[[(methylsulfonyl)oxy]methyl]-1,3-dioxolane was added. The reaction was then refluxed for about 24 hours, cooled, diluted with ether, washed with water and dried, giving about 58.7 g of the desired title compound, mp 52°–53° C.

EXAMPLE 83

3-(4-Tetradecylphenoxy)-1,2-propanediol

An about 43.5 g portion of 4-tetradecyl phenol was added in portions to a suspension of about 10.8 g of prewashed sodium hydride in dimethylformamide. The mixture was refluxed about 1½ hours, allowed to cool and about 37.8 g of 2,2-dimethyl-4-[[methylsulfonyl)oxy]methyl]-1,3-dioxolane was added. This mixture was heated to about 80° C. for about 24 hours; diluted with hexane and ether, washed with water and brine and evaporated. The residue was heated on a steam bath with about 500 ml of methanol and about 80 ml of dilute hydrochloric acid for one hour, cooled, partially evaporated, the solid collected and recrystallized from methanol, giving about 38 g of the desired title compound, mp 81.5°–83.5° C.

EXAMPLE 84

1-(4-Tetradecylphenoxy)-3-(triphenylmethoxy)-2-propanol

An about 364 mg portion of 3-(4-tetradecylphenoxy)-1,2-propanediol was dissolved in about 1.5 ml of dry pyridine and about 501 mg of tritylchloride was added. The mixture was stirred under argon for about 72 hours, ether was added and the mixture was washed with ice-cold dilute (about 1N) hydrochloric acid, sodium bicarbonate solution, brine, then dried and the solvent evaporated. The residue was recrystallized from ethanol, giving about 700 mg of the desired title compound.

EXAMPLE 85

1-[2-(Phenylmethoxy)-3-(triphenylmethoxy)propoxy]-4-tetradecyl benzene

To a solution of about 13.78 g of 1-(4-tetradecyl phenoxy)-3-(triphenylmethoxy)-2-propanol in about 45 ml of dimethylformamide was added a suspension of about 1.426 g of ether pre-washed sodium hydride in about 10 ml of dimethylformamide, followed by a solution of about 4.06 g of benzylbromide in about 5 ml of dimethylformamide. The mixture was stirred under argon for about 3 hours, quenched very slowly with water and extracted twice with about 50% ether in hexane. The organic layer was dried, filtered and the solvents removed, giving about 15.7 g of the desired title compound.

EXAMPLE 86

2-(Phenylmethoxy)-3-(4-tetradecylphenoxy)-1-propanol

An about 14.6 g portion of 1-[2-(phenylmethoxy)-3-(triphenylmethoxy)propoxy]-4-tetradecylbenzene was dissolved in about 50 ml of tetrahydrofuran. To this solution was added about 50 ml of methanol and about 100 mg of p-toluenesulfonic acid. The mixture was stirred under argon for several hours and the solvents were then removed. The residue was dissolved in ether, washed with aqueous sodium bicarbonate, dried and the ether evaporated. The residue was purified by chromatography on silica gel, eluting with hexane:ether (about 12:1), giving about 7.6 g of the desired title compound, mp 50°–51° C.

EXAMPLE 87

2-Bromoethyl 2-(phenylmethoxy)-3-(4-tetradecylphenoxy)propyl phosphate

To a solution of about 4.54 g of 2-(phenylmethoxy)-3-(4-tetradecylphenoxy)-1-propanol in about 50 ml of carbon tetrachloride was added about 2.88 g of 2-bromoethyl phosphorodichlorodate, followed by about 1.21 g of triethylamine. The mixture was stirred under argon for about 2 hours, filtered through celite and the solvent removed under reduced pressure. The residue was dissolved in about 50 ml of tetrahydrofuran, about 50 ml of about 0.5M sodium acetate was added and the mixture stirred for about 48 hours. Dilute hydrochloric acid (about 1N) and brine were added and the mixture was extracted several times with ethyl acetate. The organic layers were combined, washed with brine, dried and evaporated, giving a residue which was purified by chromatography on florisil, eluting with hexane:ether (about 1:1), giving about 5.3 g of the desired title compound.

EXAMPLE 88

4-Hydroxy-N,N,N-trimethyl-9-phenyl-7-[(4-tetradecylphenoxy)methyl]-3,5,8-trioxa-4-phosphanonan-1-aminium, 4-oxide, hydroxide, inner salt A mixture of about 4.86 g of 2-bromoethyl 2-(phenylmethoxy)-3-(4-tetradecylphenoxy)propyl phosphate, about 60 ml of about 40% aqueous trimethylamine and about 130 ml of chloroform:2-propanol:dimethylformamide (about 3:5:5) was heated at about 65° C. for about 5 hours. The volume of solvents was reduced to about ½, then about 80 ml of ethanol followed by about 638 mg of silver carbonate were added. The mixture was stirred at room temperature for one hour, filtered through celite and the solvents removed under reduced pressure. The crude material was purified by chromatography on silica gel, eluting first with chloroform:methanol:ammonium hydroxide (about 25:125:1) and then with the same constituents (about 30:30:1), giving about 3.5 g of the desired title compound.

EXAMPLE 89

2-[[Hydroxy-[2-hydroxy-3-(4-tetradecylphenoxy)-propoxy]phosphinyl]oxy]-N,N,N-trimethyl-ethanaminium, hydroxide, inner salt A mixture of about 2.85 g of 4-hydroxy-N,N,N-trimethyl-9-phenyl-7-[(4-tetradecylphenoxy)methyl]-3,5,8-trioxa-4-phosphanonan-1-aminium, 4-oxide, hydroxide, inner salt, about 0.3 g of about 5% palladium on carbon, about 30 ml of methanol and about 30 ml of glacial acetic acid was hydrogenated in a Parr shaker for about 18 hours. The catalyst was filtered off through celite and the solvent removed under reduced pressure at about 40°–50° C., giving about 2.5 g of the desired title compound, mp 180° C. (dec.).

EXAMPLE 90

4-Hydroxy-N,N,N-trimethyl-9-oxo-7-[(4-tetradecylphenoxy)methyl]-3,5,8-trioxa-4-phosphadecan-1-aminium, 4-oxide, hydroxide, inner salt A mixture of about 2.12 g of 2-[[hydroxy-[2-hydroxy-3-(4-tetradecylphenoxy)propoxy]phosphinyl]oxy]-N,N,N-trimethyl-ethanaminium, hydroxide, inner salt, about 9.44 ml of acetic anhydride, about 5.57 ml of triethylamine and about 120 ml of chloroform was refluxed for about 4 hours. The solvents were removed under reduced pressure and the crude product purified by chromatography on about 100 g of silica gel, eluting first with chloroform:methanol (about 7:3), then (about 1:1), then (about 3:7) and finally with chloroform:methanol:ammonium hydroxide (about 1:9:1), giving about 2.5 g of the desired product, IR (KBr) 1735 cm$^{-1}$.

By using the phosphorous reagents listed in Table VII, the amines of Table VIII and the appropriate starting materials prepared in Examples 81 and 82 and those listed in Table VI and by following the methods described in detail hereinabove in Examples 82–90, the compounds of this invention listed below can be prepared. These compounds can be prepared as the individual optically active R and S enantiomers or as racemic mixtures as described in the above specifications.

4-hydroxy-N,N,N-trimethyl-9-oxo-7-[(4-tetradecylphenoxy)methyl]-3,5,8-trioxa-4-phosphanonan-1-aminium, 4-oxide, hydroxide, inner salt 4-hydroxy-N,N,N-trimethyl-9-oxo-7-[(3-tetradecylphenoxy)methyl]-3,5,8-trioxa-4-phosphanonan-1-aminium, 4-oxide, hydroxide, inner salt 4-hydroxy-N,N,N-trimethyl-9-oxo-7-[(2-tetradecylphenoxy)methyl]-3,5,8-trioxa-4-phosphanonan-1-aminium, 4-oxide, hydroxide, inner salt 4-hydroxy-N,N,N-trimethyl-9-oxo-7-[(3-tridecylphenoxy)methyl]-3,5,8-trioxa-4-phosphanonan-1-aminium, 4-oxide, hydroxide, inner salt 4-hydroxy-N,N,N-trimethyl-9-oxo-7-[(2-hexadecylphenoxy)methyl]-3,5,8-trioxa-4-phosphanonan-1-aminium, 4-oxide, hydroxide, inner salt 4-hydroxy-N,N-dimethyl-9-oxo-7-[(4-tetradecylphenoxy)methyl]-3,5,8-trioxa-4-phosphanonan-1-aminium, 4-oxide, hydroxide, inner salt 4-hydroxy-N,N-dimethyl-9-oxo-7-[(3-tetradecylphenoxy)methyl]-3,5,8-trioxa-4-phosphanonan-1-aminium, 4-oxide, hydroxide, inner salt 4-hydroxy-N,N-dimethyl-9-oxo-7-[(4-dodecylphenoxy)methyl]-3,5,8-trioxa-4-phosphanonan-1-aminium, 4-oxide, hydroxide, inner salt 4-hydroxy-N,N-dimethyl-9-oxo-7-[(3-tridecylphenoxy)methyl]-3,5,8-trioxa-4-phosphanonan-1-aminium, 4-oxide, hydroxide, inner salt 4-hydroxy-N,N-dimethyl-9-oxo-7-[(2-hexadecylphenoxy)methyl]-3,5,8-trioxa-4-phosphanonan-1-aminium, 4-oxide, hydroxide, inner salt 4-hydroxy-N-ethyl-9-oxo-7-[(4-tetradecylphenoxy)methyl]-3,5,8-trioxa-4-phosphanonan-1-aminium, 4-oxide, hydroxide, inner salt 4-hydroxy-N-ethyl-9-oxo-7-[(2-tetradecylphenoxy)methyl]-3,5,8-trioxa-4-phosphanonan-1-aminium, 4-oxide, hydroxide, inner salt 4-hydroxy-N-ethyl-9-oxo-7-[(4-dodecylphenoxy)methyl]-3,5,8-trioxa-4-phosphanonan-1-aminium, 4-oxide, hydroxide, inner salt 4-hydroxy-N,N,N-trimethyl-9-oxo-7-[(4-tetradecylphenoxy)methyl]-3,5,8-trioxa-4-phosphadecan-1-aminium, 4-oxide, hydroxide, inner salt 4-hydroxy-N,N,N-trimethyl-9-oxo-7-[(3-tetradecylphenoxy)methyl]-3,5,8-trioxa-4-phosphadecan-1-aminium, 4-oxide, hydroxide, inner salt 4-hydroxy-N,N,N-trimethyl-9-oxo-7-[(2-tetradecylphenoxy)methyl]-3,5,8-trioxa-4-phosphadecan-1-aminium, 4-oxide, hydroxide, inner salt 4-hydroxy-N,N,N-trimethyl-9-oxo-7-[(3-tridecylphenoxy)methyl]-3,5,8-trioxa-4-phosphadecan-1-aminium, 4-oxide, hydroxide, inner salt 4-hydroxy-N,N,N-trimethyl-9-oxo-7-[(2-hexadecylphenoxy)methyl]-3,5,8-trioxa-4-phosphadecan-1-aminium, 4-oxide, hydroxide, inner salt 4-hydroxy-N,N-dimethyl-9-oxo-7-[(4-tetradecylphenoxy)methyl]-3,5,8-trioxa-4-phosphadecan-1-aminium, 4-oxide, hydroxide, inner salt 4-hydroxy-N,N-dimethyl-9-oxo-7-[(3-tetradecylphenoxy)methyl]-3,5,8-trioxa-4-phosphadecan-1-aminium, 4-oxide, hydroxide, inner salt 4-hydroxy-N,N-dimethyl-9-oxo-7-[(4-dodecylphenoxy)methyl]-3,5,8-trioxa-4-phosphadecan-1-aminium, 4-oxide, hydroxide, inner salt 4-hydroxy-N,N-dimethyl-9-oxo-7-[(3-tridecylphenoxy)methyl]-3,5,8-trioxa-4-phosphadecan-1-aminium, 4-oxide, hydroxide, inner salt 4-hydroxy-N,N-dimethyl-9-oxo-7-[(2-hexadecylphenoxy)methyl]-3,5,8-trioxa-4-phosphadecan-1-aminium, 4-oxide, hydroxide, inner salt 4-hydroxy-N-ethyl-9-oxo-7-[(4-tetradecylphenoxy)methyl]-3,5,8-trioxa-4-phosphadecan-1-aminium, 4-oxide, hydroxide, inner salt 4-hydroxy-N-ethyl-9-oxo-7-[(2-tetradecylphenoxy)methyl]-3,5,8-trioxa-4-phosphadecan-1-aminium, 4-oxide, hydroxide, inner salt 4-hydroxy-N-ethyl-9-oxo-7-[(4-dodecylphenoxy)methyl]-3,5,8-trioxa-4-phosphadecan-1-aminium, 4-oxide, hydroxide, inner salt 4-hydroxy-N,N,N-trimethyl-9-oxo-7-[(4-tetradecylphenoxy)methyl]-3,5,8-trioxa-4-phosphaundecan-1-aminium, 4-oxide, hydroxide, inner salt 4-hydroxy-N,N,N-trimethyl-9-oxo-7-[(3-tetradecylphenoxy)methyl]-3,5,8-trioxa-4-phosphaundecan-1-aminium, 4-oxide, hydroxide, inner salt 4-hydroxy-N,N,N-trimethyl-9-oxo-7-[(2-tetradecylphenoxy)methyl]-3,5,8-trioxa-4-phosphaundecan-1-aminium, 4-oxide, hydroxide, inner salt 4-hydroxy-N,N,N-trimethyl-9-oxo-7-[(3-tridecylphenoxy)methyl]-3,5,8-trioxa-4-phosphaundecan-1-aminium, 4-oxide, hydroxide, inner salt 4-hydroxy-N,N,N-trimethyl-9-oxo-7-[(2-hexadecyl-phenoxy)methyl]-3,5,8-trioxa-4-phosphaundecan-1-aminium, 4-oxide, hydroxide, inner salt 4-hydroxy-N,N-dimethyl-9-oxo-7-[(4-tetradecyl-phenoxy)methyl]-3,5,8-trioxa-4-phosphaundecan-1-aminium, 4-oxide, hydroxide, inner salt 4-hydroxy-N,N-dimethyl-9-oxo-7-[(3-tetradecyl-phenoxy)methyl]-3,5,8-trioxa-4-phosphaundecan-1-aminium, 4-oxide, hydroxide, inner salt 4-hydroxy-N,N-dimethyl-9-oxo-7-[(4-dodecylphenoxy)methyl]-3,5,8-trioxa-4-phosphaundecan-1-aminium, 4-oxide, hydroxide, inner salt 4-hydroxy-N,N-dimethyl-9-oxo-7-[(3-tridecylphenoxy)methyl]-3,5,8-trioxa-4-phosphaundecan-1-aminium, 4-oxide, hydroxide, inner salt 4-hydroxy-N,N-dimethyl-9-oxo-7-[(2-hexadecyl-phenoxy)methyl]-3,5,8-trioxa-4-phosphaundecan-1-aminium, 4-oxide, hydroxide, inner salt 4-hydroxy-N-ethyl-9-oxo-7-[(4-tetradecylphenoxy)methyl]-3,5,8-trioxa-4-phosphaundecan-1-aminium, 4-oxide, hydroxide, inner salt 4-hydroxy-N-ethyl-9-oxo-7-[(2-tetradecylphenoxy)methyl]-3,5,8-trioxa-4-phosphaundecan-1-aminium, 4-oxide, hydroxide, inner salt 4-hydroxy-N-ethyl-9-oxo-7-[(4-dodecylphenoxy)methyl]-3,5,8-trioxa-4-phosphaundecan-1-aminium, 4-oxide, hydroxide, inner salt 4-hydroxy-N,N,N-trimethyl-9-oxo-7-[(4-tetradecyl-phenoxy)methyl]-3,5,8-trioxa-4-phosphadodecan-1-aminium, 4-oxide, hydroxide, inner salt 4-hydroxy-N,N,N-trimethyl-9-oxo-7-[(3-tetradecyl-phenoxy)methyl]-3,5,8-trioxa-4-phosphadodecan-1-aminium, 4-oxide, hydroxide, inner salt 4-hydroxy-N,N,N-trimethyl-9-oxo-7-[(2-tetradecyl-phenoxy)methyl]-3,5,8-trioxa-4-phosphadodecan-1-aminium, 4-oxide, hydroxide, inner salt 4-hydroxy-N,N,N-trimethyl-9-oxo-7-[(3-tridecyl-phenoxy)methyl]-3,5,8-trioxa-4-phosphadodecan-1-aminium, 4-oxide, hydroxide, inner salt 4-hydroxy-N,N,N-trimethyl-9-oxo-7-[(2-hexadecyl-phenoxy)methyl]-3,5,8-trioxa-4-phosphadodecan-1-aminium, 4-oxide, hydroxide, inner salt 4-hydroxy-N,N-dimethyl-9-oxo-7-[(4-tetradecyl-phenoxy)methyl]-3,5,8-trioxa-4-phosphadodecan-1-aminium, 4-oxide, hydroxide, inner salt 4-hydroxy-N,N-dimethyl-9-oxo-7-[(3-tetradecyl-phenoxy)methyl]-3,5,8-trioxa-4-phosphadodecan-1-aminium, 4-oxide, hydroxide, inner salt 4-hydroxy-N,N-dimethyl-9-oxo-7-[(4-dodecylphenoxy)methyl]-3,5,8-trioxa-4-phosphadodecan-1-aminium, 4-oxide, hydroxide, inner salt 4-hydroxy-N,N-dimethyl-9-oxo-7-[(3-tridecylphenoxy)methyl]-3,5,8-trioxa-4-phosphadodecan-1-aminium, 4-oxide, hydroxide, inner salt 4-hydroxy-N,N-dimethyl-9-oxo-7-[(2-hexadecyl-phenoxy)methyl]-3,5,8-trioxa-4-phosphadodecan-1-aminium, 4-oxide, hydroxide, inner salt 4-hydroxy-N-ethyl-9-oxo-7-[(4-tetradecylphenoxy)methyl]-3,5,8-trioxa-4-phosphadodecan-1-aminium, 4-oxide, hydroxide, inner salt 4-hydroxy-N-ethyl-9-oxo-7-[(2-tetradecylphenoxy)methyl]-3,5,8-trioxa-4-phosphadodecan-1-aminium, 4-oxide, hydroxide, inner salt 4-hydroxy-N-ethyl-9-oxo-7-[(4-dodecylphenoxy)methyl]-3,5,8-trioxa-4-phosphadodecan-1-aminium, 4-oxide, hydroxide, inner salt 5-hydroxy-N,N,N-trimethyl-10-oxo-8-[(4-tetradecyl-phenoxy)methyl]-4,6,9-trioxa-5-phosphadecan-1-aminium, 5-oxide, hydroxide, inner salt 5-hydroxy-N,N,N-trimethyl-10-oxo-8-[(3-tetradecyl-phenoxy)methyl]-4,6,9-trioxa-5-phosphadecan-1-aminium, 5-oxide, hydroxide, inner salt 5-hydroxy-N,N,N-trimethyl-10-oxo-8-[(2-tetradecyl-phenoxy)methyl]-4,6,9-trioxa-5-phosphadecan-1-aminium, 5-oxide, hydroxide, inner salt 5-hydroxy-N,N,N-trimethyl-10-oxo-8-[(3-tridecyl-phenoxy)methyl]-4,6,9-trioxa-5-phosphadecan-1-aminium, 5-oxide, hydroxide, inner salt 5-hydroxy-N,N,N-trimethyl-10-oxo-8-[(2-hexadecyl-phenoxy)methyl]-4,6,9-trioxa-5-phosphadecan-1-aminium, 5-oxide, hydroxide, inner salt 5-hydroxy-N,N-dimethyl-10-oxo-8-[(4-tetradecyl-phenoxy)methyl]-4,6,9-trioxa-5-phosphadecan-1-aminium, 5-oxide, hydroxide, inner salt 5-hydroxy-N,N-dimethyl-10-oxo-8-[(3-tetradecyl-phenoxy)methyl]-4,6,9-trioxa-5-phosphadecan-1-aminium, 5-oxide, hydroxide, inner salt 5-hydroxy-N,N-dimethyl-10-oxo-8-[(4-dodecylphenoxy)methyl]-4,6,9-trioxa-5-phosphadecan-1-aminium, 5-oxide, hydroxide, inner salt 5-hydroxy-N,N-dimethyl-10-oxo-8-[(3-tridecylphenoxy)methyl]-4,6,9-trioxa-5-phosphadecan-1-aminium, 5-oxide, hydroxide, inner salt 5-hydroxy-N,N-dimethyl-10-oxo-8-[(2-hexadecyl-phenoxy)methyl]-4,6,9-trioxa-5-phosphadecan-1-aminium, 5-oxide, hydroxide, inner salt 5-hydroxy-N-ethyl-10-oxo-8-[(4-tetradecylphenoxy)-methyl]-4,6,9-trioxa-5-phosphadecan-1-aminium, 5-oxide, hydroxide, inner salt 5-hydroxy-N-ethyl-10-oxo-8-[(2-tetradecylphenoxy)-methyl]-4,6,9-trioxa-5-phosphadecan-1-aminium, 5-oxide, hydroxide, inner salt 5-hydroxy-N-ethyl-10-oxo-8-[(4-dodecylphenoxy)methyl]-4,6,9-trioxa-5-phosphadecan-1-aminium, 5-oxide, hydroxide, inner salt 5-hydroxy-N,N,N-trimethyl-10-oxo-8-[(4-tetradecyl-phenoxy)methyl]-4,6,9-trioxa-5-phosphaundecan-1-aminium, 5-oxide, hydroxide, inner salt 5-hydroxy-N,N,N-trimethyl-10-oxo-8-[(3-tetradecyl-phenoxy)methyl]-4,6,9-trioxa-5-phosphaundecan-1-aminium, 5-oxide, hydroxide, inner salt 5-hydroxy-N,N,N-trimethyl-10-oxo-8-[(2-tetradecyl-phenoxy)methyl]-4,6,9-trioxa-5-phosphaundecan-1-aminium, 5-oxide, hydroxide, inner salt 5-hydroxy-N,N,N-trimethyl-10-oxo-8-[(3-tridecyl-phenoxy)methyl]-4,6,9-trioxa-5-phosphaundecan-1-aminium, 5-oxide, hydroxide, inner salt 5-hydroxy-N,N,N-trimethyl-10-oxo-8-[(2-hexadecyl-phenoxy)methyl]-4,6,9-trioxa-5-phosphaundecan-1-aminium, 5-oxide, hydroxide, inner salt 5-hydroxy-N,N-dimethyl-10-oxo-8-[(4-tetradecyl-phenoxy)methyl]-4,6,9-trioxa-5-phosphaundecan-1-aminium, 5-oxide, hydroxide, inner salt 5-hydroxy-N,N-dimethyl-10-oxo-8-[(3-tetradecyl-phenoxy)methyl]-4,6,9-trioxa-5-phosphaundecan-1-aminium, 5-oxide, hydroxide, inner salt 5-hydroxy-N,N-dimethyl-10-oxo-8-[(4-dodecylphenoxy)methyl]-4,6,9-trioxa-5-phosphaundecan-1-aminium, 5-oxide, hydroxide, inner salt 5-hydroxy-N,N-dimethyl-10-oxo-8-[(3-tridecylphenoxy)methyl]-4,6,9-trioxa-5-phosphaundecan-1-aminium, 5-oxide, hydroxide, inner salt 5-hydroxy-N,N-dimethyl-10-oxo-8-[(2-hexadecyl-phenoxy)methyl]-4,6,9-trioxa-5-phosphaundecan-1-aminium, 5-oxide, hydroxide, inner salt 5-hydroxy-N-ethyl-10-oxo-8-[(4-tetradecylphenoxy)-methyl]-4,6,9-trioxa-5-phosphaundecan-1-aminium, 5-oxide, hydroxide, inner salt 5-hydroxy-N-ethyl-10-oxo-8-[(2-tetradecylphenoxy)-methyl]-4,6,9-trioxa-5-phosphaundecan-1-aminium, 5-oxide, hydroxide, inner salt 5-hydroxy-N-ethyl-10-oxo-8-[(4-dodecylphenoxy)me-thyl]-4,6,9-trioxa-5-phosphaundecan-1-aminium, 5-oxide, hydroxide, inner salt 5-hydroxy-N,N,N-trimethyl-10-oxo-8-[(4-tetradecyl-phenoxy)methyl]-4,6,9-trioxa-5-phosphadodecan-1-aminium, 5-oxide, hydroxide, inner salt 5-hydroxy-N,N,N-trimethyl-10-oxo-8-[(3-tetradecyl-phenoxy)methyl]-4,6,9-trioxa-5-phosphadodecan-1-aminium, 5-oxide, hydroxide, inner salt 5-hydroxy-N,N,N-trimethyl-10-oxo-8-[(2-tetradecyl-phenoxy)methyl]-4,6,9-trioxa-5-phosphadodecan-1-aminium, 5-oxide, hydroxide, inner salt 5-hydroxy-N,N,N-trimethyl-10-oxo-8-[(3-tridecyl-phenoxy)methyl]-4,6,9-trioxa-5-phosphadodecan-1-aminium, 5-oxide, hydroxide, inner salt 5-hydroxy-N,N,N-trimethyl-10-oxo-8-[(2-hexadecyl-phenoxy)methyl]-4,6,9-trioxa-5-phosphadodecan-1-aminium, 5-oxide, hydroxide, inner salt 5-hydroxy-N,N-dimethyl-10-oxo-8-[(4-tetradecyl-phenoxy)methyl]-4,6,9-trioxa-5-phosphadodecan-1-aminium, 5-oxide, hydroxide, inner salt 5-hydroxy-N,N-dimethyl-10-oxo-8-[(3-tetradecyl-phenoxy)methyl]-4,6,9-trioxa-5-phosphadodecan-1-aminium, 5-oxide, hydroxide, inner salt 5-hydroxy-N,N-dimethyl-10-oxo-8-[(4-dodecylphenox-y)methyl]-4,6,9-trioxa-5-phosphadodecan-1-aminium, 5-oxide, hydroxide, inner salt 5-hydroxy-N,N-dimethyl-10-oxo-8-[(3-tridecylphenox-y)methyl]-4,6,9-trioxa-5-phosphadodecan-1-aminium, 5-oxide, hydroxide, inner salt 5-hydroxy-N,N-dimethyl-10-oxo-8-[(2-hexadecyl-phenoxy)methyl]-4,6,9-trioxa-5-phosphadodecan-1-aminium, 5-oxide, hydroxide, inner salt 5-hydroxy-N-ethyl-10-oxo-8-[(4-tetradecylphenoxy)-methyl]-4,6,9-trioxa-5-phosphadodecan-1-aminium, 5-oxide, hydroxide, inner salt 5-hydroxy-N-ethyl-10-oxo-8-[(2-tetradecylphenoxy)-methyl]-4,6,9-trioxa-5-phosphadodecan-1-aminium, 5-oxide, hydroxide, inner salt 5-hydroxy-N-ethyl-10-oxo-8-[(4-dodecylphenoxy)me-thyl]-4,6,9-trioxa-5-phosphadodecan-1-aminium, 5-oxide, hydroxide, inner salt 6-hydroxy-N,N,N-trimethyl-11-oxo-9-[(4-tetradecyl-phenoxy)methyl]-5,7,10-trioxa-6-phosphaundecan-1-aminium, 6-oxide, hydroxide, inner salt 6-hydroxy-N,N,N-trimethyl-11-oxo-9-[(3-tetradecyl-phenoxy)methyl]-5,7,10-trioxa-6-phosphaundecan-1-aminium, 6-oxide, hydroxide, inner salt 6-hydroxy-N,N,N-trimethyl-11-oxo-9-[(2-tetradecyl-phenoxy)methyl]-5,7,10-trioxa-6-phosphaundecan-1-aminium, 6-oxide, hydroxide, inner salt 6-hydroxy-N,N,N-trimethyl-11-oxo-9-[(3-tridecyl-phenoxy)methyl]-5,7,10-trioxa-6-phosphaundecan-1-aminium, 6-oxide, hydroxide, inner salt 6-hydroxy-N,N,N-trimethyl-11-oxo-9-[(2-hexadecyl-phenoxy)methyl]-5,7,10-trioxa-6-phosphaundecan-1-aminium, 6-oxide, hydroxide, inner salt 6-hydroxy-N,N-dimethyl-11-oxo-9-[(4-tetradecyl-phenoxy)methyl]-5,7,10-trioxa-6-phosphaundecan-1-aminium, 6-oxide, hydroxide, inner salt 6-hydroxy-N,N-dimethyl-11-oxo-9-[(3-tetradecyl-phenoxy)methyl]-5,7,10-trioxa-6-phosphaundecan-1-aminium, 6-oxide, hydroxide, inner salt 6-hydroxy-N,N-dimethyl-11-oxo-9-[(4-dodecylphenox-y)methyl]-5,7,10-trioxa-6-phosphaundecan-1-aminium, 6-oxide, hydroxide, inner salt 6-hydroxy-N,N-dimethyl-11-oxo-9-[(3-tridecylphenox-y)methyl]-5,7,10-trioxa-6-phosphaundecan-1-aminium, 6-oxide, hydroxide, inner salt 6-hydroxy-N,N-dimethyl-11-oxo-9-[(2-hexadecyl-phenoxy)methyl]-5,7,10-trioxa-6-phosphaundecan-1-aminium, 6-oxide, hydroxide, inner salt 6-hydroxy-N-ethyl-11-oxo-9-[(4-tetradecylphenoxy)-methyl]-5,7,10-trioxa-6-phosphaundecan-1-aminium, 6-oxide, hydroxide, inner salt 6-hydroxy-N-ethyl-11-oxo-9-[(2-tetradecylphenoxy)-methyl]-5,7,10-trioxa-6-phosphaundecan-1-aminium, 6-oxide, hydroxide, inner salt 6-hydroxy-N-ethyl-11-oxo-9-[(4-dodecylphenoxy)me-thyl]-5,7,10-trioxa-6-phosphaundecan-1-aminium, 6-oxide, hydroxide, inner salt 6-hydroxy-N,N,N-trimethyl-11-oxo-9-[(4-tetradecyl-phenoxy)methyl]-5,7,10-trioxa-6-phosphadodecan-1-aminium, 6-oxide, hydroxide, inner salt 6-hydroxy-N,N,N-trimethyl-11-oxo-9-[(3-tetradecyl-phenoxy)methyl]-5,7,10-trioxa-6-phosphadodecan-1-aminium, 6-oxide, hydroxide, inner salt 6-hydroxy-N,N,N-trimethyl-11-oxo-9-[(2-tetradecyl-phenoxy)methyl]-5,7,10-trioxa-6-phosphadodecan-1-aminium, 6-oxide, hydroxide, inner salt 6-hydroxy-N,N,N-trimethyl-11-oxo-9-[(3-tridecyl-phenoxy)methyl]-5,7,10-trioxa-6-phosphadodecan-1-aminium, 6-oxide, hydroxide, inner salt 5-hydroxy-N,N,N-trimethyl-11-oxo-9-[(2-hexadecyl-phenoxy)methyl]-5,7,10-trioxa-6-phosphadodecan-1-aminium, 6-oxide, hydroxide, inner salt 6-hydroxy-N,N-dimethyl-11-oxo-9-[(4-tetradecyl-phenoxy)methyl]-5,7,10-trioxa-6-phosphadodecan-1-aminium, 6-oxide, hydroxide, inner salt 6-hydroxy-N,N-dimethyl-11-oxo-9-[(3-tetradecyl-phenoxy)methyl]-5,7,10-trioxa-6-phosphadodecan-1-aminium, 6-oxide, hydroxide, inner salt 6-hydroxy-N,N-dimethyl-11-oxo-9-[(4-dodecylphenox-y)methyl]-5,7,10-trioxa-6-phosphadodecan-1-aminium, 6-oxide, hydroxide, inner salt 6-hydroxy-N,N-dimethyl-11-oxo-9-[(3-tridecylphenox-y)methyl]-5,7,10-trioxa-6-phosphadodecan-1-aminium, 6-oxide, hydroxide, inner salt 6-hydroxy-N,N-dimethyl-11-oxo-9-[(2-hexadecyl-phenoxy)methyl]-5,7,10-trioxa-6-phosphadodecan-1-aminium, 6-oxide, hydroxide, inner salt 6-hydroxy-N-ethyl-11-oxo-9-[(4-tetradecylphenoxy)-methyl]-5,7,10-trioxa-6-phosphadodecan-1-aminium, 6-oxide, hydroxide, inner salt 6-hydroxy-N-ethyl-11-oxo-9-[(2-tetradecylphenoxy)-methyl]-5,7,10-trioxa-6-phosphadodecan-1-aminium, 6-oxide, hydroxide, inner salt 6-hydroxy-N-ethyl-11-oxo-9-[(4-dodecylphenoxy)me-thyl]-5,7,10-trioxa-6-phosphadodecan-1-aminium, 6-oxide, hydroxide, inner salt 2-[[2-(acetyloxy)-3-(4-tetradecylphenoxy)propoxy]hy-droxyphosphinyl]-N,N,N-trimethyl-ethanaminium, hydroxide, inner salt 2-[[2-(acetyloxy)-3-(3-tridecylphenoxy)propoxy]hydroxyphosphinyl]-N,N,N-trimethyl-ethanaminium, hydroxide, inner salt 2-[[2-(acetyloxy)-3-(4-dodecylphenoxy)propoxy]hydroxyphosphinyl]-N,N,N-trimethyl-ethanaminium, hydroxide, inner salt 2-[[2-(acetyloxy)-3-(2-tetradecylphenoxy)propoxy]hydroxyphosphinyl]-N,N,N-trimethyl-ethanaminium, hydroxide, inner salt 3-[[2-(acetyloxy)-3-(4-tetradecylphenoxy)propoxy]hydroxyphosphinyl]-N,N,N-trimethyl-propanaminium, hydroxide, inner salt 3-[[2-(acetyloxy)-3-(3-tridecylphenoxy)propoxy]hydroxyphosphinyl]-N,N,N-trimethyl-propanaminium, hydroxide, inner salt 3-[[2-(acetyloxy)-3-(4-dodecylphenoxy)propoxy]hydroxyphosphinyl]-N,N,N-trimethyl-propanaminium, hydroxide, inner salt 3-[[2-(acetyloxy)-3-(2-tetradecylphenoxy)propoxy]hydroxyphosphinyl]-N,N,N-trimethyl-propanaminium, hydroxide, inner salt

EXAMPLE 91

1-Hexadecyl-2-methoxybenzene

To a refluxing solution of about 35.3 g of hexadecyl iodide in tetrahydrofuran was added a solution of about 37.4 g of bromoanisole and about 4.86 g of magnesium in tetrahydrofuran which had been refluxed for about 2 hours. An about 10 ml portion of about 0.1M lithium cupric chloride was added, the mixture was refluxed about 2 hours and stirred at room temperature for about 16 hours giving about 34 g of the desired reagent.

EXAMPLE 92

2-Hexadecyl phenol

A solution of about 14.94 g of 1-hexadecyl-2-methoxybenzene in methylene chloride, under argon, was cooled to about $-78°$ C. and about 3.76 g of boron tribromide was added. The mixture was allowed to warm to room temperature, was then stirred for about 24 hours and quenched by the dropwise addition of ice-cold water. The mixture was then washed with sodium bicarbonate solution, dried and evaporated, giving about 14 g of the desired reagent, mp 54°–55° C.

EXAMPLE 93

1-[2-Methoxy-3-(triphenylmethoxy)propoxy]-4-tetradecylbenzene

To a solution of about 558 mg of 1-(4-tetradecylphenoxy)-3-(triphenylmethoxy)-2-propanol in about 5 ml of dry dimethylformamide was added a prewashed suspension of about 66 mg of sodium hydride in about 2 ml of dimethylformamide followed by about 157 mg of iodomethane. The mixture was stirred under argon for about 2 hours, quenched slowly with water and extracted twice with ether:hexane (about 1:1). The extracts were combined, dried, and the solvents evaporated, giving about 560 mg of the desired title compound.

EXAMPLE 94

2-Methoxy-3-(4-tetradecylphenoxy)-1-propanol

A mixture of about 527 mg of 1-[2-methoxy-3-(triphenylmethoxy)propoxy]-4-tetradecylbenzene, about 10 mg of p-toluenesulfonic acid and about 5 ml of methanol:tetrahydrofuran (about 1:1) was stirred under argon for about 16 hours and the solvents removed under reduced pressure. The residue was dissolved in ether:hexane (about 1:1), washed with aqueous sodium bicarbonate, brine, dried and evaporated, giving about 171 mg of the desired title compound, mp 43°–45° C.

EXAMPLE 95

2-Bromoethyl 2-methoxy-3-(4-tetradecylphenoxy)propyl phosphate

To a solution of about 2.646 g of 2-methoxy-3-(4-tetradecylphenoxy)-1-propanol in carbon tetrachloride was added a solution of about 2.016 g of 2-bromoethyl phosphorodichlorodate in about 2 ml of carbon tetrachloride followed by a solution of about 850 mg of triethylamine in carbon tetrachloride. The mixture was stirred under argon for about 2 hours, then filtered through celite and the solvents removed. The residue was dissolved in about 60 ml of tetrahydrofuran, about 60 ml of about 0.5M aqueous sodium acetate was added, the mixture stirred about 16 hours and then dilute hydrochloric acid (about 1N) and brine were added. This mixture was extracted three times with ethanol. The extracts were combined, washed with brine, dried and the solvent evaporated. The residue was chromatographed on about 60 g of florisil saturated with chloroform. The solvents used to elute were chloroform, then chloroform:methanol (about 7:3), giving about 2.9 g of the desired title compound.

EXAMPLE 96

4-Hydroxy-N,N,N-trimethyl-7-[(4-tetradecylphenoxy)methyl]-3,5,8-trioxa-4-phosphanonan-1-aminium, 4-oxide, hydroxide, inner salt A mixture of about 2.9 g of 2-bromoethyl 2-methoxy-3-(4-tetradecylphenoxy)propyl phosphate, about 30 ml of about 40% aqueous trimethylamine and about 65 ml of chloroform:2-propanol:dimethylformamide (about 3:5:5) was heated at about 65° C. for about 3 hours. The volume of solvents was reduced by about ½, then about 0.5 g of silver carbonate and about 50 ml of ethanol were added. This mixture was stirred about 45 minutes, filtered through celite and the solvents removed, giving about 2.4 g of the desired product, mp 210° C. (dec.).

By using the phosphorous reagents listed in Table VII, the amines of Table VIII and the appropriate starting materials prepared in Examples 81 and 92 and those listed in Table VI and by following the methods described in detail hereinabove in Examples 93-96, the compounds of this invention listed below can be prepared. These compounds can be prepared as the individual optically active R and S enantiomers or as racemic mixtures as described in the above specifications.

4-hydroxy-N,N,N-trimethyl-7-[(4-tetradecylphenoxy)methyl]-3,5,8-trioxa-4-phosphanonan-1-aminium, 4-oxide, hydroxide, inner salt 4-hydroxy-N,N,N-trimethyl-7-[(4-hexadecylphenoxy)methyl]-3,5,8-trioxa-4-phosphanonan-1-aminium, 4-oxide, hydroxide, inner salt 4-hydroxy-N,N,N-trimethyl-7-[(4-pentadecylphenoxy)methyl]-3,5,8-trioxa-4-phosphanonan-1-aminium, 4-oxide, hydroxide, inner salt 4-hydroxy-N,N,N-trimethyl-7-[(4-dodecylphenoxy)methyl]-3,5,8-trioxa-4-phosphanonan-1-aminium, 4-oxide, hydroxide, inner salt 4-hydroxy-N,N,N-trimethyl-7-[(3-tetradecylphenoxy)methyl]-3,5,8-trioxa-4-phosphanonan-1-aminium, 4-oxide, hydroxide, inner salt 4-hydroxy-N,N,N-trimethyl-7-[(2-tetradecylphenoxy)-methyl]-3,5,8-trioxa-4-phosphanonan-1-aminium, 4-oxide, hydroxide, inner salt
4-hydroxy-N,N,N-trimethyl-7-[(3-tridecylphenoxy)methyl]-3,5,8-trioxa-4-phosphanonan-1-aminium, 4-oxide, hydroxide, inner salt
4-hydroxy-N,N-dimethyl-7-[(4-tetradecylphenoxy)methyl]-3,5,8-trioxa-4-phosphanonan-1-aminium, 4-oxide, hydroxide, inner salt
4-hydroxy-N,N-dimethyl-7-[(4-hexadecylphenoxy)methyl]-3,5,8-trioxa-4-phosphanonan-1-aminium, 4-oxide, hydroxide, inner salt
4-hydroxy-N,N-dimethyl-7-[(4-pentadecylphenoxy)methyl]-3,5,8-trioxa-4-phosphanonan-1-aminium, 4-oxide, hydroxide, inner salt
4-hydroxy-N,N-dimethyl-7-[(4-dodecylphenoxy)methyl]-3,5,8-trioxa-4-phosphanonan-1-aminium, 4-oxide, hydroxide, inner salt
4-hydroxy-N,N-dimethyl-7-[(3-tetradecylphenoxy)methyl]-3,5,8-trioxa-4-phosphanonan-1-aminium, 4-oxide, hydroxide, inner salt
4-hydroxy-N,N-dimethyl-7-[(2-tetradecylphenoxy)methyl]-3,5,8-trioxa-4-phosphanonan-1-aminium, 4-oxide, hydroxide, inner salt
4-hydroxy-N,N-dimethyl-7-[(3-tridecylphenoxy)methyl]-3,5,8-trioxa-4-phosphanonan-1-aminium, 4-oxide, hydroxide, inner salt
2-[[2-(methoxy)-3-(4-dodecylphenoxy)propoxy]hydroxyphosphinyl]-N,N,N-trimethyl-ethanaminium, hydroxide, inner salt
2-[[2-(methoxy)-3-(4-tetradecylphenoxy)propoxy]hydroxyphosphinyl]-N,N,N-trimethyl-ethanaminium, hydroxide, inner salt
2-[[2-(methoxy)-3-(3-tridecylphenoxy)propoxy]hydroxyphosphinyl]-N,N,N-trimethyl-ethanaminium, hydroxide, inner salt
2-[[2-(methoxy)-3-(2-tetradecylphenoxy)propoxy]hydroxyphosphinyl]-N,N,N-trimethyl-ethanaminium, hydroxide, inner salt
3-[[2-(methoxy)-3-(4-dodecylphenoxy)propoxy]hydroxyphosphinyl]-N,N,N-trimethyl-propanaminium, hydroxide, inner salt
3-[[2-(methoxy)-3-(4-tetradecylphenoxy)propoxy]hydroxyphosphinyl]-N,N,N-trimethyl-propanaminium, hydroxide, inner salt
3-[[2-(methoxy)-3-(3-tridecylpbenoxy)propoxy]hydroxyphosphinyl]-N,N,N-trimethyl-propanaminium, hydroxide, inner salt
3-[[2-(methoxy)-3-(2-tetradecylphenoxy)propoxy]hydroxyphosphinyl]-N,N,N-trimethyl-propanaminium, hydroxide, inner salt

What is claimed is:

1. Compounds, including the individual R and S enantiomers and racemic mixtures, represented by the formula:

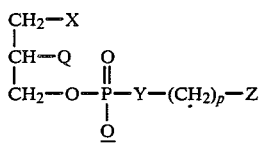

wherein: (a) X is selected from the group consisting of (i) $C_1-C_{24}$ alkyl; (ii) $C_1-C_{24}$ alkoxy; (iii)

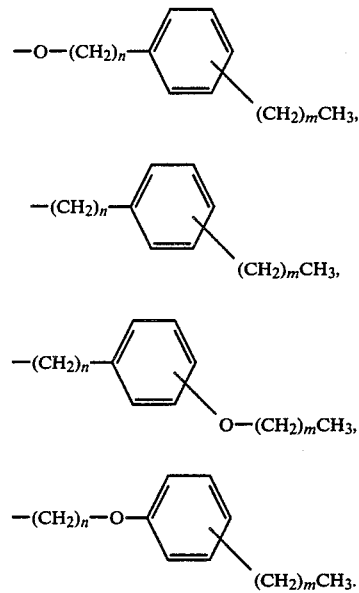

wherein n is an integer from 1 to 25 and m is an integer from 0 to 24 and the sum of n and m is less than or equal to 25; (iv) phenyl; (v) substituted phenyl wherein the substituents are selected from the group consisting of $C_1-C_{20}$ alkyl, $C_1-C_{20}$ alkoxy, halogen, trifluoromethyl, phenyl, and substituted phenyl; (vi) phenoxy; and (vii) substituted phenoxy wherein the substituents are selected from the group consisting of $C_1-C_{20}$ alkyl, $C_1-C_{20}$ alkoxy, halogen, trifluoromethyl, phenyl, and substituted phenyl; (b) Q is selected from the group consisting of:

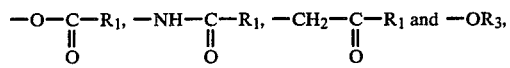

wherein $R_1$ is selected from the group consisting of (i) hydrogen; (ii) $C_1-C_4$ alkyl; (iii) $C_1-C_4$ alkoxy; and (iv) $C_1-C_4$ alkylamino and wherein $R_3$ is $C_1-C_4$ alkyl, with the provisos (i) when Q is

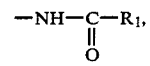

X is $C_1-C_{24}$ alkoxy or

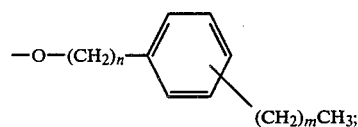

(ii) Q is not

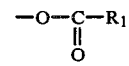

if at the same time $R_1$ is $C_1-C_4$ alkyl, X is $C_1-C_{24}$ alkoxy and Y is oxygen; (iii) Q is not $-OR_3$ if at the same time X is $C_1-C_{24}$ alkoxy and Y is oxygen; and (iv) if Q is

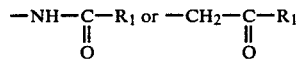

then $R_1$ is $C_1$-$C_4$ alkyl; (c) Y is oxygen or $CH_2$; (d) p is an integer from 1 to 15 with proviso that when Y is oxygen, p must be greater than 1; and (e) Z is

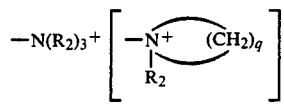

wherein $R_2$ is hydrogen or $C_1$-$C_4$ alkyl.

2. The compounds according to claim 1 wherein Q is

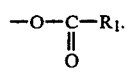

3. The compounds according to claim 1 wherein Q is

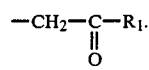

4. The compounds according to claim 1 wherein Q is

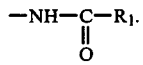

5. The compounds according to claim 1 wherein Q is —$OR_3$.
6. The compounds according to claim 2 wherein Y is oxygen.
7. The compounds according to claim 2 wherein Y is —$CH_2$.
8. The compounds according to claim 3 wherein Y is oxygen.
9. The compounds according to claim 3 wherein Y is —$CH_2$.
10. The compounds according to claim 4 wherein Y is oxygen.
11. The compounds according to claim 4 wherein Y is —$CH_2$.
12. The compounds according to claim 5 wherein Y is oxygen.
13. The compounds according to claim 5 wherein Y is —$CH_2$.
14. The compounds according to claim 6 wherein X is selected from the group consisting of $C_1$-$C_{24}$ alkyl,

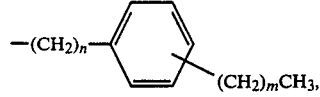

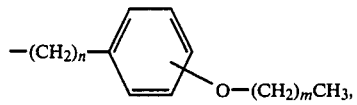

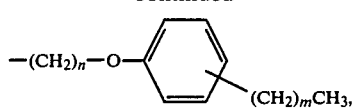

phenyl and substituted phenyl, wherein the substituents are selected from the group consisting of $C_1$-$C_{20}$ alkyl, $C_1$-$C_{20}$ alkoxy, halogen, trifluoromethyl, phenyl and substituted phenyl.

15. The compounds according to claim 6 wherein X is selected from the group consisting of $C_1$-$C_{24}$ alkoxy,

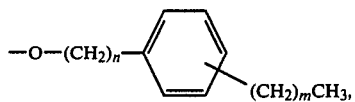

phenoxy and substituted phenoxy wherein the substituents are selected from the group consisting of $C_1$-$C_{20}$ alkyl, $C_1$-$C_{20}$ alkoxy, halogen, trifluoromethyl, phenyl and substituted phenyl.

16. The compounds according to claim 7 wherein X is selected from the group consisting of $C_1$-$C_{24}$ alkoxy,

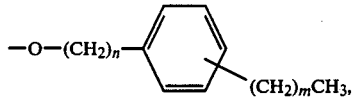

phenoxy and substituted phenoxy wherein the substituents are selected from the group consisting of $C_1$-$C_{20}$ alkyl, $C_1$-$C_{20}$ alkoxy, halogen, trifluoromethyl, phenyl and substituted phenyl.

17. The compounds according to claim 7 wherein X is selected from the group consisting of $C_1$-$C_{24}$ alkyl,

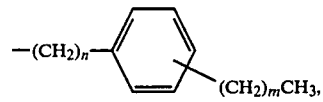

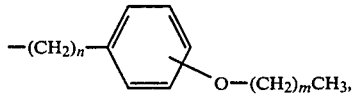

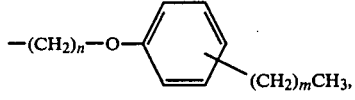

phenyl and substituted phenyl, wherein the substituents are selected from the group consisting of $C_1$-$C_{20}$ alkyl, $C_1$-$C_{20}$ alkoxy, halogen, trifluoromethyl, phenyl and substituted phenyl.

18. The compounds according to claim 8 wherein X is selected from the group consisting of $C_1$-$C_{24}$ alkyl,

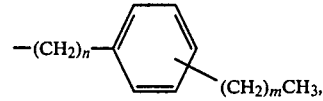

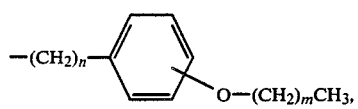

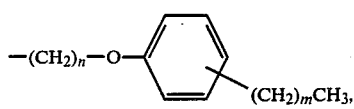

phenyl and substituted phenyl, wherein the substituents are selected from the group consisting of $C_1-C_{20}$ alkyl, $C_1-C_{20}$ alkoxy, halogen, trifluoromethy, phenyl and substituted phenyl.

19. The compounds according to claim 8 wherein X is selected from the group consisting of $C_1-C_{24}$ alkoxy,

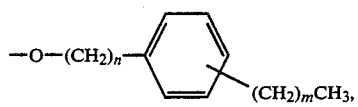

phenoxy and substituted phenoxy wherein the substituents are selected from the group consisting of $C_1-C_{20}$ alkyl, $C_1-C_{20}$ alkoxy, halogen, trifluoromethyl, phenyl and substituted phenyl.

20. The compounds according to claim 9 wherein X is selected from the group consisting of $C_1-C_{24}$ alkyl,

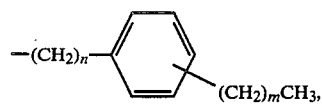

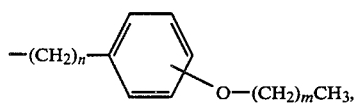

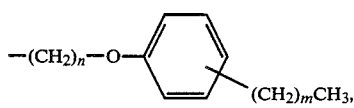

phenyl and substituted phenyl, wherein the substituents are selected from the group consisting of $C_1-C_{20}$ alkyl, $C_1-C_{20}$ alkoxy, halogen, trifluoromethyl, phenyl and substituted phenyl.

21. The compounds according to claim 9 wherein X is selected form the group consisting of $C_1-C_{24}$ alkoxy,

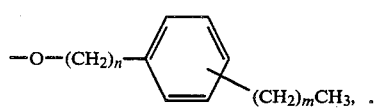

phenoxy and substituted phenoxy wherein the substituents are selected from the group consisting of $C_1-C_{20}$ alkyl, $C_1-C_{20}$ alkoxy, halogen, trifluoromethyl, phenyl and substituted phenyl.

22. The compounds according to claim 10 wherein X is selected from the group consisting of $C_1-C_{24}$ alkoxy,

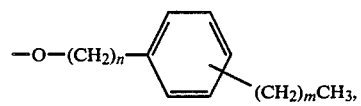

phenoxy and substituted phenoxy wherein the substituents are selected from the group consisting of $C_1-C_{20}$ alkyl, $C_1-C_{20}$ alkoxy, halogen, trifluoromethyl, phenyl and substituted phenyl.

23. The compounds according to claim 11 wherein X is selected from the group consisting of $C_1-C_{24}$ alkoxy,

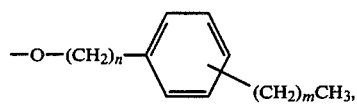

phenoxy and substituted phenoxy wherein the substituents are selected from the group consisting of $C_1-C_{20}$ alkyl, $C_1-C_{20}$ aklapoxy, halogen, trifluoromethyl, phenyl and substituted phenyl.

24. The compounds according to claim 12 wherein X is selected from the group consisting of $C_1-C_{24}$ alkyl,

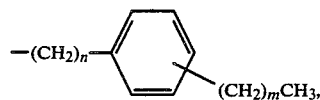

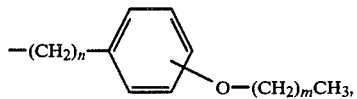

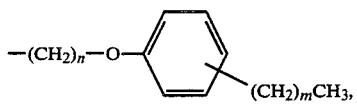

phenyl and substituted phenyl, wherein the substituents are selected from the group consisting of $C_1-C_{20}$ alkyl, $C_1-C_{20}$ alkoxy, halogen, trifluoromethyl, phenyl and substituted phenyl.

25. The compounds according to claim 12 wherein X is selected from the group consisting of $C_1-C_{24}$ alkoxy,

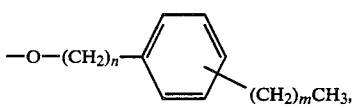

phenoxy and substituted phenoxy wherein the substituents are selected from the group consisting of $C_1-C_{20}$ alkyl, $C_1-C_{20}$ alkoxy, halogen, trifluoromethyl, phenyl and substituted phenyl.

26. The compounds according to claim 13 wherein X is selected from the group consisting of $C_1-C_{24}$ alkyl,

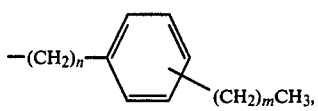

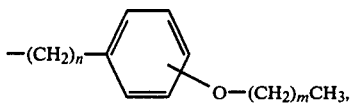

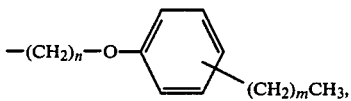

phenyl and substituted phenyl, wherein the substituents are selected from the group consisting of $C_1$-$C_{20}$ alkyl, $C_1$-$C_{20}$ alkoxy, halogen, trifluoromethyl, phenyl and substituted phenyl.

27. The compounds according to claim 13 wherein X is selected from the group consisting of $C_1$-$C_{24}$ alkoxy,

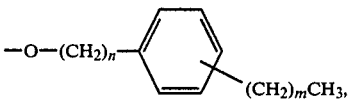

phenoxy and substituted phenoxy wherein the substituents are selected from the group consisting of $C_1$-$C_{20}$ alkyl, $C_1$-$C_{20}$ alkoxy, halogen, trifluoromethyl, phenyl and substituted phenyl.

28. A method of treating hypertension in a warm-blooded animal comprising administering to said animal an effective amount of a compound, including the individual R and S enantiomers and racemic mixture, represented by the formula:

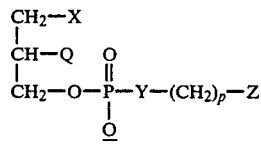

wherein: (a) X is selected from the group consisting of (i) $C_1$-$C_{24}$ alkyl; (ii) $C_1$-$C_{24}$ alkoxy; (iii)

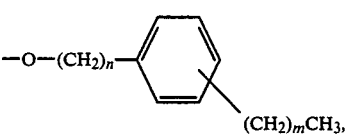

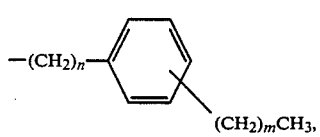

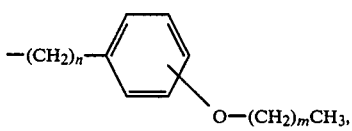

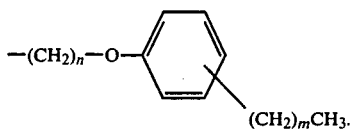

wherein n is an integer from 1 to 25 and m is an integer from 0 to 24 and the sum of n and m is less than or equal to 25; (iv) phenyl; (v) substituted phenyl wherein the substituents are selected from the group consisting of $C_1$-$C_{20}$ alkyl, $C_1$-$C_{20}$ alkoxy, halogen, trifluoromethyl, phenyl and substituted phenyl; (vi) phenoxy; and (vii) substituted phenoxy wherein the substituents are selected from the group consisting of $C_1$-$C_{20}$ alkyl, $C_1$-$C_{20}$ alkoxy, halogen, trifluoromethyl, phenyl and substituted phenyl; (vi) phenoxy; and (vii) substituted phenoxy wherein the substituents are selected from the group consisting of $C_1$-$C_{20}$ alkyl, $C_1$-$C_{20}$ alkoxy, halogen, trifluoromethyl, phenyl and substituted phenyl; (b) Q is selected from the group consisting of

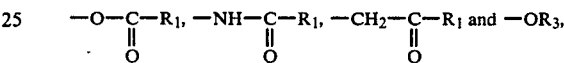

wherein $R_1$ is selected from the group consisting of (i) hydrogen; (ii) $C_1$-$C_4$ alkyl; (iii) $C_1$-$C_4$ alkoxy; and (iv) $C_1$-$C_4$ alkylamino and wherein $R_3$ is $C_1$-$C_4$ alkyl, with the provisos: (i) when Q is

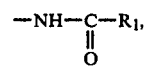

X is $C_1$-$C_{24}$ alkoxy or

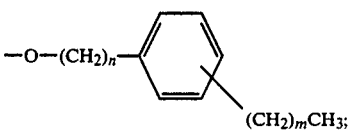

(ii) Q is not

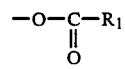

if at the same time $R_1$ is $C_1$-$C_4$ alkyl, X is $C_1$-$C_{24}$ alkoxy and Y is oxygen; (iii) Q is not —$OR_3$ if at the same time X is $C_1$-$C_{24}$ alkoxy and Y is oxygen; (iv) if Q is

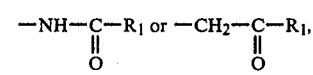

then $R_1$ is $C_1$-$C_4$ alkyl; (c) Y is oxygen or $CH_2$; (d) p is an integer from 1 to 15 with the proviso that when Y is oxygen, p must be greater than 1; and (e) Z is

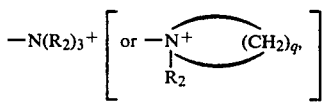

wherein $R_2$ is hydrogen or $C_1$-$C_4$ alkyl.

29. A pharmaceutical composition comprising an antihypertensive effective amount of a compound, including the individual R and S enatiomers and racemic mixture, represented by the formula:

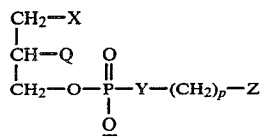

wherein: (a) X is selected from the group consisting of (i) $C_1$-$C_{24}$ alkyl; (ii) $C_1$-$C_{24}$ alkoxy; (iii)

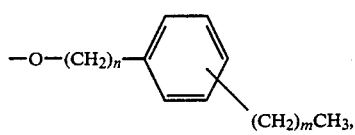

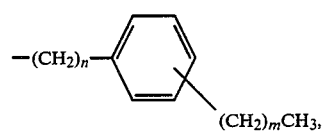

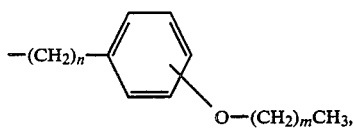

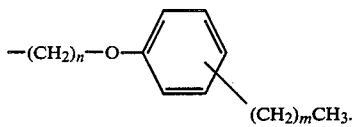

wherein n is an integer from 1 to 25 and m is an integer from 0 to 24 and the sum of n and m is less than or equal to 25; (iv) phenyl; (v) substituted phenyl wherein the substitutents are selected from the group consisting of $C_1$-$C_{20}$ alkyl, $C_1$-$C_{20}$ alkoxy, halogen, trifluoromethyl, phenyl and substituted phenyl; (vi) phenoxy; and (vii) substituted phenoxy wherein the substituents are selected from the group consisting of $C_1$-$C_{20}$ alkyl, $C_1$-$C_{20}$ alkoxy, halogen, trifluoromethyl, phenyl and substituted phenyl; (b) Q is selected from the group consisting of

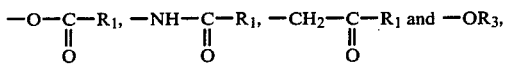

wherein $R_1$ is selected from the group consisting of (i) hydorgen; (ii) $C_1$-$C_4$ alkyl; (iii) $C_1$-$C_4$ alkoxy; and (iv) $C_1$-$C_4$ alkylamino and wherein $R_3$ is $C_1$-$C_4$ alkyl with the provisos; (i) when Q is

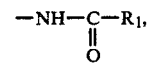

X is $C_1$-$C_{24}$ alkoxy or

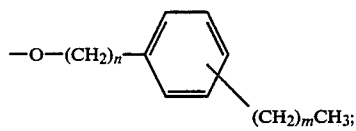

(ii) Q is not

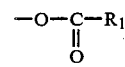

if at the same time $R_1$ is $C_1$-$C_4$ alkyl, X is $C_1$-$C_{24}$ alkoxy and Y is oxygen; (iii) Q is not —$OR_3$ if at the same time X is $C_1$-$C_{24}$ alkoxy and Y is oxygen; (iv) if Q is

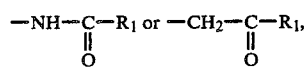

then $R_1$ is $C_1$-$C_4$ alkyl; (c) Y is oxygen or $CH_2$; (d) p is an integer from 1 to 15 with the proviso that when Y is oxygen, p must be greater than 1; and (e) Z is

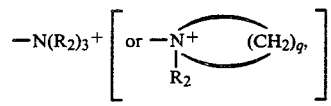

wherein $R_2$ is hydrogen or $C_1$-$C_4$ alkyl in a pharmaceutically acceptable carrier.

* * * * *